(12) United States Patent
Amit et al.

(10) Patent No.: US 12,630,831 B2
(45) Date of Patent: *May 19, 2026

(54) SYNTHETIC NON-CODING RNAS

(71) Applicant: TECHNION RESEARCH & DEVELOPMENT FOUNDATION LIMITED, Haifa (IL)

(72) Inventors: Roee Amit, Tel Aviv (IL); Noa Katz, Tirat Carmel (IL)

(73) Assignee: TECHNION RESEARCH & DEVELOPMENT FOUNDATION LIMITED, Haifa (IL)

( * ) Notice: Subject to any disclaimer, the term of this patent is extended or adjusted under 35 U.S.C. 154(b) by 1193 days.

This patent is subject to a terminal disclaimer.

(21) Appl. No.: 17/036,257

(22) Filed: Sep. 29, 2020

(65) Prior Publication Data

US 2021/0095296 A1     Apr. 1, 2021

Related U.S. Application Data

(60) Provisional application No. 62/907,676, filed on Sep. 29, 2019.

(51) Int. Cl.
| | |
|---|---|
| *C07H 21/00* | (2006.01) |
| *C12N 15/115* | (2010.01) |
| *C12N 15/67* | (2006.01) |
| *C12P 21/02* | (2006.01) |
| *C12N 15/10* | (2006.01) |

(52) U.S. Cl.
CPC ............. *C12N 15/67* (2013.01); *C07H 21/00* (2013.01); *C12P 21/02* (2013.01); *C12N 15/1037* (2013.01); *C12N 15/115* (2013.01)

(58) Field of Classification Search
CPC ................ C12N 15/67; C12N 15/1037; C12N 15/115; C07H 21/00; C12P 21/02; G16B 20/20; G16B 40/20
See application file for complete search history.

(56) References Cited

U.S. PATENT DOCUMENTS

| | | | |
|---|---|---|---|
| 10,624,849 B2 | 4/2020 | Leonard et al. | |
| 2007/0116718 A1 | 5/2007 | Weidanz et al. | |
| 2010/0261214 A1 | 10/2010 | Loibner | |
| 2013/0164845 A1 | 6/2013 | Polach | |
| 2020/0317746 A1 | 10/2020 | Leonard | |
| 2021/0095296 A1 | 4/2021 | Amit et al. | |

FOREIGN PATENT DOCUMENTS

| | | | | |
|---|---|---|---|---|
| CN | 112375149 A | 2/2021 | | |
| WO | WO-2013103614 A1 * | 7/2013 | ........... | C12N 15/111 |
| WO | 2015081229 A2 | 6/2015 | | |
| WO | WO-2020142676 A1 * | 7/2020 | ............... | C12N 9/78 |
| WO | 2021022008 A1 | 2/2021 | | |
| WO | 2021051153 A1 | 3/2021 | | |

OTHER PUBLICATIONS

Lunde (et al. 2007. RNA-binding proteins: modular design for efficient function. Nat. Rev. Mol. Cell Biol. 8:479-490) (Year: 2007).*
Kwon (et al. 2016. Structure of Human DROSHA. Cell 164[1-2]:81-90) (Year: 2016).*
Masliah (et al. 2018. Structural basis of siRNA recognition by TRBP double-stranded RNA binding domains. EMBO J 37[6]:e97089) (Year: 2018).*
Katz (et al. 2018. An in vivo binding assay for RNA-binding proteins based on repression of a reporter gene. BioRxiv. Posted Apr. 13, 2018) (Year: 2018).*
U.S. Appl. No. 17/780,404, filed May 2022.*
U.S. Appl. No. 18/192,487, filed Aug. 2023.*
U.S. Appl. No. 18/507,493, filed Jan. 2024.*
Corley (et al. 2020. How RNA binding proteins interact with RNA: molecules and mechanisms. Mol. Cell 78[1]:9-29) (Year: 2020).*
Vergani (et al. 2021. DICER: structure, function, and regulation. Biophys Rev. 13:1081-1090) (Year: 2021).*
Insana (et al. 2024. Improved selection of canonical proteins for reference Proteomes. NAR Genom Bioinformat 6:lqae066) (Year: 2024).*
Wikipedia (Dicer; Helicase. Available at Wikipedia.org. Accessed Jul. 11, 2024) (Year: 2024).*
Hynes (and Kakumani. 2024. Regulatory role of RNA-binding proteins in microRNA biogenesis. Front. Mol. Biosci. 11:1374843) (Year: 2024).*
Shechner (et al. 2015. Multiplexable, locus-specific targeting of long RNrnAs with CRIScrisPR-Display. Nature Methods 12[7]:664-673 (Year: 2015).*
Hirao (et al. 1999. The limits of specificity: An experimental analysis with RNA aptamers to MS2 coat protein variants. Molec. Divers. 4:75-889) (Year: 1999).*
White (et al. 2001. Generation of Species Cross-reactive Aptamers Using "Toggle" SELEX. Molec. Ther. 4[6]:567-573) (Year: 2001).*
Lim (and Peabody. 2002. RNA recognition site of PP7 coat protein. Nuc. Ac. Res. 30[19]:4138-4144) (Year: 2002).*
Wu (et al. 2015. Synonymous modification results in high-fidelity gene expression of repetitive protein and nucleotide sequences. Genes Develop. 29:876-886) (Year: 2015).*
Koo, P. K., Anand, P., Paul, S. B., & Eddy, S. R. (2018). Inferring sequence-structure preferences of ma-binding proteins with convolutional residual networks. BioRxiv, 418459.

(Continued)

*Primary Examiner* — Nancy J Leith
*Assistant Examiner* — Ruth Sophia Arieti
(74) *Attorney, Agent, or Firm* — The Roy Gross Law Firm, LLC; Roy D. Gross

(57) ABSTRACT

Synthetic RNA molecules comprising at least two RNA-binding protein (RBP)-binding motifs, wherein the at least two RBP-binding motifs bind the same first RBP and comprise non-identical sequences are provided. Synthetic RNA molecules comprising an RBP-binding motif that binds two orthogonal RBPs, comprising at least three RBP-binding motifs for three orthogonal RBPs or comprising a first RBP-binding motif, a second RBP-binding motif, a regulatory element and an open reading frame wherein the first and second RBP-binding motifs cooperatively enhance translation of the open reading frame are also provided. Compositions, cells and methods of use or generating the synthetic RNA molecules are also provided.

9 Claims, 33 Drawing Sheets

Specification includes a Sequence Listing.

(56) References Cited

OTHER PUBLICATIONS

Allaway, G. P., Davis-Bruno, K. L., Beaudry, G. A., Garcia, E. B., Wong, E. L., Ryder, A. M., & Maddon, P. J. (1995). Expression and characterization of CD4-IgG2, a novel heterotetramer that neutralizes primary HIV type 1 solates. AIDS research and human retroviruses, 11(5), 533-539.

Taskova M, Mantsiou A, Astakhova K. Synthetic Nucleic Acid Analogues in Gene Therapy: An Update for Peptide-Oligonucleotide Conjugates. Chembiochem. Sep. 5, 2017;18(17):1671-1682. doi: 10.1002/cbic.201700229. Epub Jul. 24, 2017. PMID: 28614621.

Williams BA, Chaput JC. Synthesis of peptide-oligonucleotide conjugates using a heterobifunctional crosslinker. Curr Protoc Nucleic Acid Chem. Sep. 2010;Chapter 4:Unit4.41. doi: 10.1002/0471142700. nc0441s42. PMID: 20827717; PMCID: PMC2947322.

H. Guo, J. Ryan, A. Mallet, X. Song, V. Pabst, A. Decrulle, A. Lindner. Spatial engineering of E. coli with addressable phase-separated RNAs. bioRxiv Jul. 2, 2020; 182527; doi: https://doi.org/10.1101/2020.07.02.182527.

Langan RA, Boyken SE, Ng AH, Samson JA, Dods G, Westbrook AM, Nguyen TH, Lajoie MJ, Chen Z, Berger S, Mulligan VK, Dueber JE, Novak WRP, El-Samad H, Baker D. De novo design of bioactive protein switches. Nature. Aug. 2019;572(7768):205-210. doi: 10.1038/s41586-019-1432-8. Epub Jul. 24, 2019. PMID: 31341284; PMCID: PMC6733528.

Koodli RV, Keep B, Coppess KR, Portela F; Eterna participants, Das R. EternaBrain: Automated RNA design through move sets and strategies from an Internet-scale RNA videogame. PLoS Comput Biol. Jun. 27, 2019;15(6):e1007059. doi: 10.1371/journal.pcbi. 1007059. PMID: 31247029; PMCID: PMC6597038.

Urbanek MO, Galka-Marciniak P, Olejniczak M, Krzyzosiak WJ. RNA imaging in living cells—methods and applications. RNA Biol. 2014;11(8):1083-95. doi: 10.4161/rna.35506. PMID: 25483044; PMCID: PMC4615301.

Tutucci E, Vera M, Biswas J, Garcia J, Parker R, Singer RH. An improved MS2 system for accurate reporting of the mRNA life cycle. Nat Methods. Jan. 2018; 15(1):81-89. doi: 10.1038/nmeth. 4502. Epub Nov. 13, 2017. PMID: 29131164; PMCID: PMC5843578.

Lim F, Spingola M, Peabody DS. The RNA-binding site of bacteriophage Qbeta coat protein. J Biol Chem. Dec. 13, 1996;271(50):31839-45. doi: 10.1074/jbc.271.50.31839. PMID: 8943226.

Witherell GW, Uhlenbeck OC. Specific RNA binding by Q beta coat protein. Biochemistry. Jan. 10, 1989;28(1):71-6. doi: 10.1021/bi00427a011. PMID: 2706270.

Gasperini M, Starita L, Shendure J. The power of multiplexed functional analysis of genetic variants. Nat Protoc. Oct. 2016;11(10):1782-7. doi: 10.1038/nprot.2016.135. Epub Sep. 1, 2016. PMID: 27583640; PMCID: PMC6690347.

Park Y, Kellis M. Deep learning for regulatory genomics. Nat Biotechnol. Aug. 2015;33(8):825-6. doi: 10.1038/nbt.3313. PMID: 26252139.

Katz N, Cohen R, Atar O, Goldberg S, Amit R. An Assay for Quantifying Protein-RNA Binding in Bacteria. J Vis Exp. Jun. 12, 2019;(148). doi: 10.3791/59611. PMID: 31259904.

Johansson HE, Dertinger D, LeCuyer KA, Behlen LS, Greef CH, Uhlenbeck OC. A thermodynamic analysis of the sequence-specific binding of RNA by bacteriophage MS2 coat protein. Proc Natl Acad Sci U S A. Aug. 4, 1998;95(16):9244-9. doi: 10.1073/pnas.95.16. 9244. PMID: 9689065; PMCID: PMC21323.

Spingola M, Peabody DS. MS2 coat protein mutants which bind Qbeta RNA. Nucleic Acids Res. Jul. 15, 1997;25(14):2808-15. doi: 10.1093/nar/25.14.2808. PMID: 9207028; PMCID: PMC146832.

Tsai MC, Manor O, Wan Y, Mosammaparast N, Wang JK, Lan F, Shi Y, Segal E, Chang HY. Long noncoding RNA as modular scaffold of histone modification complexes. Science. Aug. 6, 2010;329(5992):689-93. doi: 10.1126/science. 1192002. Epub Jul. 8, 2010. PMID: 20616235; PMCID: PMC2967777.

Amit R, Garcia HG, Phillips R, Fraser SE. Building enhancers from the ground up: a synthetic biology approach. Cell. Jul. 8, 2011;146(1):105-18. doi: 10.1016/j.cell.2011.06.024. PMID: 21729783; PMCID: PMC3155781.

Brunwasser-Meirom M, Pollak Y, Goldberg S, Levy L, Atar O, Amit R. Using synthetic bacterial enhancers to reveal a looping-based mechanism for quenching-like repression. Nat Commun. Feb. 2, 2016;7:10407. doi: 10.1038/ncomms10407. PMID: 26832446; PMCID: PMC4740811.

Levo M, Segal E. In pursuit of design principles of regulatory sequences. Nat Rev Genet. Jul. 2014; 15(7):453-68. doi: 10.1038/nrg3684. Epub Jun. 10, 2014. PMID: 24913666.

Ausländer, S., Ausländer, D., Muller, M et al. Programmable single-cell mammalian biocomputers. Nature 487, 123-127 (2012). https://doi.org/10.1038/nature11149.

Hocine S, Raymond P, Zenklusen D, Chao JA, Singer RH. Single-molecule analysis of gene expression using two-color RNA labeling in live yeast. Nat Methods. Feb. 2013; 10(2):119-21. doi: 10.1038/nmeth.2305. Epub Dec. 23, 2012. PMID: 23263691; PMCID: PMC3899799.

Polymenidou M. The RNA face of phase separation. Science. May 25, 2018;360(6391):859-860. doi: 10.1126/science.aat8028. PMID: 29798872.

N. Katz, R. Cohen, O. Solomon, B. Kaufmann, O. Atar, Z. Yakhini, S. Goldberg, R. Amit. An in Vivo Binding Assay for RNA-Binding Proteins Based on Repression of a Reporter Gene. ACS Synth. Biol. 7, 2765-2774 (2018). https://doi.org/10.1021/acssynbio.8b00378.

N. Katz, E. Tripto, S. Goldberg, O. Atar, Z. Yakhini, Y. Orenstein, R. Amit, Overcoming the design, build, test (DBT) bottleneck for synthesis of nonrepetitive protein-RNA binding cassettes for RNA applications. bioRxiv, 2020, doi:10.1101/2019.12.24.886168.

Levy L, Anavy L, Solomon O, Cohen R, Brunwasser-Meirom M, Ohayon S, Atar O, Goldberg S, Yakhini Z, Amit R. A Synthetic Oligo Library and Sequencing Approach Reveals an Insulation Mechanism Encoded within Bacterial σ54 Promoters. Cell Rep. Oct. 17, 2017;21(3):845-858. doi: 10.1016/j.celrep.2017.09.063. PMID: 29045849.

Wittmann A, Suess B. Engineered riboswitches: Expanding researchers' toolbox with synthetic RNA regulators. FEBS Lett. Jul. 16, 2012;586(15):2076-83. doi: 10.1016/j.febslet.2012.02.038. Epub Feb. 28, 2012. PMID: 22710175.

Wroblewska L, Kitada T, Endo K, Siciliano V, Stillo B, Saito H, Weiss R. Mammalian synthetic circuits with RNA binding proteins for RNA-only delivery. Nat Biotechnol. Aug. 2015;33(8):839-41. doi: 10.1038/nbt.3301. Epub Aug. 3, 2015. PMID: 26237515; PMCID: PMC4532950.

Katz, N., Tripto, E., Granik, N et al. Overcoming the design, build, test bottleneck for synthesis of nonrepetitive protein-RNA cassettes. Nat Commun 12, 1576 (2021). https://doi.org/10.1038/s41467-021-21578-6.

Delebecque CJ, Lindner AB, Silver PA, Aldaye FA. Organization of intracellular reactions with rationally designed RNA assemblies. Science. Jul. 22, 2011;333(6041):470-4. doi: 10.1126/science. 1206938. Epub Jun. 23, 2011. PMID: 21700839.

Delebecque CJ, Silver PA, Lindner AB. Designing and using RNA scaffolds to assemble proteins in vivo. Nat Protoc. Oct. 2012;7(10):1797-807. doi: 10.1038/nprot.2012.102. Epub Sep. 6, 2012. PMID: 22955695.

Wilner OI, Shimron S, Weizmann Y, Wang ZG, Willner I. Self-assembly of enzymes on DNA scaffolds: en route to biocatalytic cascades and the synthesis of metallic nanowires. Nano Lett. May 2009;9(5):2040-3. doi: 10.1021/hl900302z. PMID: 19323557.

Ke Y, Ong LL, Shih WM, Yin P. Three-dimensional structures self-assembled from DNA bricks. Science. Nov. 30, 2012;338(6111):1177-83. doi: 10.1126/science.1227268. PMID: 23197527; PMCID: PMC3843647.

Katz, N., Cohen, R., Solomon, O., Kaufmann, B., Atar, O., Yakhini, Z., Goldberg S., Amit, R. RBP-RNA interactions in the 5' UTR lead to structural changes that alter translation. bioRxiv 2018. 174888; doi: https://doi.org/10.1101/174888.

(56)         References Cited

OTHER PUBLICATIONS

Granik, N., Katz, N., Goldberg, S., Amit, R. Synthetic liquid-liquid phase separated RNA-protein biocondensates reveal a bi-phasic cytosol in *E.coli*. bioRxiv 2020. 682518; doi: https://doi.org/10.1101/682518.

Kaufmann, B., Willinger, O., Eden, N., Kermas, L., Anavy, L., Solomon, Oz., Atar, O., Yakhini, Z., Goldberg, S., Amit, R. Identifying triplex binding rules in vitro leads to creation of a new synthetic regulatory tool in vivo bioRxiv 2019.12.25.888362; doi: https://doi.org/10.1101/2019.12.25.888362.

Buenrostro, J. D., Araya, C. L., Chircus, L. M., Layton, C. J., Chang, H. Y., Snyder, M. P., & Greenleaf, W. J. (2014). Quantitative analysis of RNA-protein interactions on a massively parallel array reveals biophysical and evolutionary landscapes. Nature biotechnology, 32(6), 562-568. https://doi.org/10.1038/nbt.2880.

Colantoni A, Rupert J, Vandelli A, Tartaglia GG, Zacco E. Zooming in on protein-RNA interactions: a multi-level workflow to identify interaction partners. Biochem Soc Trans. Aug. 28, 2020;48(4):1529-1543. doi: 10.1042/BST20191059. PMID: 32820806; PMCID: PMC7458403.

Zhang S, Zhou J, Hu H, Gong H, Chen L, Cheng C, Zeng J. A deep learning framework for modeling structural features of RNA-binding protein targets. Nucleic Acids Res. Feb. 29, 2016;44(4):e32. doi: 10.1093/nar/gkv1025. Epub Oct. 13, 2015. PMID: 26467480; PMCID: PMC4770198.

Al-Shuhaib, M.B.S., Hashim, H.O. and Al-Shuhaib, J.M., 2022. Most Deleterious Missense Variants of Angiotensin-converting Enzyme 2 Gene have Extremely Low Frequencies and a Little Impact on the Binding Affinity with the SARS-CoV-2 Spike.

Katz, N., Cohen, R., Solomon, O., Kaufmann, B., Atar, O., Yakhini, Z., Goldberg, S. and Amit, R., 2018. An in vivo binding assay for RNA-binding proteins based on repression of a reporter gene. ACS Synthetic Biology, 7(12), pp. 2765-2774. doi: 10.1021/acssynbio.8b00378. Epub Nov. 13, 2018. PMID: 30408420.

Katz, N., Cohen, R., Solomon, O., Kaufmann, B., Atar, O., Yakhini, Z., Goldberg, S. and Amit, R., 2019. Synthetic 5' UTRs can either up-or downregulate expression upon RNA-binding protein binding. Cell Systems, 9(1), pp. 93-106. doi: 10.1016/j.cels.2019.04.007. Epub May 22, 2019. PMID: 31129060.

Cohen, R., (2019) Understanding regulation of translation through RNA structure and investigating regulatory synthetic long non-coding RNA (sIncRNAs) [Research Thesis, Degree of Master of Science in Biotechnology & Food Engineering, theTechnion—Israel Institute of Technology], 78pp.

Koo, P.K., Anand, P., Paul, S.B. and Eddy, S.R., 2018. Inferring sequence-structure preferences of RNA-binding proteins with convolutional residual networks. BioRxiv, p. 418459. DOI:10.1101/418459.

* cited by examiner

SEQ ID NO: 307

10k variants

Qβ-wt

PP7-wt

SEQ ID NO: 306

MS2-wt

SEQ ID NO: 308

Edit Distance

SEQ ID NO: 306

SEQ ID NO: 307

SEQ ID NO: 308

SYNTHETIC NON-CODING RNAS

CROSS REFERENCE TO RELATED APPLICATIONS

This application claims the benefit of priority of U.S. Provisional Patent Application No. 62/907,676, filed Sep. 29, 2019, the contents of which are all incorporated herein by reference in their entirety.

REFERENCE TO AN ELECTRONIC SEQUENCE LISTING

The contents of the electronic sequence listing (TECH-P-0162-US corrected.xml; Size: 387,134 bytes; and Date of Creation: Jul. 6, 2025) is herein incorporated by reference in its entirety.

FIELD OF INVENTION

The present invention is in the field of synthetic RNA molecules and biological scaffolding.

BACKGROUND OF THE INVENTION

For the past two decades, synthetic biologists have built a portfolio of increasingly sophisticated biological circuits that are able to perform logical functions inside living cells. Such circuits are made from "biological parts" which are biochemical analogs of electronic components that are routinely used for the design of electrical circuits. Unfortunately, unlike their electronic counterparts, connecting biological parts to form circuits often fails. This is mostly due to the fact that many parts are short sequences of DNA or RNA, and connecting them introduces unpredictable and undesirable sequence effects. As a result, many iterations of trial and error are often needed before a successful design is achieved. This is termed the design, build, test (DBT) cycle in synthetic biology and is considered to be a major bottleneck for progress in the field. Specifically, the field is lacking computational methods that allow users to reliably design their system of choice without going through multiple time-consuming DBT cycles.

The challenge of formulating such algorithms is rooted in the large space of biomolecules that make-up the biological parts, and the variety of interactions that are possible between them. This translates to a plethora of molecular mechanisms, each governed by differing kinetics, thermodynamic parameters, and free-energy considerations. Consequently, modelling these systems necessitates case-specific kinetic and/or thermodynamic modelling approaches to devise a reliable design algorithm. In recent years, several studies have demonstrated such algorithms for diverse RNA-, DNA- and protein-based applications, with varying degrees of success. Notable examples include the Cello algorithm and the Ribosome-binding-site calculator, which are limited to bacterial chassis at the present time.

Reliable algorithms are especially needed for the design of RNA-centric functional modules for various applications. Another RNA-based system where a reliable design algorithm can help bring about the full potential of the technology is the encoding of multiple repeats of phage coat protein (CP) binding elements on an RNA molecule of choice. Such cassettes have been utilized in many studies for a variety of applications including gene editing and RNA-tracking. However, a limited understanding of CP-binding in vivo has forced cassette designs into incorporating repeated hairpinlike sequence elements, making them cumbersome to synthesize using current oligo-based technology. Subsequent steps, including cloning and genome maintenance, are also badly affected by the repeat nature of the cassette. Finally, repeat sequence elements are notoriously unstable, thus damaging protein binding to the cassette and causing occupancy-related experimental noise. Consequently, these limitations hinder the utility of these cassettes for robust quantitative measurements as well as expansion to more complex multi-genic applications. There is a therefore a great need to for repetitive binding elements that can be incorporated repeatedly into RNA molecules.

Synthetic scaffolds that allow for the bridging of proteins, DNA and RNA are greatly in need. Specifically, a modular scaffold that can be arranged to bridge the components of any known pathways would be greatly advantageous. Further, the ability to bind not just but also induce phase separation, would greatly widen the repertoire of scaffold targets.

SUMMARY OF THE INVENTION

The present invention provides synthetic RNA molecules comprising at least two RNA-binding protein (RBP)-binding motifs, wherein the at least two RBP-binding motifs bind the same first RBP and comprise non-identical sequences are provided; synthetic RNA molecules comprising an RBP-binding motif that binds two orthogonal RBPs; synthetic RNA molecules comprising at least three RBP-binding motifs for three orthogonal RBPs and synthetic RNA molecules comprising a first RBP-binding motif, a second RBP-binding motif, a regulatory element and an open reading frame wherein the first and second RBP-binding motifs cooperatively enhance translation of the open reading frame are also provided. Compositions, cells and methods of use comprising the synthetic RNA molecules are also provided. As are methods of generating variant sequences of an RBP-binding motif comprising performing OL and ML.

According to a first aspect, there is provided a synthetic RNA molecule, comprising at least two RNA-binding protein (RBP)-binding motifs, wherein the at least two RBP-binding motifs bind a same first RBP and comprise non-identical sequences.

According to another aspect, there is provided a synthetic RNA molecule comprising an RNA-binding protein (RBP)-binding motif, wherein the RBP-binding motif binds two orthogonal RBPs, wherein the orthogonal RBPs do not bind to each other's canonical binding motifs.

According to another aspect, there is provided a synthetic RNA molecule comprising at least three RNA-binding protein (RBP)-binding motifs, wherein each RBP-binding motif binds a different orthogonal RBP, wherein the orthogonal RBPs do not bind to each other's canonical binding motifs.

According to another aspect, there is provided a method for designing a variant sequence of at least one RNA-binding protein (RBP)-binding motif, the method comprising:

a. receiving as input a dataset comprising a plurality of variant sequences of a canonical binding motif of the RBP, and a binding score for each variant sequence of the plurality, wherein each variant comprises at least one nucleotide change from the canonical binding motif, b. training a machine learning model on the variant sequences and labels containing the binding score;

c. applying the trained machine learning model to a plurality target variant sequences to determine a binding score for each target variant sequence of the plurality; and d. selecting at least one target variant sequence with a binding score above a predetermined threshold; thereby designing a variant sequence of at least one RBP-binding motif.

According to another aspect, there is provided a method comprising:

at a training stage, training a machine learning model on a training set comprising:

(i) a plurality of variant sequences of a canonical binding motif of an RBP, wherein each variant comprises at least one nucleotide change from the canonical binding motif, and (ii) labels identifying a binding score associated with each of the variant sequences; and at an inference stage, applying the trained machine learning model to a target variant sequence of the canonical binding motif of the RBP, to determine a binding score.

According to another aspect, there is provided a method of producing a synthetic RNA molecule comprising at least two RNA-binding protein (RBP)-binding motifs, wherein the at least two RBP-binding motifs bind a first RBP and comprise non-identical sequences, the method comprising a. performing a method of the invention, b. selected at least two different target variant sequences with a binding score above a predetermined threshold, and c. inserting the at least two target variant sequences into a synthetic RNA molecule;

thereby producing the synthetic RNA molecule.

According to another aspect, there is provided a method of inducing phase separation in a cell, the method comprising expressing in the cell a synthetic RNA molecule comprising at least four RNA-binding protein (RBP)-binding motifs and the RBP, thereby inducing phase separation in a cell, optionally wherein the four RBP-binding motifs comprise non-identical sequences.

According to another aspect, there is provided a synthetic RNA molecule comprising at least one first RBP-binding motif, at least one second RBP-binding motif, at least one open reading frame and at least one regulatory element wherein the regulatory element is operatively linked to the open reading frame, the at least one first RBP-binding motif and the at least one second RBP-binding motifs are 3' to the promoter and 5' to the open reading frame and the at least one first RBP-binding motif and the at least one second RBP-binding motifs separately repress translation of the open reading frame and cooperatively enhance translation of the open reading frame.

According to another aspect, there is provided a method of enhancing or repressing expression of an open reading frame in a cell, the method comprising contacting the cell with a synthetic RNA molecule of the invention and the first RBP, the second RBP or both the first and the second RBP, thereby tuning expression of the open reading frame.

According to another aspect, there is provided a method of labeling a cell, comprising a. expressing in the cell at least one synthetic RNA of the invention; and b. expressing in the cell a chimeric protein comprising at least one RNA-binding domain of an RBP and at least one detectable moiety, wherein the synthetic RNA molecule comprises at least one RBP-binding motif that binds the at least one RNA-binding domain of an RBP, thereby labeling the cell.

According to another aspect, there is provided a method of attracting a nucleic acid molecule to at least one non-RNA binding peptide, comprising contacting a. at least one synthetic RNA molecule of the invention, wherein the synthetic RNA molecule comprises at least a first RBP-binding domain; and b. a first chimeric protein comprising at least one RNA-binding domain that binds the first RBP-binding domain and the non-RNA binding peptide;

thereby attracting a nucleic acid molecule to a non-RBP or functional fragment thereof.

According to another aspect, there is provided a method of attracting a first peptide to a second peptide, comprising contacting a. at least one synthetic RNA molecule of the invention, wherein the synthetic RNA molecule comprises at least a first RBP-binding domain and a second RBP-binding domain;

b. a first chimeric protein comprising at least one RNA-binding domain that binds the first RBP-binding domain and the first peptide; and c. a second chimeric protein comprising at least one RNA-binding domain that binds the second RBP-binding domain and the second peptide, thereby attracting the first peptide to the second peptide.

According to some embodiments, the molecule comprises at least 5 first RBP-binding motifs that bind the same first RBP and comprise non-identical sequences.

According to some embodiments, the molecule comprises at least 20 first RBP-binding motifs that bind the same RBP and comprise non-identical sequences.

According to some embodiments, each non-identical first RBP-binding motif comprises at least 5 nucleotide differences from a canonical first RBP-binding motif.

According to some embodiments, each non-identical first RBP-binding motif comprises at least 5 nucleotide differences from all other all other RBP-binding motifs in the molecule.

According to some embodiments, the first RBP is a phage coat protein.

According to some embodiments, the phage coat protein is selected from PCP, QCP and MCP.

According to some embodiments, the molecule is devoid of a canonical first RBP-binding motif.

According to some embodiments, the molecule further comprises at least two RBP-binding motifs to a same second RBP, wherein the first RBP and the second RBP are different proteins.

According to some embodiments, the at least two RBP-binding motifs to a second RBP comprise non-identical sequences.

According to some embodiments, the molecule comprises at least 5 second RBP-binding motifs that bind the same RBP and optionally comprise non-identical sequences.

According to some embodiments, each second RBP-binding motif comprises at least 5 nucleotide differences from a canonical second RBP-binding motif, from all other RBP-binding motifs in the molecule or both.

According to some embodiments, the second RBP is a phage coat protein, optionally wherein the phage coat protein is selected from PCP, QCP and MCP.

According to some embodiments, the at least two first RBP-binding motifs and the at least two second RBP-binding motifs are orthogonal to each other.

According to some embodiments, the molecule comprises at least one RBP-binding motif that binds both the first RBP and the second RBP.

According to some embodiments, the molecule further comprises at least two RBP-binding motifs to a same third RBP, wherein the first RBP, the second RBP and third RBP are different proteins.

According to some embodiments, the synthetic RNA molecule does not encode a protein.

According to some embodiments, the molecule further comprises at least one regulatory element upstream of the at least two RBP-binding motifs and wherein the at least one regulator element is operatively linked to the at least two RBP-binding motifs.

According to some embodiments, the at least one regulatory element is a promoter.

According to some embodiments, the at least one regulatory element is a mammalian promoter.

According to some embodiments, the molecule further comprises at least one open reading frame and at least one regulatory element wherein the regulatory element and the at least two first RBP-binding motifs are operatively linked to the open reading frame.

According to some embodiments, the at least two RBP-binding motifs repress translation of the open reading frame upon binding of the RBP to one motif and cooperatively enhance translation of the open reading frame upon binding of the RBP to at least two motifs.

According to some embodiments, the at least two RBP-binding motifs individually repress translation of the open reading frame and cooperatively enhance translation of the open reading frame.

According to some embodiments, the regulatory element, the at least two first RBP-binding motifs and at least two second RBP-binding motifs are operatively linked to the open reading frame, and wherein the at least two first RBP-binding motifs and the at least two second RBP-binding motifs separately repress translation of the open reading frame and cooperatively enhance translation of the open reading frame.

According to some embodiments, the target variant sequence comprises at least five nucleotide changes from the canonical binding motif.

According to some embodiments, the target variant sequence comprises a different number of nucleotides than the canonical binding motif.

According to some embodiments, the RBP is a phage coat protein. According to some embodiments, the phage coat protein is selected from PCP, QCP and MCP.

According to some embodiments, the plurality of variant sequences of a canonical binding motif of an RBP comprises at least 10000 different variant sequences.

According to some embodiments, the method comprises at the inference stage, applying the trained machine learning model to a plurality of target variant sequences to determine a binding score for each target variant sequence of the plurality and selecting at least one target variant sequence with a binding score above a predetermined threshold.

According to some embodiments, the binding score is a relative numerical evaluation of binding of the RBP to the variant sequence inside a cell and wherein a magnitude of the binding score correlates to a magnitude of binding.

According to some embodiments, a binding score above zero indicates binding of the RBP to the sequence variant.

According to some embodiments, the binding score is determined in an in vivo binding assay comprising:

a. expressing in a cell a nucleic acid molecule comprising a promoter and a variant sequence of the plurality of variant sequences operatively linked to an open reading frame;

b. expressing in the cell the RBP; and c. detecting expression of the open reading frame and calculating inhibition of expression as compared to expression from the nucleic acid molecule in the absence of the RBP, wherein a magnitude of inhibition is proportional to the binding score.

According to some embodiments, the cell is a mammalian cell.

According to some embodiments, the in vivo binding assay further comprises detecting expression of the open reading frame before step (b).

According to some embodiments, the variant sequence is inserted into a region 5' to the open reading frame wherein binding of the RBP to the region inhibits translation of the open reading frame, optionally wherein the region is a ribosomal initiation region of the open reading frame.

According to some embodiments, the expressing the RBP comprises transferring to the cell a vector comprising an inducible promoter operatively linked to an open reading frame encoding the RBP and inducing the promoter.

According to some embodiments, the open reading frame encodes a detectable protein. According to some embodiments, the detectable protein is a fluorescent protein.

According to some embodiments, the binding assay is a high-throughput assay comprising receiving an oligo-library comprising a plurality of nucleic acid molecules each comprising a variant sequences of the plurality of variant sequences inserted 3' to a promoter operably linked to an open reading frame encoding a fluorescent molecule and 5' to the open reading frame, expressing the oligo-library in cells capable of transcribing from the promoter, expressing the RBP in the cell, sorting the cells by fluorescence and determining a sequence of the variant sequence in the sorted cells.

According to some embodiments, the method further comprises performing the high-throughput assay.

According to some embodiments, the sorting comprises FACS, the determining comprises next-generation sequencing or both.

According to some embodiments, the expressing the at least one synthetic RNA comprises introducing into the cell a DNA molecule comprising a DNA sequence that encodes the at least one synthetic RNA operably linked to a transcription-regulatory element, and wherein the method is for measuring the effect of the regulatory element in the cell.

According to some embodiments, the attracting is in vitro.

According to some embodiments, the attracting occurs within a cell and the contacting comprises introducing the at least one RNA molecule and the first chimeric protein into the cell.

According to some embodiments, the method further comprises contacting a duplex nucleic acid molecule that comprises a sequence that binds to at least one NDBM in the synthetic RNA.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

correspond to the rates by which the slncRNA-RBP complexes leave/re-enter the nucleoid phase, and $$k_+^{out}, k_+^{in}$$

correspond to the insertion/shedding rates of the slncRNA-RBP complexes from the dilute to the droplet phase. The biphasic model is an extension of the simple rate-equation gene expression model and leads to a Super-Poisson distribution of RNA for any RNA species (see SI). (10B) (left) Background fluorescence signal for the PP7-4x slncRNA expressed from a multi-copy plasmid (yellow) and single-copy plasmid (red). (right) Distribution of the number of slncRNA-RBP complexes within the puncta for each case. (10C) (left and middle) Typical images of fluorescent bacteria in stationary phase, which are very different than the 2-puncta image obtained for exponentially growing cells (right). A close examination shows "bridging" or spreading of puncta (bottom-left), and emergence of an additional punctum in the middle of the cell (bottom-middle).

Figure 11:
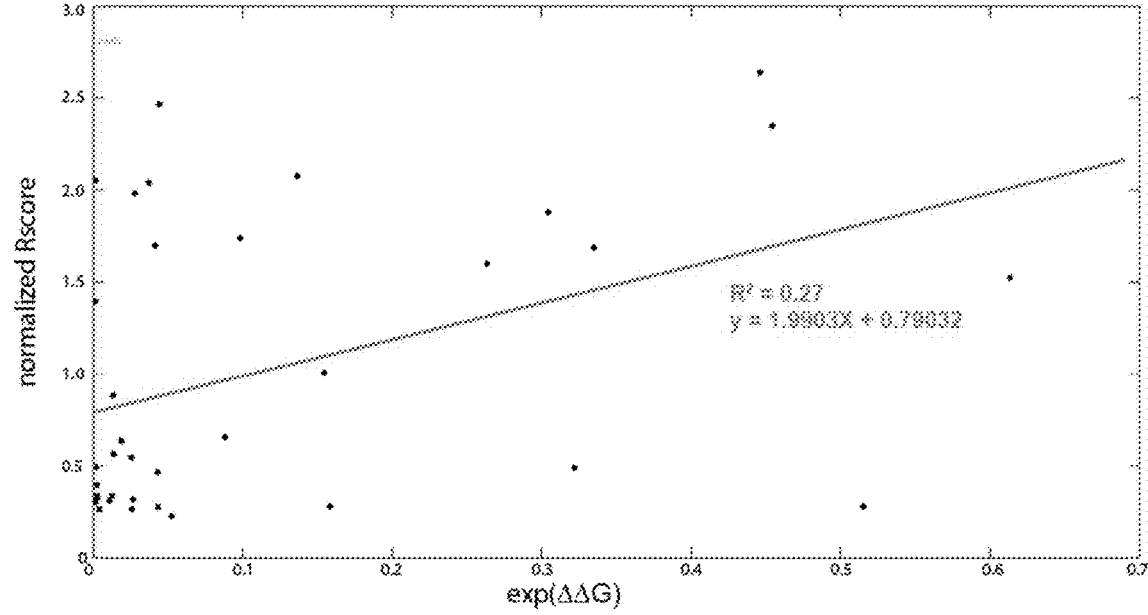

FIG. 11. Conversion of $R_{score}$ to $K_d$. Experimental normalized $R_{score}$ as a function of $\Delta\Delta G$ results of a previous study for 37 mutual binding sites. Only binding sites with measurable affinity—$R_{score}$ (>3.5) and $\Delta\Delta G$ (>−6.66169) are taken into account. The linear regression results are presented in blue, along with its goodness of fit ($R^2$).

Figure 12:
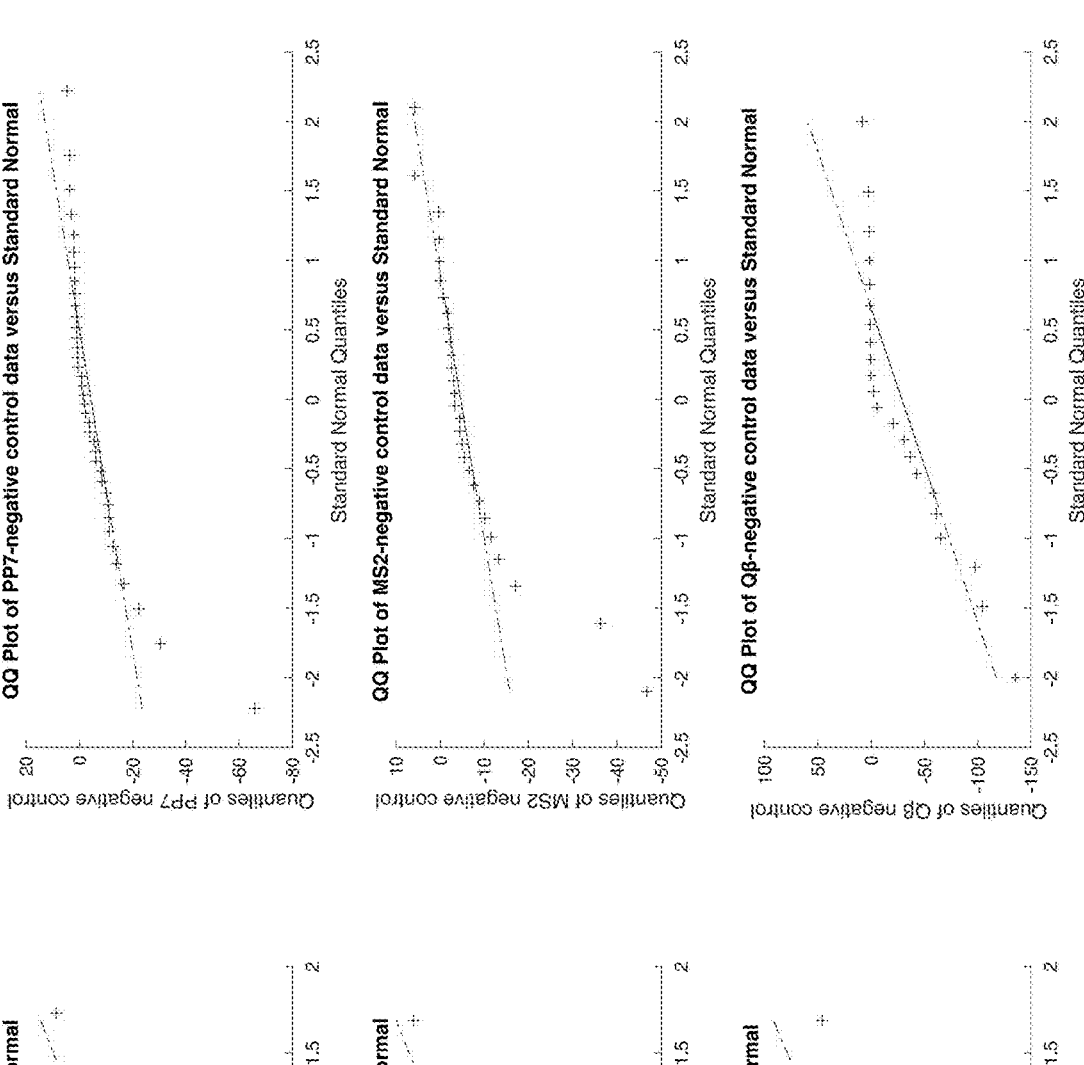
Figure 12:
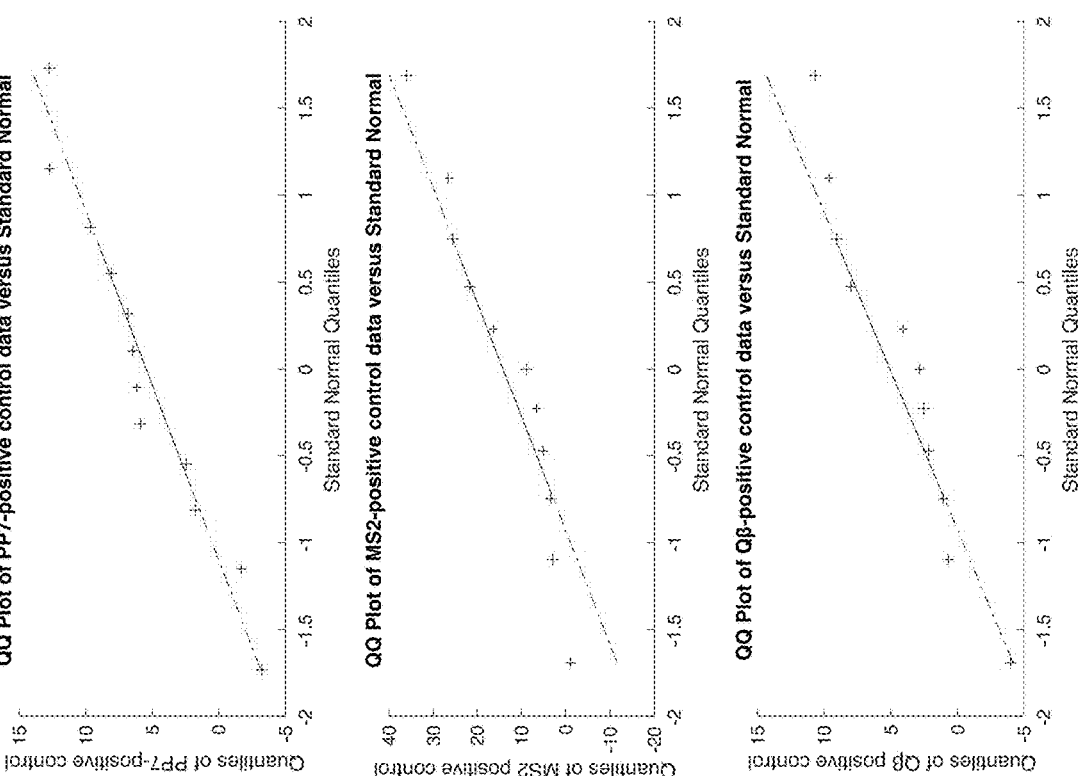

FIG. 12. QQ-plot computation for the $R_{score}$ of positive and negative controls. Positive (left) and negative (right) controls for (top) PCP, (middle) MCP, and (bottom) QCP.

Figure 13:
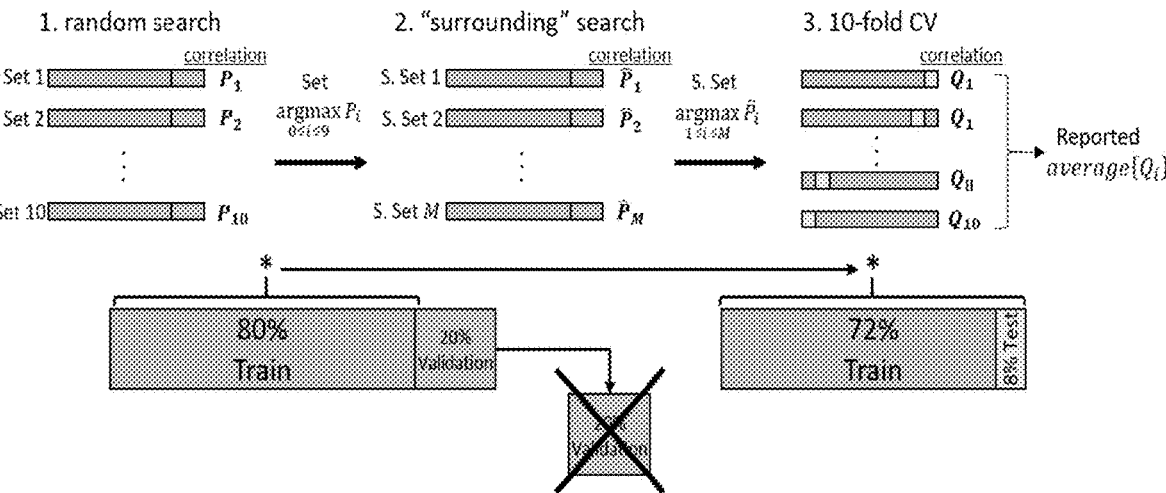

FIG. 13. Illustration of the hyper-parameters optimization process. (left to right) Stage 1—repeating 10 times: randomly selecting hyper-parameters and training the model on 80% of the available data and testing it on the remaining 20%. Stage 2—selecting the set of parameters from stage 1 achieving the maximum Pearson correlation, and repeating M times (M depends on the type of model and the set selected in step 1): performing grid search in the surrounding of the set selected in stage 1, training and testing on the same 80% and 20% of data as in stage 1, respectively. Stage 3—selecting the set of parameters from stage 2 achieving the maximum Pearson correlation, discarding 20% of the data that was used as the validation set in stages 1 and 2, and performing 10-fold cross-validation on the data that was used as training data in stages 1 and 2.

DETAILED DESCRIPTION OF THE INVENTION

The present invention, in some embodiments, provides synthetic RNA molecules comprising at least two RNA-binding protein (RBP)-binding motifs, wherein the at least two RBP-binding motifs bind the same first RBP and comprise non-identical sequences are provided. Synthetic RNA molecules comprising an RBP-binding motif that binds two orthogonal RBPs, comprising at least three RBP-binding motifs for three orthogonal RBPs or comprising a first RBP-binding motif, a second RBP-binding motif, a regulatory element and an open reading frame wherein the first and second RBP-binding motifs cooperatively enhance translation of the open reading frame are also provided. Compositions, cells and methods of use or generating the synthetic RNA molecules are also provided.

Previous findings have determined that specificity in phage CP binding to RNA is determined by the structural elements formed by specific sequence motifs. This implies that for a given phage CP, many different sequences may become potential binding sites by folding into a common functional structure. The DBT problem for phage CP-binding cassette design can thus be solved by generating a database of functional binding sites that are divergent from a sequence perspective, and then utilizing different sequences with the same functional structure in place of multiple repeats of the same wild type (WT) sequence. The emergence in recent years of high-throughput oligo library (OL) based-experiments provides a platform for testing hundreds of thousands of potential binding-site variants. While extremely useful for identifying functional variants, the OL scale is much smaller than the available sequence space for ~20 nt-long binding sites, and thus many functional variants are not sampled. Recently-developed machine-learning (ML) algorithms provide the necessary tool for computationally expanding the variant database to millions of potentially functional sequences, using the OL as an empirical training dataset. The result is an ML algorithm which can computationally score any sequence for the desired functionality.

This work is based on the surprising finding that application of a combined OL-ML approach to the design of phage CP RNA binding sites yields hundreds of heretofore unknown binding motifs. Indeed, some of these binding motifs are even superior to the canonical binding motif. An OL of many candidate sites was generated for the phage CPs of MS2 (MCP), PP7 (PCP), and Qβ (QCP). The function of the resulting RNA hairpins was evaluated in a massively-parallel in vivo expression assay in bacteria, and subsequently ML tools were utilized to train on the OL sequences and their experimental function binding scores to computationally discover and experimentally verify novel sequences that can bind the phage CPs with high affinity. Consequently, it is demonstrated that sequences with non-repeating elements can be reliably designed, synthesized, and cloned, and, once transcribed, exhibit the functionality expected from the original repeated hairpins in mammalian cells. This achievement enables researchers to rapidly design functional customized cassettes for RNA-based applications in any organism, effectively eliminating the DBT bottleneck for this technology. This is highly significant, as it is the 3-dimensional structure of a motif that determines binding and binding cannot be readily assessed just by examining nucleotide sequence. This approach also allows for the determination of single motifs that bind multiple, naturally orthogonal, RBPs, something that heretofore could not be done.

By a first aspect, there is provided a synthetic RNA molecule comprising at least one RNA-binding protein (RBP) binding motif.

The term "ribonucleotide" and the phrase "ribonucleic acid" (RNA) refer to a modified or unmodified nucleotide or polynucleotide comprising at least one ribonucleotide unit. A ribonucleotide unit comprises a hydroxyl group attached to the 2' position of a ribosyl moiety that has a nitrogenous base attached in N-glycosidic linkage at the 1' position of a ribosyl moiety, and a moiety that either allows for linkage to another nucleotide or precludes linkage. In some embodiments, the RNA does not comprise a DNA base. In some embodiments, the RNA molecule is a hybrid RNA-DNA molecule.

As used herein, the term "synthetic RNA" refers to a man-made, artificial RNA. In some embodiments, a synthetic RNA is not found in nature. In some embodiments, a synthetic RNA is purified RNA. In some embodiments, a synthetic RNA comprises a purity of at least 80, 85, 90, 95, 97, 98, 99 or 100% purity. Each possibility represents a separate embodiment of the invention. In some embodiments, a synthetic RNA is produced by a method that does not include transcription. In some embodiments, a synthetic RNA is not produced in a cell or nucleus. In some embodiments, the synthetic RNA is not polyadenylated. In some embodiments, the synthetic RNA does not comprise a 5' cap. In some embodiments, the synthetic RNA comprises a non-natural nucleic acid base. In some embodiments, the synthetic RNA comprises thymine.

In some embodiments, the synthetic RNA is a non-coding RNA. In some embodiments, the synthetic RNA does not encode a protein. In some embodiments, the synthetic RNA does not comprise an open reading frame. In some embodiments, the synthetic RNA is not a microRNA (miR). In some embodiments, the synthetic RNA is not a small interfering RNA (siRNA). In some embodiments, the synthetic RNA is not a heterologous nuclear RNA. In some embodiments, the synthetic RNA is not part of a heterologous nuclear ribo-protein. In some embodiments, the synthetic RNA is not any one of a microRNAs (miRNAs), small interfering RNAs (siRNAs), small nuclear RNAs (snRNAs), small nucleolar RNAs (snoRNAs), small temporal RNAs (stRNAs), anti-gene RNAs (agRNAs), piwi-interacting RNAs (piRNAs) or other short regulatory nucleic acid molecule. In some embodiments, the synthetic RNA cannot be translated. In some embodiments, the synthetic RNA does not have a function in nature.

In some embodiments, the synthetic RNA comprises a modification. In some embodiments, the synthetic RNA comprises an artificial base. In some embodiments, the synthetic RNA comprises an artificial secondary structure. In some embodiments, synthetic RNA comprises at most 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1250, 1500, 1750, 2000, 2500, 3000, 3500, 4000, 4500, 5000, 5500, 6000, 6500, 7000, 7500, 8000, 8500, 9000, 9500, or 10000 nucleotides. Each possibility represents a separate embodiment of the invention. In some embodiments, the synthetic RNA is a short RNA. In some embodiments, synthetic RNA comprises at least, 10, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1250, 1500, 1750, 2000, 2500, 3000, 3500, 4000, 4500, or 5000 nucleotides. Each possibility represents a separate embodiment of the invention. In some embodiments, the synthetic RNA comprises only one binding site and is short. It will be understood by a skilled artisan that the more binding sites present in the molecule the longer the molecule will be.

In some embodiments, the synthetic RNA comprises at least one RBP-binding motif. In some embodiments, the synthetic RNA comprises at least two RBP-binding motifs. In some embodiments, the synthetic RNA comprises at least three RBP-binding motifs. In some embodiments, the synthetic RNA comprises at least 2, 3, 4, 5, 6, 7, 8, 9, 10, 12, 14, 15, 16, 18, 20, 25, 30, 35, 40, 45, 50, 60, 70, 80, 90 or 100 RBP-binding motifs. Each possibility represents a separate embodiment of the invention. In some embodiments, the RBP is a mammalian protein. In some embodiments, the RBP is a human protein. In some embodiments, the RBP is not a mammalian protein. In some embodiments, the RBP is not a human protein. In some embodiments, the RBP is a eukaryotic protein. In some embodiments, the RBP is a prokaryotic protein. In some embodiments, the RBP is a viral protein. In some embodiments, the RBP is a phage protein. In some embodiments, the RBP is a capsid. In some embodiments, the RBP is a capsid coat protein. In some embodiments, the phage protein is a phage capsid coat protein. In some embodiments, the phage coat protein is selected from PCP, QCP and MCP. In some embodiments, the phage coat protein is PCP. In some embodiments, the phage coat protein is QCP. In some embodiments, the phage coat protein is MCP.

In some embodiments, the synthetic RNA comprises at most 15, 20, 25, 30, 35, 40, 45, 50, 55, 60, 65, 70 or 75 RBP-binding motifs. Each possibility represents a separate embodiment of the invention. In some embodiments, the synthetic RNA comprises between 1-100, 1-90, 1-80, 1-70, 1-60, 1-55, 1-50, 1-45, 1-40, 1-35, 1-30, 1-25, 1-20, 1-15, 1-10, 1-5, 2-100, 2-90, 2-80, 2-20, 2-60, 2-55, 2-50, 2-45, 2-40, 2-35, 2-30, 2-25, 2-20, 2-15, 2-10, 2-5, 3-100, 3-90, 3-80, 370, 360, 3-55, 3-50, 3-45, 3-40, 3-35, 3-30, 3-25, 3-20, 3-15, 3-10, 3-5, 5-100, 5-90, 5-80, 5-70, 5-60, 5-55, 5-50, 5-45, 5-40, 5-35, 5-30, 5-25, 5-15, or 5-10 RBP-binding motifs. Each possibility represents a separate embodiment of the invention. In some embodiments, the synthetic RNA comprises between 5-20 RBP-binding motifs. Each possibility represents a separate embodiment of the invention.

In some embodiments, the Bacteriophage or phage is selected from PP7, MS2, GA and Qbeta (Qβ). In some embodiments, the phage is PP7. In some embodiments, the phage is MS2. In some embodiments, the phage is GA. In some embodiments, the phage is Qβ. In some embodiments, the Bacteriophage or phage is selected from PP7, MS2 and Qβ. In some embodiments, PP7 is *Pseudomonas* phage PP7. In some embodiments, MS2 is *Escherichia* virus MS2. In some embodiments, Qβ is *Escherichia* virus Qbeta. In some embodiments, the PP7 coat protein is PCP. In some embodiments, the MS2 coat protein is MCP. In some embodiments, the Qβ coat protein is QCP.

In some embodiments, a first RBP-binding motif and a second RBP-binding motif are separated by a spacer or linker. In some embodiments, the spacer or linker is an RNA sequence. In some embodiments, the spacer is at least 1, 2, 3, 4, 5, 6, 7, 8, 9, 10, 15, 20, 25, 30, 35, 40, 45, 50, 55, 60, 65, or 70 nucleotides. Each possibility represents a separate embodiment of the invention. In some embodiments, the spacer is at most 5, 10, 15, 20, 25, 30, 35, 40, 45, 50, 55, 60, 65, 70, 75, 80, 85, 90, 95, or 100 nucleotides. Each possibility represents a separate embodiment of the invention. In some embodiments, the spacer is between 10-70, 10-65, 10-60, 10-55, 10-50, 10-45, 10-40, 10-35, 10-30, 20-70, 20-65, 20-60, 20-55, 20-50, 20-45, 20-40, 20-35, 20-30, 30-70, 30-65, 30-60, 30-55, 30-50, 30-45, 30-40, 40-70, 40-65, 40-60, 40-55, 40-50, or 40-45 nucleotides. Each possibility represents a separate embodiment of the invention. In some embodiments, the spacer is between 40-65 nucleotides. In some embodiments, the length of an RBP-binding motif and an adjacent spacer is between 50-75 nucleotides.

In some embodiments, the length of the synthetic RNA is between 20-6000, 40-6000, 60-6000, 100-6000, 130-6000, 150-6000, 180-6000, 200-6000, 230-6000, 250-6000, 280-6000, 300-6000, 350-6000, 400-6000, 450-6000, 500-6000, 1000-6000, 20-5000, 40-5000, 60-5000, 100-5000, 130-5000, 150-5000, 180-5000, 200-5000, 230-5000, 250-5000, 280-5000, 300-5000, 350-5000, 400-5000, 450-5000, 500-5000, 1000-5000, 20-4000, 40-4000, 60-4000, 100-4000, 130-4000, 150-4000, 180-4000, 200-4000, 230-4000, 250-4000, 280-4000, 300-4000, 350-4000, 400-4000, 450-4000, 500-4000, 1000-4000, 20-3000, 40-3000, 60-3000, 100-3000, 130-3000, 150-3000, 180-3000, 200-3000, 230-3000, 250-3000, 280-3000, 300-3000, 350-3000, 400-3000, 450-3000, 500-3000, 1000-3000, 20-2000, 40-2000, 60-2000, 100-2000, 130-2000, 150-2000, 180-2000, 200-2000, 230-2000, 250-2000, 280-2000, 300-2000, 350-2000, 400-2000, 450-2000, 500-2000, 1000-2000, 20-1500, 40-1500, 60-1500, 100-1500, 130-1500, 150-1500, 180-1500, 200-1500, 230-1500, 250-1500, 280-1500, 300-1500, 350-1500, 400-1500, 450-1500, 500-1500, 1000-1500, 20-1000, 40-1000, 60-1000, 100-1000, 130-1000, 150-1000, 180-1000, 200-1000, 230-1000, 250-1000, 280-1000, 300-1000, 350-1000, 400-1000, 450-1000, or 500-1000 nucleotides. Each possibility represents a separate embodiment of the invention. In some embodiments, the length of the synthetic RNA is between 280-1600 nucleotides.

In some embodiments, the RBP-binding motifs in the synthetic RNA bind the same RBP. In some embodiments, the at least two RBP-binding motifs bind the same RBP. In some embodiments, the RBP-binding motifs in the synthetic RNA comprise different sequences. In some embodiments, the RBP-binding motifs in the synthetic RNA comprise non-identical sequences. In some embodiments, the at least two RBP-binding motifs comprise different sequences. In some embodiments, the at least two RBP-binding motifs comprise non-identical sequences.

In some embodiments, the RBP is a first RBP and it binds a first RBP-binding motif. In some embodiments, the RBP is a second RBP and it binds a second RBP-binding motif. In some embodiments, the RBP is a third RBP and it binds a third RBP-binding motif. In some embodiments, the first and second RBPs are the same RBP. In some embodiments, the first and second RBPs are different RBPs. In some embodiments, the first, second and third RBPs are different RBPs.

In some embodiments, the RNA molecule comprises at least 2, 3, 4, 5, 6, 7, 8, 9, 10, 12, 14, 15, 16, 18, 20, 25, 30, 35, 40, 45, 50, 55, 60, 65, 70, 75, 80, 85, 90, 95 or 100 first RBP-binding motifs that bind the same first RBP. Each possibility represents a separate embodiment of the invention. In some embodiments, the RNA molecule comprises at least 5 first RBP-binding motifs that bind the same first RBP. In some embodiments, the RNA molecule comprises at least 10 first RBP-binding motifs that bind the same first RBP. In some embodiments, the RNA molecule comprises at least 20 first RBP-binding motifs that bind the same first RBP. In some embodiments, the RNA molecule comprises at least 50 first RBP-binding motifs that bind the same first RBP. In some embodiments, the first RBP-binding motifs comprise different sequences. In some embodiments, the first RBP-binding motifs comprise non-identical sequences.

In some embodiments, each different or non-identical RBP-binding motif comprises at least 1, 2, 3, 4, 5, 6, 7, 8, 9 or 10 nucleotide difference from every other different or non-identical RBP-binding motif Each possibility represents a separate embodiment of the invention. In some embodiments, each different or non-identical RBP-binding motif comprises at least 2 nucleotide difference from every other different or non-identical RBP-binding motif. In some embodiments, each different or non-identical RBP-binding motif comprises at least 5 nucleotide difference from every other different or non-identical RBP-binding motif. In some embodiments, the nucleotide differences are from all other RBP-binding motifs in the molecule.

In some embodiments, each different or non-identical RBP-binding motif comprises at least 1, 2, 3, 4, 5, 6, 7, 8, 9 or 10 nucleotide difference from a canonical RBP-binding motif Each possibility represents a separate embodiment of the invention. In some embodiments, each different or non-identical RBP-binding motif comprises at least 2 nucleotide difference from a canonical RBP-binding motif. In some embodiments, each different or non-identical RBP-binding motif comprises at least 5 nucleotide difference from a canonical RBP-binding motif.

Canonical RBP-binding motifs are well known in the art and can be found for myriad RBPs. For example, the canonical binding motif for PCP is UAAGGAGUUUAUAUGGAAACCCUUA (SEQ ID NO: 306), the canonical motif for QCP is AUGCAUGUCUAAGACAGCAU (SEQ ID NO: 307), and the canonical motif for MCP is ACAUGAGGAUCACCCAUGU (SEQ ID NO: 308). In some embodiments, the canonical binding motif for PCP is SEQ ID NO: 306. In some embodiments, the canonical binding motif for QCP is SEQ ID NO: 307. In some embodiments, the canonical binding motif for MCP is SEQ ID NO: 308. In some embodiments, the synthetic RNA molecule is devoid of a canonical RBP-binding motif.

In some embodiments, the RNA comprises an RBP-binding motif to a first RBP and an RBP-binding motif to a second RBP. In some embodiments, the second RBP is a different RBP than the first RBP. In some embodiments, the RNA comprises at least two RBP-binding motifs to the second RBP. In some embodiments, the at least two RBP-binding motifs to the second RBP comprise different sequences. In some embodiments, the at least two RBP-binding motifs to the second RBP comprise non-identical sequences.

In some embodiments, the RNA comprises an RBP-binding motif to a first RBP, an RBP-binding motif to a second RBP and an RBP-binding motif to a third RBP. In some embodiments, the third RBP is a different RBP than the first RBP. In some embodiments, the third RBP is a different RBP than the second RBP. In some embodiments, the third RBP is a different RBP than the first RBP and the second RBP. In some embodiments, the RNA comprises at least two RBP-binding motifs to the third RBP. In some embodiments, the at least two RBP-binding motifs to the third RBP comprise different sequences. In some embodiments, the at least two RBP-binding motifs to the third RBP comprise non-identical sequences.

In some embodiments, the RBPs are orthogonal to each other. In some embodiments, the at first and second RBPs are orthogonal to each other. In some embodiments, the first, second and third RBPs are orthogonal to each other. As used herein, the term "orthogonal" refers to proteins, RNAs or systems that are mutually exclusive and do not overlap. In some embodiments, orthogonal RBPs bind to different canonical binding motifs. In some embodiments, orthogonal RBPs do not bind to the same canonical binding motif. In some embodiments, orthogonal RBPs do not bind to the same naturally occurring binding motifs. In some embodiments, the first binding motif/s and the second binding motif/s are orthogonal to each other. In some embodiments, orthogonal binding motifs bind a mutually exclusive repertoire of RBPs. In some embodiments, the orthogonal binding motifs do not bind the same proteins. In some embodiments, the orthogonal binding motif does not bind a protein that binds another binding motif in the synthetic RNA. In some embodiments, the synthetic RNA comprises at least one RBP-binding motif that binds both the first and second RBPs. In some embodiments, the synthetic RNA comprises at least one RBP-binding motif that binds at least two RBPs. In some embodiments, the synthetic RNA comprises at least one RBP-binding motif that binds the first, second and third RBPs. In some embodiments, RNA-binding motif binds at least two orthogonal RBPs. In some embodiments, RNA-binding motif binds at least three orthogonal RBPs.

In some embodiments, the spacer is configured to reduce steric hinderance. In some embodiments, the spacer is of a length sufficient to separate a first bound RBP and a second bound RBP. In some embodiments, the spacer comprises any nucleic acid sequence. In some embodiments, the spacer comprises any nucleic acid sequence that does not bind an RBP. In some embodiments, the spacer comprises any nucleic acid sequence that does not bind another molecule. In some embodiments, the spacer comprises a sequence with complex secondary structure. In some embodiments, the spacer comprises a sequence devoid of complex secondary structure. In some embodiments, the spacer comprises a sequence that does not form a secondary structure with any of the motifs in the synthetic RNA. In some embodiments, the spacer is a unique nucleotide barcode. In some embodiments, the spacer comprises a unique nucleotide barcode. In some embodiments, the spacer or linker comprises a secondary structure. In some embodiments, the secondary structure reduces interaction between the spacer and a binding motif. In some embodiments, the secondary structure reduces interaction between the spacer and an RBP-binding motif. In some embodiments, the secondary structure has a binding energy at least equal to the binding energy of the RBP-binding motif. In some embodiments, the secondary structure has a binding energy at least equal to the binding energy of the RBP-binding motif. In some embodiments, the binding energies are about equal. In some embodiments, the binding energy of the spacer's secondary structure is its self-assembly energy. That is, it is energetically more advantageous for the spacer to form its secondary structure than for it to bind a binding motif. In some embodiments, the spacer forms a hairpin. In some embodiments, the spacer forms a stable secondary structure. In some embodiments, the spacer stabilizes the conformation of the binding motif. In some embodiments, the stabilization increases the binding affinity of the binding motif for its target.

In some embodiments, the synthetic RNA comprises a barcode. In some embodiments, the barcode is one or more nucleic acid molecules. Nucleic acid molecules, such as DNA strands, present an unlimited number of barcoding options. As used throughout the invention "barcode", and "DNA barcode", are interchangeable with each other and have the same meaning. The nucleic acid molecule serving as a DNA barcode is a polymer of deoxynucleic acids or ribonucleic acids or both and may be single-stranded or double-stranded, optionally containing synthetic, non-natural or altered nucleotide bases.

In some embodiments, the synthetic RNA molecule comprises a tag. In some embodiments, the synthetic RNA molecule further comprises a tag. In some embodiments, the tag is an RNA tag. In some embodiments, the tag is a detectable moiety. In some embodiments, the tag is a fluorescent moiety. In some embodiments, tag is optically detectable. In some embodiments, the tag is a barcode.

In some embodiments, the synthetic RNA molecule does not encode a protein. In some embodiments, the synthetic RNA molecule does encode a protein. In some embodiments, the protein is a polypeptide. In some embodiments, the synthetic RNA comprises an open reading frame. In some embodiments, the open reading frame encodes a protein.

As used herein, the terms "peptide", "polypeptide" and "protein" are used interchangeably to refer to a polymer of amino acid residues. In another embodiment, the terms "peptide", "polypeptide" and "protein" as used herein encompass native peptides, peptidomimetics (typically including non-peptide bonds or other synthetic modifications) and the peptide analogues peptoids and semipeptoids or any combination thereof. In another embodiment, the peptides polypeptides and proteins described have modifications rendering them more stable while in the body or more capable of penetrating into cells. In one embodiment, the terms "peptide", "polypeptide" and "protein" apply to naturally occurring amino acid polymers. In another embodiment, the terms "peptide", "polypeptide" and "protein" apply to amino acid polymers in which one or more amino acid residue is an artificial chemical analogue of a corresponding naturally occurring amino acid.

In some embodiments, the RNA further comprises at least one regulatory element. In some embodiments, the regulatory element is upstream of the RBP-binding motif. In some embodiments, upstream is 5' to. In some embodiments, the regulatory element is downstream of the RBP-binding motif. In some embodiments, downstream is 3' to. In some embodiments, the RBP-binding motif is within the regulatory element. In some embodiments, the regulatory element and the RBP-binding motif are operatively linked. In some embodiments, the RBP-binding motif controls the regulatory element. In some embodiments, binding of the RBP to the binding motif modulates the function of the regulatory element. The term "operably linked" is intended to mean that the nucleotide sequence of interest is linked to the regulatory element or elements in a manner that allows for combined regulation by the regulatory element and the nucleotide sequence. In some embodiments, the nucleotide sequence is the RBP-binding motif.

In some embodiments, the regulatory element is a promoter. In some embodiments, the regulatory element is an enhancer. In some embodiments, the regulatory element is a repressor. In some embodiments, the regulatory element is an insulator. Regulatory elements are well known in the art and any regulatory element may be used. In some embodiments, the regulatory element is a transcription regulatory element. In some embodiments, the regulatory element is a translation regulatory element. In some embodiments, the RBP-binding motif is within the ribosome binding site. In some embodiments, the RBP-binding motif is within the ribosome initiation region.

In some embodiments, the regulatory element is a bacterial regulatory element. In some embodiments, the regulatory element is a mammalian regulatory element. In some embodiments, the regulatory element is a eukaryotic regulatory element. In some embodiments, the regulatory element is a prokaryotic regulatory element. In some embodiments, the promoter is a bacterial promoter. In some embodiments, the promoter is a mammalian promoter. In some embodiments, the promoter is a eukaryotic promoter. In some embodiments, the promoter is a prokaryotic promoter.

In some embodiments, RNA further comprises an open reading frame. In some embodiments, the open reading frame is operatively to the regulatory element and the RBP-binding motif. In some embodiments, the open reading frame is operatively to the regulatory element. In some embodiments, the open reading frame is operatively to the RBP-binding motif. In some embodiments, the RBP-binding motif is in an untranslated region (UTR) of the open reading frame. In some embodiments, the RBP-binding motif regulates translation of the open reading frame. In some embodiments, the RBP-binding motif is in a 5' UTR of the open reading frame. In some embodiments, the RBP-binding motif is operably linked to the open reading frame. In some embodiments, the RBP-binding motif is upstream to the open reading frame. In some embodiments, the RBP-binding motif is within the ribosome binding site of the open reading frame. In some embodiments, the RBP-binding motif is within the ribosome initiation region of the open reading frame. In some embodiments, binding of the RBP to the motif represses transcription by the promoter. In some embodiments, binding of the RBP to the motif enhances transcription by the promoter. In some embodiments, binding of the RBP to the motif represses translation of the open reading frame. In some embodiments, binding of the RBP to the motif enhances translation of the open reading frame. In some embodiments, binding of the first RBP to the RBP-binding motif represses translation of the open reading frame. In some embodiments, binding of the first RBP to the RBP-binding motif represses translation. In some embodiments, binding of the second RBP to the RBP-binding motif represses translation of the open reading frame. In some embodiments, binding of the second RBP to the RBP-binding motif represses translation. In some embodiments, the RBP-binding motifs repress translation upon binding of an RBP. In some embodiments, the RBP-binding motifs repress translation upon binding of either the first or the second RBP, but not both RBPs. In some embodiments, binding of both the first and second RBP to the first and second RBP-binding motifs, respectively, cooperatively enhances translation by the promoter. In some embodiments, the first and second RBP-binding motifs, respectively, cooperatively enhances translation. In some embodiments, the enhanced translation occurs in the presence of the first RBP. In some embodiments, the enhanced translation occurs in the presence of the second RBP. In some embodiments, the enhanced translation occurs in the presence of the first RBP, second RBP or both. In some embodiments, binding of both the first and second RBP to the first and second RBP-binding motifs, respectively, cooperatively enhances translation of the open reading frame. In some embodiments, the at least two RBP-binding motifs act cooperatively and upon binding of an RBPs enhance translation of the open reading frame. In some embodiments, binding of the same RBP to the first and second binding motifs enhances translation. In some embodiments, binding of different RBPs to the first and second binding motifs enhances translation. In some embodiments, binding of different RBPs to the first and second binding motifs represses translation. In some embodiments, binding of an RBP to the first RBP-binding motif or second RBP-binding motif in a molecule without the other RBP-binding motif represses translation and binding of an RBP to the first RBP-binding motif or the second RBP-binding motif in a molecule with both motifs enhances translation. In some embodiments, each RBP-binding motif separately represses translation. In some embodiments, the two RBP-binding motifs cooperatively enhance translation. In some embodiments, binding of the RBP-binding motif in the 5' UTR enhances translation. In some embodiments, binding of the RBP-binding motif in the ribosome initiation region does not enhance translation. In some embodiments, binding of a first RBP to a RBP-binding motif of a second RBP enhances translation.

In some embodiments, the first RBP-binding motif is in a ribosome initiation region of the open reading frame and the second RBP-binding motif is in the 5' UTR of the open reading frame. In some embodiments, the first RBP-binding motif and the second RBP-binding motif are separated by at least 1 nucleotide. In some embodiments, the first RBP-binding motif and the second RBP-binding motif are separated by at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35 nucleotides. Each possibility represents a separate embodiment of the invention. In some embodiments, the first RBP-binding motif and the second RBP-binding motif are separated by at least 25 nucleotides. In some embodiments, the first RBP-binding motif and the second RBP-binding motif are separated by at least 30 nucleotides. In some embodiments, the first RBP-binding motif and the second RBP-binding motif are separated by at least 20 nucleotides. In some embodiments, the first RBP-binding motif and the second RBP-binding motif are separated by at most 25, 26, 27, 28, 29, 30, 31, 32, 33, 34, 35, 36, 37, 38, 39, 40, 45, 50, 55, 56, 60, 65, 70, 75, 80, 85, 90, 95 or 100 nucleotides. Each possibility represents a separate embodiment of the invention. In some embodiments, the first RBP-binding motif and the second RBP-binding motif are separated by at most 30 nucleotides. In some embodiments, the first RBP-binding motif and the second RBP-binding motif are separated by at most 35 nucleotides. In some embodiments, the first RBP-binding motif and the second RBP-binding motif are separated by at most 40 nucleotides. In some embodiments, the first RBP-binding motif and the second RBP-binding motif are separated by 34 nucleotides. In some embodiments, the first RBP-binding motif and the second RBP-binding motif are separated by 28 nucleotides.

In some embodiments, the RNA molecule is linked to a polypeptide. In some embodiments, the RNA molecule further comprises a linker. In some embodiments, the RNA molecule further comprises a polypeptide. In some embodiments, the polypeptide is linked to the RNA molecule by the linker. In some embodiments, the RNA molecule is linked at its 5' terminus. In some embodiments, the RNA molecule is linked at its 3' terminus. In some embodiments, the RNA molecule is linked by a phosphate of its backbone. In some embodiments, the phosphate is the most 3' phosphate. In some embodiments, the phosphate is the most 5' phosphate. In some embodiments, polypeptide is linked at its N-terminus. In some embodiments, the polypeptide is linked at its C-terminus. In some embodiments, the linker is an amide linker. In some embodiments, the linker is a Succimidyl 4-(N-maleimidomethyl)cyclohexane-1-carboxylate (SMCC) linker. Linkers for linking nucleic acids (and specifically RNA) and protein are well known in the art. Any appropriate linker that retains functionality of the RNA, the polypeptide or both may be used. In some embodiments, the linker retains the functionality of the RNA and polypeptide. In some embodiments, the linker is of a sufficient length to allow free movement of the RNA and the polypeptide. It will be understood by a skilled artisan that in order for an RNA molecule of the invention to bind its target it must form the correct secondary structure. Similarly, the polypeptide may also require a proper secondary or tertiary structure in order to bind. A linker is selected such that each of the RNA and the polypeptide can form their respective proper structures without interaction with the other.

In some embodiments, the polypeptide is not a complete protein. In some embodiments, the polypeptide comprises or consists of a fragment of a protein. In some embodiments, the polypeptide comprises or consists of a domain of a protein. In some embodiments, the polypeptide comprises at least 5, 10, 15, 20, 25, 30, 35, 40, 45, or 50 amino acids. Each possibility represents a separate embodiment of the invention. In some embodiments, the polypeptide comprises not more than 15, 20, 25, 30, 35, 40, 45, 50, 55, 60, 65, 70, 75, 80, 85, 90, 95, 100, 125, 150, 175, 200, 250, 300, 350, 400, 450 or 500 amino acids. Each possibility represents a separate embodiment of the invention.

In some embodiments, the polypeptide is a human polypeptide. In some embodiments, the polypeptide is not a human polypeptide. In some embodiments, the polypeptide is a mammalian polypeptide. In some embodiments, the polypeptide is a eukaryotic polypeptide. In some embodiments, the polypeptide is a prokaryotic polypeptide. In some embodiments, the polypeptide is a viral polypeptide. In some embodiments, the virus is herpes simplex virus. In some embodiments, the polypeptide comprises or consists of an activation domain. In some embodiments, the activation domain is a transcriptional activation domain. In some embodiments, the activation domain is a transactivation domain. In some embodiments, the activation domain is from a viral protein. In some embodiments, the viral protein is VP16. In some embodiments, the transactivation domain of herpes VP16 comprises or consists of the sequence PAGALDDFDLDML (SEQ ID NO: 305). In some embodiments, the polypeptide comprises or consists of 1, 2, or 3 copies of the domain. In some embodiments, there is a linker between at least 2 of the domains. In some embodiments, the domains are connected directly, without a linker.

In some embodiments, linking an RNA molecule of the invention to a polypeptide increases penetrance of the RNA into a cell. In some embodiments, linking an RNA molecule of the invention to a polypeptide increases penetrance of the RNA into a nucleus. In some embodiments, linking an RNA molecule of the invention to a polypeptide increases binding of the RNA to a target duplex. In some embodiments, linking an RNA molecule of the invention to a polypeptide increases altered transcription of a target molecule comprising a target duplex. In some embodiments, linking an RNA molecule of the invention to a polypeptide increases transcription of a target molecule comprising a target duplex.

In some embodiments, the synthetic RNA molecule is lyophilized. In some embodiments, the synthetic RNA molecule is in a solution. In some embodiments, the synthetic RNA molecule is suspended in water, or an aqueous buffer. Buffers for suspension of nucleic acid molecules are well known in the art and include, but are not limited to TE, TBE, TAE, and EDTA buffers. Any known nucleic acid buffer may be for resuspending the synthetic RNA molecule of the invention. In some embodiments, the synthetic RNA molecule is in a cell.

By another aspect, there is provided a synthetic RNA-peptide fusion molecule, comprising a synthetic RNA molecule and a polypeptide. In some embodiments, the synthetic RNA molecule is an RNA molecule of the invention.

By another aspect, there is provided a method of increasing penetrance of a nucleic acid molecule into a nucleus of a cell, the method comprising linking the nucleic acid molecule to a polypeptide. In some embodiments, the method further comprises introducing the linked nucleic acid molecule into a cytoplasm of a cell. In some embodiments, the nucleic acid is RNA.

By another aspect, there is provided a composition comprising a synthetic molecule of the invention. In some embodiments, the synthetic molecule makes up at least 80%, 85%, 90%, 95%, 97%, 99% or 100% of the composition. Each possibility represents a separate embodiment of the invention. In some embodiments, the composition further comprises a buffer. In some embodiments, the buffer is a nucleic acid buffer. In some embodiments, the buffer is a storage buffer. In some embodiments, the buffer is a binding buffer. In some embodiments, the buffer mimics physiological conditions. In some embodiments, the buffer mimics cytoplasmic conditions.

By another aspect, there is provided a kit comprising,
    a. at least one synthetic RNA molecule of the invention; and
    b. at least one chimeric protein comprising at least one RNA-binding domain of an RBP and at least one peptide that is not a fragment of the RBP;
wherein said synthetic RNA molecule comprises at least one RBP-binding motif that binds the at least one RNA binding domain of an RBP.

By another aspect, there is provided a cell comprising,
    a. at least one synthetic RNA molecule of the invention; and
    b. at least one chimeric protein comprising at least one RNA-binding domain of an RBP and at least one peptide that is not a fragment of the RBP;
wherein said synthetic RNA molecule comprises at least one RBP-binding motif that binds the at least one RNA binding domain of an RBP.

In some embodiments, the chimeric protein is a fusion protein. In some embodiments, the chimeric protein comprises an RBP. In some embodiments, the chimeric protein comprises an RNA-binding domain of an RBP. In some embodiments, the chimeric protein comprises more than one RNA-binding domain of an RBP. In some embodiments, the chimeric protein comprises a fragment of an RBP capable of binding to RNA. In some embodiments, the chimeric protein comprises a functional fragment of an RBP. In some embodiments, the chimeric protein comprises a derivative of an RBP or functional fragment thereof that binds RNA.

As used herein, a "fragment" refers to a partial polypeptide that makes up part of the larger protein or protein domain. In some embodiments, a fragment comprises at least 10, 20, 30, 40 or 50 amino acids. Each possibility represents a separate embodiment of the invention. In some embodiments, a fragment comprises at most 20, 30, 40, 50, 60, 70, 80, 90 or 100 amino acids. Each possibility represents a separate embodiment of the invention.

As used herein, a "derivative" refers to a polypeptide sequence that is based off or modified from a different polypeptide sequence. In some embodiments, a derivative is a mutant of a peptide. A derivative may comprise a chemical modification, post translational modification, artificial amino acid, or the like.

As used herein, a "chimeric protein" refers to a protein with at least one region of amino acids from a first protein and a second region of amino acids from a second protein. In some embodiments, a region is a fragment of a protein. In some embodiments, a region from a protein is a functional fragment. In some embodiments, a chimeric protein is not a naturally occurring protein. In some embodiments, the RNA-binding domain or RBP is attached to a peptide that is not from that same RBP. In some embodiments, the peptide that is not a fragment of the RBP is a non-RNA binding peptide.

As used herein, the term "attached" refers to any method of connecting two peptide fragments such that they make a single new peptide. The term "attached" may be exchanged with linked, bound, covalently bound, or operatively linked.

In some embodiments, the chimeric protein comprises a first fragment and a second fragment, wherein the first fragment is an RNA-binding domain of an RBP and the second fragment is not from that RBP. In some embodiments, RBP and fragment not from the RBP are from different species. In some embodiments, the RBP and fragment not from the RBP are from different genera. In some embodiments, the RBP and fragment not from the RBP are from different families. In some embodiments, the RBP and fragment not from the RBP are from different orders. In some embodiments, the RBP and fragment not from the RBP are from different classes. In some embodiments, the RBP and fragment not from the RBP are from different phyla. In some embodiments, the RBP and fragment not from the RBP are from different kingdoms. In some embodiments, the RBP and fragment not from the RBP are from different domains.

In some embodiments, the non-RBP protein is a detectable moiety. In some embodiments, the detectable moiety is a fluorescent moiety. In some embodiments, detectable is detectable by microscopy. In some embodiments, detectable is detectable by FACS.

In some embodiments, peptide that is not a fragment from the RBP is a protein. In some embodiments, the peptide is a functional fragment or derivative of a protein. In some embodiments, the peptide is an enzyme. In some embodiments, the peptide is part of a biological pathway. In some embodiments, the pathway is a signaling pathway. In some embodiments, the peptide is part of a biological structure. In some embodiments, the peptide is part of a multiprotein complex. In some embodiments, the structure is a subcellular structure. In some embodiments, the structure is a degradome. In some embodiments, the structure is a degradosome.

In some embodiments, the kit or cell comprises at least two chimeric protein. In some embodiments, the at least two chimeric proteins comprise different RNA-binding domains. In some embodiments, the at least two chimeric proteins comprise different peptides not from the RBP. In some embodiments, the at least two chimeric proteins comprise the same RNA-binding domain and different peptides not from the RBP. In some embodiments, the at least two chimeric proteins comprise different RNA-binding domains and the same peptide not from the RBP. In some embodiments, the two peptides not from the RBP are from the same biological pathway or structure. In some embodiments, the two peptides not from the RBP are from the same signaling pathway. In some embodiments, the two peptides not from the RBP are from the same biological structure. In some embodiments, the peptide not from the RBP is a detectable moiety. In some embodiments, detectable moiety is a fluorescent moiety. In some embodiments, the at least two chimeric proteins comprise different fluorescent moieties.

By another aspect, there is provided a method of labeling a cell comprising a. introducing into the cell at least one synthetic RNA of the invention; and b. introducing into the cell a chimeric protein comprising at least one RNA-binding domain of an RBP and at least one detectable moiety, wherein the synthetic RNA molecule comprises at least one RBP-binding motif that bind the at least one RBA-binding domain of an RBP, thereby labeling the cell.

By another aspect, there is provided a method of attracting a nucleic acid molecule to at least one non-RNA binding peptide, comprising contacting a. at least one synthetic RNA molecule of the invention, wherein the synthetic RNA molecule comprises at least one RBP-binding domain; and b. a first chimeric protein comprising at least one RNA-binding domain that binds the first RBP-binding domain and the non-RNA binding peptide;

thereby attracting a nucleic acid molecule to a non-RBP or functional fragment thereof.

By another aspect, there is provided a method of attracting a first peptide to a second peptide, comprising contacting a. at least one synthetic RNA molecule of the invention, wherein the synthetic RNA molecule comprises at least a first RBP-binding domain and a second RBP-binding domain;

b. a first chimeric protein comprising at least one RNA-binding domain that binds the first RBP-binding domain and the first peptide; and c. a second chimeric protein comprising at least one RNA-binding domain that binds the second RBP-binding domain and the second peptide, thereby attracting the first peptide to the second peptide.

Introduction of a gene, RNA, nucleic acid or protein into a live cell will be well known to one skilled in the art. As used herein, "introduction" refers to exogenous addition of a gene, protein or compound into a cell. It does not refer to increasing endogenous expression of a gene, protein or compound. Examples of such introduction include, but are not limited to transfection, lentiviral infection, nucleofection, or transduction. In some embodiments, the introducing occurs ex vivo. In some embodiments, the introducing occurs in vivo. In some embodiments, the introducing occurs in vivo or ex vivo. In some embodiments, the introduction comprises introducing a vector comprising the gene of interest.

The vector may be a DNA plasmid delivered via non-viral methods or via viral methods. The viral vector may be a retroviral vector, a herpesviral vector, an adenoviral vector, an adeno-associated viral vector or a poxviral vector. The promoters may be active in mammalian cells. The promoters may be a viral promoter.

In some embodiments, the vector is introduced into the cell by standard methods including electroporation (e.g., as described in From et al., Proc. Natl. Acad. Sci. USA 82, 5824 (1985)), Heat shock, infection by viral vectors, high velocity ballistic penetration by small particles with the nucleic acid either within the matrix of small beads or particles, or on the surface (Klein et al., Nature 327. 70-73 (1987)), and/or the like.

In some embodiments, mammalian expression vectors include, but are not limited to, pcDNA3, pcDNA3.1 (±), pGL3, pZeoSV2(±), pSecTag2, pDisplay, pEF/myc/cyto, pCMV/myc/cyto, pCR3.1, pSinRep5, DH26 S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

In some embodiments, expression vectors containing regulatory elements from eukaryotic viruses such as retroviruses are used by the present invention. SV40 vectors include pSVT7 and pMT2. In some embodiments, vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

In some embodiments, recombinant viral vectors, which offer advantages such as lateral infection and targeting specificity, are used for in vivo expression. In one embodiment, lateral infection is inherent in the life cycle of, for example, retrovirus and is the process by which a single infected cell produces many progeny virions that bud off and infect neighboring cells. In one embodiment, the result is that a large area becomes rapidly infected, most of which was not initially infected by the original viral particles. In one embodiment, viral vectors are produced that are unable to spread laterally. In one embodiment, this characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

In one embodiment, plant expression vectors are used. In one embodiment, the expression of a polypeptide coding sequence is driven by a number of promoters. In some embodiments, viral promoters such as the 35S RNA and 19S RNA promoters of CaMV [Brisson et al., Nature 310:511-514 (1984)], or the coat protein promoter to TMV [Takamatsu et al., EMBO J. 6:307-311 (1987)] are used. In another embodiment, plant promoters are used such as, for example, the small subunit of RUBISCO [Coruzzi et al., EMBO J. 3:1671-1680 (1984); and Brogli et al., Science 224:838-843 (1984)] or heat shock promoters, e.g., soybean hsp17.5-E or hsp17.3-B [Gurley et al., Mol. Cell. Biol. 6:559-565 (1986)]. In one embodiment, constructs are introduced into plant cells using Ti plasmid, Ri plasmid, plant viral vectors, direct DNA transformation, microinjection, electroporation and other techniques well known to the skilled artisan. See, for example, Weissbach & Weissbach

[Methods for Plant Molecular Biology, Academic Press, NY, Section VIII, pp 421-463 (1988)]. Other expression systems such as insects and mammalian host cell systems, which are well known in the art, can also be used by the present invention.

It will be appreciated that other than containing the necessary elements for the transcription and translation of the inserted coding sequence (encoding the polypeptide), the expression construct of the present invention can also include sequences engineered to optimize stability, production, purification, yield or activity of the expressed polypeptide.

In some embodiments, introduction of a gene of interest comprises introduction of an inducible vector, wherein administration of a drug to the cell will induce expression of the gene of interest. Drug inducible vectors are well known in the art, some non-limiting examples include tamoxifen-inducible, tetracycline-inducible and doxycycline-inducible. In some embodiments, the inducible-vector is introduced to the MSC ex-vivo and the MSC is contacted with the inducing drug in-vivo. In this way expression of the induced gene, and as a result priming or differentiation of the MSC, only occurs in-vivo. In some embodiments, priming or differentiation of the MSC only occurs after the MSC has homed to a location in the body of a subject.

In some embodiments, introducing comprises introducing a modified mRNA. The term "modified mRNA" refers to a stable mRNA that maybe introduced into the cytoplasm of the cell and will there be translated to protein. Such a mRNA does not require transcription for protein expression and thus will more quickly produce protein and is subject to less regulation. Modified mRNAs are well known in the art.

The terms "expression", "expressing" and the like, as used herein, refer to the biosynthesis of a genetic product, including the transcription and/or translation of said genetic product. Thus, expression of a nucleic acid molecule may refer to transcription of the nucleic acid fragment (e.g., transcription resulting in production of the synthetic RNA) and/or translation of RNA into a precursor or mature protein (polypeptide).

In some embodiments, expressing comprises transfection, nucleofection of the synthetic RNA into the cell. In some embodiments, a vector comprising the synthetic RNA is expressed in the cell. Any method of bringing the RNA into the cell, that is known in the art, may be used. In some embodiments, expressing the chimeric protein comprises expressing an expression vector in the cell. In some embodiments, the expressing comprises transfection, nucleofection or lentiviral transduction.

In some embodiments, expressing the at least one synthetic RNA comprises introducing into the cell a DNA molecule comprising a DNA sequence that encodes the at least one synthetic RNA operably linked to a transcription-regulatory element. In some embodiments, the transcription-regulatory element is a promoter. In some embodiments, the promoter is an endogenous promoter of interest. In some embodiments, the method is for measuring the effect of the regulatory element is the cell. Other examples of regulatory elements include, but are not limited to, promoter, cis-regulatory elements, insulators, microRNA binding sites, enhancers, silencers, and trans-regulatory elements. A skilled artisan will appreciate that multiple elements, as well as combinations of elements can be tested in this way, and that any shade of color can be produced by using a specific combination of binding sites for the detectable molecules.

In some embodiments, the contacting is in solution. In some embodiments, the contacting is in an environment suitable for RNA-protein binding. In some embodiments, the contacting is in an environment suitable for DNA-RNA, and/or RNA-protein binding. In some embodiments, the solution is binding buffer. In some embodiments, contacting comprises placing the synthetic RNA and chimeric protein in the same solution. In some embodiments, contacting comprises introducing the synthetic RNA and chimeric protein into the same cell.

In some embodiments, the nucleic acid is an RNA. In some embodiments, the nucleic acid is a DNA. In some embodiments, the nucleic acid is a synthetic nucleic acid.

In some embodiments, the method comprises contacting more than one synthetic RNA. In some embodiments, the method comprises contacting more than one chimeric protein. In some embodiments, the method further comprises contacting a duplex nucleic acid molecule that comprises a sequence that binds to at least one NDBM in the synthetic RNA. In some embodiments, the method is for attracting more than one non-RNA binding peptide, and comprises expressing at least two chimeric proteins, wherein the proteins comprise different non-RBP peptides.

A skilled artisan will appreciate that the method can be performed with any number of chimeric proteins and not just one or two. Indeed, construction of a multiprotein complex or pathways can be achieved by the method of the inventions using distinct RBP-binding domains and RNA binding fragments attached to all the proteins of the complex or pathway. In the methods of the invention, the synthetic RNA acts as a scaffold bringing together different proteins, duplex nucleic acids or all of the above. In some embodiments, the first and second RBP-binding domains are different. In some embodiments, the first and second RBP-binding domains are the same. In some embodiments, the first and second RBP-binding domains bind the same RBP.

In some embodiments, the method is performed in vitro. In some embodiments, the method is performed ex vivo. In some embodiments, the method is performed in vivo. In some embodiments, the method is performed in a cell. In some embodiments, the method is performed in a subject. In some embodiment, the method is a computerized method.

By another aspect, there is provided a method for designing a variant sequence of at least one RBP-binding motif, the method comprising:

a. receiving as input a dataset comprising a plurality of variant sequences of a canonical binding motif of said RBP, and a binding score for each variant sequence of the plurality, wherein each variant comprises at least one nucleotide change from the canonical binding motif, b. training a machine learning model on the variant sequences and labels containing the binding score;

c. applying the trained machine learning model to a plurality target variant sequences to determine a binding score for each target variant sequence of the plurality; and d. selecting at least one target variant sequence with a binding score above a predetermined threshold;

thereby designing a variant sequence of at least one RBP-binding motif.

By another aspect there is provided, a computer program product comprising a non-transitory computer-readable storage medium having program code embodied thereon, program code executable by at least one hardware processor to perform a method of the invention.

By another aspect, there is provided a method comprising: at a training stage, training a machine learning model on a training set comprising:

(i) a plurality of variant sequences of a canonical binding motif of an RBP, and (ii) labels identifying a binding score associated with each of the variant sequences; and at an inference stage, applying the trained machine learning model to a target variant sequence of the canonical binding motif of the RBP, to determine a binding score.

In some embodiments, the target variant sequence comprises at least 1 nucleotide change from a canonical binding motif. In some embodiments, the target variant sequence comprises at least 2 nucleotide change from a canonical binding motif. In some embodiments, the target variant sequence comprises at least 5 nucleotide change from a canonical binding motif. In some embodiments, the target variant sequence comprises at least 1, 2, 3, 4, 5, 6, 7, 8, 9 or 10 nucleotide changes from a canonical binding motif. Each possibility represents a separate embodiment of the invention. In some embodiments, the target variant sequence comprises between 1-10 nucleotide changes from a canonical binding motif. In some embodiments, the target variant sequence comprises between 2-10 nucleotide changes from a canonical binding motif. In some embodiments, the target variant sequence comprises between 1-8 nucleotide changes from a canonical binding motif. In some embodiments, the target variant sequence comprises between 2-8 nucleotide changes from a canonical binding motif.

In some embodiments, the plurality of variant sequences comprises at least 1,000 variant sequences. In some embodiments, the plurality of variant sequences comprises at least 5,000 variant sequences. In some embodiments, the plurality of variant sequences comprises at least 10,000 variant sequences. In some embodiments, the variant sequences are different variant sequences. In some embodiments, the plurality of variant sequences comprises between 1000 and 50000 variant sequences. In some embodiments, the plurality of variant sequences comprises between 1000 and 20000 variant sequences. In some embodiments, the plurality of variant sequences comprises between 5000 and 50000 variant sequences. In some embodiments, the plurality of variant sequences comprises between 5000 and 20000 variant sequences. In some embodiments, the plurality of variant sequences comprises between 10000 and 50000 variant sequences. In some embodiments, the plurality of variant sequences comprises between 10000 and 20000 variant sequences.

In some embodiments, the plurality of variant sequences comprises at least 500 variant sequences that bind the RBP. In some embodiments, the plurality of variant sequences comprises at least 1000 variant sequences that bind the RBP. In some embodiments, the plurality of variant sequences comprises at least 2000 variant sequences that bind the RBP. In some embodiments, the plurality of variant sequences comprises between 500-2000 variant sequences that bind the RBP. In some embodiments, the plurality of variant sequences comprises between 500-3000 variant sequences that bind the RBP. In some embodiments, the plurality of variant sequences comprises between 1000-2000 variant sequences that bind the RBP. In some embodiments, the plurality of variant sequences comprises between 1000-3000 variant sequences that bind the RBP. In some embodiments, the plurality of variant sequences comprises at least 10% variant sequences that bind the RBP. In some embodiments, the plurality of variant sequences comprises at least 15% variant sequences that bind the RBP. In some embodiments, the plurality of variant sequences comprises at least 20% variant sequences that bind the RBP. In some embodiments, the plurality of variant sequences comprises at least 25% variant sequences that bind the RBP. In some embodiments, the plurality of variant sequences comprises at least 30% variant sequences that bind the RBP. In some embodiments, the plurality of variant sequences comprises at most 50% variant sequences that bind the RBP. In some embodiments, the plurality of variant sequences comprises at most 60% variant sequences that bind the RBP. In some embodiments, the plurality of variant sequences comprises at most 70% variant sequences that bind the RBP. In some embodiments, the plurality of variant sequences comprises between 10 and 50% variant sequences that bind the RBP. In some embodiments, the plurality of variant sequences comprises between 10 and 30% variant sequences that bind the RBP. In some embodiments, the plurality of variant sequences comprises between 10 and 25% variant sequences that bind the RBP. In some embodiments, the plurality of variant sequences comprises between 10 and 20% variant sequences that bind the RBP. In some embodiments, binding to the RBP is binding above a predetermined threshold. In some embodiments, the threshold is a score of above zero. In some embodiments, the threshold is a score above 3.5.

In some embodiments, the inference stage comprises applying the trained machine learning model to a plurality of target variant sequences. In some embodiments, the apply the trained machine learning model to a plurality of target variant sequences comprises determining a binding score for each target variant sequence of the plurality. In some embodiments, the apply the trained machine learning model to a plurality of target variant sequences comprises selecting at least one target variant sequence with a binding score above a predetermined threshold. In some embodiments, the apply the trained machine learning model to a plurality of target variant sequences comprises selecting all target variant sequences with a binding score above a predetermined threshold.

In some embodiments, the binding score is a relative numerical evaluation of binding of the RBP. In some embodiments, binding of the RBP is binding of the RBP to the variant sequence. In some embodiments, the binding is within a cell. In some embodiments, the binding is inside a cell. In some embodiments, the binding is in a cytoplasm of a call. In some embodiments, the binding is in a nucleus of a cell. In some embodiments, the binding score correlates to a magnitude of binding. In some embodiments, the binding score is proportional to a magnitude of binding. In some embodiments, a binding score above zero indicates binding. In some embodiments, a binding score above 3.5 indicates binding. In some embodiments, the binding score is determined in vivo. In some embodiments, the binding score is determined in a cell.

In some embodiments, the binding score is determined in an in vivo binding assay. In some embodiments, the in vivo binding assay comprises expressing in a cell a nucleic acid molecule comprising a regulatory element and a variant sequence of the plurality of variant sequences operatively linked to an open reading frame. In some embodiments, the regulatory element is a promoter. In some embodiments, the regulatory element is operatively linked to the open reading frame. In some embodiments, the variant sequence is downstream of the regulatory element. In some embodiments, the variant sequence is upstream of the open reading frame. In some embodiments, the variant sequence is in the 5′ UTR of the open reading frame. In some embodiments, the variant sequence is in a ribosome initiation region of the open reading frame. In some embodiments, binding of the RBP to the variant sequence inhibits translation of the open reading frame. In some embodiments, binding of the RBP to the region inhibits translation of the open reading frame.

In some embodiments, the in vivo binding assay comprises expressing the RBP in the cell. In some embodiments, expressing in the cell comprises contacting the cell with the RBP. In some embodiments, expressing in the cell comprises expressing a nucleic acid molecule comprising an open reading frame encoding the RBP. In some embodiments, expressing comprises contacting. In some embodiments, expressing comprises transferring. In some embodiments, expressing comprises transfecting. It will be understood by a skilled artisan that any method of expressing nucleic acids in a cell may be used. These methods are well known in the art and include, for example, transfection, nucleofection and lipofection. In some embodiments, the nucleic acid molecule is a vector. In some embodiments, the nucleic acid molecule comprises a regulatory element operatively linked to the open reading frame. In some embodiments, the regulatory element is an inducible regulatory element.

In some embodiments, the regulatory element is active in the cell. In some embodiments, the cell is a mammalian cell. In some embodiments, the regulatory element is a promoter. In some embodiments, the regulatory element is a mammalian regulatory element. In some embodiments, the cell is a eukaryotic cell. In some embodiments, the cell is a prokaryotic cell. In some embodiments, the cell is a bacterial cell.

In some embodiments, the in vivo binding assay comprises detecting expression of said the reading frame. In some embodiments, detecting expression is detecting the protein encodes by the open reading frame. In some embodiments, detecting expression is detecting translation of the open reading frame. In some embodiments, the protein is a detectable protein. In some embodiments, the detectable protein is a fluorescent protein. In some embodiments, the detecting is by microscopy. In some embodiments, the detecting is by FACS. In some embodiments, detecting is quantifying. In some embodiments, detecting is measuring.

In some embodiments, the in vivo binding assay comprises calculating inhibition of expression. In some embodiments, the inhibition is as compared to expression from the nucleic acid molecule in the absence of the RBP. In some embodiments, the method further comprises detecting expression before step (b). In some embodiments, the method further comprises detecting expression after step (a). In some embodiments, the method further comprises detecting expression in the absence of the RBP. In some embodiments, the RBP is expressed from an inducible promoter, and the method further comprises detecting expression after (b) but before induction of the inducible promoter. In some embodiments, the method further comprises inducing the promoter. In some embodiments, inducing the promoter comprises adding the inducing agent. Inducible promoters and the compositions that can be added to induce their expression are well known in the art and any such induction may be used.

In some embodiments, a magnitude of inhibition is proportional to the binding score. In some embodiments, the magnitude of inhibition correlates with the binding score. In some embodiments, the binding score is calculated from the magnitude of inhibition. In some embodiments, the magnitude of inhibition is converted into the binding score. It will be understood that positive binding score represent increases binding which causes increased inhibition.

In some embodiments, the binding assay is a high-throughput assay. In some embodiments, the binding assay is a massively parallel assay. In some embodiments, the assay comprises receiving an oligo-library comprising a plurality of nucleic acid molecule each comprising a variant sequence of the plurality of variant sequences. In some embodiments, the assay comprises producing the oligo-library. In some embodiments, the variant sequence is inserted 3' to a regulatory element. In some embodiments, the regulatory element is operably linked to an open reading frame. In some embodiments, the open reading frame encodes a detectable protein. In some embodiments, the variant sequence is inserted 5' to the open reading frame. In some embodiments, the variant sequence is inserted in the 5' UTR of the open reading frame. In some embodiments, the binding assay comprises expressing the oligo-library in cells. In some embodiments, the cells are capable of transcribing the open reading frame. In some embodiments, the regulatory element is active in the cells. In some embodiments, the binding assay comprises expressing the RBP in the cells. In some embodiments, the binding assay comprises separating the cell by expression of the detectable protein. In some embodiments, the detectable protein is a fluorescent protein, and the separating comprises sorting the cells by fluorescence. In some embodiments, the separating is cell sorting. In some embodiments, the sorting is FACS sorting. In some embodiments, the binding assay comprises determining a sequence of a variant sequence in the sorted cells. In some embodiments, individual sorted cells are grown and sequenced. In some embodiments, a bin of sorted cells is sequenced. In some embodiments, a group of cells with equivalent fluorescence is sequenced. In some embodiments, the group comprises a range of fluorescence. In some embodiments, the sequencing is Sanger sequencing. In some embodiments, the sequencing is deep sequencing. In some embodiments, the sequencing is massively parallel sequencing. In some embodiments, the sequencing is next generation sequencing (NGS). In some embodiments, the sequencing comprises high throughput sequencing. In some embodiments, the method comprises performing the in-vivo binding assay. In some embodiments, the method comprises performing the high-throughput assay.

By another aspect, there is provided a method of producing a synthetic RNA molecule of the invention, the method comprising: performing a method of the invention, selecting a target variant sequences and inserting the selected variant sequences into a synthetic RNA molecule, thereby producing a synthetic RNA molecule of the invention.

By another aspect, there is provided a method of producing a synthetic RNA molecule of the invention, the method comprising: performing a method of the invention for a first RBP, repeating the method of the invention for a second RBP, selecting at least one target variant sequence that binds both the first and second RBP, inserting the selected variant sequence into a synthetic RNA molecule, thereby producing a synthetic RNA molecule of the invention.

In some embodiments, the method further comprises performing the method on the invention for a second RBP, selecting a second target variant sequence, and inserting the selected second variant sequence into the synthetic RNA molecule. In some embodiments, at least two variant sequences are selected. In some embodiments, at least two of the first variants are selected. In some embodiments, at least two of the second variants are selected. In some embodiments, the method further comprises performing the method of the invention for a third RBP, selecting a third target variant sequence, and inserting the selected third variant sequence into the synthetic RNA molecule. In some embodiments, the selected target variant sequence comprises a binding score above a predetermined threshold.

In some embodiments, the method comprises producing an output of a binding score of the target variant sequence. In some embodiments, the method comprises producing an output of target variant sequences that bind the RBP. In some embodiments, the method comprises producing an output of target variant sequences that bind two different RBPs. In some embodiments, the method comprises producing an output of target variant sequences that are orthogonal. In some embodiments, the method comprises producing an output of target variant sequences that bind above a predetermined threshold.

As used herein, the terms "electronic document" and "electronic file" are interchangeable and refer broadly to any document/file containing data and stored in a computer-readable format. Electronic document formats may include, among others, Portable Document Format (PDF), Digital Visual Interface (DVI), text files (txt), Comma Separated Vector (CSV), binary files, NumPy array files (npy), PostScript, word processing file formats, such as docx, doc, and Rich Text Format (RTF), and/or XML Paper Specification (XPS).

In some embodiments, the labels denote the identity of the sequence. In some embodiments, the labels denote the sequence. In some embodiments, the sequence is the sequence of the RBP-binding motif. In some embodiments, the label denotes the identity of the RBP-binding motif.

According to some embodiments, the system further comprises means for producing the plurality of electronic documents. In some embodiments, the system further comprises a nanopore. In some embodiments, the system further comprises a nanopore apparatus. In some embodiments, the means for producing the plurality of electronic documents is the nanopore apparatus.

In some embodiments, the present invention may be configured for automatic document classification based, at least in part, on content-based assignment of one or more predefined categories (classes) to documents. By classifying the content of a document, it may be assigned one or more predefined classes or categories, thus making it easier to manage and sort. Such classes may be specific families of proteins, proteins with particular functions, proteins from particular sources or any class of protein or category of protein such as would be useful to the user.

Typically, multi-class machine learning classifiers are trained on a training set of documents, where each document belongs to one of a certain number of distinct classes (e.g., invoices, scientific papers, resumes, letters). The training set may be labeled with the correct classes (e.g., for supervised learning), or may not be labeled (e.g., in the case of unsupervised learning). Following a training stage, the classifier may be able to predict the most probable class for each document in a test set of documents. Although document classification may be based on textual content alone, for some types of documents, the task of classification can be significantly enhanced by also generating features from the visual structure of the document. This is based on the idea that documents in the same category often also share similar layout and structure features.

In some embodiments, following a multi-modal training stage, a trained classifier of the present invention may be configured for classifying electronic documents based on a multi-modal input comprising both representations of the documents. In other embodiments, the trained classifier may be configured for classifying electronic documents based on only a single modality input (e.g., textual content or raster image alone), with improved classification accuracy as compared to a classifier which has been trained solely based on a single modality.

In some embodiments, the present invention may employ one or more types of neural networks to further generate data representations of the multi-modal inputs. For example, raw input text from an electronic document may be processed so as to generate a data representation of the text as a fixed-length vector. Similarly, images of the electronic document (e.g., thumbnails or raster images) may be processed to extract image features.

In some embodiments, the neural network models employed by the present invention to generate textual data representations may be selected from the group consisting of Neural Bag-of-Words (NBOW); recurrent neural network (RNN), Recursive Neural Tensor Network (RNTN); Dynamic Convolutional Neural Network (DCNN); Long short-term memory network (LSTM); and recursive neural network (RecNN). See, e.g., Pengfei Liu et al., "Recurrent Neural Network for Text Classification with Multi-Task Learning", Proceedings of the Twenty-Fifth International Joint Conference on Artificial Intelligence (IJCAI-16). Convolutional neural network (CNN) may be used, e.g., to extract image features which represent the physical visual structure of a document.

In some embodiments, the present invention may further be configured for employing a common representation learning (CRL) framework, for learning a common representation of the two views of data (i.e., textual and visual). CRL is associated with multi-view data that can be represented in multiple forms. The learned common representation can then be used to train a model to reconstruct all the views of the data from each input. CRL of multi-view data can be categorized into two main categories: canonical-based approaches and autoencoder-based methods. Canonical Correlation Analysis (CCA)-based approaches comprise learning a joint representation by maximizing correlation of the views when projected to the common subspace. Autoencoder (AE) methods learn a common representation by minimizing the error of reconstructing the two views. AE-based approaches use deep neural networks that try to optimize two objective functions. The first objective is to find a compressed hidden representation of data in a low-dimensional vector space. The other objective is to reconstruct the original data from the compressed low-dimensional subspace. Multi-modal autoencoders (MAE) are two-channeled models which specifically perform two types of reconstructions. The first is the self-reconstruction of view from itself, and the other is the cross-reconstruction where each view is reconstructed from the other. These reconstruction objectives provide MAE the ability to adapt towards transfer learning tasks as well. In the context of CRL, each of these approaches has its own advantages and disadvantages. For example, though CCA based approaches outperform AE based approaches for the task of transfer learning, they are not as scalable as the latter.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire. Rather, the computer readable storage medium is a non-transient (i.e., not-volatile) medium.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

By another aspect, there is provided a method of inducing phase separation in a cell, the method comprising expressing in the cell a synthetic RNA molecule comprising at least three RBP-binding motifs and the RBP, thereby inducing phase separation in the cell.

In some embodiments, the synthetic RNA molecule is a molecule of the invention. In some embodiments, the RNA molecule is a non-coding RNA. In some embodiments, the RNA does not encode a protein. In some embodiments, the method is devoid of expressing any molecules other than the synthetic RNA and the RBP.

In some embodiments, the at least four RBP-binding motifs comprises non-identical sequences. In some embodiments, the at least four RBP-binding motifs comprises different sequences. In some embodiments, the different sequences comprise at least 1 nucleotide difference from each other. In some embodiments, the different sequences comprise at least 1 nucleotide difference from the canonical binding motif. In some embodiments, the synthetic RNA is devoid of the canonical binding motif. In some embodiments, at least three RBP-binding motifs is at least four RBP-binding motifs. In some embodiments, the synthetic RNA comprises at least one binding motif for a first RBP and at least a second binding motif for a second RBP and wherein the first and second RBPs are different RBPs.

As used herein, the term "about" when combined with a value refers to plus and minus 10% of the reference value. For example, a length of about 1000 nanometers (nm) refers to a length of 1000 nm+−100 nm.

It is noted that as used herein and in the appended claims, the singular forms "a," "an," and "the" include plural referents unless the context clearly dictates otherwise. Thus, for example, reference to "a polynucleotide" includes a plurality of such polynucleotides and reference to "the polypeptide" includes reference to one or more polypeptides and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements or use of a "negative" limitation.

In those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

Various embodiments and aspects of the present invention as delineated hereinabove and as claimed in the claims section below find experimental support in the following examples.

EXAMPLES

Generally, the nomenclature used herein, and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, CT (1994); Mishell and Shiigi (eds), "Strategies for Protein Purification and Characterization—A Laboratory Course Manual" CSHL Press (1996); all of which are incorporated by reference. Other general references are provided throughout this document.

Methods

Bacterial Oligo Library Work

Construction of the oligo library. 10,000 mutated versions of the WT binding sites of the phage CPs of PP7 (FIG. 1A-E), MS2 and Qβ, were designed and positioned at two positions within the ribosomal initiation region. Each of the designed 10 k sites were positioned either one or two nucleotides downstream to the mCherry start codon, resulting in 20 k different configurations. The following OL was ordered from Agilent: 100 k oligos, each 210 bp long containing the following components: BamHI restriction site, barcode (five for each variant), constitutive promoter (cPr), ribosome binding site (RBS), mCherry start codon, one or two bases (denoted by δ), the variant binding site, ~60 bp of the mCherry gene, and an ApaLI restriction site. The OL was then cloned using a restriction-based cloning strategy. Briefly, the 100 k-variant ssDNA library from Agilent was amplified in a 96-well plate using PCR, purified, and merged into one tube. Following purification, dsDNA was cut using BamHI-hf and ApaLI and cleaned. Resulting DNA fragments were ligated to the target plasmid containing an mCherry open reading frame and a terminator, using a 1:1 ratio. Ligated plasmids were transformed to E. Cloni® cells (Lucigen) and plated on 37 large agar plates with Kanamycin antibiotics in order to conserve library complexity. Approximately two million colonies were scraped and transferred to an Erlenmeyer for growth. After O/N growth, plasmids were extracted using a maxiprep kit (Agilent), their concentration was measured, and they were stored in an Eppendorf tube in −20° C.

Construction of RBP-GFP fusions. RBP sequences lacking a stop codon were amplified via PCR of either Addgene or custom-ordered templates. MCP, PCP and QCP were cloned into the RBP plasmid between restriction sites KpnI and AgeI, immediately upstream of a GFP gene lacking a start codon, under the pRhlR promoter (containing the rhlAB las box38) and induced by C4-HSL. The backbone contained an Ampicillin (Amp) resistance gene. The resulting fusion-RBP plasmids were transformed into E. coli TOP10 cells. After Sanger sequencing, positive transformants were made chemically competent and stored at −80° C. in 96-well format.

Double Transformation of OL and RBP-GFP plasmids. Note: the following two sections were conducted three times, one for each RBP-GFP fusions.

OL DNA was transformed into ~300 chemically competent bacterial cell in 100 ul aliquots containing one of the RBP-mCeulean plasmids in 96-well format. After transformation, cells were grown in 2 L liquid LB with twice the concentration of the antibiotics—Kanamycin and Ampicillin—overnight at 37° C. and 250 rpm. After growth glycerol stocks were made by centrifugation, re-suspension in 30 ml LB, mix 1.2 ml with 400 ul 80% glycerol—20% LB solution and stored in −80° C.

Induction-based Sort-Seq OL assay. One full glycerol stock of the library was dissolved in 500 ml of LB with antibiotics and grown overnight at 37° C. and 250 rpm. In the morning, the bacterial culture was diluted 1:50 into 100 ml of semi-poor medium consisting of 95% bioassay buffer (BA: for 1 L—0.5 g Tryptone [Bacto], 0.3 ml Glycerol, 5.8 g NaCl, 50 ml 1M MgSO4, 1 ml 10×PBS buffer pH 7.4, 950 ml DDW) and 5% LB. The inducer, N-butanoyl-L-homoserine Lactone (C4-HSL), was pipetted manually to a final concentration of one out of six final concentrations: 0 uM, 0.02 uM, 0.2 uM, 2 uM, 20 uM, and 200 uM. Cells were grown at 37° C. and 250 rpm to mid-log phase (OD600 of ~0.6) as measured by a spectrophotometer and taken to the FACS for sorting.

During sorting by the FACSAria II (BD Biosciences) cell sorter each inducer level culture was sorted into eight bins of increasing mCherry levels spanning the entire fluorescence range except for 5% at the higher end (bin 1—low mCherry to bin 8—high mCherry), and constant GFP levels (for example, the 0 mM culture were sorted according to zero GFP fluorescence, the 0.02 uM culture to slightly positive GFP fluorescence, and so on). Sorting was done at a flow rate of ~20,000 cells per second. 300 k cells were collected in each bin for the entire 6×8 bin matrix. After sorting, the binned bacteria were transferred to 10 ml LB+KAN+AMP growth culture and shaken at 37° C. and 250 rpm overnight. In the morning, cells were prepared for sequencing (see below) and glycerol stocks were made by mixing 1 ml of bacterial solution with 500 ul 80% glycerol—20% LB solution and stored in −80° C.

Sequencing. Cells were lysed (TritonX100 0.1% in 1×TE: 15 μl, culture: 5 μl, 99° C. for 5 min and 30° C. for 5 min) and the DNA from each bin was subjected to PCR with a different 5' primer containing a specific bin-inducer level barcode. PCR products were verified in an electrophoresis gel and cleaned using PCR Clean-Up kit. Equal amounts of DNA (2 ng) from 16 bins were joined to one 1.5 ml microcentrifuge tube for further analysis, to a total of three tubes. This procedure was conducted three times, one for each RBP-GFP fusions.

Each one of the three samples were sequenced on an Illumina HiSeq 2500 Rapid Reagents V2 50 bp 465 single-end chip. 20% PhiX was added as a control. This resulted in ~540 million reads, about 180 million reads per RBP.

Mammalian Cassette Microscopy Experiments

Construction of mammalian expression plasmids. Three plasmids were ordered from Addgene containing PCP-3xGFP (#75385), MCP-3xBFP (#75384), and N22-3xmCherry (#75387), and they were used to create the following two plasmids: MCP-3xmCherry and QCP-3xBFP. In brief, using two restriction enzymes, BamHI and MluI, the plasmids were restricted, and PCR conducted with the same restriction sites added as primers on both MCP and QCP. After PCR purification, the product was restricted with the same two enzymes and ligated to the matching plasmids. Then, the Top10 *E. coli* cells were transformed and screened for positive clones. All plasmids used in the microscopy experiments were sequence-verified via Sanger sequencing.

RNA binding site cassettes were ordered from IDT as g-blocks. They were restricted and ligated to a vector downstream of a CMV promoter using the restriction enzyme EcoRI. Then, the Top10 *E. coli* cells were transformed and screened for positive clones. All plasmids used in the microscopy experiments were sequence-verified via Sanger sequencing and are available at Addgene.

Mammalian Microscopy Assay

1. Cell culture: The Human Bone Osteosarcoma Epithelial Cell line was incubated and maintained in 100×20 mm cell culture dishes under standard cell culture conditions at 37° C. in humidified atmosphere containing 5% $CO_2$ and were passaged at 80-85% confluence. Cells were washed once with 1×PBS, and subsequently treated with 1 mL trypsin/EDTA (ethylenediaminetetraacetic acid, Biological Industries) followed by incubation at 37° C. for 3-5 minutes. DMEMcomplete, complemented with 10% FBS and final concentrations of 100 U penicillin plus 100 µg streptomycin, was added and transferred into fresh DMEMcomplete in subcultivation ratios of 1:10.

2. Fluorescent microscopy experiments: Before the experiment, U2OS cells were seeded on 60 mm glass-bottom imaging dishes. Transient transfection was performed with Polyjet (Invivogen) transfection reagent according to the manufacturer's instructions. Typical DNA for transfection was 150 ng from RBP-3xFP and 850 ng from the cassette plasmid. After inoculation for 24-48 hours, the growth medium was removed and replaced with Leibovitz L15 medium with 10% FBS. During microscopy, the sample was kept at 37° C.

Microscopy was carried out on a Nikon Ti-E eclipse epifluorescent microscope. Images were taken with a 40× oil immersion objective and the following excitation lasers: 585 nm for mCherry, 490 nm for GFP, 400 nm for BFP. The images were recorded with the Xion EMCCD camera. The microscope was controlled with NIS Elements imaging software. Time-lapse movies of a single Z-plane were recorded with, 1500 ms exposure time and time intervals between frames were 30 seconds.

Responsiveness score. Note: the following analysis procedure was conducted three times, once for each RBP.

1. Read normalization and filtration. Read numbers were normalized by percentage of bacteria in each bin from the total library, given by the FACS during sorting. This is done in order to be able to compare between numbers of reads of the same variant in different bins.

$$N_{reads}(i, j, k) = R_{reads}(i, j, k) \times \% \, cells(j, k), \qquad \text{Eq. 1}$$

$$i = 1:100,000$$

$$j = 1:6$$

$$k = 1:8$$

where $N_{reads}(i,j,k)$ and $R_{reads}$ are the number of normalized and raw reads per variant, bin, and inducer concentration respectively. % cells(j,k) corresponds to the percentages of the cells in each bin per inducer concentration during sorting from the entire library as supplied by the sorter.

Two cut-offs were introduced on the variant read counts: (i) only inducer levels that had above 30 reads for all eight bins were taken into account; and (ii) only variants that had more than 300 reads in total for the entire 6×8 matrix were taken into account.

2. Estimation of mean mCherry levels (µ) per inducer concentration from reads per variant. For each inducer concentration j, there is an 8-bin histogram for which there is a need to calculate the mCherry averaged fluorescence of variant i µ(i,j) for all variants. First, for every variant $N_{reads}$ are renormalize by the total number of reads obtained for that inducer level (each column in the read matrix and color bar, FIG. 2E (left)-top).

$$\tilde{N}_{reads}(i, j, k) = \frac{N_{reads}(i, j, k)}{\Sigma_{k=1}^{8} N_{reads}(i, j, k)}, \qquad \text{Eq. 2}$$

$$i = 1:100,000$$

$$j = 1:6$$

$$k = 1:8$$

Next, the bin index (=1:8) was convert to mCherry fluorescence (Bin(i,j,k)). This is done by retrieving the maximum mCherry fluorescence value that was assigned to each bin by the sorter. Then, the cumulative renormalized reads are computed by adding all the normalized reads successively from the lowest to the highest fluorescent bin as follows:

$$\tilde{N}_{reads}^{cum}(i, j, k) = \sum_{l=1}^{k} \tilde{N}_{reads}(i, j, l), \qquad \text{Eq. 3}$$

$$i = 1:100,000$$

$$j = 1:6$$

$$k = 1:8$$

Figure 2A:
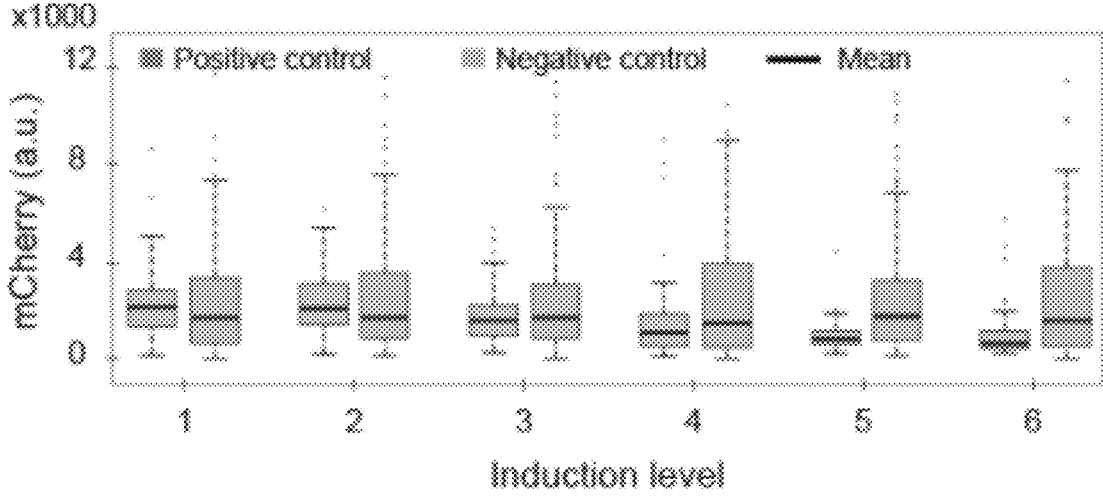
FIGS. 2A-G. Responsiveness analysis and results. (2A) Boxplots of mCherry levels for the positive and negative control variants at each of the six induction levels for PCP-GFP. (2B) Schema for responsiveness score ($R_{score}$) analysis. (Left & middle) Linear regression was conducted for each of the 100 k variants, and two parameters were extracted: slope and goodness of fit ($R^2$). The third parameter is the standard deviation (STD) of the fluorescence values at the three highest induction levels. (Right) Location of the positive control (dark green stars) and negative control (red stars) in the 3D-space spanned by the three parameters. Both populations (positive and negative) were fitted to 3D-Gaussians, and simulated data points were sampled from their probability density functions (pdfs) (orange for negative and green for positive). Based on these pdfs the $R_{score}$ was calculated. (2C) (Left) Heatmap of normalized mCherry expression for the ~20 k variants with PCP. Variants are sorted by $R_{score}$. Black and red lines are positive and negative controls, respectively, and the grey graph is the $R_{score}$ as a function of variant. (Right) "Zoom-in" on the 2,000 top-$R_{score}$ binding sites for PCP. (2D) (Left) 3D-representation of the $R_{score}$ for every binding site in the library and all RBPs. Responsive binding sites, i.e. sites with $R_{score}$>3.5, are colored red for PCP, green for MCP, and orange for QCP. (Right) "Zoom-in" on the central highly concentrated region. Source data are provided as a Source Data file. Altogether, there was identified 1868, 1144, and 2624 binding sites (i.e $R_{score}$>3.5) for PCP, MCP, and QCP respectively. In addition, there were additional 3736, 1460, and 4682 "non-classified" binding sites (i.e 0<$R_{score}$<3.5) for PCP, MCP and QCP, while the rest were determined to be non-binding ($R_{score}$<0). (2E) (Top-Left) A sample 6×8 matrix obtained for each variant. (Bottom-Left) Collapsing the matrix to a vector of integrated mCherry level for every inducer value. (Middle) Sample list for PCP of unsorted non-renormalized 6-long vectors displayed as heatmap. (Right) Renormalized heatmap displaying unsorted PCP responsive variants. (2F-G) $R_{score}$ Sorted heat-maps of (2F) MCP, and (2G) QCP with the OL. Positive and negative control are depicted in black and red, respectively.
Figure 2B:
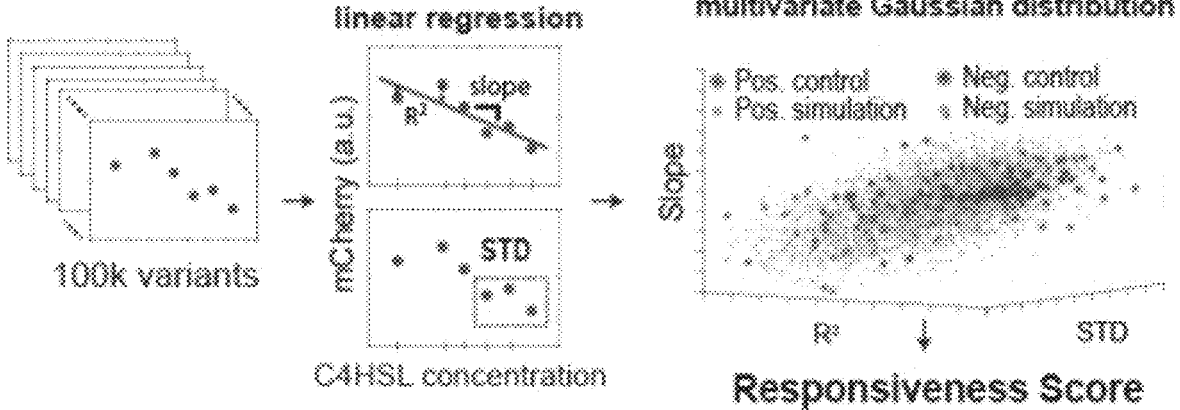
Figure 2C:
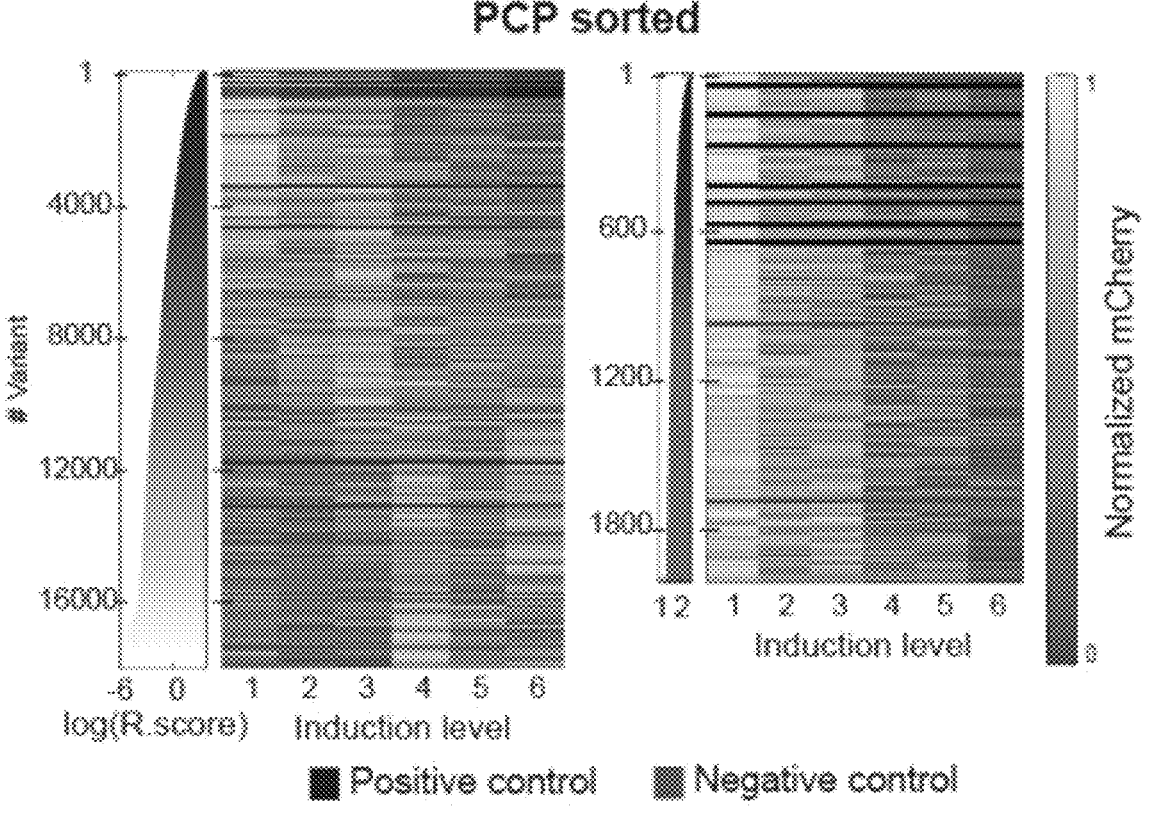
Figures 2D, 2E:
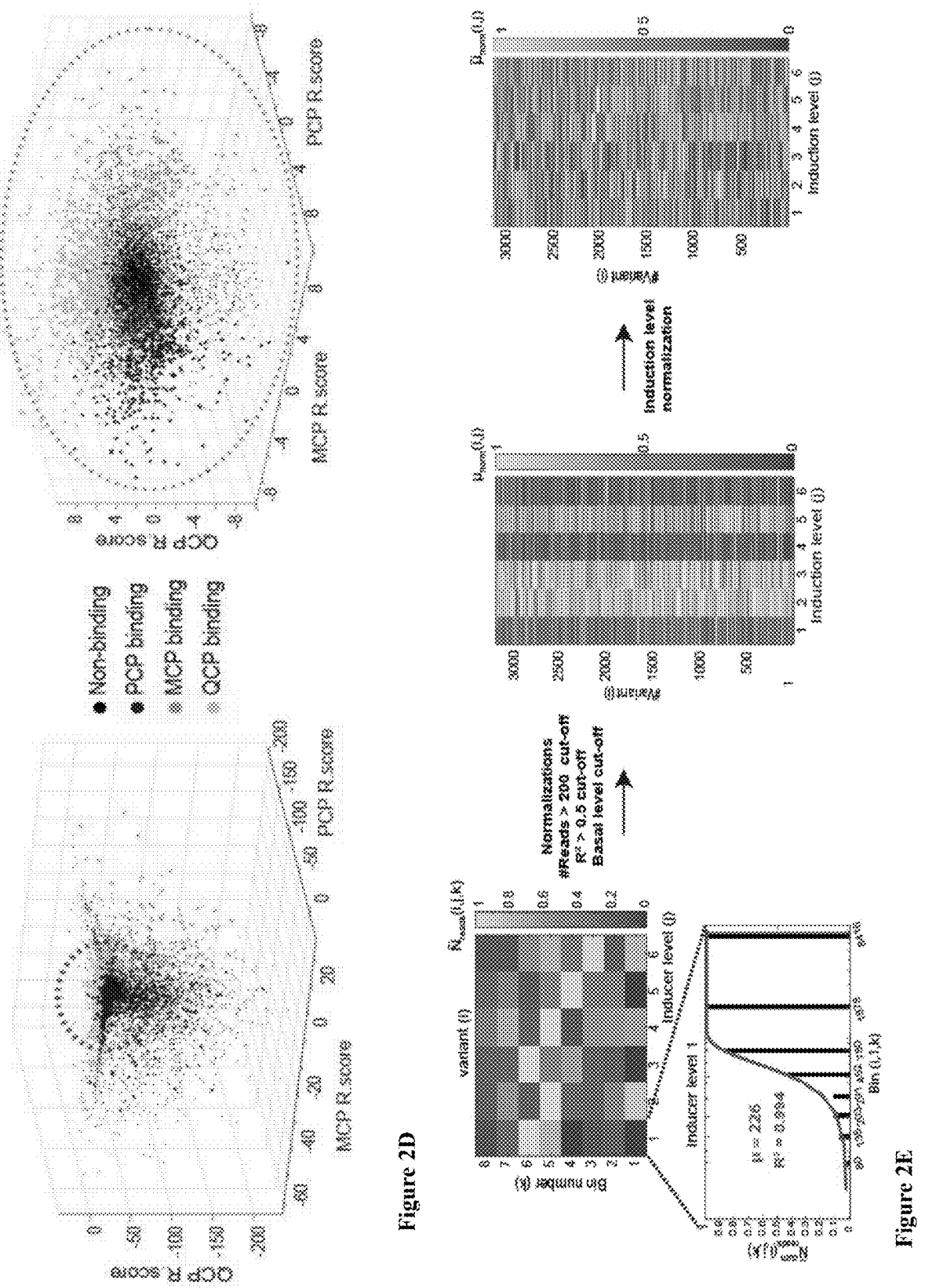

Finally, to compute µ(i,j), the cumulative renormalized read values are fit to a cumulative Gaussian as follows:

$$\tilde{N}_{reads}^{cum}(i, j, k) = 0.5 + 0.5 \, erf\left(\frac{Bin(i, j, k) - \mu(i, j)}{\sigma(i, j)\sqrt{2}}\right), \qquad \text{Eq. 4}$$

$$i = 1:100,000$$

$$j = 1:6$$

$$k = 1:8$$

where σ(i,j) is the standard deviation for mCherry fluorescence extracted from the fitting procedure (see FIG. 2E (Left)-bottom for sample calculation). Note, only induction levels that had a goodness of fit higher than 0.5 were taken into account in the final analysis.

3. Fluorescence level normalization and filtration. Since each inducer concentration experiment was carried out in different conditions (e.g. duration of incubation on ice, O/N shaking, binning time) and at a different time (different days), mCherry levels assigned for each bin varied greatly as a function of experiment as well as overall fluorescence recorded. Therefore, to quantify this systematic error, first there was computed a normalized mean fluorescence level ($\mu_{norm}$) per variant as follows:

$$\mu_{norm}(i, j) = \frac{\mu(i, j)}{\max\{\mu(i, j); j = 1:6\}}, \qquad \text{Eq. 5}$$

$$i = 1:100,000$$

$$j = 1:6.$$

To ascertain the scope of the problem presented by the systematic error, in FIG. 2E (Middle) there is plotted a heat-map of $\mu_{norm}$ values consisting of 3000 variants for PCP. Here, low fluorescence was recorded for induction levels 1, 4, and 6, while higher levels were recorded for induction levels 2, 3, and 5, respectively. These results are consistent with the fact that the induction experiments of level 1, 4, and 6 were carried out on the same day, while those of 2, 3, and 5 on a separate day.

Next, to accommodate for these systematic discrepancies in the data, for each inducer level the $\mu_{norm}$ for all the negative control variants that were introduced into the OL were extracted (220 variants for PCP, 160 variants for MCP and QCP). The average $\mu_{norm}$ for all negative controls per inducer level is then computed to obtain $\mu_{neg}(j)$. Finally, all $\mu_{norm}(i,j)$ values were rescaled by $\mu_{neg}(j)$ to eliminate the systematic error from the average fluorescence level as follows:

$$\tilde{\mu}_{norm}(i, j) = \frac{\mu_{norm}(i, j)}{\mu_{neg}(j)}, \qquad \text{Eq. 6}$$

$$i = 1:100,000$$

$$j = 1:6.$$

FIG. 2E (Right) shows that this rescaling operation successfully compensated for the systematic error. Note, that since the experiment is based on detecting a repression effect as a function of inducer, the variants that displayed averaged mCherry levels at the three lowest concentrations below 15% of the averaged mCherry levels at the three lowest concentrations of the positive control were filtered out.

4. Calculating the responsiveness score ($R_{score}$). To characterize binding to the variants, an empirical score was computed which quantifies how similar a given variant's mCherry levels were to either the positive or negative controls. The score, termed the responsiveness score ($R_{score}$), is proportional to the binding affinity $K_d$ (see below) provided that the $R_{score}$ obtained for the various negative and positive controls are distributed in a Gaussian fashion. Quantile-quantile (QQ) plots for testing how the positive and negative controls fit to a Gaussian distribution are presented in FIG. 12.

To derive an expression for the $R_{score}$, there was first computed two n-dimensional probability density functions defining the probability in an n-dimensional space to find either the CP binding or non-binding positive and negative controls, respectively. The parameters were selected according to the maximum likelihood criterion.

$$pdf(pos, n) = \qquad \text{Eq. 7}$$

$$\frac{\exp\left(-\frac{1}{2}(\tilde{\mu}_{norm}(pos, n) - \text{mean}(\tilde{\mu}_{norm}(pos, n)))^T \Sigma^{-1} \atop (\tilde{\mu}_{norm}(pos, n) - \text{mean}(\tilde{\mu}_{norm}(pos, n)))\right)}{\sqrt{(2\pi)^3 |\Sigma|}},$$

$$pos = \text{positive controls}$$
$$n = n_1, n_2, \ldots, n_N$$

$$pdf(neg, n) = \frac{\exp\left(-\frac{1}{2}(\tilde{\mu}_{norm}(neg, n) - \text{mean}(\tilde{\mu}_{norm}(pos, n)))^T \atop \Sigma^{-1}(\tilde{\mu}_{norm}(neg, n) - \text{mean}(\tilde{\mu}_{norm}(pos, n)))\right)}{\sqrt{(2\pi)^3 |\Sigma|}}, \qquad \text{Eq. 8}$$

$$neg = \text{negative controls}$$
$$n = n_1, n_2, \ldots, n_N$$

Where the set $\{n_j\}$ corresponds to n independent parameters by which one can describe the fluorescence measurement of each variant, and $\Sigma$ is the covariance matrix. For example, one such set is the six-dimensional set corresponding to the fluorescence measurements for each inducer level.

Using these probability density functions, one can compute the probability that an n-dimensional vector i belongs to each of these distributions, as follows:

$$p(i,\text{pos}) \equiv p(\tilde{\mu}_{reg}(i,n)|pdf(\text{pos},n)),$$

$$p(i,\text{neg}) \equiv p(\tilde{\mu}_{reg}(i,n)|pdf(\text{neg},n)) \qquad \text{Eq.9:}$$

which allows us to define the responsiveness score ($R_{score}$) as follows:

$$R_{score}(i) \equiv \log\left(\frac{p(i, pos)}{p(i, neg)}\right). \qquad \text{Eq. 10}$$

A higher $R_{score}$ indicates a more likely grouping to the CP binding positive control, while a lower score indicates a more likely grouping to the non-binding negative control.

In the analysis carried out herein, it was chosen to reduce the parameter space to a 3-dimensional space consisting of the following components: the slope (m) and goodness of fit ($R^2$) to a simple linear fit of the rescaled fluorescence $\tilde{\mu}_{norm}(i,j)$ to inducer concentration values. The third component is a standard deviation (std) of $\tilde{\mu}_{norm}(i,j)$ computed at the three highest concentration induction bins. This new vector is termed:

$$\left\{\tilde{\mu}_{norm}(i, j), \begin{array}{l} i = 1:100,000 \\ j = 1:6 \end{array}\right\} \to \left\{\tilde{\mu}_{reg}(i, n), \begin{array}{l} i = 1:100,000 \\ n = m, R^2, std \end{array}\right\} \qquad \text{Eq. 11}$$

Based on the 3-dimensional space ($R^2$, m, and std) a multivariant Gaussian fit was conducted for the positive and negative control populations (see FIG. 2A-D), which in turn allowed the computing of the 3-dimensional pdf(pos,n) and pdf(neg,n). Finally, the $R_{score}$ was computed for each non-control variant by averaging the score over as many barcodes which past the filters (each variant appeared in the library 5 times). The results of this computation are presented in the heatmaps of FIG. 2A-G, which are arranged in accordance with decreasing $R_{score}$.

5. Calculating $\Delta\Delta G$ for high-affinity variants. Up to this point, the $R_{score}$ was developed to sort the different variants, but there was no investigation of what it means physically or from a binding perspective. The approach relied on mapping the behavior of the positive binding controls and non-binding negative controls in some three-dimensional parameter space, and computing the likelihood that a given variant would belong to one or the other group. The $R_{score}$ is the log of the ratio of the two computations. In principle, $R_{score}$ can be computed from any number of probability density functions. The original 6D space consisting of the 6 inducer concentrations could have been used, or any other combination. In the computation below, the 6D space is mapped to a 1D space of binding affinities that can be in principle computed from each 6-vector using a Hill function fit. In the case of such a mapping, eqn. 7 and 8 can be replaced with the following terms:

$$pdf(pos, n) = \frac{1}{\sigma_{pos}\sqrt{(2\pi)}}\exp\left(-\frac{1}{2}\left(\frac{K_d^n - K_d^{pos}}{\sigma_{pos}}\right)^2\right), \qquad \text{Eq. 12}$$

$pos$ = positive controls $n = n_1, n_2, \dots, n_N$ $$pdf(neg, n) = \frac{1}{\sigma_{neg}\sqrt{(2\pi)}}\exp\left(-\frac{1}{2}\left(\frac{K_d^n - K_d^{neg}}{\sigma_{neg}}\right)^2\right),$$

$neg$ = negative controls $n = n_1, n_2, \dots, n_N$

In such a case, the probability for a given variant to have a $K_d$ similar to the positive and negative control distributions is given by:

$$p(i, pos) \equiv p\left(K_d^i | pdf(pos, n)\right) \qquad \text{Eq. 13}$$

$$p(i, neg) \equiv p\left(K_d^i | pdf(neg, n)\right)$$

One can then compute $R_{score}(i)$ similar to Eq. 10 in the following manner:

$$R_{score}(i) = \log\left[\left(\frac{\sigma_{neg}}{\sigma_{pos}}\right)\exp\left(-\frac{1}{2}\left(\frac{K_d^i - K_d^{pos}}{\sigma_{pos}}\right)^2 + \frac{1}{2}\left(\frac{K_d^i - K_d^{neg}}{\sigma_{neg}}\right)^2\right)\right] \qquad \text{Eq. 14}$$

If one assumes for simplicity that $\sigma_{pos} \sim \sigma_{neg} \sim \sigma$ one gets:

$$R_{score}(i) = \frac{K_d^{pos} - K_d^{neg}}{\sigma^2}K_d^i + \frac{(K_d^{neg})^2 - (K_d^{pos})^2}{\sigma^2} \qquad \text{Eq. 15}$$

which implies that the $R_{score}(i)$ for a given variant is proportional to its $K_d$.

Finally, it is noted that the expressions derived in equations 14 and 15 have the following general form to a reasonable first approximation:

$$R_{score}(i) = a + bK_d^i + O\left((K_d^n)^2\right) \cong a + bK_d^i \qquad \text{Eq. 16}$$

This then allows one to convert any $R_{score}$ value to binding affinity provided there is a reasonable approximation to a and b.

Given the fact that:

$$\Delta G = -k_B T \ln K_d, \qquad \text{Eq. 17:}$$

the binding energy can be estimated from $R_{score}$ values. Lari, A. et al. "Live-Cell Imaging of mRNP-NPC Interactions in Budding Yeast" Methods Mol. Biol. 2038, 131-150 (2019) previously derived the $\Delta\Delta G$ for MCP with over 100 k variants, 609 of them were present in the OL variants. There was a screen for the high affinity variants by setting thresholds of $\Delta\Delta G > -6.667$ and $R_{score} > 3.5$, which left us with 37 data points. In order to derive the $\Delta\Delta G$ for PCP and QCP using the same equation, the $R_{score}$ values were normalized by the mean calculated value for the MS2-WT strain. A linear regression, as presented in FIG. 11, was then implemented and a and b derived. Using these values, $\Delta\Delta G$ was calculated for every high-affinity variant with all three RBPs.

$$\Delta\Delta G(i) = \ln\frac{\frac{R.score(i)}{R.score(wt)} - a}{b}, i = 1:100,000 \qquad \text{Eq. 18}$$

6. Non-parametric analysis of the OL data. In order to validate the Gaussian-parametric approach in this analysis, a simple non-parametrized computation, called Average Nearest Neighbor (ANN), was carried out. In this case, each variant is characterized by a 6-dimensional vector representing the mean mCherry fluorescence for six inducer concentrations. For each variant, the average squared Euclidean distance in a 6-dimensional space was calculated from the positive and negative control variants respectively, as follows:

$$S_{pos}^k = \frac{1}{N_{pos}}\sum_{i=1}^{N_{pos}}\sum_{j=1}^{6}\left(x_j^k - x_j^i\right)^2 \qquad \text{Eq. 19}$$

$$S_{neg}^k = \frac{1}{N_{neg}}\sum_{i=1}^{N_{neg}}\sum_{j=1}^{6}\left(x_j^k - x_j^i\right)^2,$$

Where, $$x_j^k$$

corresponds to the $j^{th}$ inducer concentration (varying from 1 to 6) of the $k^{th}$ variant, $$x_j^i$$

corresponds to the $j^{th}$ inducer concentration of the $i^{th}$ positive or negative controls variants. $N_{pos}$ and $N_{neg}$ correspond to the number of positive and negative control variants, respectively.

$$s_{pos}^k$$

and $$s_{neg}^k$$

correspond to the average squared Euclidean distance of a variant k to the positive and negative control variants, respectively. The logarithm of the ratio of the average distances (negative to positive controls—to ensure values that can correlate with parametrized $R_{score}$) was taken to obtain a non-parametrized responsiveness score for the $k^{th}$ variant.

$$R_{score}^{ANN}(k) \equiv \log\left(\frac{s_{neg}^k}{s_{pos}^k}\right),$$  Eq. 20

Machine-learning methods. Two types of models to predict the binding preferences were developed, represented as the responsiveness score, of the three RNA binding proteins (RBPs): WT-specific and whole-library. Herein is described in detail the models, the choice of hyper-parameters and their training on experimental data. First, the features common to the two models are covered; then, details relevant to each of the two model types separately are provided.

Figure 1A:
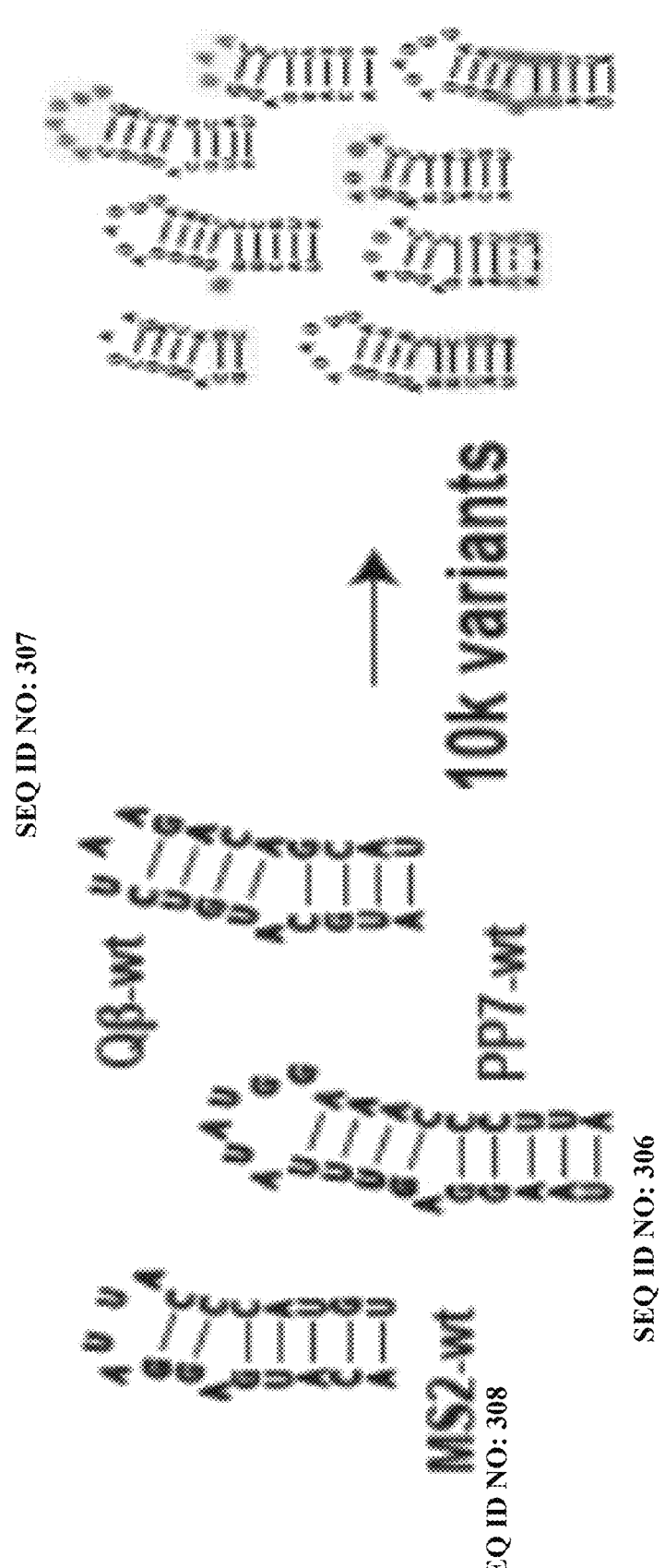
FIGS. 1A-E: iSort-Seq overview in *E. coli*. (1A) (Top) Wild-type binding sites for MS2 (SEQ ID NO: 308), PP7 (SEQ ID NO: 306) and QB (SEQ ID NO: 307) phage coat proteins and illustrations of the 20k mutated variants created based on their sequences. (Bottom) Composition of the OL library. Histogram of the number of PP7-based variants (blue), QB-based variants (orange), and MS2-based variants (green) with different edit distances from the MS2-WT binding site. (1B) Each putative binding site variant was encoded on a 210 bp oligo containing the following components: restriction site, barcode, constitutive promoter (cPr), ribosome binding site (RBS), mCherry start codon, one or two bases (denoted by δ), the sequence of the variant tested, and the second restriction site. Each configuration was encoded with five different barcodes, resulting in a total of 100k different OL variants. The OL was then cloned into a vector and transformed into an *E. coli* strain expressing one of three RBP-GFP fusions under an inducible promoter (iPr). The transformation was repeated for all three fusion proteins. Variants in FIGS. 1A and 1B are representative variants and blurring is intentional. (1C) The schema illustrates the behavior of a high-affinity strain: when no inducer is added, mCherry is expressed at a certain basal level that depends on the mRNA structure and sequence. When inducer (C4-HSL) is added, the RBP binds the mRNA and blocks the ribosome from mCherry translation, resulting in a down-regulatory response as a function of inducer concentration. (1D) The experimental flow for iSort-Seq. Each library is grown at 6 different inducer concentrations, and sorted into eight bins with varying mCherry levels and constant RBP-GFP levels. This yields a 6×8 matrix of mCherry levels for each variant at each induction level. (Bottom) An illustration of the experimental output of a high-affinity strain (V1) and a no-affinity strain (V2). (1E) Histograms of the edit distance of the sequences in the library of MCP, QCP, and PCP to the different wild types. The library contains sequences with high similarity to each of the wild types, with larger distances to the wild type of the other proteins.
Figure 1A:
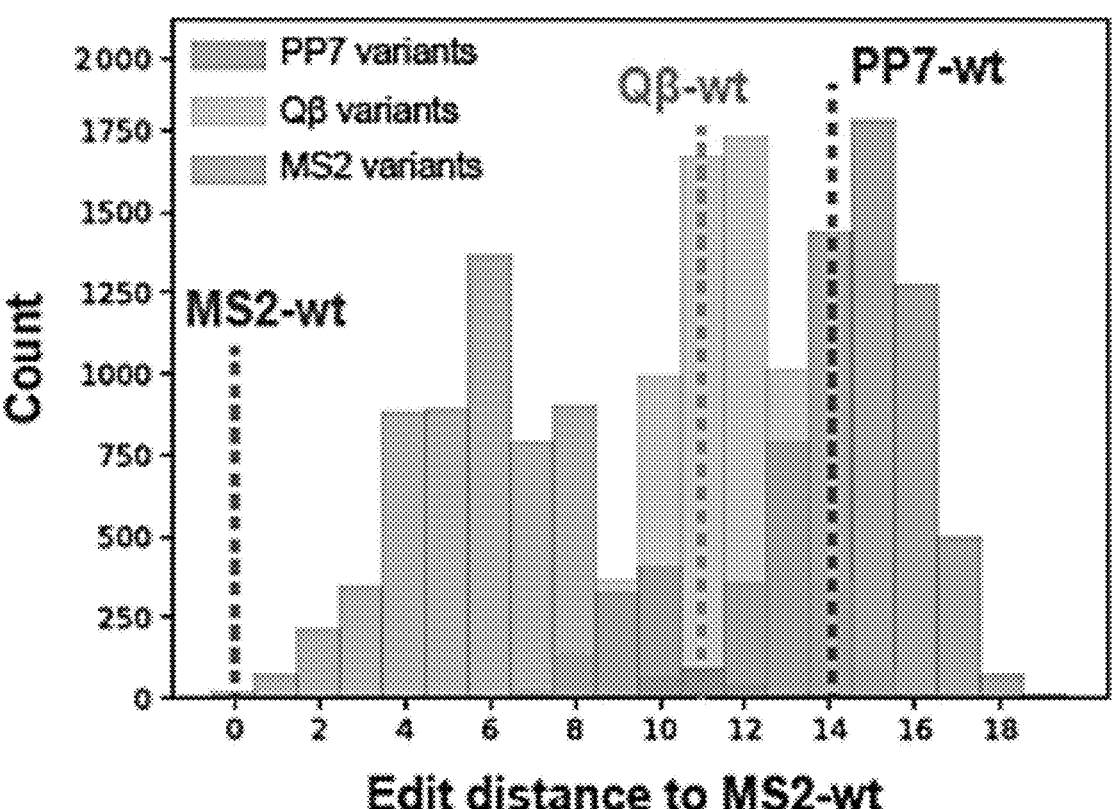
Figure 1B:
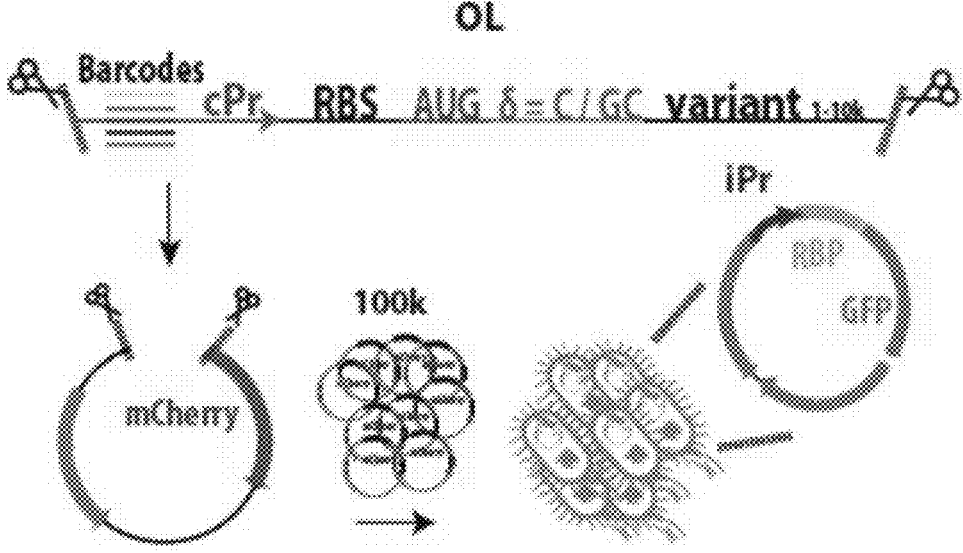
Figures 1C, 1D:
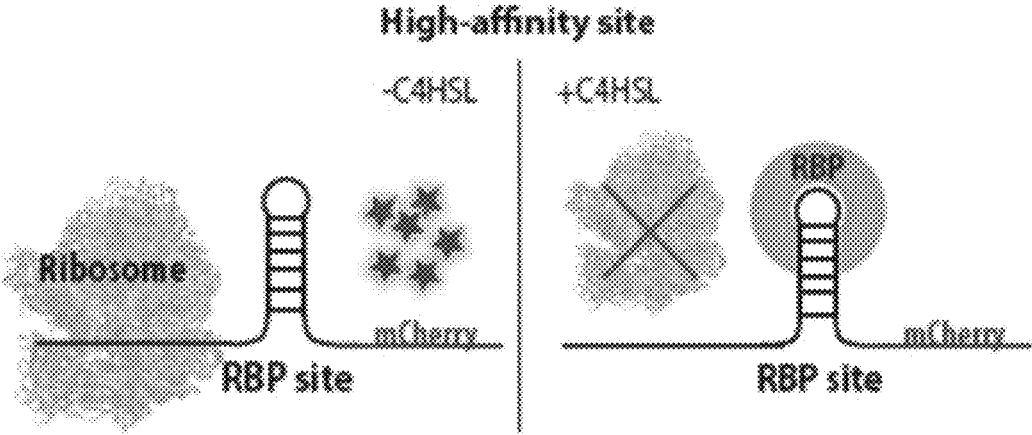
Figure 1E:
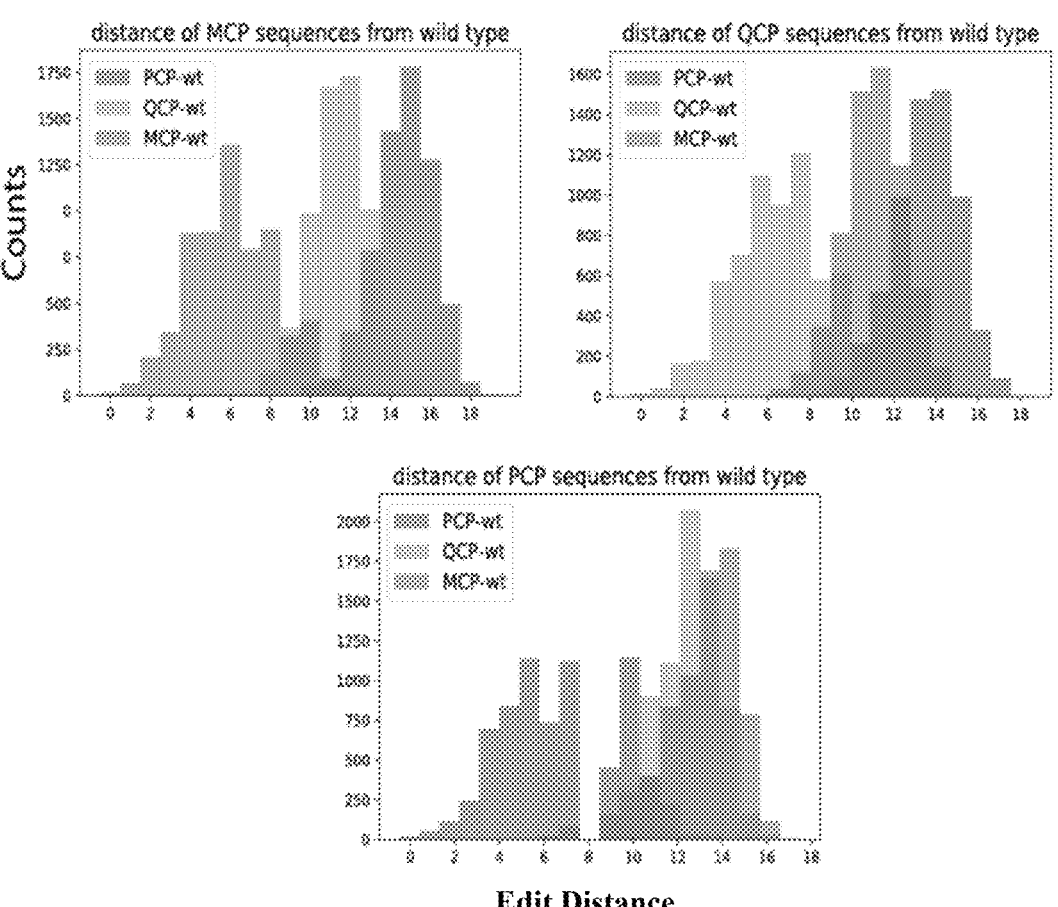

Dataset. The dataset contains $R_{score}$ of three proteins (MCP, PCP and QCP) to approximately 17,000 sequences (PCP 17,177, MCP 17,213, QCP 16,041, and 12,245 in the intersection of the three). All sequences were either a variant of a known WT binding site of one of the three proteins or a non-similar sequence that was used as control (PCP 42, MCP 40, QCP 38). The edit distance of the derived sequences from their WT mostly span 4 to 8 mutations or indels (FIG. 1E). The binding intensity score ($R_{score}$) empirically spanned the range of −281 to 47. Each sequence has a positional feature, which defines its prefix and suffix, i.e. upstream and downstream flanking sequences, respectively. The prefix is either C ($\delta$=5) or GC ($\delta$=6) and the corresponding suffix is one out of three options: T, CT or no suffix. The choice of suffix is done in a way that guarantees no shift in the reading frame.

Data encoding. To provide the sequence data as input to the computational framework used, it first needs to be transformed to numerical values. Each sequence was encoded using a traditional one-hot encoding of the sequence. Each nucleotide is converted to a four-bit vector with one bit set in the position corresponding to that nucleotide and all other positions set to zero. This way an L-long sequence is transformed into a 4×L binary matrix. L is either the WT length in the WT-specific model or 50 in the whole-library model.

Model evaluation. 10-fold cross-validation (CV) was performed to evaluate the binding models. The dataset was partitioned randomly into 10 equal-sized folds. Then, the model was trained and tested 10 times, each time using a different fold as the test set and the other nine folds combined as the training set. Two measurements were used to gauge model performance: Pearson correlation and area under the receiver operating curve (AUC). Pearson correlation measures the linear agreement between two vectors and is a common measure to evaluate intensity prediction. AUC is a common measure to evaluate classification of positive and negative data points. Positive (i.e. binding) sequences were defined as those having a binding intensity greater than 3.5, and negatives as those having intensity smaller than 3.5.

This threshold was computed as the averaged $R_{score}$ of non-zero positive control variants minus one standard deviation:

Pos. control thershold =  Eq. 21

$$\frac{\Sigma_1^3 \text{mean}(R_{score}(pos_{control}, i)) - \sigma(R_{score}(pos_{control}, i))}{3},$$

$$i = PCP, MCP, QCP$$

Parameters search. A hyper parameter search procedure, identical to the hyper-parameter search process of Graph-Prot, was used to optimize model performance. Given the amount of computation required for the optimization phase, all hyper-parameters were evaluated on a set of 20% of the available data. More specifically, the data was divided into two parts, 80% as training set and 20% as a validation set. Then, a set of parameters from the parameter space defined for each of the models was randomly selected (Tables 1 and 2), trained on the training set and the trained model was tested on the validation set. This step was repeated 10 times. From the 10 random parameters sets, the best performing set was selected based on the achieved Pearson correlation between predicted and measured scores of the validation set. The second step of the search was "fine tuning" of the chosen parameter set. In this step, sets of parameters were tested in the surrounding of the set that was selected during the first step in the same manner, i.e. training the models on the training set and evaluating them the validation set. The "fine-tuning" step is based on the results of the first random stage, and thus can be generalized to any set of parameters.

The sequences used to determine the optimal parameter values, i.e. that validation set comprising of 20% of the data, were then discarded for the cross-validated performance assessment procedure. After discarding the validation set, the final reported model evaluation is by 10-fold CV on the remaining training set comprising of 80% of the data. This process of parameters selection was done for each protein and for each of the models separately. This process is summarized in FIG. 13.

WT-Specific Binding Model

Figure 3A:
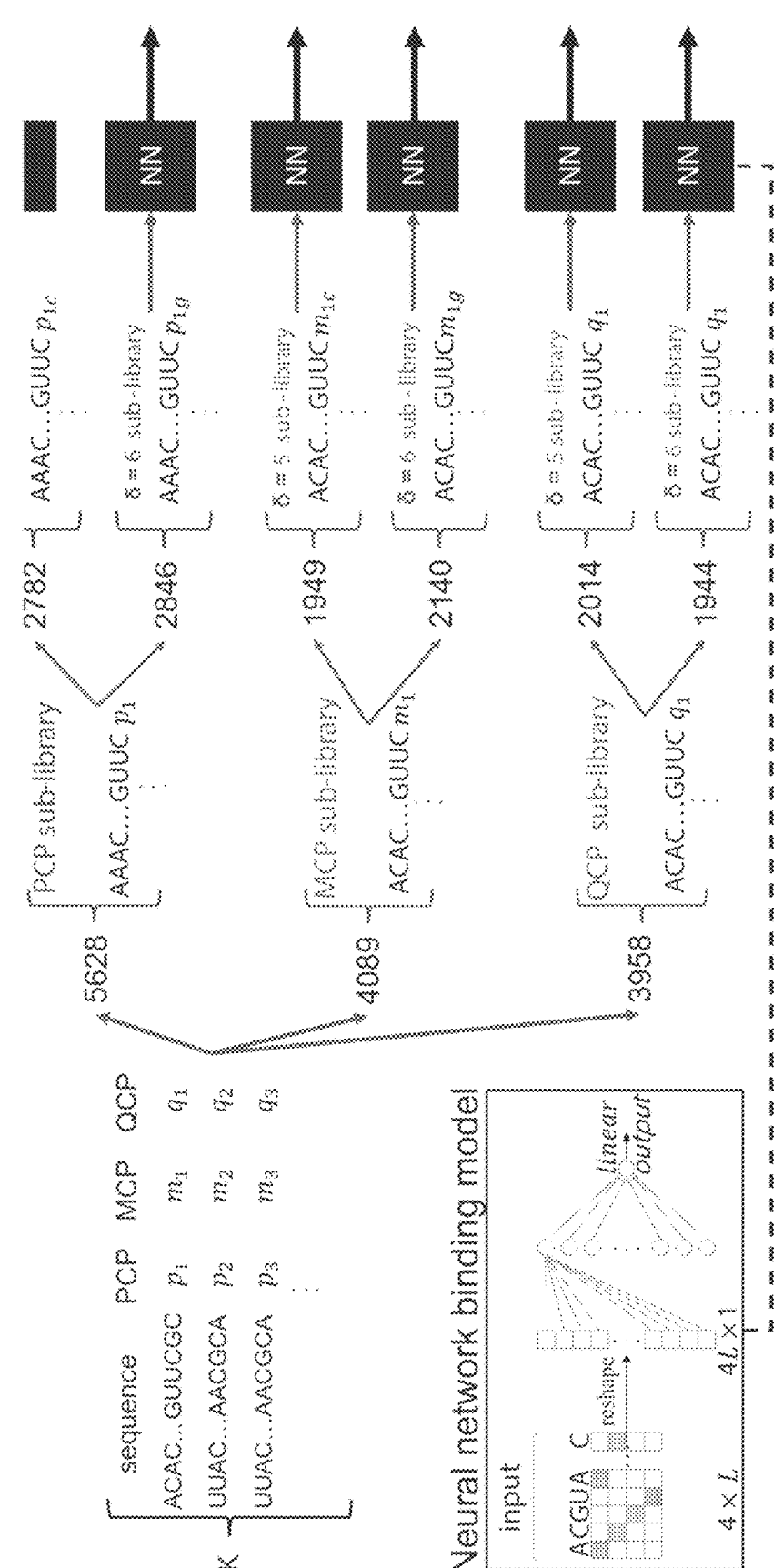
FIGS. 3A-G. Analysis of MCP, PCP, and QCP RNA-binding sequence preferences. (3A) Scheme for the data preparation and neural network architecture (inset) used. (3B) Average Pearson correlation of 10-fold cross-validation computed for the WT-specific sub-libraries (i.e. PCP, MCP, and QCP with PP7-based, MS2-based, and QB-based binding sites respectively at either δ=5 (left) and δ=6 (middle)), and for the whole library CNN model (right). (3C) mCherry basal levels for the six WT-specific sub-libraries. (3D) Illustrations of the model predictions for the three sub-libraries for any single- or double-nucleotide structure-preserving mutation. Each binding site is shown, with the wild-type sequence (SEQ ID NO: 306-308) indicated as white or black dots inside the squares. Each square is divided to the four possible options of nucleotide identity, with the colors representing the predicted change in $R_{score}$ with respect to the wild-type for each option. (3E) Comparison of the $R_{score}$ values between C and GC prefixes for the same binding sites of MCP (Left), QCP (Middle), and PCP (Right). For all proteins, there is effectively little to no correlation between expression levels and the position of the variants within the ribosomal initiation region. (3F) Comparison between the Gaussian-parametrized $R_{score}$ computation and the non-parametrized. $R_{score}$ computation (Left panels) X-Y scatter plot of the Gaussian-parametrized $R_{score}$ (X-axis) vs the non-parametrized $R_{score}$. (Right panels) Cross-correlation computations between the Gaussian-parametrized to the non-parametrized $R_{score}$. The correlation is computed for multiple subsets of variants. Each value on the x-axis corresponds to the last-value on any subset as ordered by the Gaussian-parametrized $R_{score}$. Note, the correlation falls with increasing subset size due to the increased inclusion of non-binders which are expected to be randomly positioned in both the parametrized and non-parametrized spaces. (3G) Comparison of structure-conserving ML mutation analysis for the non-parametrized (left panels) vs the Gaussian-parametrized (right panels) approach.
Figure 3B:
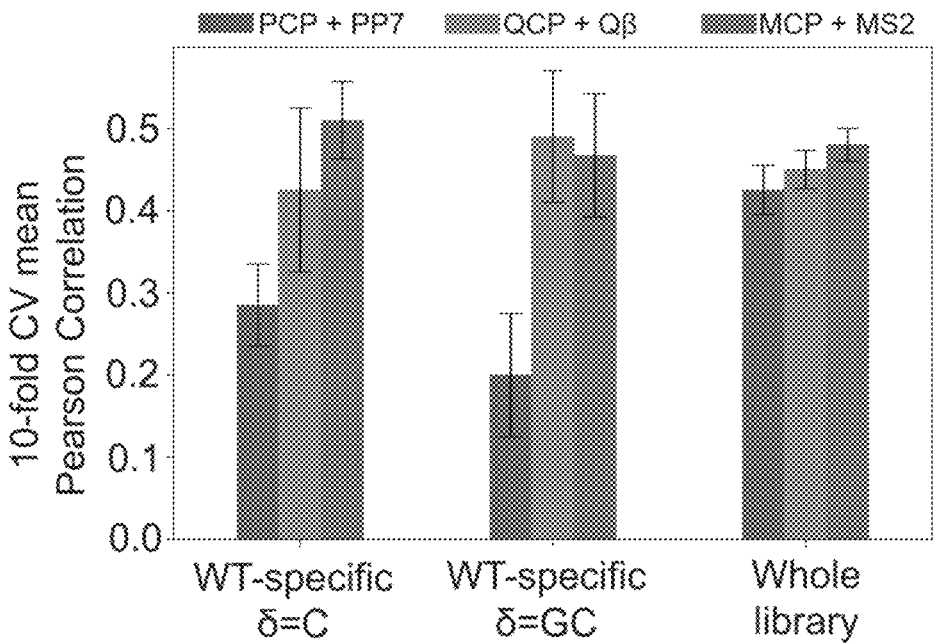
Figure 3C:
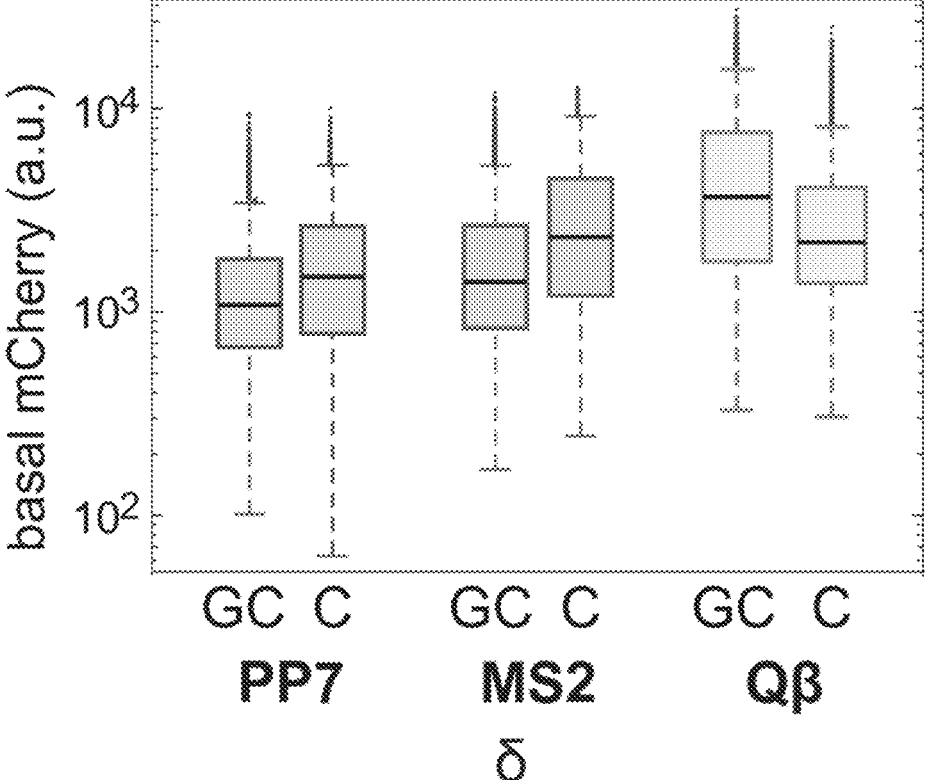
Figure 3D:
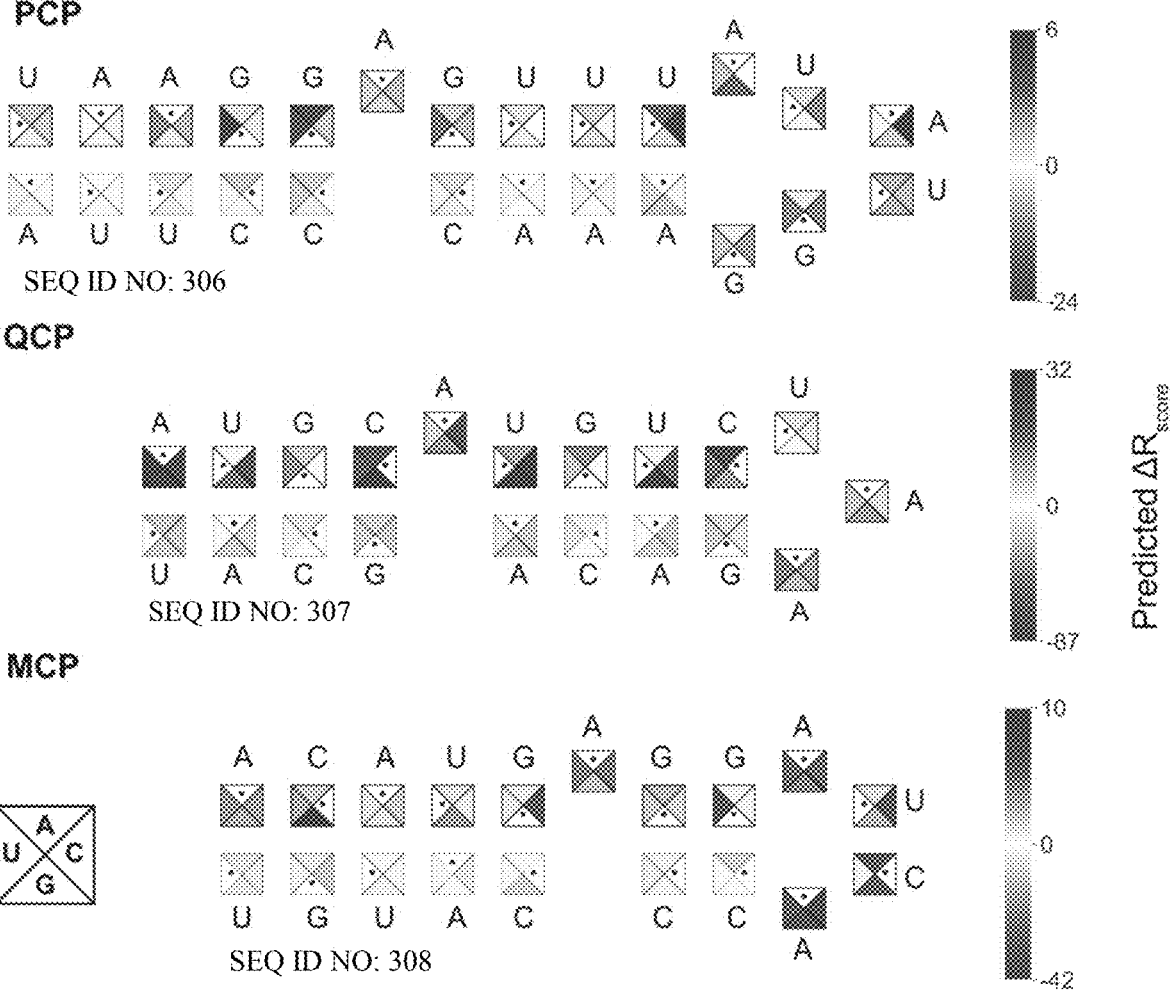
Figure 3E:
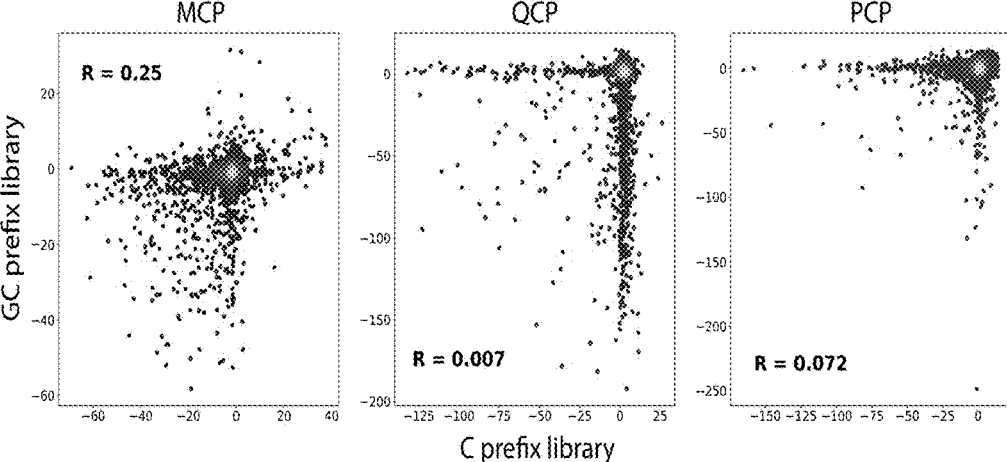
Figure 3F:
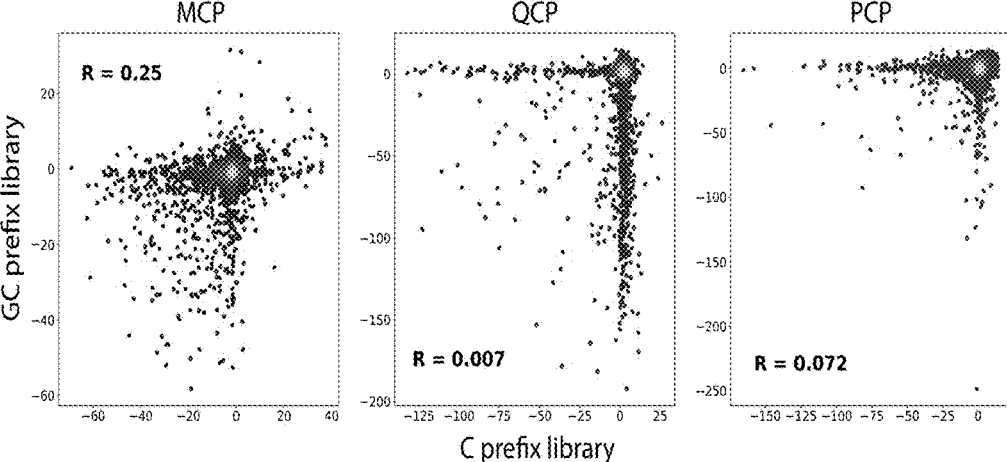

Dataset division. First a model based on a WT and its variants of the same length was developed. For this aim, a different subset of the data for each protein was used. The protein-specific subset contained only the sequences that have the same length as its WT binding site (MS2—19 nt, Qβ—20 nt, PP7—25 nt). Then, the subset was again split by the prefix of the sequence (C or GC). The rationale for the second split is the low correlation in binding intensities observed between $\delta$=5 and $\delta$=6 positions (FIG. 3F). This process is summarized in FIG. 3A.

Model description and optimization. Each WT-specific model is composed of 1-2 hidden layers with 10-40 nodes and one output layer with a single node (FIG. 3A). Each protein and its sub-library have different parameters that were chosen specifically for it. This optimization process was done as described under the Parameters search section above. The details of the parameters examined are described in Table 1.

TABLE 1

Parameters search space for WT-specific model. (Left) The parameter space for
each of the two steps of the hyper parameters search. (Right) The final models'
parameters. Unless noted otherwise, the range specified is of stride 1.

| | Parameter space | | Final parameters (protein, prefix) | | | | | |
| | Initial space | Surrounding space | | | | | | |
| Parameter | | | MCP-C | MCP-GC | QCP-C | QCP-GC | PCP-C | PCP-GC |
| --- | --- | --- | --- | --- | --- | --- | --- | --- |
| Nodes | 5-50 | ±5 | 22 | 30 | 25 | 10, 10 | 22 | 9, 9 |
| Layers | 1-3 | — | 1 | 2 | 1 | 2 | 1 | 2 |
| Activation function | identity, tanh, relu | — | Relu | relu | Relu | relu | relu | relu |
| Epochs | 20, 30 . . . 100 | ±15 (strides of 5) | 30 | 35 | 30 | 40 | 20 | 30 |

In addition to the parameters in Table, which are unique
to each model, there are additional parameters that are
common to all of them: learning rate 0.001 (default), batch
size 8, optimizer ADAM, loss function MSE (mean squared
error) and dropout probability of 0.2 for each hidden layer.
The output layer consisted of one node with the identity
activation function.

Evaluation. Overall, the WT-specific models achieved
good prediction performance, i.e. an average Pearson cor-
relation between ~0.3 to 0.5 in 10-fold CV (FIG. 3B). As
explained before, the sub-library of each RBP was divided
in to two sub-libraries based on its prefix. A model specific
for each of the two sub-libraries was trained and tested in
10-fold CV. The better performing model out of these two
was then chosen according to its average Pearson correlation
in 10-fold CV, and it was used in the downstream analysis.
This resulted in using the δ=5 library for MCP and PCP, and
the δ=6 library for QCP.

Whole-Library Binding Model

Padding sequences for whole-library models. Next, there
was developed a protein-specific binding model based on the
whole library of RNA sequences and their responsiveness
scores. Since the binding sites have different lengths, they
need to be converted to have equal lengths for the learning
process. All sequences were padded to the same length of 50
nt. The binding sites were part of an RNA transcript. Hence,
they were upstream-padded with the flanking 9 or 8 nt
upstream followed by C or GC prefix (respectively) accord-
ing to their position; overall 10 nt were added upstream.
Downstream-padding of the sequences was done by their
flanking transcriptomic context up to a full length of 50 nt.

(SEQ ID NO: 1)
AATTGTGAGCGCTCACAATTATGATAGATTCAATTGGATTAATTAAAGAG

GAGAAAGGTACCCATG.

The upstream nucleotides used are:

(SEQ ID NO: 2)
GTGAGCAAGGGCGAGGAGGATAACATGGCCATCATCAAGGAGTTCATGCG

CTTCAAGGTGCACATGGAGGGCTCCGTGAACGGCCACAGAGTTCGAGATCG

AGGGCGAGGGCGAGGGCCGCCCCTACGAGGGCACCCAGACCGCCAAGCTG

AAGGTGACCAAGGGTGGCCCCCTGCCCTTCGCCTGGGACATCCTGTCCCC

TCAGTTCATGTACGGCTCCAAGGCCTACGTGAAGCACC.

The padding of the binding sites does not invalidate the
models. Since these flanks are constant, and the first layer of
the model is a convolution layer, which extracts local
sequence features, they do not have any impact on model
performance.

RNA secondary structure information. For the whole-
library binding model, the one-hot encoded sequence infor-
mation was augmented by RNA secondary structure infor-
mation. The RNAfold algorithm (Vienna package) was used
to predict the structure of each sequence. The input to
RNAfold is the binding site, and it outputs the predicted
secondary structure in parenthesis notation, i.e. opening and
closing parenthesis for base-pairs and a dot for unpaired
nucleotide.

Figure 4A:
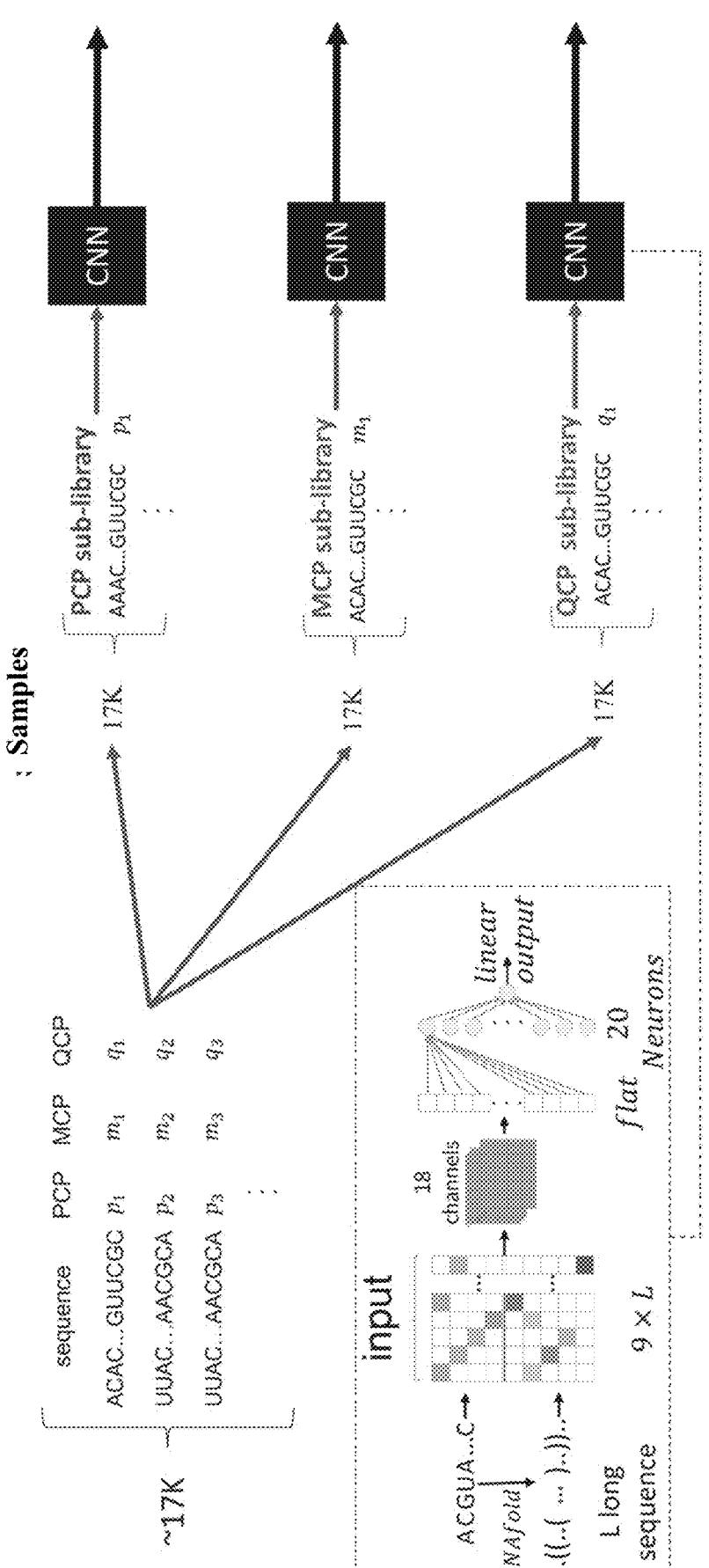
FIGS. 4A-D. Analysis of MCP, PCP, and QCP RNA-binding structure preferences. (4A) A scheme for the data preparation and neural network architecture (inset) used for the protein-specific convolutional neural network model based on the whole library. Various binding sites were generated with a predefined structure different from the wild-type and used the whole-library models to predict their responsiveness score. (4B) Predicted $R_{score}$ distributions for binding sites that differ in the length of the upper stem (left) or the loop (right) for PCP (top row), MCP (middle row), and QCP (bottom row). Stem and loop lengths were varied by ±2 base-pairs and nucleotides, respectively. (4C) Density maps for predicted $R_{score}$ for either no bulge (left-column) or a 2-nucleotide bulge (right-column) mutation of a wild-type-like structure for PCP-response (top-row), MCP-response (middle-row), and QCP-response (bottom-row). (4D) Bar charts of performance evaluation of the whole library model with the structural contribution. Performance accuracy is reported by an average over 10-fold cross-validation (CV) of (Left) AUC for the whole-library models, and (Right) Pearson correlation for both models. The data shows that for all cases when the model was trained with structural informa- tion its performance improved (p-value<$10^{-5}$ paired Wil- coxon rank-sum test compared with adding random struc- tural information).

This notation was converted into an encoding of RNA
structural contexts. This was done by a MATLAB script that
encodes the RNA structure as a one-hot matrix with one bit
set in each column for the corresponding structural context.
For a binding site of length n, the n-long parenthesis
annotation is transformed to a 5×n binary matrix. The
structural contexts used were lower stem (LS), bulge (B),
upper stem (US), loop (L), and no-hairpin (N). The one-hot
encoded structure matrix outside of the binding site was set
to zero. The RNA structure matrix was concatenated to the
sequence matrix (FIG. 4A). In total, for a sequence of length
L, this results in a binary matrix of size (4+5)×L.

Model description and optimization. The model is com-
posed of one convolution layer, one hidden layer and an
output layer (FIG. 4A). The optimization of the model was
done in the same manner as described above. Briefly, 10
random parameters sets were tested, and the best preforming
one was chosen followed by fine tuning.

TABLE 2

Parameters search for whole-library models. (Left) The parameter
space for each of the two steps of the hyper parameters
search and (Right) the final model's parameters. Unless
noted otherwise, the range specified is of stride 1.

| | Parameter space | | Final parameters | | |
| | | Surrounding | | | |
| Parameter | Initial space | space | MCP | QCP | PCP |
| --- | --- | --- | --- | --- | --- |
| Nodes | 5-40 | ±5 | 25, 25 | 22 | 20 |
| Layers | 1-3 | – | 2 | 1 | 1 |
| Kernel length | 4-10 | ±3 | 5 | 9 | 10 |

TABLE 2-continued

Parameters search for whole-library models. (Left) The parameter
space for each of the two steps of the hyper parameters
search and (Right) the final model's parameters. Unless
noted otherwise, the range specified is of stride 1.

| | Parameter space | | Final parameters | | |
| | | Surrounding | | | |
| Parameter | Initial space | space | MCP | QCP | PCP |
| --- | --- | --- | --- | --- | --- |
| Kernel number | 4-35 | ±5 | 6 | 9 | 6 |
| Epochs | 10, 20 . . . 100 | ±15 (strides of 5) | 25 | 30 | 15 |

In addition to the parameters in Table 2, which are unique to each model, there are additional parameters that are common to all of them: learning rate 0.001, batch size 16, optimizer ADAM, loss function MSE (mean squared error), activation function for the convolution and hidden layers is 'relu'. The output layer consists of one node with the identity activation function.

Evaluation. The prediction performance achieved by the whole-library models are similar to the WT-specific ones, i.e. an average Pearson correlation greater than 0.42 for each of the three proteins (FIG. 3B). The performance as a binary classifier (motivated by the downstream application of generating non-repetitive binding site cassettes) was an average AUC greater than 0.57 (empirical p-values reflecting the frequency of AUC values of random shuffles greater than the ones achieved were smaller than $10^{-3}$). In addition to achieving better average Pearson correlation over the three proteins than the WT-specific models, this whole-library model has the advantage that it can be applied to a binding site of any length, and not just that of the WT. This enables the prediction of binding of all three proteins to the same sequence set.

To showcase the contribution of RNA structure to the whole-library models, whole library models were compared with and without the additional RNA structure information. A slight increase in prediction performance was observed (FIG. 4D) when the structural information was added for all three proteins. To assign statistical significance to this observation, a model was trained on 80% of the data and tested on the remaining 20%. For each partition of the data this train and test was performed with and without the structural context. 100 repetitions of this process were performed, and the improvement evaluated using a paired Wilcoxon rank-sum test. This resulted in a significant improvement in the results when using the structural context (p-value<$10^{-5}$ for each of the three proteins).

Structure binding preference analysis. The structural binding preferences was inspected by altering the binding site structure and predicting its binding intensity by the ML model. Three different structure alterations were made: bulge-, loop- and upper-stem-length altering mutations. To conduct this analysis in a way that is independent from sequence effects all added nucleotides were added as a uniform vector (i.e. [0.25,0.25,0.25,0.25]).

To increase the upper-stem length, n positions (n=1,2) were randomly selected. A base-pair with a structure context of an upper stem (i.e. A-U or C-G) was then inserted to that position. Thus, other structure elements of the binding site were not affected. Shortening of the upper stem was done by randomly deleting base-paired nucleotides. Increasing the length of the loop was done by randomly selecting n positions (n=1,2) and inserting in that position nucleotides with the structure context of a loop. Shortening of the loop was done by randomly deleting n nucleotides from it.

Increasing bulge size was done by adding one nucleotide with the appropriate structure context. Deleting the bulge was done by simply removing the bulge nucleotide. All sequences were examined by RNAfold and showed the desired structure. The padding of these sequences was done in the same way described earlier.

Generation of sequences for experimental validation. To test the predicted binding cassette generated according to the models' predictions, one million synthetic binding sites were created. One million random sequences were generated that are in hamming distance of 3-7 from one of the WT binding sites. Overall, one million out of 1.5 billion options were randomly selected. Because the number of possible variants rises as the length of the sequence, uniform selection of sequences will result in more variants of the long WT (PCP, 25-nt long) and less variants of the short WT (MCP, 19-nt). To overcome this bias, the random selection was divided into three parts; in each part 333,333 sequences from the variants of one WT were randomly selected. The binding intensity of each of the proteins to the set of one million sequences were computed using the whole-library models. Then, to experimentally validate model accuracy, a sample out of the one million was chosen. Ten sequences were selected that are single binders (i.e. bound by a single protein and not by the two others), and ten that are double binders (i.e. bound by two proteins and not by the third). As a reminder, binders are defined as having a binding score greater than 3.5, and non-binders as having a score smaller than 3.5. All are in hamming distance of at least 4 from one another and all were not included in the original experimental library.

Data and Software Availability. The software and code are publicly available: ML code and data via github.com/OrensteinLab/SynRBPbind/; Fasta files are available at NCBI's Sequence Read Archive (SRA) submission #: SUB6905641; A web-tool for cassette design called CARBP is available at: https://roee-amit.technion.ac.il/our-research/software/.

Bacterial strains. *E. coli* BL21-DE3 cells which encode the gene for T7 RNAP downstream from an inducible pLac/Ara promoter was used for all reported experiments. *E. coli* TOP10 (Invitrogen, Life Technologies, Cergy-Pontoise) was used for cloning procedures.

Addgene plasmids. The following plasmids were used: pCR4-24XPP7SL (Addgene plasmid #31864; http://n2t.net/addgene:31864; RRID: Addgene_31864) and pBAC-lacZ (Addgene plasmid #13422; http://n2t.net/addgene:13422; RRID: Addgene_13422).

Construction of the binding sites cassettes plasmids. The cassette sequence containing 5 PP7-wt and 4 Qβ-wt binding sites with randomized spacer sequences was ordered from GenScript, Inc. (Piscataway, NJ), as part of a Puc57 plasmid, flanked by EcoRI and HindIII restriction sites.

(SEQ ID NO: 303)

cctaggcgattatgacgttattctactttgattgt<u>gatgcatgtctaagac</u>

<u>agcatc</u>gcctgctggtcgtgactaaggagtttatatggaaacccttacgag acaatgctaccttaccggtcgggcccacttgtttttacccatg<u>atgcatgt</u>

<u>ctaagacagcatc</u>gcctgctggtcgtgactaaggagtttatatggaaaccc ttagaaacagccgtcgccttgaagccgagaaca<u>atgcatgtctaagacagc</u>

<u>at</u>atggattgcctgtctgttaaggagtttatatggaaaccccttacatcagg

-continued

```
cttcgcagtatgcaacgcttgcgatgcatgtctaagacagcatttcaccgc tttcctaagtaaggagtttatatggaaaccccttagtactaactcgcagatg catgtctaagacagcatcagaaacgtcacgtcctggc. Qβ and PP7 binding sites marked in underline and bold respectively.
``` pBAC-lacZ backbone plasmid was obtained from Addgene (plasmid #13422). Both insert and vector were digested using the above restriction sites and ligated to form BAC-Qβ-5x-PP7-4x.

The Qβ-10x cassette was ordered from Twist Bioscience (San Francisco, CA), flanked by BamHI restriction sites. Insert and pSMART BAC (Lucigen, Middleton, WI) vector were digested with BamHI and ligated to form BAC-Qβ-10x. The binding site sequence (SEQ ID NO: 304)
```
gaattcttacaaaggaactgtaacagtccttctcgtgctgatcgtgacttg gatgtccaagacaccaacgagacaatgctaccttaccgtcggcccacttgt ttttacccatgacatgacgagatactcgcatgtcgcctgctggtcgtgaca tgcatgtctaagacagcatgaaacagccgtcgccttgaagccgagaacatt gcatgtcgaagacagcaaatggattgggtctccaattcctgtctgtttcca tgactaagtcaggaacatcaggatcgcagtatgcaacgcttgcgatgcatt gcaaagcaagcatttcaccgctttcctaagaaggatagtaatgactacctt gtactaactcgcagatcgaactctaagagtcgatcagaaacgtcacgtcct ggcaaccatgtcagggacaggtttggaagaattc. (Qβ binding sites marked as underline),
```

Design and Construction of Fusion-RBP Plasmids. Fusion-RBP plasmids were constructed as previously reported in Katz et al., 2018, "An in Vivo Binding Assay for RNA-Binding Proteins Based on Repression of a Reporter Gene", *ACS Synth Biol* 7:2765-2774, herein incorporated by reference in its entirety. Briefly, RBP sequences lacking a stop codon were amplified via PCR off either Addgene or custom-ordered templates. All RBPs presented (PCP, and QCP) were cloned into the RBP plasmid between restriction sites KpnI and AgeI, immediately upstream of an mCerulean gene lacking a start codon, under the so-called RhlR promoter containing the rhlAB las box (Medina et al., 2003) and induced by N-butyryl-L-homoserine lactone (C4-HSL) (Cayman Chemicals, Ann Arbor, Michigan). The backbone contained either an Ampicillin (Amp) or Kanamycin (Kan) resistance gene depending on experiment. mCerulean gene was replaced by mCherry using restriction cloning between sites XbaI and AgeI.

Sample preparation. BL21-DE3 cells expressing the two plasmid system (single copy plasmid containing the binding sites array, and a multicopy plasmid containing the fluorescent protein fused to an RNA binding protein) were grown overnight in 5 ml Luria Broth (LB), in 37° with appropriate antibiotics (CM, AMP), and in the presence of two inducers—1.6 ul Isopropyl β-D-1-thiogalactopyranoside (IPTG) (final concentration 1 mM), and 2.5 ul C4-HSL (final concentration 6 μM) to induce expression of T7 RNA polymerase and the RBP-FP respectively. Overnight culture was diluted 1:100 into 3 ml solution of BioAssay (BA)-LB (95%-5% v:v) with appropriate antibiotics and induced with 1 μl IPTG (final concentration 1 mM) and 1.5 μl C4-HSL (final concentration 60 μM). For stationary phase tests, cells were diluted into 3 ml Dulbecco's Phosphate-Buffered Saline (PBS) (Biological Industries, Israel) with similar quantities of induction and antibiotics. Culture was shaken for 3 hours in 37° before being applied to a gel slide (3 ml PBS×1, mixed with 0.045 g SeaPlaque low melting Agarose (Lonza, Switzerland), heated for 20 seconds and allowed to cool for 25 minutes). 1.5 μl cell culture was deposited on a gel slide and allowed to settle for an additional 30 minutes before imaging.

Cell lysis and extract analysis. Two strains of BL21-DE3 cells, one expressing both the Qβ-mCherry fusion protein and the Qβ-10x binding sites cassette, and the other expressing only the fusion protein, were grown overnight in 10 ml LB with appropriate antibiotics in 37° C. Following overnight growth cultures were diluted 1/100 into two vials of 500 ml Terrific Broth (TB), with appropriate antibiotics and full induction (150 μl IPTG and 250 μl C4-HSL) and grown in 37° C. to $OD_{600}>10$. Cells were harvested, resuspended in 45 ml of buffer (50 mM Tris-HCl pH 7.0, 100 mM NaCl and 0.02% $NaN_3$), disrupted by four passages through an EmulsiFlex-C3 homogenizer (Avestin Inc., Ottawa, Canada), and centrifuged (13,300 RPM for 30 min) to obtain a soluble extract. Turbidity was measured using a plate reader (Tecan, F200) at $OD_{600}$. Flow cytometry measurements were done using MACSQuant VYB flow cytometer (Miltenyi Biotec, Auburn, CA).

Microscopy. Gel slide was kept at 37° inside an Okolab microscope incubator (Okolab, Italy). A time lapse experiment was carried out by tracking a field of view for 60 minutes on Nikon Eclipse Ti-E epifluorescent microscope (Nikon, Japan) using the Andor iXon Ultra EMCCD camera at 6 frames-per-minute with a 250 msec exposure time per frame to avoid photo-bleaching and sufficient recovery of fluorescence signal. Excitation was performed at 585 [nm] (mCherry) wavelengths by a CooLED (Andover, UK) PE excitation system.

Quantification of the fraction of cells presenting puncta was done by taking 10-15 snapshots of different fields of view (FOV) containing cells. The number of cells showing puncta and the total number of fluorescent cells in the FOV were counted manually.

Image Analysis. The brightest spots (top 10%) in the field of view were tracked over time and space via the imageJ MosaicSuite plugin. A typical field of view usually contained dozens of cells, a portion of which were not fluorescent while others presented distinct bright speckles, localized at the cell poles.

The tracking data, (x,y,t coordinates of the bright spots centroids), together with the raw microscopy images were fed to a custom built Matlab (The Mathworks, Natick, MA) script designed to normalize the relevant spot data. Normalization was carried out as follows: for each bright spot, a 14-pixel wide sub-frame was extracted from the field of view, with the spot at its center. Each pixel in the sub-frame was classified to one of three categories according to its intensity value. The brightest pixels were classified as 'spot region' and would usually appear in a cluster, corresponding to the spot itself. The dimmest pixels were classified as 'dark background', corresponding to an empty region in the field of view. Lastly, values in between were classified as 'cell background'. Classification was done automatically using Otsu's method. From each sub-frame, two values were extracted, the mean of the 'spot region' pixels and the mean of the 'cell background' pixels, corresponding to spot intensity value and cell intensity value. This was repeated for each spot from each frame in the data, resulting in sequences of intensity vs. time for the spot itself and for the cell background.

Signal Analysis. A noise model is a assumed comprised of both additive and exponential components, corresponding to fluorescent proteins (bound or unbound) not relating to the spot itself, and photobleaching. This can be described as follows:

$$y(t)=(S(t)+c(t)) \cdot f(t) \qquad (0.1)$$

$$c(t)=c_0(t) \cdot f(t) \qquad (0.2)$$

where y(t) is the observed spot signal, S(t) is the underlying spot signal which is extracted, c(t) is the observed cell background signal, $c_0(t)$ is the underlying background signal and f(t) is the photobleaching component.

To find S(t), one assumes:

$$c_0(t) \approx c_0 = \text{const} \qquad (0.3)$$

This leads to:

$$\frac{y(t)}{c(t)} = \frac{S(t)+c_0}{c_0} \qquad (0.4)$$

$$S(t) = c_0\left(\frac{y(t)}{c(t)}\right) - c_0 = c_0\left(\frac{y(t)}{c(t)} - 1\right) \qquad (0.5)$$

To get y(t), one filters the measured spot signal with a moving average of span 13, in order to remove high frequency noise effects, and smooth out fluctuations (see section—Identifying burst events). To get c(t), the measured cell background signal is fit to a $3^{rd}$ degree polynomial (fitting to higher degree polynomials did not change the results). This is done to capture the general trend of the signal while completely eliminating fluctuations due to random noise.

Identifying burst events. The total fluorescence is assumed to be comprised of three distinct signal processes: biocondensate fluorescence, background fluorescence and noise. It is further assumed that background fluorescence is slowly changing, as compared with biocondensate fluorescence which depends on the dynamic and frequent insertion and shedding events occurring in the droplet. Finally, noise is considered to be a symmetric, memory-less process. Based on these assumptions, a "signal-burst" event is defined as a change or shift in the level of signal intensity leading to either a higher or lower new sustainable signal intensity level. To identify such shifts in the base-line fluorescence intensity, a moving-average filter of 13 points (i.e. 2 minutes) is used to smooth the data. The effect of such an operation is to bias the fluctuations of the smoothed noisy signal in the immediate vicinity of the bursts towards either a gradual increase or decrease in the signal. Random single fluctuations, which do not settle on a new baseline level are not expected to generate a gradual and continuous increase or decrease over multiple time-points in a smoothed signal. Following this, contiguous segments of gradual increase or decrease are searched for and record only those whose probability for occurrence is 1 in 1000 or less given a Null hypothesis of randomly fluctuating noise.

To translate this probability to a computational threshold, the intensity difference distribution for every trace separately is first computed. This distribution is computed by collecting all the instantaneous differences in signal ($\Delta S(t_i)$ $=S(t_i)-S(t_{i-1})$) and binning them. Given a particular trace the likelihood for observing an instantaneous signal increase event in a time-point ($t_i$) can therefore be computed as follows:

$$P_{inc} = \frac{N(\Delta S(t_i) > 0)}{N_{tot}} \qquad (0.6)$$

where $N(\Delta S(t_i)>0)$ and $N_{tot}$ correspond to the number of increasing instantaneous events and total number of events in a trace respectively. Likewise, the number of decreasing instantaneous events is defined as:

$$p_{dec} = \frac{N(\Delta S(t_i) < 0)}{N_{tot}} \qquad (0.7)$$

This in turn allows one to compute the number of consecutive instantaneous signal increase events (m) to satisfy the 1 in 1000 threshold for a significant signal increase burst event m as follows:

$$p_{inc}^m = \frac{1}{2^{10}} \Rightarrow m\log_2(p_{inc}) = -10 \Rightarrow m = \frac{-10}{\log_2(p_{inc})} \qquad (0.8)$$

The threshold is calculated for each signal separately and is usually in the range of 7-13 time points. An analogous threshold is calculated for decrements in the signal and is typically in the range [m−1, m+1].

To account for the presence of the occasional strong instantaneous noise fluctuations appearing in experimental signals, isolated reversals are allowed in the signal directionality (e.g. an isolated one time point decrease in an otherwise continuous signal increase environment). Furthermore, since the moving average filter itself can induce correlations in the signal, it was determined that the minimum allowed threshold is the moving average window span. This means that any calculated threshold lower than the moving average size is increased to this bare minimum.

Each trace is marked with the number of events whose duration exceeds the threshold and define those as bursts. Segments within the signal that are not classified as either a negative or positive burst event are considered unclassified. Unclassified segments are typically signal elements whose noise profile does not allow us to make a classification into one or the other event-type. For each identified segment the amplitude ($\Delta I$) is recorded, as is the duration ($\Delta t$). Sample trace are marked with the classification positive "burst", negative "burst", and non-classified events in green, red, and blue, respectively. The segment analysis is confined between the first and last significant segments identified in a given signal, since one cannot correctly classify signal sections that extend beyond the observed trace.

Estimating the signal amount per slncRNA-RBP complex. Given the fact that one cannot directly infer the fluorescence intensity associated with a single RNA-RBP complex, the distributions was fitted with a modified Poisson function of the form:

$$p(I) = \frac{\lambda^{\frac{I}{k_0}} e^{-\lambda}}{\left(\frac{I}{k_0}\right)!} \qquad (0.9)$$

where I is the experimental fluorescence amplitude, $\lambda$ is the Poisson parameter (rate), and $k_0$ is a fitting parameter whose value corresponds to the amplitude associated with a single RBP-bound slncRNA molecule within the burst. For each rate it was chosen to fit $k_0$ such that it minimizes the deviation (MSE) from the experimental data.

Numerical simulations of signal types. To check that the analysis is consistent with an underlying random burst signal, three types of base signals were simulated with added noise components. For each simulation type, 1000 signals of 360 time-points were simulated and analyzed using the same data analysis process described in the methods section.

Flat constant signals, gradually ascending signals, and signals containing multiple burst events were simulated. Two noise components were added to all signals, based on the noise model. White Gaussian noise of magnitude 40 [A.U] peak-to-peak amplitude, matching the value estimated from experimental traces, and an exponential component, simulating photobleaching.

The burst-detection algorithm described above was then applied and it was found that for the flat signal positive and negative bursts (green and red respectively) and non-classified events are detected. However, a closer examination of the results reveals that the burst amplitude width is smaller by a factor of ~5-10 as compared with the experimental data bursts, and the total number of events observed (458 positive, 452 negative, and 298 non-classified segments found) is significantly smaller than the experimental data, indicating roughly 1 event per signal, as expected from the base assumption that a rare noise event occurs once in a thousand time points. For the gradually increasing signal with additional noise, a negligible number of negative burst-like events was detected by the algorithm, with a pronounced bias towards positive events (1111 positive, 9 negative and 467 non-classified). The scarcity of events can be explained by the positive bias in the signal which results in a steep increase in the statistical threshold for event identification. Similar simulations with a decreasing signal show a mirror image of amplitude distribution (data not shown).

Finally, a signal designed to mimic the interpretation of the experimental data containing randomly distributed instantaneous bursts, both increasing and decreasing with multiple possible amplitudes was analyzed. The simulated signals resulted in a symmetric amplitude distribution, comprising of non-Gaussian or skewed amplitude distributions. Additionally, the range of amplitudes observed is 2-3× larger as compared with the case for the constant signal, with the non-classified amplitudes presenting a wider distribution. A total of 2298 positive, 1831 negative and 2489 non-classified segments were found.

Estimating statistical significance of burst events in all traces recorded. To compute whether or not the number of burst events identified via the algorithm is statistically significant, a constant base-line intensity amplitude is simulated with overlaid white Gaussian noise. For each numerical trace, 360 times points (corresponding to a ~60 minute experimental trace) were simulated and the total number of "increasing" and "decreasing" burst events was identified in accordance with the algorithm described in detailed above. Here, m=10 (see eqn. 1.8) consecutive increasing or decreasing instantaneous signal difference events was used as the threshold. There were identified 458 and 298 increasing and decreasing burst events respectively in 1000 simulated traces with constant baseline. By comparison, there were found 2298 and 1831 increasing and decreasing burst events respectively in 1000 simulated traces containing bursts, which using Fisher's test yield a p-value of 4e−309 and 2e−310 for the significance of the increasing and decreasing burst findings.

This statistical test was repeated for experimental data, comparing the PP7-4x data against traces measured from cell containing only PP7-mCherry with no expression of the RNA cassettes, using the latter as a baseline akin to the constant signal simulations. There were identified 7 increasing and 6 decreasing burst events in 150 traces gathered from the cells lacking RNA binding sites, while for the PP7-4x data there was identified 112 increasing and decreasing burst events in 255 experimental traces, which using Fisher's test yields a p-value of 2e−13.

Signal Analysis Parameter Selection.

Subframe length. As part of the analysis process, the immediate surroundings of each discovered bright spot are recorded as a sub-frame containing the spot at its center, from this sub-frame the mean spot intensity and mean background intensity are calculated. The selection of the sub-frame length used to calculate the background intensity is an important parameter in the analysis process that might bring about unwanted noise into the resulting statistics. A large sub-frame might include other cells, with possibly different bright spots of themselves, inserting a bias into both the cell background intensity, and spot intensity signals. On the other hand, a small sub-frame might not have a sufficient spot-to-background area ratio, resulting in an underestimated cell background signal.

To select the appropriate sub-frame length the Qβ-10x data was analyzed with sub-frames of different lengths—10, 14, 20, and 30 pixels. The criteria for this selection process are the mean ratio between cell area to spot area; percentage of frames where this ratio is less than one; and the ratio between the spot mean intensity to the cell mean intensity without any filtering or fitting. These criteria are designed to find the length that does not cause an overestimation of cell background against spot or vice versa (as could be the case where more than one bright spot fall inside the sub-frame). From these tests it was learned that lengths of 10 and 14 pixels result in a mean ratio of less than two (i.e. on average the sizes of the bright spot and of its surrounding environment are equal). However, a sub-frame length of 10 pixels results in nearly a fifth of frames where the cell background is less than one and thus potentially underestimated. Finally, the intensity ratios show that the mean ratio does not vary much between the different options, however the spread is more conserved for lengths of 10 and 14 pixels. Following these tests, a sub-frame length of 14 pixels was chosen for the analysis process.

Moving average span. The moving average window span is an important component in the signal analysis process. It is used both as a noise reduction filter, and as a means to bias sharp signal jumps (See Methods). The filter span plays another significant role, as it is the minimal allowed length for a burst duration. Choosing a small value might introduce false positives into the statistics, while a large value would cause many actual burst events to be discarded. To find the optimal span length the number of events found in a simulated flat signal were compared, such a signal should not produce any bursts under noise-less conditions. For this there were simulated 1000 constant signals, 360 time points each, with an added white Gaussian noise and an exponential component and applied the data analysis procedure. An ideal result for this test would be less than one event of each type, i.e. positive and negative bursts, per signal. It was further shown that using intermediate span length values (9-13 time points), has little effect on the qualitative nature of the results.

Following these tests, a span of 13 time points was decided upon. This value results in one event or less of each type per simulated signal, while still allowing us to record the statistical nature of the experimental signals.

To verify that burst events that occur after a non-classified period lasting 2.5 minutes or longer are not biased, a statistical test was performed for randomness where the null hypothesis is that events are in random order. The tests yielded p-values of 0.7 for PP7-4x, 0.03 for Qβ-5x, 0.4 for Qβ-10x, and 0.5 for PP7-24x. Indicating that the burst events do appear at random at the 1% significance level.

Theoretical Model. Liquid-liquid phase separation has been recently modelled by Klosin et al., 2020, "Phase separation provides a mechanism to reduce noise in cells", Science 367:464-468, herein incorporated by reference in its entirety. In this section the Klosin model is expanded to a case where the bacterial cell has initially a dense-nucleoid and dilute phase, and the RNA is transcribed within the nucleoid phase. If the RNA is sufficiently multivalent, a droplet forms within the dilute phase background. the model will describe the rates by which RNA is transcribed, exchanged between the nucleoid and dilute phases, and at which conditions it will form a biocondensate within the dilute phase.

Thermodynamic Model Assumptions. It is assumed a cell contains two phases: a dense nucleoid phase and dilute cytosolic phase. The nucleoid phase fills 75% of the cell volume and the dilute phase occupies mostly the cell pole regions. A synthetic and multivalent long non-coding RNA molecule (slncRNA) containing multiple binding sites for an RNA-binding protein (RBP) is then expressed, as is the RBP as a fusion with an mCherry fluorescent protein. Given these assumptions, one can now write a free energy as follows (an expansion of the Klosin free energy):

$$F = V_n f_n(\phi_n) + V_+ f_+(\phi_+) + V_- f_-(\phi_-) + \Gamma_n A_n + \Gamma_- A_-  \tag{0.10}$$

Where, following Klosin's notations, $V_n$, $V_+$, $V_-$ correspond to the volume of the nucleoid, dilute and droplet phases. Similarly, $\phi_n$, $\phi_+$, and $\phi_-$ correspond to the volume fractions of each phase, and $f_n$, $f_+$, $f_-$ correspond to the free energy density of each phase. $\Gamma_n$ and $\Gamma_-$ are the nucleoid and droplet phase surface tensions with corresponding area $A_n$ and $A_-$. In addition, it is noted that the total slncRNA-RBP complex present in the system at steady state is:

$$N_T = N_n + N_+ N_-  \tag{0.11}$$

Where $N_n$, $N_+$, and $N_-$ correspond to the number of molecular complexes in the nucleoid, dilute, and droplet phases respectively.

Kinetic Model. In the following, the kinetic model is derived describing such a system according to the schematic presented in FIG. 4A. Here it is assumed that a single promoter located within the nucleoid phase encodes the slncRNA, which immediately leads to the formation of the slncRNA-RBP complex. Molecular complexes then diffuse around the nucleoid phase and are transported out of the nucleoid phase into the dilute cytosolic phase at a rate proportional to their diffusion coefficient times their volume fraction defined according to the Klosin model as follows:

$$k_n^{out} = \frac{6 D_n V_n^3}{\upsilon}  \tag{0.12}$$

Where $\upsilon$ corresponds to the unit volume, i.e. the volume of a single molecule, and $D_n$ corresponds to the diffusion constant within the nucleoid phase, which is assumed to be different than the one in the cytosolic or dilute phase. Note, this is due to the Stokes-Einstein equation which to a first approximation defines the diffusion coefficient as:

$$D = \frac{k_B T}{6 \pi \eta r}  \tag{0.13}$$

Where $\eta$, the dynamic viscosity, is expected to vary for the dilute and nucleoid phases.

Given the above definitions, the goal of the model analyzed below is to estimate the rate of increasing signal bursts, which corresponds to $$k_+^{out}$$

in the schematic of FIG. 4A.

Evaluating the model. To evaluate the model, it is assumed that the all three liquid phases are permeable and allow exchange of slncRNA-RBP molecular complexes. This implies that each phase can be modeled as a state within a Master equation context, with rates controlling the transition between each state. Given this assumption, one can now write a Master equation model for the kinetics of this multiphasic system in accordance with the schematic shown in FIG. 4A.

$$\begin{pmatrix} \partial_t p_n(N) \\ \partial_t p_+(N) \\ \partial_t p_-(N) \end{pmatrix} =  \tag{0.14}$$

$$\begin{pmatrix} -(N\gamma_n + k_t + k_n^{out})p_n(N) + k_n^{in} p_+(N) + \\ k_t p_n(N-1) + (N+1)\gamma_n P_n(N+1) \\ -(N\gamma_+ + k_n^{in} + k_+^{out})p_+(N) + k_n^{out} P_n(N) + \\ k_+^{in} p_-(N) + (N+1)\gamma_+ p_+(N+1) \\ -(N\gamma_- + k_+^{in})p_-(N) + k_+^{out} p_+(N) + (N+1)\gamma_- p_-(N+1) \end{pmatrix}$$

Which can be written in vector form as follows:

$$\frac{d}{dt}\vec{p}(N) = \left[ \hat{K} - \hat{R} - N\hat{\Gamma} \right]\vec{p}(N) + \hat{R}\vec{p}(N-1) + (N+1)\hat{\Gamma}\vec{p}(N+1)  \tag{0.15}$$

$$\text{Where, } \hat{K} = \begin{pmatrix} -k_n^{out} & k_n^{in} & 0 \\ k_n^{out} & -(k_n^{in} + k_+^{out}) & k_+^{in} \\ 0 & k_+^{out} & -k_+^{in} \end{pmatrix},  \tag{0.16}$$

$$\hat{R} = \begin{pmatrix} k_t & 0 & 0 \\ 0 & 0 & 0 \\ 0 & 0 & 0 \end{pmatrix},$$

$$\hat{\Gamma} = \begin{pmatrix} \gamma_n & 0 & 0 \\ 0 & \gamma_+ & 0 \\ 0 & 0 & \gamma_- \end{pmatrix}$$

In order to determine $$k_+^{out},$$

the zeroth moment of the master equation is evaluated as follows:

$$\overrightarrow{M_0} = \begin{pmatrix} M_0^n \\ M_0^+ \\ M_0^- \end{pmatrix} = \begin{pmatrix} \sum_{N=1}^{\infty} p_n(N) \\ \sum_{N=1}^{\infty} p_+(N) \\ \sum_{N=1}^{\infty} p_-(N) \end{pmatrix} \qquad (0.17)$$

with the following condition:

$$\vec{u} \cdot \overrightarrow{M_0} = 1 \qquad (0.18)$$

ensuring that the total probability for the kinetic system to be in one of the states adds up to 1.

Next, the zeroth moment is evaluated in steady state, which allows the use of the following assumptions:

$$k^t = 0 \qquad (0.19)$$

$$\gamma_n = \gamma_+ = \gamma_- = 0$$

$$k_n^{in} = k_+^{out}$$

Where the last equation implies that the rate of exit from the dilute phase is the same, regardless of direction.

Plugging these to the following equation:

$$0 = [\hat{K} - N\hat{T}]\overrightarrow{M_0} + [\hat{R} + N\hat{T}]\overrightarrow{M_0} \qquad (0.20)$$

$$\hat{K} \cdot \overrightarrow{M_0} = 0 \qquad (0.21)$$

This then allows writing the following set of equations:

$$-k_n^{out}M_0^n + k_n^{in}M_0^+ = 0 \qquad (0.22)$$

$$k_n^{out}M_0^n - (k_n^{in} + k_+^{out})M_0^+ + k_+^{in}M_0^- = 0$$

$$k_+^{out}M_0^+ - k_+^{in}M_0^- = 0$$

$$M_0^n + M_0^+ + M_0^- = 1$$

which allows solving for $$k_+^{out}$$

as follows:

$$M_0^+ = \frac{k_+^{in}}{k_+^{out}}M_0^- = \frac{k_n^{out}}{k_n^{in}}M_0^n \qquad (0.23)$$

Plugging in the third assumption:

$$k_+^{in} = k_n^{out}\frac{M_0^n}{M_0^-} \qquad (0.24)$$

$$k_+^{out} = k_n^{out}\left(\frac{M_0^n}{M_0^+}\right) = \frac{6D_n V_n^{1/3}}{\upsilon}\phi_n\left(\frac{M_0^n}{M_0^+}\right) \qquad (0.25)$$

Showing that the burst of signal increases should occur at a rate that is proportional to the complex's volume fraction within the nucleoid phase.

Implication of bi-phasic cellular model to transcription. Given the bi-phasic model, the Fano factor should be computed for a general mRNA that does not necessarily phase separate in the dilute cytosol phase to a third droplet phase. In this case equation 2.7 is simplified as follows:

$$\hat{K} = \begin{pmatrix} -k_n^{out} & k_n^{in} \\ k_n^{out} & -k_n^{in} \end{pmatrix}, \hat{R} = \begin{pmatrix} k_t & 0 \\ 0 & 0 \end{pmatrix}, \hat{\Gamma} = \begin{pmatrix} \gamma_n & 0 \\ 0 & \gamma_+ \end{pmatrix} \qquad (0.26)$$

Here, it is assumed that each phase is characterized by a different degradation rate. Degradation is a process by which an RNAase is assumed to diffuse around until it finds its target. If one accepts the assumption that each phase is characterized by a different diffusion coefficient, then the rate of degradation should also vary in accordance. However, for the sake of simplicity, there is assumed a constant degradation rate across the cell, and thus one gets:

$$\hat{K} = \begin{pmatrix} -k_n^{out} & k_n^{in} \\ k_n^{out} & -k_n^{in} \end{pmatrix}, \hat{R} = \begin{pmatrix} k_t & 0 \\ 0 & 0 \end{pmatrix}, \hat{\Gamma} = \begin{pmatrix} \gamma & 0 \\ 0 & \gamma \end{pmatrix} \qquad (0.27)$$

Evaluating the zeroth moment. In this case, the zeroth moment is defined as follows:

$$\overrightarrow{M_0} = \begin{pmatrix} M_0^n \\ M_0^+ \end{pmatrix} \equiv \begin{pmatrix} \sum_{N=1}^{\infty} p_n(N) \\ \sum_{N=1}^{\infty} p_+(N) \end{pmatrix} \qquad (0.28)$$

leading to the following equations $$-k_n^{out}M_0^n + k_n^{in}M_0^+ = 0 \qquad (0.29)$$

$$M_0^n + M_0^+ = 1$$

which allows us to solve for the different components:

$$M_0^+ = \frac{k_n^{out}}{k_n^{out} + k_n^{in}} \qquad (0.30)$$

$$M_0^n = \frac{k_n^{in}}{k_n^{out} + k_n^{in}}$$

Evaluating the first moment. The first moment is defined as follows:

$$\overrightarrow{M_1} = \begin{pmatrix} M_1^n \\ M_1^+ \end{pmatrix} \equiv \begin{pmatrix} \sum\limits_{N=1}^{\infty} N p_n(N) \\ \sum\limits_{N=1}^{\infty} N p_+(N) \end{pmatrix} \tag{0.31}$$

from which one can calculate the mean number of molecules per cell as follows:

$$\langle N \rangle = \vec{u} \cdot \overrightarrow{M_1} = M_1^n + M_1^+ \tag{0.32}$$

Next, the Master equation is evaluated for the first moment in steady state as follows:

$$0 = (\hat{K} - \hat{\Gamma} + \hat{R})\overrightarrow{M_1} + \hat{R}\overrightarrow{M_0} \tag{0.33}$$

To obtain an expression for the mean, one multiplies equation 20 by the unitary vector to obtain:

$$k = \frac{k_t k_n^{in}}{k_n^{out} + k_n^{in}} = \vec{u} \cdot \hat{\Gamma} \cdot \overrightarrow{M_1} = \gamma \langle N \rangle \tag{0.34}$$

Evaluating the second moment and the Fano factor. The second moment is defined as follows:

$$\overrightarrow{M_2} = \begin{pmatrix} M_2^n \\ M_2^+ \end{pmatrix} \equiv \begin{pmatrix} \sum\limits_{N=1}^{\infty} N^2 p_n(N) \\ \sum\limits_{N=1}^{\infty} N^2 p_+(N) \end{pmatrix} \tag{0.35}$$

$$\vec{u} \cdot \overrightarrow{M_2} = M_2^n + M_2^+ = \langle N^2 \rangle \tag{0.36}$$

Using Sanchez et al., 2011, "Effect of Promoter Architecture on the Cell-to-Cell Variability in Gene Expression", *PLoS Computational Biology* 7:e1001100, herein incorporated by reference in its entirety, in steady state one gets the following matrix equation:

$$0 = 2\vec{u} \cdot \hat{R} \cdot \overrightarrow{M_1} + \vec{u} \cdot \hat{R} \cdot \overrightarrow{M_0} - 2\vec{u} \cdot \hat{\Gamma} \cdot \overrightarrow{M_2} + \vec{u} \cdot \hat{\Gamma} \cdot \underline{M_1} \tag{0.37}$$

which reduces to:

$$\vec{u} \cdot \hat{\Gamma} \cdot \overrightarrow{M_2} = \vec{u} \cdot \hat{R} \cdot \overrightarrow{M_1} + k \tag{0.38}$$

$$\langle N^2 \rangle = \frac{\vec{u} \cdot \hat{R} \cdot \overrightarrow{M_1}}{\gamma} + \langle N \rangle \tag{0.39}$$

This then allows one to define a Fano factor as follows:

$$F_n = \frac{\langle N^2 \rangle - \langle N \rangle^2}{\langle N \rangle} = 1 + \frac{1}{\langle N \rangle}\left( \frac{\vec{u} \cdot \hat{R} \cdot \overrightarrow{M_1}}{\gamma} - \langle N \rangle^2 \right) \tag{0.40}$$

which after further evaluation reduces to (see also Sanchez et al.—eq. 19):

$$F_n = 1 + \langle N \rangle \left( \frac{k_n^{out}}{k_n^{in}} \right)\left( \frac{\gamma}{\gamma + k_n^{out} + k_n^{in}} \right) = 1 + \left( \frac{k_t k_n^{out}}{\gamma + k_n^{out} + k_n^{in}} \right) \tag{0.41}$$

Which is a signature of a super-Poisson distribution as was observed experimentally in bacteria. Therefore, even if one assumes nothing additional about the standard biological dogma, having two phases which exchange molecules between them is sufficient for generating the deviation from Poisson behavior that was previously attributed to transcriptional bursting. As a result, if one accepts the experimental evidence for the existence of these two phases, the super-Poisson distributions of mRNA that was previously observed is an immediate consequence of this physical state.

Example 1: Induction-Based Sort-Seq (iSort-Seq)

It was recently shown that placing a hairpin in the ribosomal initiation region of bacteria can lead to a ~×10-100 fold repression effect when bound to an RNA-binding protein (RBP). The magnitude of the effect allowed adaptation of this in vivo binding assay to a high-throughput OL experiment. 10,000 mutated versions of the single WT binding sites of PCP, MCP and QCP were designed, and positioned at two positions within the ribosomal initiation region (FIG. 1A top). The library consists of three sub-libraries within the original library: binding sites that mostly resemble either the MS2-wt site, the PP7-wt site, or the Qβ-wt site (FIG. 1A bottom and FIG. 1E). Semi-random mutations, both structure-altering and structure-preserving, as well as deliberate mutations at positions which previous studies have shown to be crucial for binding were introduced. Additionally, there was incorporated into the library several dozens of control variants. Previously confirmed variants were used as positive and negative controls as follows: positive controls are binding sites that exhibited a strong fold-repression response, and negative control variants are either random sequences or hairpins which did not exhibit a fold-repression response.

Each of the designed 10 k single binding-site variants was incorporated downstream to an mCherry start codon (FIG. 1b) at each of the two positions (spacers δ=C or δ=GC) to ensure high basal expression and enable detection of a down-regulatory response, resulting in 20 k different OL variants. Each variant was ordered with five different barcodes, resulting in a total of 100 k different OL sequences.

The second component of the system included a fusion of one of the three phage CPs to green fluorescent protein (GFP) (FIG. 1B) under the control of an inducible promoter. Thus, there were created three libraries in *E. coli* cells; each with a different RBP but the same 100k binding site variants. In order to characterize the dose response of the variants, each library was first separated to six exponentially expanding cultures grown in the presence of one of six inducer concentration for RBP-GFP fusion induction. If the RBP was able to bind a particular variant, a strong fold-repression effect ensued, resulting in a reduced mCherry expression profile (FIG. 1C). Each inducer-concentration culture was sorted into eight predefined fluorescence bins, which resulted in a 6×8 fluorescence matrix for each variant, corresponding to its dose-response behavior. This adaptation of Sort-Seq is called "induction Sort-Seq" (iSort-seq—for details see Methods). As an example, presented is a high-affinity, down-regulatory dose-response for a positive variant (FIG. 1D—bottom V1), and a no-affinity variant exhibiting no apparent regulatory effect as a function of induction (FIG. 1D—bottom V2).

Example 2: Calculating Binding Scores

Preliminary analysis of the sequencing data was conducted to generate mCherry levels per RBP and inducer concentration for each variant (FIG. 2E and Methods). Variants for which too little reads were acquired were eliminated (see Methods). To ascertain the validity of the assay, the behavior of the control variants was first characterized (FIG. 2A). A linear-like down-regulatory effect as a function of RBP induction is observed for the positive control variants (green), while no response in mCherry levels is observed for the negative controls (red). Additionally, the spread in mCherry at high induction levels is significantly smaller for the positive control than that of the negative control variants.

Next, to sort the variants in accordance with their likelihood of binding the RBP (i.e. similarity of their dose-response to the positive control's), the following computation was carried out. First, all variants were characterized by calculating a vector composed of three components: the slope of a linear regression, its goodness of fit (R2), and standard deviation of the fluorescence value at the three highest induction bins (FIG. 2B-middle). Next, two multivariate Gaussian distributions were computed using the empirical 3-component vectors that were extracted for the positive and negative controls and for the given RBP, to yield a probability distribution function (pdf) for both the responsive and non-responsive variants, respectively (FIG. 2B—right). The two populations are relatively well-separated from one another, presenting two distinct clusters with minor overlap. Finally, the "Responsiveness score" for each variant (Rscore—see Methods) was defined as the logarithm of the ratio of the probabilities computed by the responsive pdf to the non-responsive pdf. This score was computed for each unique barcode, and the final result for a sequence variant was averaged over up to five vectors, one for every variant barcode that passes the read-number and basal-level thresholds (FIG. 2E and Methods).

Figures 2F, 2G:
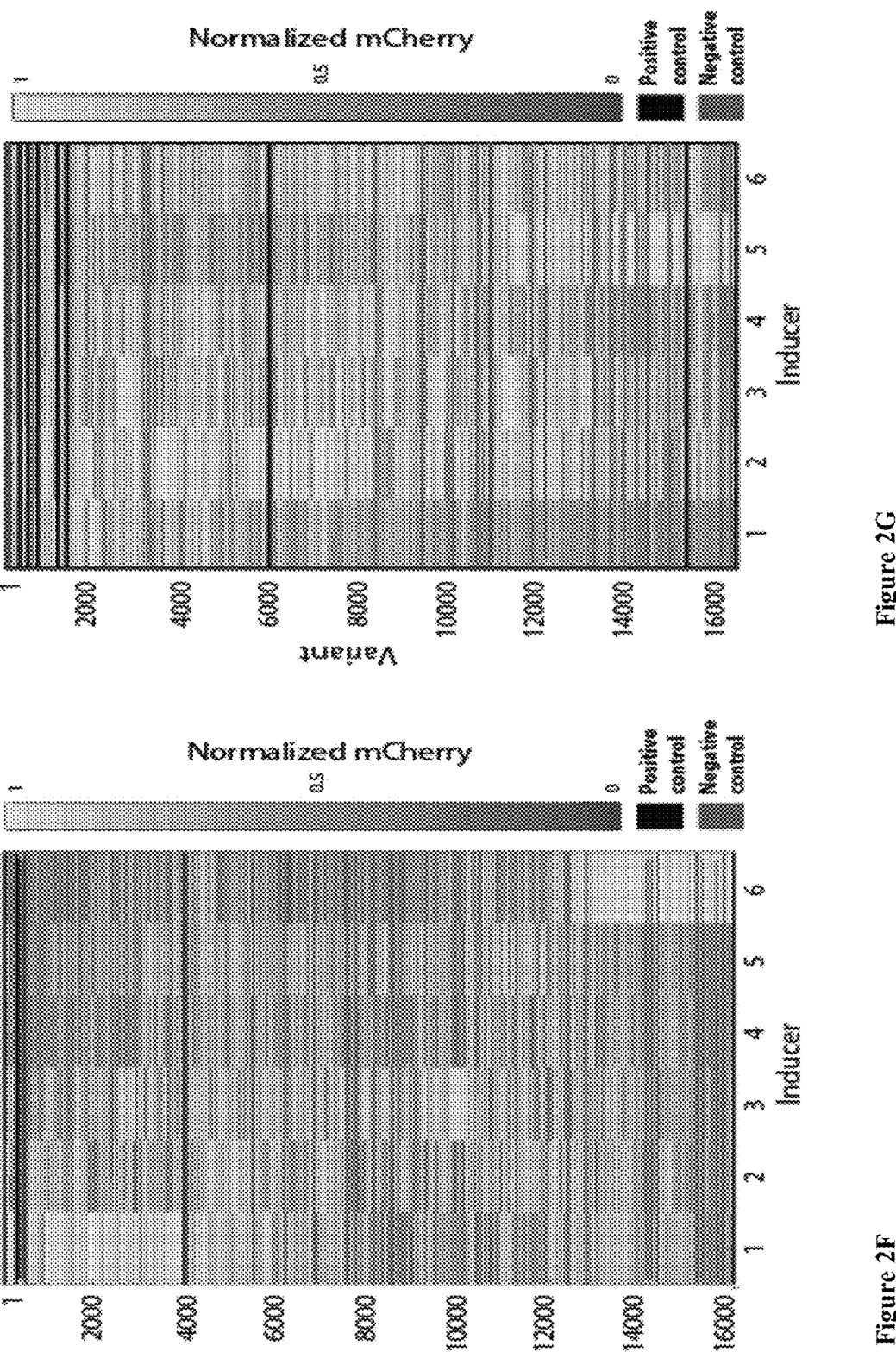

In FIG. 2C, on the left, there is plotted the expression heatmap of the ~18 k variants with PCP sorted (top to bottom) by decreasing Rscore (FIG. 2F-G for MCP and QCP respectively). The plot shows that 5470 variants exhibit an apparent down-regulatory response, defined as log(Rscore) >0, corresponding to having a larger probability to belonging to the positive control distribution as compared with the negative. By comparison (FIG. 2F-G), MCP and QCP yielded 2604 and 7306 such variants, respectively. This indicates that while QCP may be the most promiscuous RBP in the library (i.e. tolerates a more varied set of binding sites), MCP is likely to be the most limited in terms of binding specificity. A closer observation of the top of the list (top 2000, FIG. 2C—right) indicates that for a high Rscore, a rapid reduction in fluorescence is detected in the second bin, which indicates that these variants also seem to exhibit the strongest binding affinity. Sorted Rscore values for the top 100 variants for each RBP as well as the $\Delta\Delta G$ values derived from those scores (FIG. 2F-G and Methods) are available in Table 3. Next, the Rscore obtained for all three RBPs, was plotted for each variant (FIG. 2D). The plot is overlayed with colored dots corresponding to the variants with Rscore>3.5 in each list, corresponding to the most specific variants. The plots reveal very little overlap between the subsets of variants that are highly responsive to the different RBPs, indicating that the vast majority of these highly-responsive binding sites are orthogonal (i.e. respond to only one RBP), which was expected for PCP & MCP and PCP & QCP, but not necessarily for MCP & QCP whose WT sites are not mutually orthogonal.

TABLE 3

Top 100 variant motifs for each RBP

| Sequence (QCP) | SEQ ID NO: | R.score | Sequence (MCP) | SEQ ID NO: | R.score | Sequence (PCP) | SEQ ID NO: | R.score |
|---|---|---|---|---|---|---|---|---|
| auuuacuucuaagagagaaau | 3 | 29.373 | acgcaugaggaacaccaau | 103 | 46.739 | uaaagacguuauaaggaacgcuuua | 203 | 17.806 |
| aaucgagaaaauaugguuuccgauu | 4 | 28.698 | acaugagcaucagccaugg | 104 | 42.737 | uuucgacauuauauggaaugcgaaa | 204 | 17.649 |
| gaauaaggauuaccuauuc | 5 | 28.460 | acauaaggauuaccuaugu | 105 | 40.285 | ggaguuuauauggaaaccc | 205 | 17.310 |
| uaagacaguauuaccugcuua | 6 | 26.215 | gcaugagaaccaucccaugu | 106 | 37.642 | uaucgagaaauauuggguuuccgaua | 206 | 16.384 |
| uaaggacuuuaauauguaaagccuua | 7 | 25.254 | ugaagacgauuacgcuuca | 107 | 37.410 | aaucgaguauaauauaccgauu | 207 | 16.344 |
| acauaaaggauuaccuaugu | 8 | 25.102 | acgugaggaucaccaccgg | 108 | 36.137 | uuuggacuuuauauggaaagccaaa | 208 | 16.093 |
| ccguaauaauuauauacgg | 9 | 24.141 | acaugaggauuaccuaugu | 109 | 36.014 | auaccacuuauaauggaaagggguau | 209 | 16.034 |
| auacaguucuaagaacguau | 10 | 23.673 | acgugaggaucaccacgc | 110 | 35.828 | auagcacaauaauauauggauuggcuau | 210 | 15.983 |
| aaugcacaugcuaacaugcauu | 11 | 22.598 | acgagacgaucacgcucgu | 111 | 35.644 | cagagauuucauaugggaaacucug | 211 | 15.667 |
| aaugcacauuauaugaauggcauu | 12 | 21.799 | aguugaccauuaggcaacu | 112 | 35.551 | uauggagauuauacgcaauccaua | 212 | 15.648 |
| uacagauuucauuaugggaaacugua | 13 | 21.642 | acgugaggaucaccacgu | 113 | 35.172 | uuuccacuuuauauggaaagggaaa | 213 | 15.636 |
| uaaggaguuuuauguaaacccuua | 14 | 20.682 | uaaggaauuugauccuua | 114 | 32.034 | aauggacaaaaauauggguuugccaau | 214 | 15.525 |
| uaaugaguuuacaucgaaaccauua | 15 | 20.057 | acacgaggaucaccgguc | 115 | 31.706 | aaucgacaauauuaugggauucgauu | 215 | 15.524 |
| uaaggauuucgauuggaaaccuua | 16 | 19.770 | acuuaaggaucaccuaagu | 116 | 31.523 | caagagaguauauugggacacucug | 216 | 15.454 |
| aaacaacuccagaguguuu | 17 | 19.555 | ggaugaggaucaccaccu | 117 | 31.327 | uaagggaguuuauauggaaccccuua | 217 | 15.300 |
| uaaccacaauaauauggauuggguua | 18 | 19.401 | cgaugaggaucaccaucu | 118 | 31.114 | auuccaguuuauauggaaaacggaau | 218 | 15.253 |
| aaggauaaugacuaccuu | 19 | 19.294 | acaacacgauuacgguugu | 119 | 31.037 | uuuccagaauauaugggauuccgaaa | 219 | 14.976 |
| acauacgaauuaucuaugu | 20 | 19.136 | agaacacgauuacgguucu | 120 | 30.794 | uaaccacuuuauauggaaagggua | 220 | 14.917 |
| uaucgagauuauauaugggaauccgaua | 21 | 18.515 | agaugaggaucaccaucu | 121 | 30.279 | aaacgacaauauuauggguuucgguuu | 221 | 14.781 |
| uaaggcaauuauuaccgaauuccuua | 22 | 18.426 | acuacaggacuaccguagu | 122 | 30.091 | uauaggaguuuauauggaaacccuaua | 222 | 14.518 |
| acaugacgauuaccgcaugu | 23 | 18.354 | acauaaggauuaccaugu | 123 | 29.324 | uaaccagaaaaauauggguuucgguua | 223 | 14.404 |
| aaaguuguuuaugguggaaacacuuu | 24 | 17.995 | agaagaccauuaggcuucu | 124 | 29.125 | acaugagcgaauaugaucgccaugu | 224 | 14.332 |
| auccaugucaaagacaggau | 25 | 17.990 | gcuugaggaucaccaagu | 125 | 29.070 | cuaggaguuuauaccgaaacccuag | 225 | 14.321 |
| uaaggaguuucacaguaaacccuua | 26 | 17.810 | agaucaccauuagggaucu | 126 | 28.927 | uaggaauuguauauggacaauccua | 226 | 14.252 |

TABLE 3-continued

Top 100 variant motifs for each RBP

| Sequence (QCP) | SEQ ID NO: | R. score | Sequence (MCP) | SEQ ID NO: | R. score | Sequence (PCP) | SEQ ID NO: | R. score |
|---|---|---|---|---|---|---|---|---|
| aguuauugcuaagcaaaacu | 27 | 17.538 | aguugagcauuagccaacu | 127 | 28.790 | uaauaaacucauaugggaguaauua | 227 | 14.193 |
| auacgagaauauaugggauuccguau | 28 | 17.462 | agaugaggaucacccaucg | 128 | 28.690 | aaaggagauuauaugaaauccccuuu | 228 | 14.051 |
| uaagggguuuuguucgaaacccuua | 29 | 17.248 | agaugagaaauaauccaucu | 129 | 28.297 | caaugagcguauauggacgccaug | 229 | 14.031 |
| augucaaaugcuuaaacauugacau | 30 | 17.234 | aauggagaauauauggauucccauu | 130 | 27.493 | aaggaguuuauaugaaacccuu | 230 | 13.935 |
| uaagcacauaauaugguauggcuua | 31 | 17.102 | acacgaggaucacccgugu | 131 | 26.842 | ugaguaauucauaugggaauaucuca | 231 | 13.924 |
| uaaggcguuuggcucuaaacccuua | 32 | 17.006 | agaugagcaauagccaucu | 132 | 26.593 | caaugaguucauuaggaaccauug | 232 | 13.705 |
| uugggaguccaagacaccaa | 33 | 16.885 | agaugaggacuacccaucu | 133 | 26.570 | auuccgagauuauauggaauccgaau | 233 | 13.677 |
| auacauugauaaucaaguau | 34 | 16.709 | acaugaggauuaccaugu | 134 | 26.538 | uaaugagucgauaugcgaccauua | 234 | 13.644 |
| aaaugacaaaauauaugggguuugccauu | 35 | 16.669 | agaagagcauuagccuucu | 135 | 26.433 | caguaaguucauauggaacuacug | 235 | 13.638 |
| uaagcacaguaucaggacuggcuua | 36 | 16.503 | augaggaucacccaguua | 136 | 25.918 | aaucgagaaauaaugguuuccgauu | 236 | 13.587 |
| uaaggagguagcccuua | 37 | 16.325 | aacaugaggaucacccaug | 137 | 25.778 | uaugcaguauauaugggaucgcaua | 237 | 13.296 |
| acaucgagauacucgcaugu | 38 | 16.323 | acaugaggauuaccaugu | 138 | 25.441 | uacgagucaauauauggugaccgua | 238 | 13.198 |
| uaaggaguuuuugacaaacccuua | 39 | 16.103 | uaaggaguuucguguuaaacccuua | 139 | 24.866 | aaucgacauuauaugggaaugcgauu | 239 | 13.150 |
| uaagguguuucuaccaaacccuua | 40 | 16.026 | acauguaaggauuuaccuacaugu | 140 | 24.658 | aauggcacuuuauaugggaaaggcauu | 240 | 13.083 |
| uaagguguuuaaggguuaaacccuua | 41 | 16.022 | acaugaggaucacccaugu | 141 | 24.415 | uaaccagaauaauaugggaucgguua | 241 | 13.037 |
| uacagaacuuaauaugggaagucgua | 42 | 15.861 | acauauaucuaagauaaugu | 142 | 23.787 | auugcacauuauaugggaauggcaau | 242 | 13.009 |
| gcuauaaggauugccauagc | 43 | 15.788 | auacgagaauauaugggauuccguau | 143 | 23.705 | uuugcacuuuauaugggaaaggcaaa | 243 | 12.986 |
| auacaugcuaacacaguau | 44 | 15.724 | aguugagcaguagccaacu | 144 | 23.652 | uacgagcuuauaugggaagcucgua | 244 | 12.955 |
| auguauguccaagacaacau | 45 | 15.653 | uaaagcgccuuauaugaaggccuuua | 145 | 23.605 | auuccagaauuauaugggaaucggaau | 245 | 12.937 |
| uugcaugugaagacagcaa | 46 | 15.627 | acgugagcaucagccaugu | 146 | 23.278 | uuugcaguauauaugggauuacgcaaa | 246 | 12.851 |
| uaaaaauuuuaucagcaaauuuua | 47 | 15.508 | auacgaggaauacccguau | 147 | 23.235 | aaacgacauuaauaugguaugcguuu | 247 | 12.845 |
| auacgagauuauauggaauccguau | 48 | 15.401 | acauguaggauuaccacaugu | 148 | 23.140 | uaacgacaacauaauaugggauugcguua | 248 | 12.815 |
| aguacacgauuacgcuacu | 49 | 15.081 | acuugaccauuaggcaagu | 149 | 22.463 | gaaguaguaauauggacaccuuc | 249 | 12.771 |
| aaaggucuuuaugugugaagcccuuu | 50 | 14.915 | aagugaggaauacccacauu | 150 | 21.837 | uaaggaguuuauaugggaaacccuua | 250 | 12.752 |

TABLE 3-continued

Top 100 variant motifs for each RBP

| Sequence (QCP) | SEQ ID NO: | R.score | Sequence (MCP) | SEQ ID NO: | R.score | Sequence (PCP) | SEQ ID NO: | R.score |
|---|---|---|---|---|---|---|---|---|
| gaagaauugauauggcaaaucuuc | 51 | 14.901 | uaaugaggaauuaccauua | 151 | 21.805 | uaaggaguuuguauguaaacccuua | 251 | 12.739 |
| uaaggguguuuuaagaaacccuua | 52 | 14.758 | acuacaggauuacgguagu | 152 | 21.713 | uaaggaguuuauauggaaacccuua | 252 | 12.731 |
| uguacacgauuacgguaca | 53 | 14.691 | uaaggaguuauuaugguaaacccuua | 153 | 21.654 | aaaccacaauauauggauuggggguu | 253 | 12.618 |
| aacgaugcuaagacacguu | 54 | 14.673 | augcacaugaggauuaacccaugug | 154 | 21.650 | uaagcacauuauaaggaauggcuua | 254 | 12.609 |
| uaucgacaaaauauggguuugcgaua | 55 | 14.671 | augcgaggauuacccgcau | 155 | 21.648 | aaacgagauuauauggaauccguuu | 255 | 12.501 |
| acuacaccauuaggguagu | 56 | 14.580 | acacgaggaucacccgugg | 156 | 21.321 | uaacaaguauauaaaggauuacuguua | 256 | 12.499 |
| auugcacuuauauauggaaggcaau | 57 | 14.580 | agcaugaggauuaacccaagcu | 157 | 21.259 | uaagaaacuuauauggaaguucuua | 257 | 12.465 |
| auagcaugcuaagacagcuau | 58 | 14.292 | gcacgaggaucacccgugu | 158 | 21.055 | uuucgagaaaauauggguuuccgaaa | 258 | 12.453 |
| gugaauaucuaagauaucac | 59 | 14.237 | acuugaggaucaccaagu | 159 | 20.973 | gagguaguuuuauauggaaacaccuc | 259 | 12.398 |
| guuuacuucuaagagaaac | 60 | 14.231 | agaacaccauuagggguucu | 160 | 20.456 | auacgacuuuauauggaaagcguau | 260 | 12.339 |
| acauauguauugauacaugu | 61 | 14.222 | caauaaggauuaaccuauug | 161 | 20.372 | uuuccagauuauauauggaaucggaaa | 261 | 12.304 |
| uaagcacaauauauggauugcguua | 62 | 14.175 | uaaggaguuucaggacaaaacccuua | 162 | 20.366 | uaauugaaguuauauggaaacucauua | 262 | 12.285 |
| acaugaagaacauuaauucucaugu | 63 | 14.012 | aacaugaggauuaacccaugu | 163 | 20.359 | uaucgagaauauauggaauucgcaua | 263 | 12.284 |
| uagccaagaagagucugcua | 64 | 14.011 | ugaacacgauuacgguca | 164 | 20.306 | aauggagaaauauggguuucccauu | 264 | 12.269 |
| augcauguacaaagacagcau | 65 | 13.936 | uaagaaacuuauauggaaguucuua | 165 | 20.129 | uaucgacuuuauauggaaagcgaua | 265 | 12.186 |
| augcauugcaaagcaagcau | 66 | 13.911 | agaagaggaauuaccccucu | 166 | 20.085 | aaucagaauauauggaauuccgauu | 266 | 12.182 |
| uaaggaguuuuguuguaaacccuua | 67 | 13.861 | aguguaggacuaccaccacu | 167 | 20.078 | aaucgaguuuauauggaaaccgauu | 267 | 12.161 |
| uaaggaguuuaaguuuaaacccuua | 68 | 13.836 | acuggaggaucaccccccagu | 168 | 19.906 | augcacauuauauggauugcauu | 268 | 12.151 |
| uacggaguccauauggggacccgua | 69 | 13.765 | aaaccagaaauauuauauggguuucggguuu | 169 | 19.900 | aauccacuuuauauggaaaggggauu | 269 | 12.141 |
| uaaggaguuuauggaaacccuua | 70 | 13.751 | augucagaugauguuaaacaucgacau | 170 | 19.872 | uaagcacuauauauggauuaggcuua | 270 | 12.124 |
| aaaacaugcuagagacaguuu | 71 | 13.741 | acguaagaauuauucuacgu | 171 | 19.791 | auucgacagauauauggguaucgcauu | 271 | 12.121 |
| uaagcaaaguacaucuacuuugcuua | 72 | 13.674 | agaacacgcauuagcguucu | 172 | 19.776 | uaaccagguauaugcaaccggguua | 272 | 12.081 |
| aaugcacaauauauaggauuggcauu | 73 | 13.662 | acgugaggaucaccgcgu | 173 | 19.707 | gcaauagcuauauggagacauugc | 273 | 12.075 |
| agaugauaauuguacaucu | 74 | 13.613 | acaugaggaucacccaugc | 174 | 19.543 | uaucgacaauauauggaguugcgaua | 274 | 12.064 |
| aaaccagaauauauaugggauucgguuu | 75 | 13.539 | guauagaggaucaccccaugc | 175 | 19.495 | caaggaguuuauauguaaacccuug | 275 | 12.032 |

TABLE 3-continued

Top 100 variant motifs for each RBP

| Sequence (QCP) | SEQ ID NO: | R.score | Sequence (MCP) | SEQ ID NO: | R.score | Sequence (PCP) | SEQ ID NO: | R.score |
|---|---|---|---|---|---|---|---|---|
| uaaggauuuauaauggaaccuua | 76 | 13.504 | augacaaguuaacugucau | 176 | 19.204 | uuucgacaauauauggauugcgaaa | 276 | 12.029 |
| aaaggcguugauauggcaaccuuu | 77 | 13.477 | agcugacgaauacgcagcu | 177 | 18.980 | aaagcacaauauauggauuggcuuu | 277 | 11.981 |
| uugcgaguccaagacugcaa | 78 | 13.430 | auucgagauuauauggaauccgaau | 178 | 18.907 | gaauuaguccauaugggacaauuc | 278 | 11.972 |
| aaacgagauuauauggaauccguuu | 79 | 13.407 | acuacagagauuaccguagu | 179 | 18.601 | uaaugcacuuauauggcaaugcauua | 279 | 11.737 |
| uaaggauuuauaauggaaccuua | 80 | 13.392 | uaaggguuuuuuaagaaacccuua | 180 | 18.514 | uuucgagauuauauggaauccgaaa | 280 | 11.680 |
| uuagcacaauauauggauuggcuaa | 81 | 13.365 | uaggagaaggucccua | 181 | 18.149 | uaaagaaguuauauggaacucuuua | 281 | 11.641 |
| gauugauuuuuaugacaaaacaauc | 82 | 13.340 | auaugaggaauaaccauau | 182 | 17.926 | uaaggaguuuguauugaaaacccuua | 282 | 11.574 |
| aaagaagucaaagacuuu | 83 | 13.327 | acaugaggauuaaccaugu | 183 | 17.654 | uguugaccauuaggcaaca | 283 | 11.505 |
| aaggaacuguaacagucccu | 84 | 13.231 | acgugaggaacaccacgu | 184 | 17.628 | uaaccacauauauggauugcguua | 284 | 11.476 |
| augcaagacugacugauucgcau | 85 | 13.213 | uagugaguguauauggacaccacua | 185 | 17.589 | uuuggagaaauauauggauuccccaaa | 285 | 11.429 |
| auuugaguaauuaccaaau | 86 | 13.163 | uaaggaaguuuauauggaaacucccuua | 186 | 17.311 | aaacgacaaauauauggauugcguuu | 286 | 11.412 |
| uaaggcguuucuugauuaaacccuua | 87 | 13.161 | uaaaagaguuauuaaggaaacccuuua | 187 | 16.986 | auuccaguauauauauggauuacgggaau | 287 | 11.344 |
| guucagaucuaagaucgaac | 88 | 13.119 | acaagaccaauagccuugu | 188 | 16.964 | uaucgacaauauauggauugcgaua | 288 | 11.325 |
| uaaggguuuucucggaacccuua | 89 | 13.091 | acugagggauuuaacccagu | 189 | 16.560 | aauugcaguauauauggauugcgauu | 289 | 11.268 |
| acaugauacgauacguacaugu | 90 | 13.061 | uaacgagaaaauaaucauuuccguua | 190 | 16.454 | uauggacaauauauggauugccaua | 290 | 11.266 |
| agauauccauucgguaucu | 91 | 13.054 | uuguggaguaccccaca | 191 | 16.449 | uuuggagaauauauggauucccaaa | 291 | 11.251 |
| aucgaacucuaagagucgau | 92 | 13.051 | acaugaggauuaaccaugu | 192 | 16.286 | aaagcaguauauauggauuacgcuuu | 292 | 11.247 |
| uuugcacauaauauggguauggcaaa | 93 | 13.037 | auuggacauuauauggaugccaau | 193 | 16.248 | aauggaguauauauggauuacccauu | 293 | 11.245 |
| uaaggguuuuuuaagaaacccuua | 94 | 13.033 | uaaggguuuuuuaagaaacccuua | 194 | 16.092 | uuuccagauuauauggaauccggaaa | 294 | 11.162 |
| uaugagguuauguaauggauuacccuua | 95 | 12.983 | acugaauaauuacaucagu | 195 | 15.911 | uaaggaguauauauguauacccuua | 295 | 11.112 |
| uaugcacaauauauggauuggcaua | 96 | 12.975 | uaaggacgauacgccuua | 196 | 15.870 | ugaauauuguauauggacaaaauuca | 296 | 11.105 |
| cacgugaauuauccagug | 97 | 12.906 | auuaagaggacuaccuaau | 197 | 15.836 | gcaagauuucauauggaaaacuugc | 297 | 11.100 |
| uaaggaaguuuauauggaaacuccuua | 98 | 12.819 | aguucagcauuagcgaacu | 198 | 15.794 | uuagcacuuuauauggaaaggcuaa | 298 | 11.082 |
| ggucagaucuaagaucgacc | 99 | 12.805 | aaacgagaauuauccguuu | 199 | 15.680 | uuucgacuuuauauggaaagcgaaa | 299 | 11.065 |

TABLE 3-continued

Top 100 variant motifs for each RBP

| Sequence (QCP) | SEQ ID NO: | R. score | Sequence (MCP) | SEQ ID NO: | R. score | Sequence (PCP) | SEQ ID NO: | R. score |
|---|---|---|---|---|---|---|---|---|
| uacggauuuugauagaaaccgua | 100 | 12.772 | aaaccuguuuacacggaaacgguuu | 200 | 15.656 | acgcaggauaaauaccgcgu | 300 | 11.041 |
| uucgaugacuaagucacgaa | 101 | 12.770 | gaauaaggauuaccuauuc | 201 | 15.533 | auuggaguaaauauggguuacccaau | 301 | 10.990 |
| aguacaggauuuaccguacu | 102 | 12.740 | uaacgagaaaauaucauuuuccguua | 202 | 15.448 | uuuggacaaauauggguuugccaaa | 302 | 10.938 |

Example 3: RBP Binding Sequence Preferences

Using empirical Rscore values and associated binding site sequences as training set, an ML-based method that predicts the Rscore values for every mutation in the WT sequences was developed. First a model was built specific to each protein and its WT binding site length to validate the OL measurements on prior knowledge of the proteins' binding specificities. To do so, a neural network was used that receives as input the sequence of a binding site the same length as the WT sequences (25 nt for PP7-wt, 19 nt for MS2-wt, and 20 nt for Qβ-wt) and outputs a single score. A specific network was trained for each of the three RBP-OL experiments and the two positions where the binding sites were embedded within the ribosomal initiation region (FIGS. 3A and 3F), resulting in a total of six different models. Such a model preserves the positional information for each feature, i.e. the position of each nucleotide in the WT binding site. To choose the prefix (S) in which more robust scores were measured, the average Pearson correlation over 10-fold CV was examined. The correlations for the most robust position yielded values of 0.28 for PCP with PCP-based sites and δ=C, 0.48 for MCP with MCP-based sites and δ=C, and 0.45 for QCP with QCP-based sites and δ=GC (FIG. 3B). Interestingly, the variant group with higher Pearson correlation was also characterized by higher basal mCherry expression levels (FIG. 3C), which in turn resulted in a higher fold repression effect. Thus, higher correlation, meaning more robust predictability, correlated with higher fold-repression, which provided additional validity to the analysis.

In order to better understand the relationship between binding site sequence and binding, a protein-specific model was developed based on the whole library, which was termed the whole-library model. This model, as opposed to the WT-specific model, enables binding prediction to any site, i.e. of length different than the WT-site length. The model is based on a convolutional neural network (CNN) and receives as input nearly all of the oligo library sequences (~17,000). As with the protein-specific NN-model, the average Pearson correlation over 10-fold CV was examined (FIG. 3B—right) with the CNN model and there was found a significant improvement in Pearson correlation for PCP, while the correlation for MCP and QCP remained approximately the same. The whole library model was used to analyze the effect of structure-conserving mutations in each of the WT binding-site sequences (FIG. 3D). The ML model's results are presented as "binding rules" depicted in illustrations for each of the three RBPs binding site. The schemas represent the predicted change in responsiveness with respect to the wild-type sequence for every single-nucleotide mutation (SNP) in the loop or the bulge region, and every di-nucleotide mutation (DNP) preserving stem structure in the stem regions. For instance, in the schema for PCP (FIG. 3D—top), mutating the bulge from A to C, U, or G reduces the binding site's predicted responsiveness. By contrast, mutating the top base-pair in the upper stem from a U-A to a C-G, and the third nucleotide in the loop from an A to a C are both predicted to increase the responsiveness score with respect to the wild type binding site. A clear characteristic of PCP is the tolerance to DNPs in the stem regions, which is reflected by the dominance of the blue colors or light red (indicating a small reduction in responsiveness with respect to the wild-type binding sites), while there are only a few bases where single mutations are found to abolish binding (e.g. UGG portion of the loop). It is important to note that the results for PCP broadly correlate with past work which found the loop and the bulge regions to be critical for PCP binding, while sequence variations in the stems did not alter binding significantly. For QCP (FIG. 3D—middle), a significantly different picture emerges. The results indicate that the WT sequence used, as referred to in the literature, has a lower Rscore than many mutated versions of it. The bulge, for instance, has a higher Rscore with C, G, or U instead of the wild-type A. The data seems to indicate that QCP prefers a four nucleotide K-rich (i.e. G/U) stem and a U/C bulge mini-motif. This motif is apparent throughout the binding site, as can be seen from the blue-colored nucleotides of both the lower and upper stems. For MCP (FIG. 3D—bottom), a tolerance to DNPs in the lower stem emerges from the analysis, while a strong sensitivity to SNPs in the bulge, upper stem, and the loop regions is revealed. Past analysis also highlighted the sensitivity to mutations in the loop and the bulge regions, indicating that the in vivo environment does not alter the overall binding characteristics of MCP.

Figure 3G:
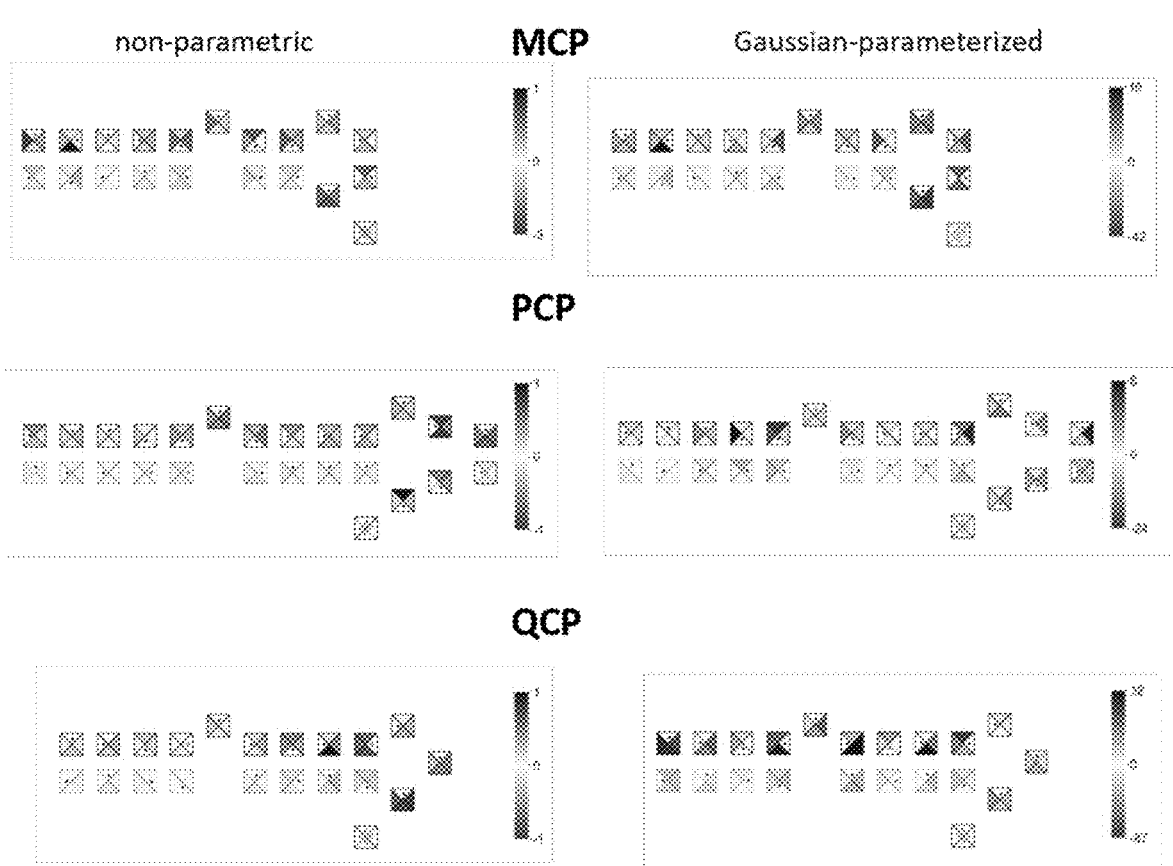

Finally, to provide a sanity check on the structural findings, the original Sort-seq data was reanalyzed using an Average Nearest Neighbor (ANN) approach (see Methods), and a non-parametrized Rscore was calculated. The cross-correlation between the non-parametrized and the Gaussian-parametrized Rscore was first computed (FIG. 3G) and an average Pearson correlation coefficient of ~0.5 was obtained between both sets of scores for all three proteins. The whole-library CNN model was then retrained using the non-parametrized scores, and Pearson correlation values of 0.42, 0.41, and 0.33 were obtained for PCP, MCP, and QCP as compared with 0.42, 0.46, and 0.44 respectively with the Gaussian-parametrized Rscore. Next, the binding preferences were recomputed and visualized on the structures as shown in FIG. 3D (FIG. 3H). The figure shows that the predicted changes in responsiveness from the wild-type computed with the non-parametrized Rscore are similar to the ones computed with the Gaussian-parametrized Rscore. While there is some deviation, because of the noisy nature of the original experimental dataset, most trends are sustained.

Example 4: RBP Binding Structure Preferences

In order to better understand the relationship between binding site structure and binding, the CNN model was extended to also include structural information (FIG. 4A). This model, as opposed to the whole-library model, incorporates both the sequence and secondary structure of the RNA binding site, as calculated by RNAfold. All three CNNs showed improved predictive performance when the structural data was added into the network (FIG. 4D).

This model was used to analyze the effect of structure-altering mutations on protein binding. To do so, various binding sites were generated with a predefined structure and the whole-library models was used to predict their responsiveness score. Specifically, at three types of mutations were examined: alteration of upper-stem length, alteration of loop length, and alteration of bulge size. Overall, upper-stem length plays a big role in binding affinity for all three RBPs, though not equally (FIG. 4B—left). PCP seems to be the most resilient to longer upper-stems, while MCP can relatively tolerate an upper-stem consisting of a single base-pair but is intolerant to stems of three base-pairs or longer. Finally, QCP exhibits tolerance to a two-base-pair stem, but a relative intolerance to any other length. Interestingly, this is consistent with QCP's known weak binding affinity to the MS2-WT binding site.

Varying the loop-length suggests increased flexibility for all three RBPs (FIG. 4B—right). PCP is the most resilient, displaying a viable binding affinity to loops that range from five to seven nucleotides in length. MCP is slightly less tolerant, displaying flexibility to structures containing loops that are three and four nucleotides in length, with some binding also observed for a small percentage of structures containing loops that are five nucleotides in length. As for QCP's affinity to short stems, this result is also consistent with MCP's recorded low affinity to the Qβ-WT binding site. Finally, QCP is the least flexible CP, exhibiting affinity to loops that are two nucleotides in lengths, and some affinity to structures with loops of length five.

Figure 4C:
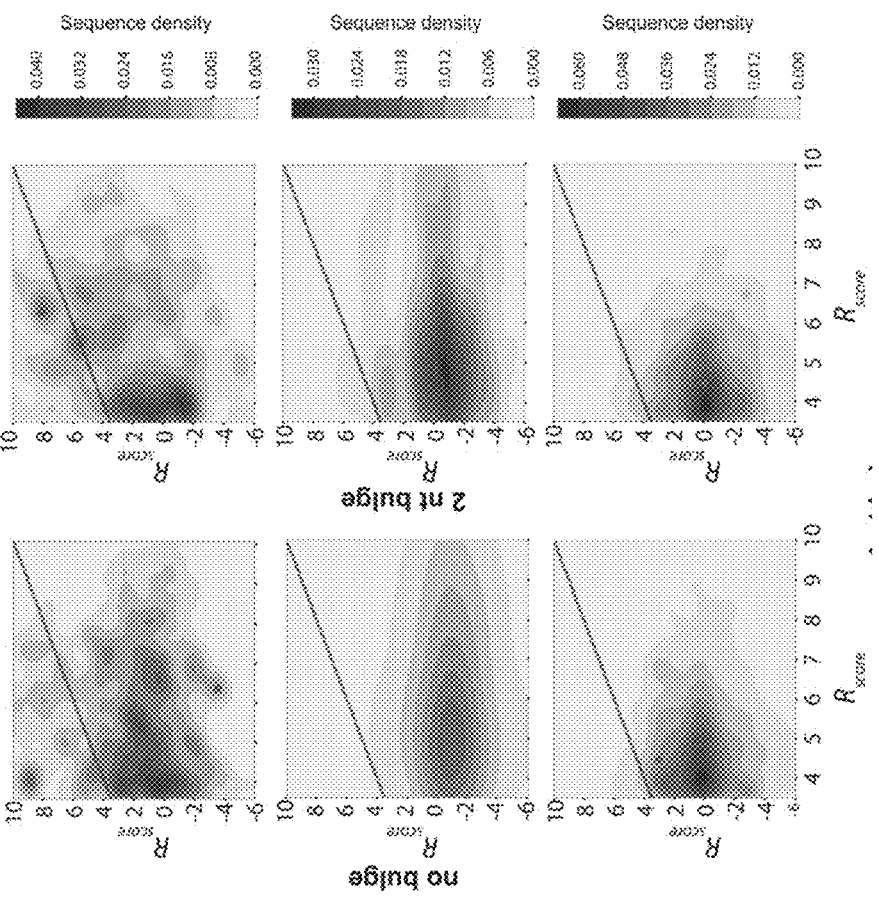
Figure 4B:
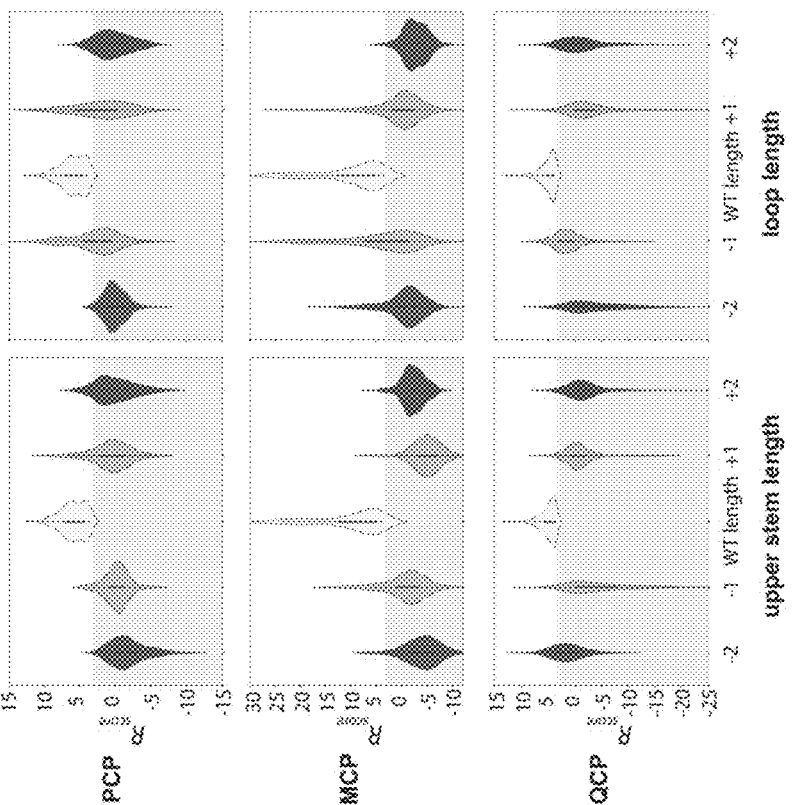
Figure 4D:
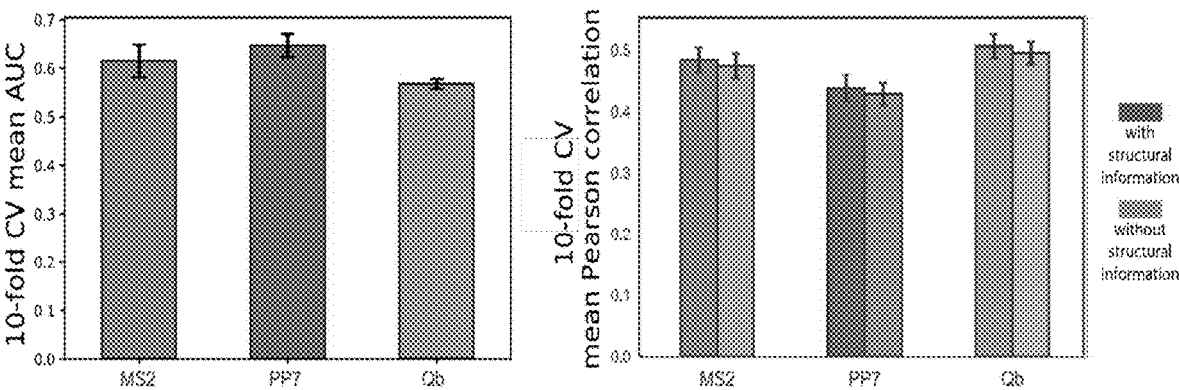

Finally, examining the importance of the bulge, a high variation in tolerance to mutations for the three RBPs is observed (FIG. 4C). PCP can tolerate and even have higher affinity with sequences that either have no bulge, or a two-nucleotide bulge. This is depicted by a non-negligible variant density above the 3.5 threshold. MCP, on the other hand, has negligible tolerance for variants with no bulge, and very low tolerance for those with a two-nucleotide bulge. This sensitivity correlates with MCP previous structure and sequence dependencies of the loop and upper stem (FIGS. 3D and 4B). QCP displays some tolerance to both bulge mutations, though much less than PCP.

In summary, the structural analysis indicates that all three proteins prefer different structures, with some overlap that can create cross-binding (e.g. MCP to Qβ-WT). PCP seems to prefer a structure with an upper stem of length four base-pairs or longer and a variable loop size ranging from five to seven nucleotides with some sequence specificity. MCP is constrained in both structure and sequence specificity needing a bulge separating a lower and upper stem, two base-pair upper stem, and a loop length of three to five nucleotides in length with a conserved sequence signature. Finally, QCP seems to display a binding signature consistent with a repeat concatemer of 4-K-rich-stem-bulge sequence and structural motif.

Example 5: Validations—New Cassettes for RNA Imaging

Figure 5A:
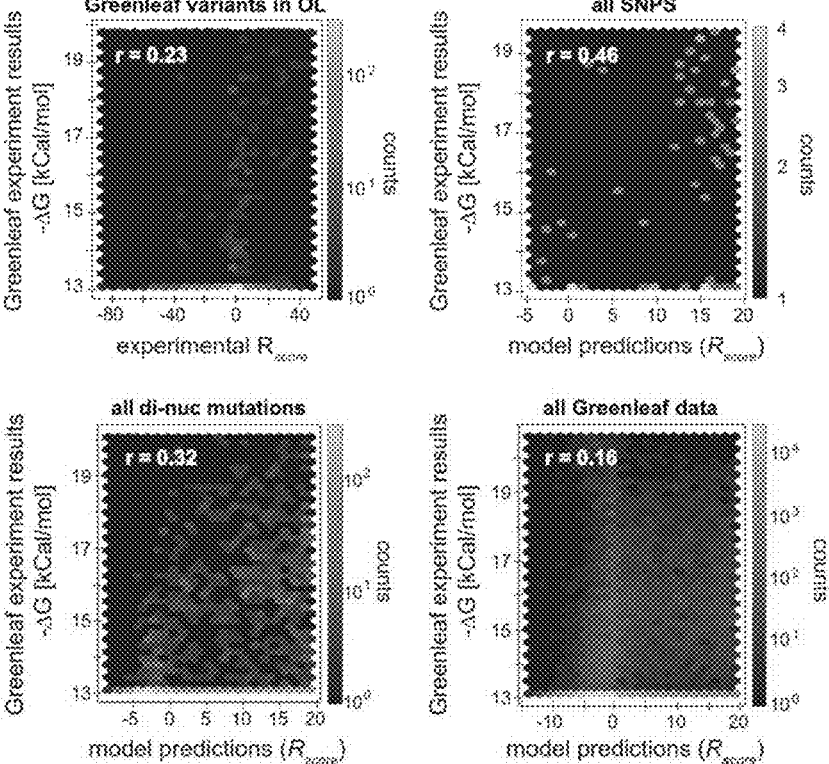
FIGS. 5A-G. Validations: cassettes for RNA imaging in U2OS cells. (5A) $R_{score}$ comparison to ΔG results of a previous study that reported MCP binding to more than 129 k sequences. Each plot (from left-to-right) represents Pear- son correlation coefficient using: the experimental measure- ments for variants that were both in the OL and in the in vitro study, the $R_{score}$ values predicted by the ML model for all single-mutation variants, for all double-mutation variants, and for the entire set of 129,248 mutated variants. (5B) Experiment design for the three cassettes based on the experimental binding sites. High $R_{score}$ binding sites were incorporated into a ten-site cassette downstream to a CMV promoter. When the matching RBP-3xFP is added (MCP- 3xBFP is shown), it binds the binding-site cassette and creates a fluorescent spot. (5C) The results for all three cassettes transfected with the matching RBP-3xFP plasmid into U2OS cells and imaged by fluorescence microscopy for detection of fluorescentfoci. For each experiment, both the relevant fluorescent channel and the merged images with the differential interference contrast (DIC) channel are pre- sented. (5D) Experimental design for the orthogonality experiment: two separate cassettes with 10 predicted mutated sites for either MCP only or QCP only, respectively, were designed and transfected together with both MCP- 3xmCherry and QCP-3xBFP, into U2OS cells. (5E) Results for the orthogonality experiment: a cell presenting non- overlapping fluorescentfoci from both fluorescent channels, indicating binding of MCP and QCP to different targets. Fluorescent wavelengths used in these experiments are: 400 nm for BFP, 490 nm for GFP, and 585 nm for mCherry. (5F-G) Micrographs of negative controls for fluorescent experiments in U2OS cells. (5F) Microscopy images of RBP-3xFP with plasmid containing no binding sites cas- settes (puc19). (5G) Additional negative control images, where RBP-3xFP plasmids were transfected with non-cog- nate cassettes. For each experiment, both the relevant fluo- rescent channel and the merged images with the differential interference contrast (DIC) channel are presented, and fluo- rescent wavelengths used in these experiments were: 400 nm for BFP and 490 nm for GFP. For both panels, no fluorescent foci were detected.

To validate both the experimental measurements and model predictions, the results were compared to a previous study that measured high-throughput in vitro RNA-binding of MCP (Buenrostro, J. D. et al. "Quantitative analysis of RNA-protein interactions on a massively parallel array for mapping biophysical and evolutionary landscapes", Nat Biotechnol 32, 562-568 (2014) herein incorporated by reference in its entirety). In the study, the researchers employed a combined high-throughput sequencing and single molecule approach to quantitatively measure binding affinities and dissociation constants of MCP to more than $10^7$ RNA sites using a flow-cell and in vitro transcription. The study reported $\Delta G$ values for over 120 k variants, which formed a rich dataset to test correlation with the measured and predicted Rscore values. First, Pearson correlation coefficient of the purely experimental measurements were computed for variants that were both in the library and in the in vitro study. The result (FIG. 5A—left) indicates a positive and statistically significant correlation (R=0.23). Next, Rscore values were predicted using the WT-specific model for all the reported variants of the in vitro study (FIG. 5A, left-to-right), and a strong correlation (R=0.46) was found for single-mutations variants, a moderate correlation (R=0.32) for double-mutation variants and a weak correlation (R=0.16) with the entire set of 129,248 mutated variants.

Given the large difference between the experiments and the different sets of variants used (e.g. in vitro vs. in vivo, microscopy-based vs. flow cytometry-based), the positive correlation coefficients (p-values<0.0002 for all reported coefficients) indicate a good agreement for both sets of experimental data, and a wide applicability for the learned binding models for MCP.

Figure 5B:
Figure 5B:
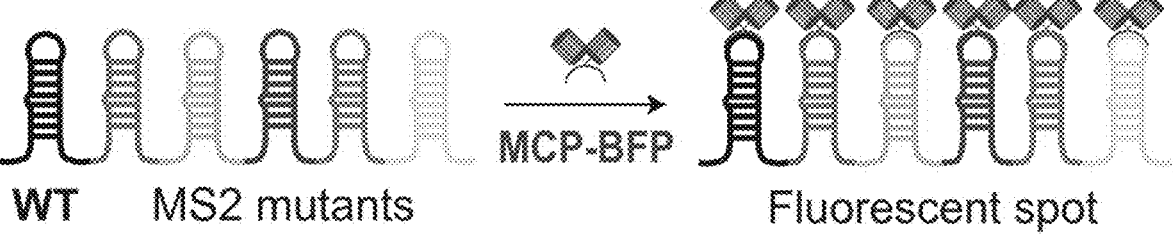
Figure 5C:
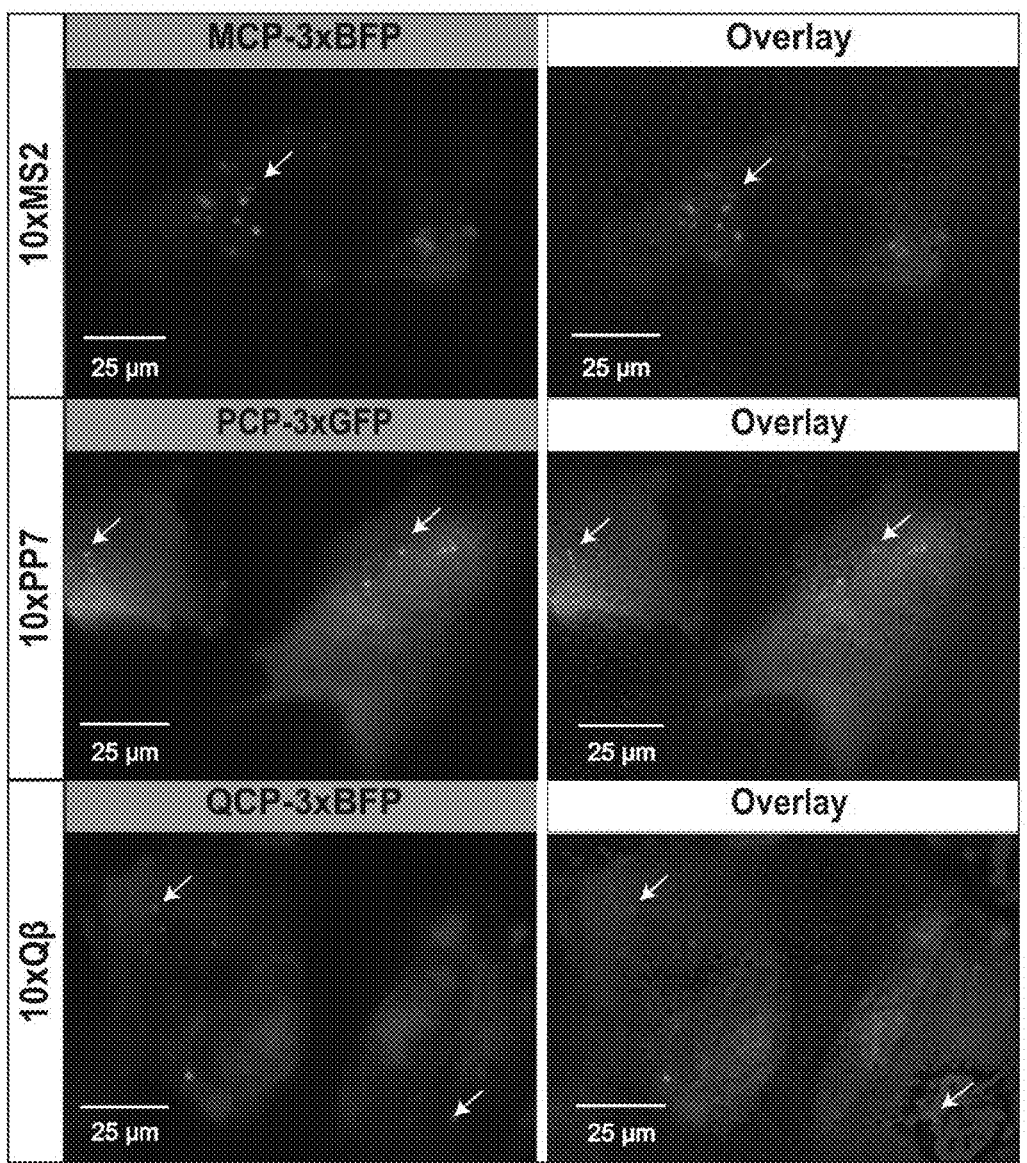
Figure 5D:
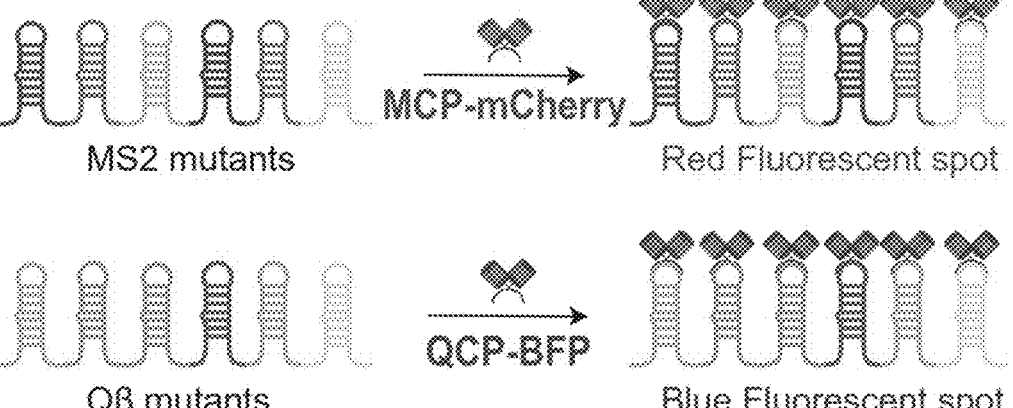
Figure 5E:
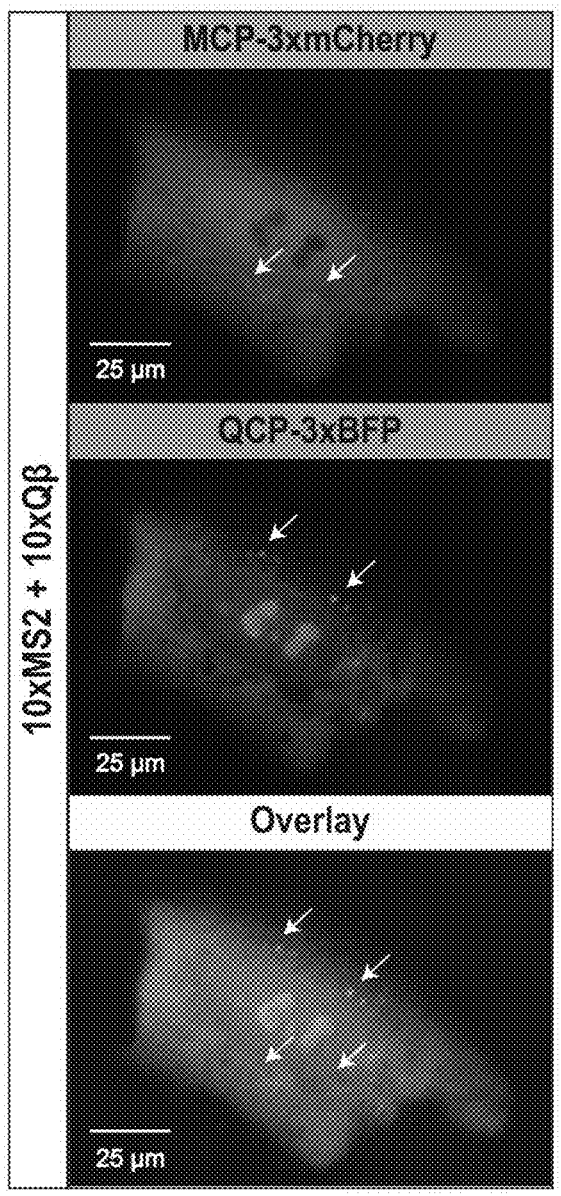
Figure 5G:
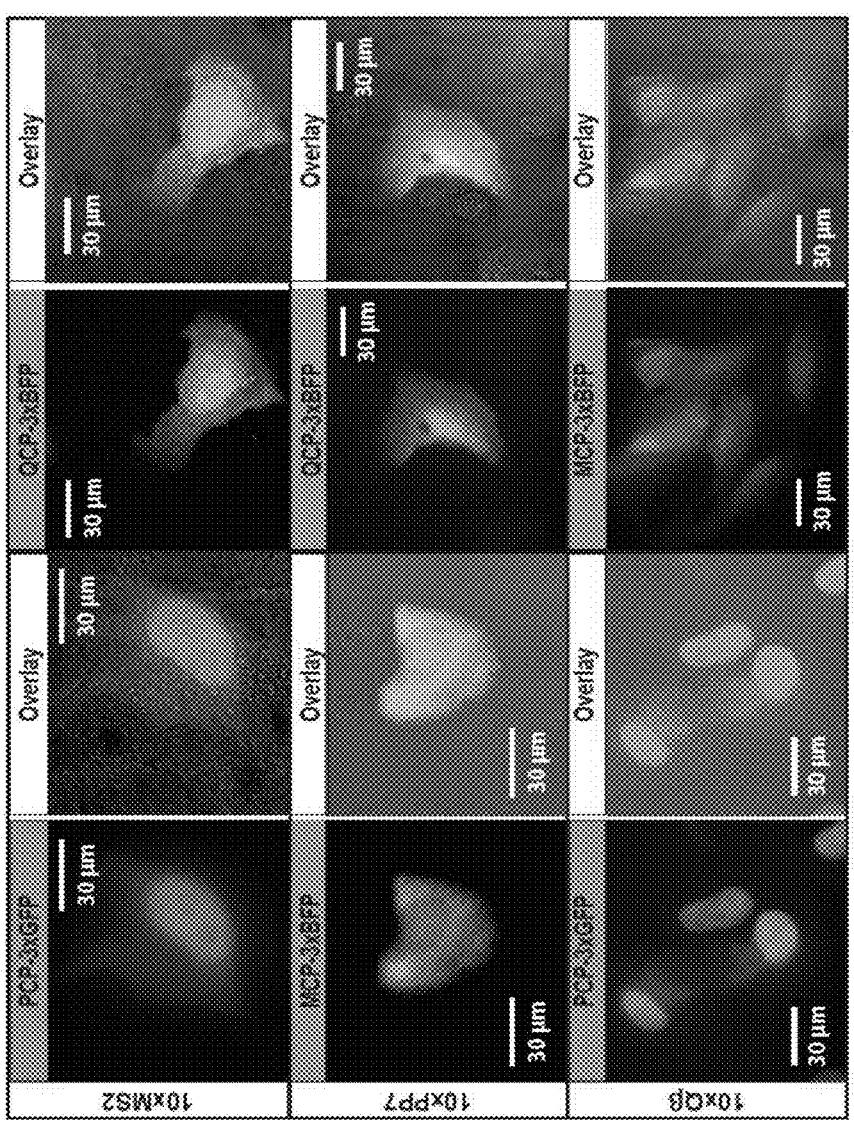
Figure 5F:
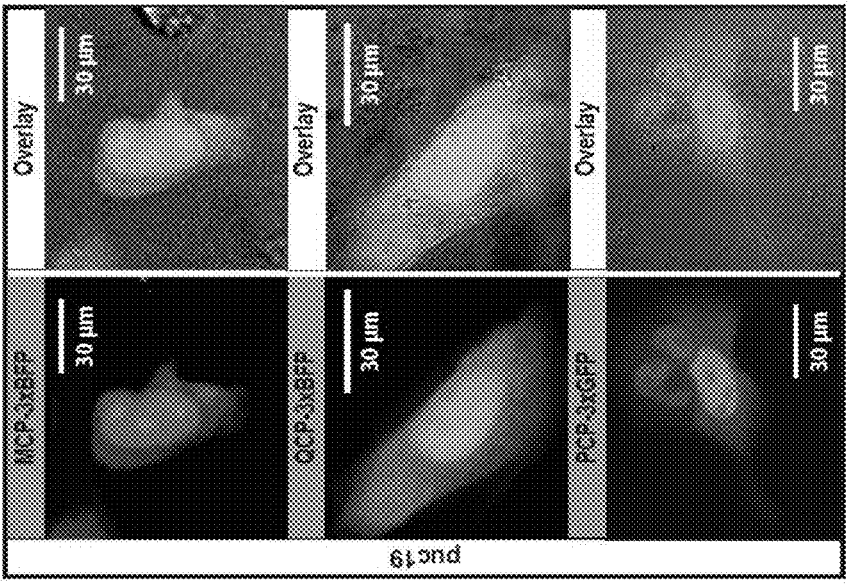

To further validate the results of the experiment and test the wider applicability of the findings, new cassettes were generated containing multiple non-repetitive RBP binding sites identified by the experimental dataset and they were tested in mammalian cells. Once labelled with a fusion of the RBP to a fluorescent protein, functional cassettes appear as trackable bright fluorescent foci. Three binding site cassettes were designed based on library variants that were identified as highly responsive for each RBP (FIG. 5B). Each cassette was designed with ten different binding sites, all characterized by a large edit distance (i.e. at least 5) from the respective WT site and from each other, thus creating a sufficiently non-repeating cassette that IDT was able to synthesize in three working days. In addition, all selected binding sites exhibited non-responsive behavior to the two other RBPs in the experiment. The cassettes were cloned into a vector downstream to a CMV promoter for mammalian expression and transfected them into U2OS cells together with one of the RBP-3xFP plasmid encoding either PCP-3xGFP, MCP-3xBFP, or QCP-3xBFP. In a typical cell (FIG. 5C), all three cassettes generated more than five fluorescent puncta, dispersed throughout the cytoplasm. The puncta were characterized by rapid mobility within the cytoplasm, and a lack of overlap with static granules or distinct features which also appear in the DIC channel. Negative control experiments, where RBP-3xFP plasmids were transfected with either an empty plasmid (puc19) or non-cognate binding site cassettes, did not show such puncta (FIG. 5F-G).

To expand to orthogonal and simultaneous imaging of multiple promoters, two additional cassettes were ordered with MS2 and Qβ variants, respectively, and co-transfected with a plasmid encoding for both of the matching fusion proteins: MCP-3xmCherry and QCP-3xBFP (FIG. 5D). For each cassette, the sites were chosen with two constraints: to minimize repeat sequences and to maximize orthogonality to the other RBP (e.g. both MS2-WT and Qβ-WT binding sites were not included as they exhibit cross-responsiveness and are thus not orthogonal). In FIG. 5E sample cell images depicting single and double channel views were plotted. The images show that both cassettes produce a spatially distinct set of puncta (FIG. 5E—top and middle), which can be definitively associated with one of the two proteins (FIG. 5E—bottom). This indicates that the binding sites are sufficiently orthogonal to allow tracking of more than one cassette simultaneously. Moreover, there is little difference between the number of puncta of the two sequences and the fluorescent intensity for all puncta seem to fluctuate unimpeded in all three directions (x, y and z) inside the cell. Taken together, the microscopy experiments conducted in mammalian cells demonstrate the universal applicability of the results obtained from the high-responsiveness binding sites identified in the OL experiment to the advancement of RNA imaging in a variety of cell types.

Example 6: De Novo Design of Dual-Binding Site Cassettes

Figures 6A, 6B:
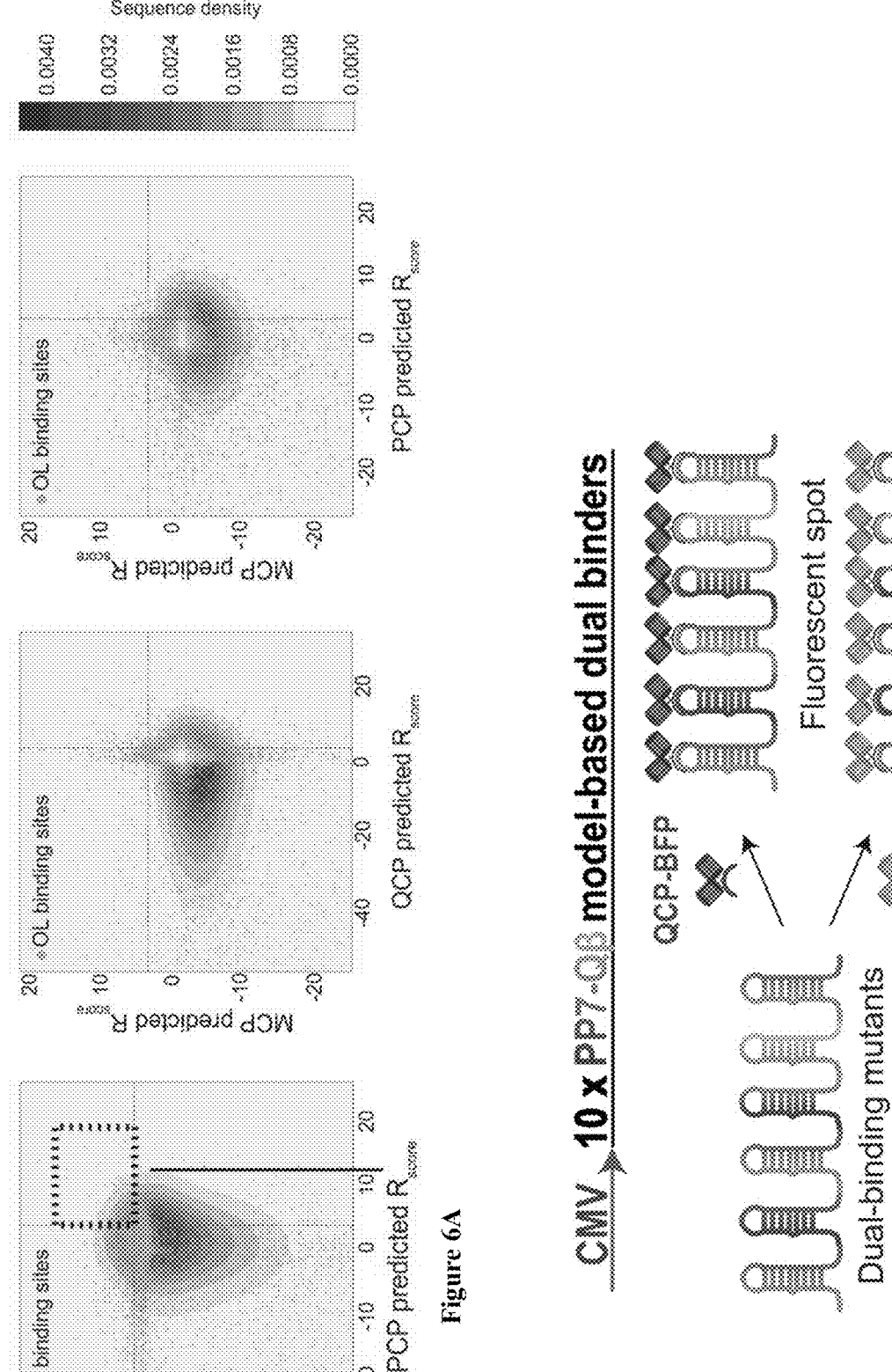
FIGS. 6A-G. De novo design of dual-binding site cas- settes in U2OS cells. (6A) 2D density plots (pink-red scale) depicting the predicted $R_{score}$ values for one million ML variants binding to (left-to-right): PCP and QCP, MCP and QCP, and MCP and PCP. QCP-PCP dual-binding variants are located in the black dashed square. Blue-white dots represent the experimental OL variants. (6B) Based on the dual-binding mutants for QCP and PCP from the model predictions, an additional cassette was designed. (6C) Results for the dual-binding experiment. Fluorescentfoci can be observed for the cassette expressed with either PCP- 3xGFP or QCP-3xBFP. For both experiments, both the relevant fluorescent channel and the merged images with the DIC channel are presented. Fluorescent wavelengths used in these experiments are: 400 nm for BFP and 490 nm for GFP. (6D) Evaluation of prediction accuracy based on size of the training set. For each training set size, a random set of more than 1,000 training-set variants was withheld for computa- tional testing post-training. Performance is reported as aver- age Pearson correlation over 10 random training and test sets (and standard deviation in shade). (6E) Microscopy images of PCP-3xBFP with a cassette containing binding sites predicted by the ML model. Both the relevant fluorescent channel and the merged images with the differential inter- ference contrast (DIC) channel are presented, and the fluo- rescent wavelength used was 490 nm. (6F-G) Scatter plots of mCherry expression in cells with increasing QCP added. QCP was added to cells (6F) expressing a reporter construct with a QCP binding site in the 5' UTR and an MCP variant binding site in the ribosome initiation region and (6G) expressing a reporter construct with an MCP variant binding site in the 5' UTR and the ribosome initiation region.

Finally, to further validate the predictive power of this system, cassettes were created with binding sites that did not exist in the experimental library. The whole-library was used to predict de novo functional binding site sequences, which could bind multiple RBPs. To do so, all possible variants with Hamming distance 3-7 to one of the three WTsv were generated. From this set of sequences, one million sequences were randomly selected and the models were used to predict the responsiveness score for each of the three RBPs. In FIG. 6A, the variant density distribution is plotted based on a predicted Rscore values. The plots show that the highest density of sequences appears at Rscore values that hover around 0 for all three proteins. The plots further show that there is a bias towards negative responsiveness values for all three proteins in the computed sequences. This is consistent with having a small region of sequence space which facilitates specific binding, which in turn is easy to abolish with a small number of mutations. In contrast, high responsiveness scores are only computed for a small number of the sequences, as can be seen by the sharp gradient in the density plot for positive responsiveness values. Finally, each plot shows a non-negligible region where the same sequence exhibits a high responsiveness score for both RBPs. These sequences are predicted to be dual binders. By overlaying the empirical responsiveness score for all the variants in the library (white and blue dots), it was observed that the dual-binder region is inhabited by a handful of experimental variants for each possible RBP pair.

Figure 6C:
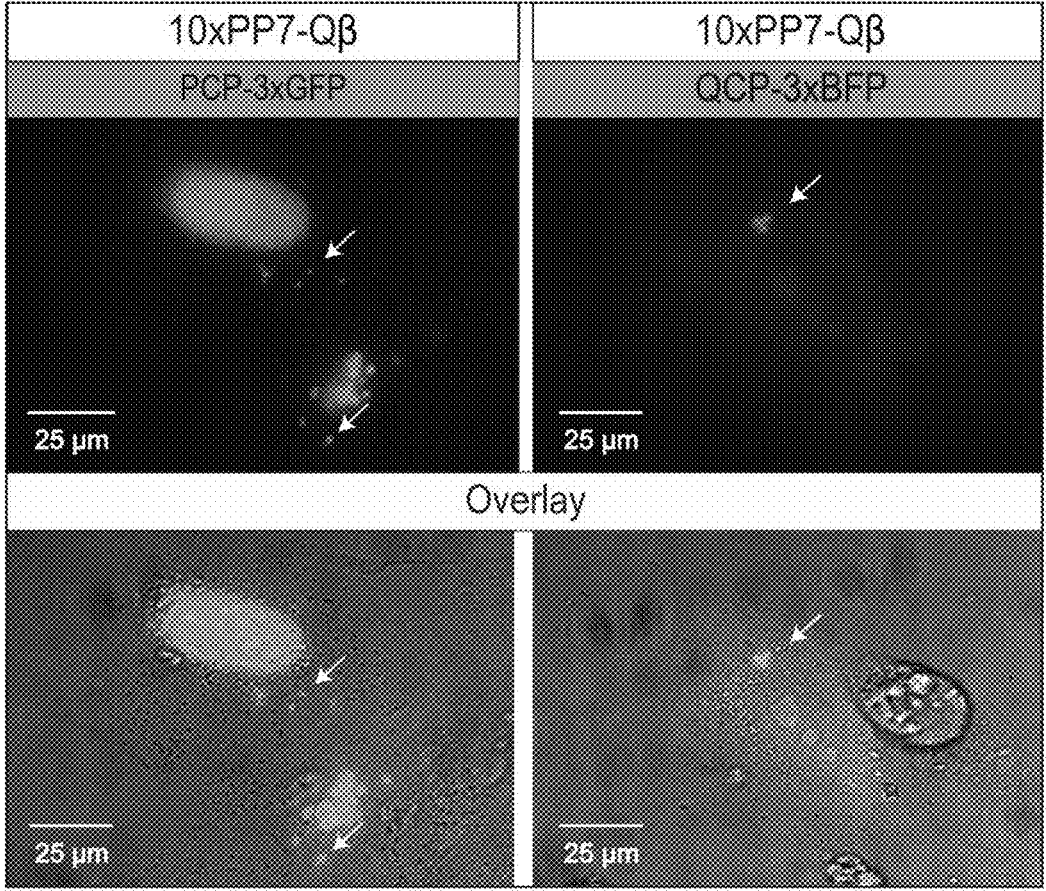
Figure 6D:
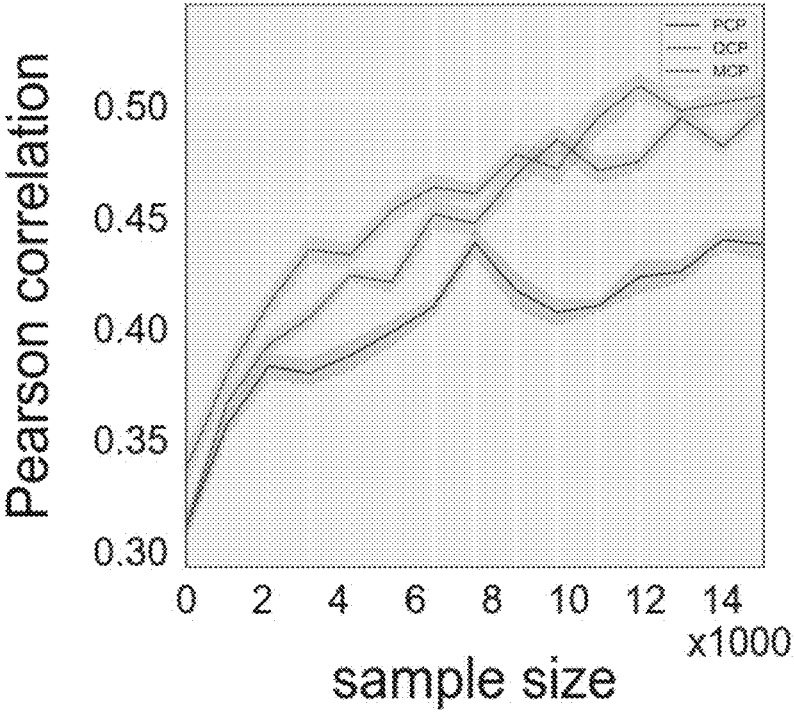
Figure 6E:
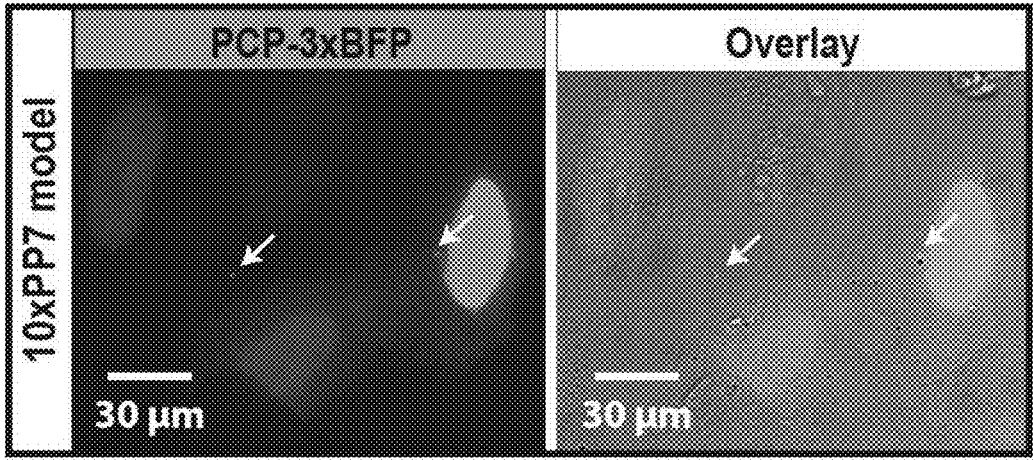
Figure 6F:
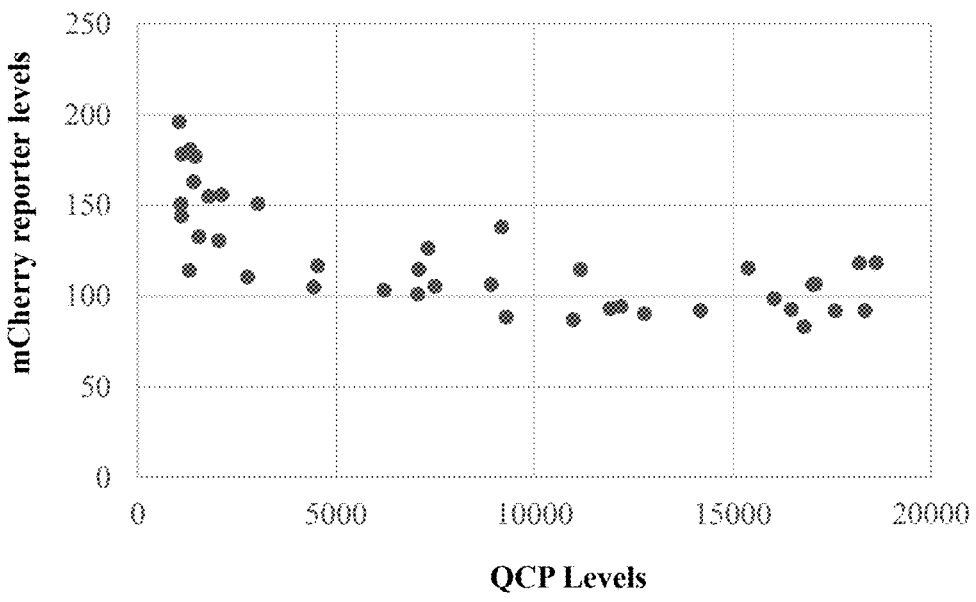

To test the predictions of the whole-library models experimentally, another 10× binding site cassette was designed (FIG. 6B), where each binding site was selected from the set of predicted sequences whose responsiveness scores for QCP and PCP were both above 3.5 (see dashed square in FIG. 6B—left panel). Therefore, the cassette is expected to generate fluorescent foci when bound by either QCP or PCP. As before, the cassette was cloned into a vector downstream of a CMV promoter for mammalian expression and transfected it into U2OS cells together with a plasmid encoding for either PCP-3xGFP or QCP-3xBFP. In FIG. 6C, fluorescent and DIC images were plotted for PCP (left) and QCP (right), depicting bright fluorescent foci that are located outside of the nucleus and which do not overlap with a DIC feature. The plots show distinct puncta observed with both relevant RBPs confirming the dual binding nature of the cassette. An additional cassette containing predicted PP7 sites also presented mobile fluorescent foci when tested in a similar manner with PCP-3xGFP (FIG. 6F). Consequently, these images support the model's ability to accurately predict MCP, PCP, and QCP binding sequences with known function with respect to all three RBPs.

Figure 6G:
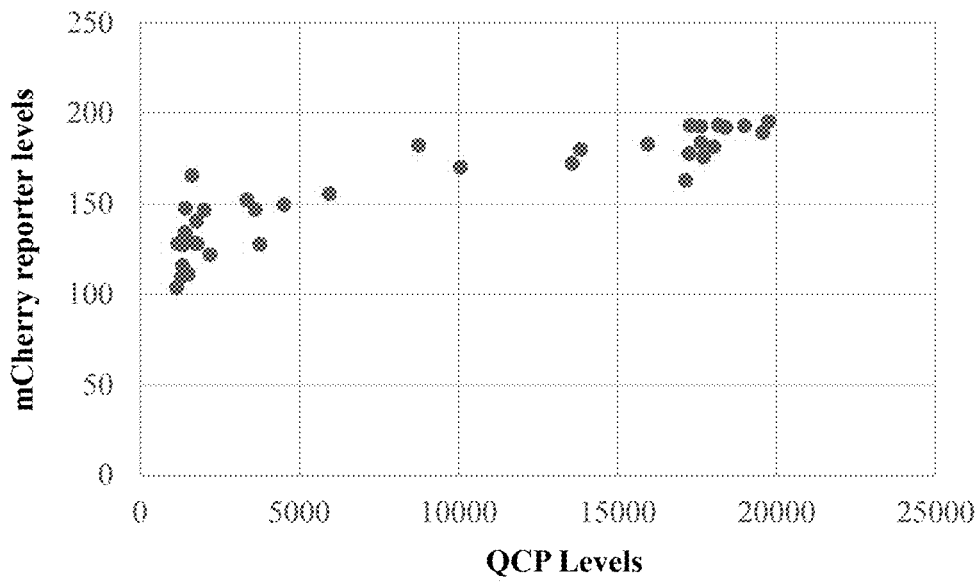

These dual binding cassettes lead to an unexpected discovery. A cassette was generated containing a MCP variant binding site (a single nucleotide change) inserted into either the 5' UTR and the ribosome initiation site. This variant comprises a single mutation from the canonical binding site and was predicted not to bind to QCP or PCP. When only one copy of this variant was inserted at either of the two locations, addition of MCP resulted in repression of mCherry translation. Indeed, when the variant was inserted at both locations the addition of MCP also resulted in repression. When this MCP-binding variant was inserted at the ribosomal initiation region and the canonical QCP site was inserted in the 5' UTR the addition of QCP also lead to repression in a dose dependent manner (FIG. 6F). This is expected as the binding of QCP in the 5' UTR is sufficient to repress translation. However, unexpectedly when both the 5' UTR site and the ribosome initiation site contained the MCP variant the addition of QCP lead to an upregulation of mCherry levels (FIG. 6G). This upregulation was also dose dependent, as increasing amounts of QCP lead to increasing mCherry levels. This shows that the two binding sites act cooperatively, and that the cooperative action can convert repression into enhancement. This cooperative effect was also observed with other combinations of binding motifs, and indeed appears to be a widespread mechanism for exerting transcriptional upregulation and not just downregulation via RBP binding.

Example 7: Synthetic RNA-Protein Complexes are Phase Separated In-Vitro and In-Vivo Liquid-liquid phase separation (LLPS), the process by which a homogeneous solution separates into molecularly dense and dilute liquid phases, has been connected to a wide range of natural cellular processes in virtually all forms of life. In cells, LLPS results in the formation of membrane-less compartments containing a high-concentration mix of biomolecules (e.g. proteins, RNA and proteins, etc.) Examples of such compartments include paraspeckles, stress granules, and nuclear speckles among others. Given the ubiquity of these compartments in cells, it was hypothesized that it was possible to engineer a synthetic, orthogonal, and programmable phase separation system, and thereby provide an additional level of control over gene expression in synthetic systems (i.e. signal amplification and attenuation). As described hereinabove, co-expression of the coat-protein-bound RNA cassettes yields bright puncta, which can be tracked in living cells. Given the similarities between the puncta signal attained from these cassettes and natural liquid-liquid phase separated puncta such as paraspeckles, it was hypothesized that these synthetic modular RNA scaffolds can trigger liquid-liquid phase separation within different cell types, and that the observed puncta correspond to synthetic biocondensates.

Figure 7A:
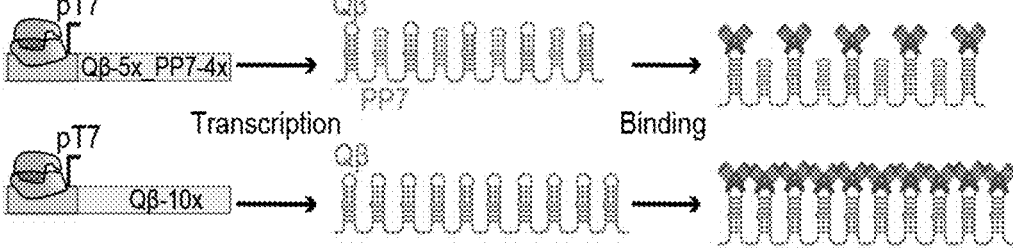
FIGS. 7A-E: Synthetic liquid-liquid phase separated droplets within bacterial cells. (7A) Construct diagram depicting pT7 expression of the two new slncRNA cassettes used in this study, in the presence of Qβ-mCherry. (7B) (left) Fluorescent image of cell expressing the Qβ-5x-PP7-4x slncRNA together with Qβ-mCherry. (right) Heatmap depic- tion of the image on left showing puncta within cells. (7C) Cell fraction showing puncta as a function of cassette-type. Note, PP7-4x and Qβ-5x indicate the Qβ-5x-PP7-4x cassette expressed together with PP7-mCherry or Qβ-mCherry, respectively. Error bars indicate standard deviation. (7D) Turbidity (absorption) measurements of cell lysates that either contain the Qβ-5x-PP7-4x slncRNA (right) or not (middle). (7E) (Left) E. coli cell lysates containing both Qβ-mCherry and the Qβ-10x slncRNA. (Top) Flow cytom- etry side scatter vs forward scatter plot showing a second population at high side-scatter values that are consistent with denser particles. (Bottom) Image showing a clear DIC slide and a fluorescent image depicting a dense layer of sub- micron resolution puncta. (Right) E. coli cell lysates con- taining only Qβ-mCherry. (Top) FSC vs SSC image which does not show distinct population of particles at higher side-scatter values. (Bottom) a similar microscopy pictures showing only a handful of fluorescent puncta.
Figure 7B:
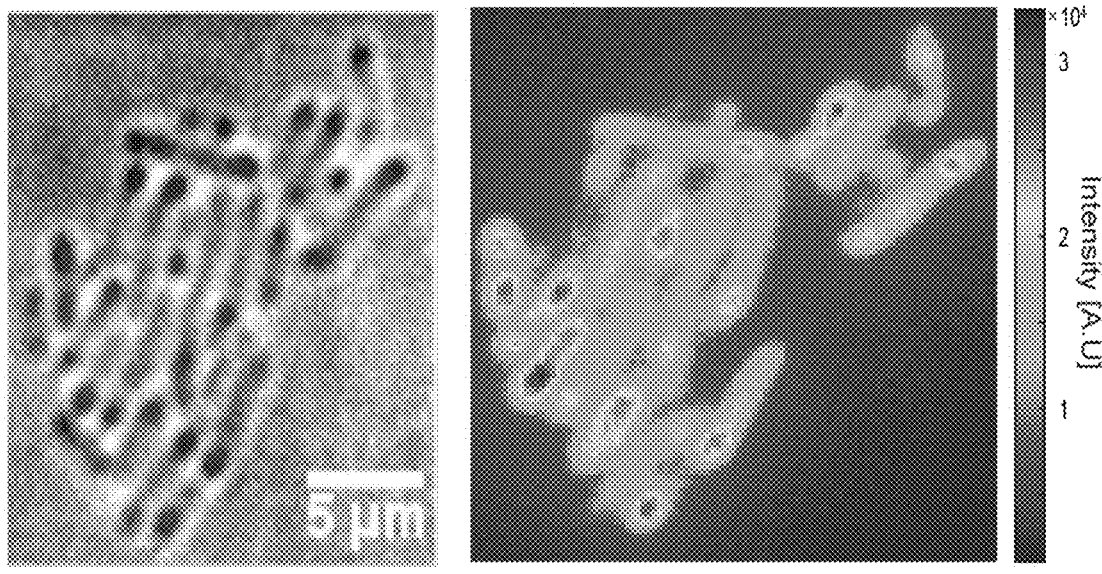
Figure 7C:
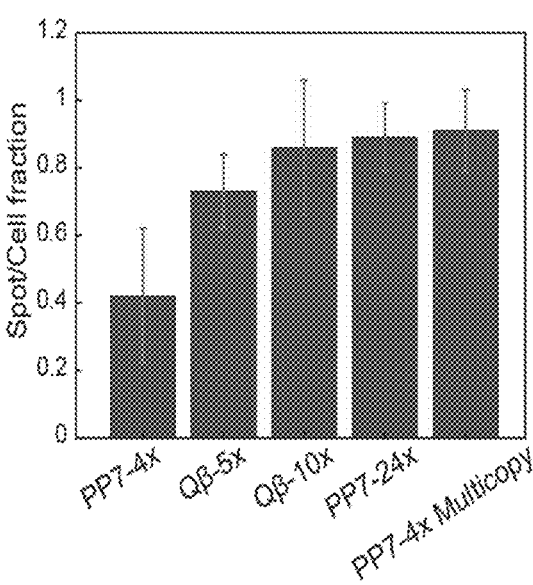
Figure 7D:
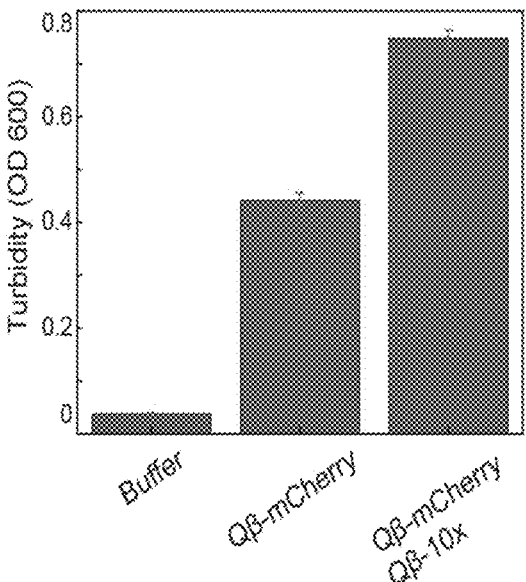

In order to prove this hypothesis, two synthetic long non-coding RNA (slncRNA) binding-site cassettes were designed using the engineered binding sites. The first slncRNA, Qβ-5x_PP7-4x, consisted of five native Qβ and four native PP7 binding sites, in an interlaced manner. The second slncRNA, Qβ-10x, consisted of ten novel high-affinity Qβ binding sites (FIG. 7A). The new slncRNA cassettes and the PP7-24x cassette from Hocine, et al., 2013, "Single-molecule analysis of gene expression using two-color RNA labeling in live yeast", Nature Methods 10:119-121, herein incorporated by reference in its entirety, were each cloned downstream to a pT7 promoter on a single copy plasmid and transformed into BL21-DE3 E. coli cells, together with a plasmid encoding for either Qβ-mCherry or PP7-mCherry fusion proteins from an inducible promoter. Single cells expressing the cassettes and RBPs were imaged every 10 seconds for 60 minutes under constant conditions on an epifluorescent microscope. For all cassettes used in the experiment, the images revealed formation of various puncta at the majority of cell poles (FIG. 7B). Quantifying the fraction of cells that display at least one punctum reveals a dependence on the number of binding sites, in accordance with the multivalency model of LLPS formation (FIG. 7C). To provide further evidence that these puncta are phase-separated liquid droplets, cells expressing the Qβ-mCherry fusion protein only, and cells expressing both the fusion protein and the binding site cassette consisting of ten Qβ binding sites were lysed. Next, the turbidity of the cell lysates was measured. The results (FIG. 7D) show a 1.7-fold increase in turbidity (measured at OD600), a known signature of a liquid suspension containing phase separated droplets. The cell lysates were further examined via flow

US 12,630,831 B2

Figure 7E:
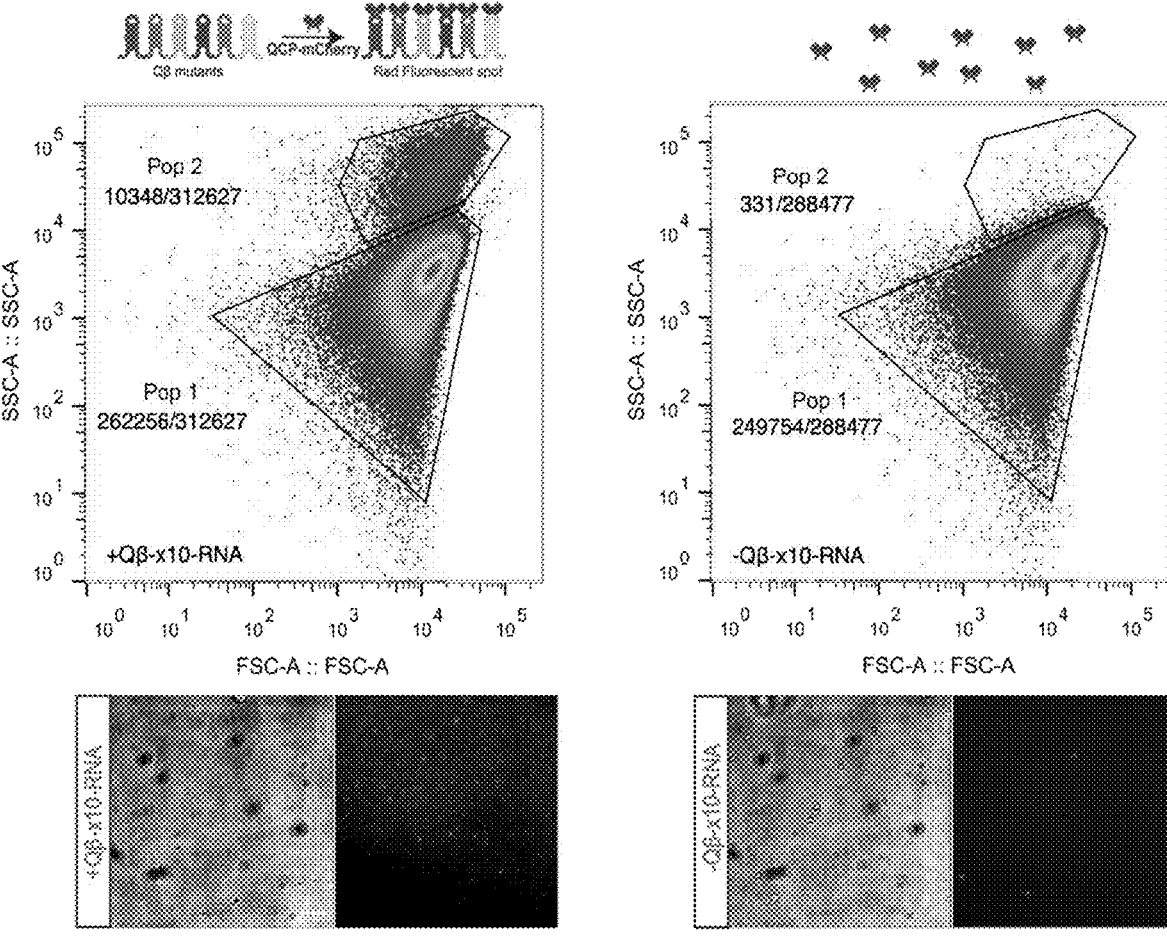

81
82 cytometer and the existence of a second population charac-
terized by denser particles that are mixed within a dilute
liquid in the lysate containing the binding sites cassette were
verified (FIG. 7E).

Example 8: Intensity Measurements Reveal Free
Exchange with the Cytoplasm

Figure 8A:
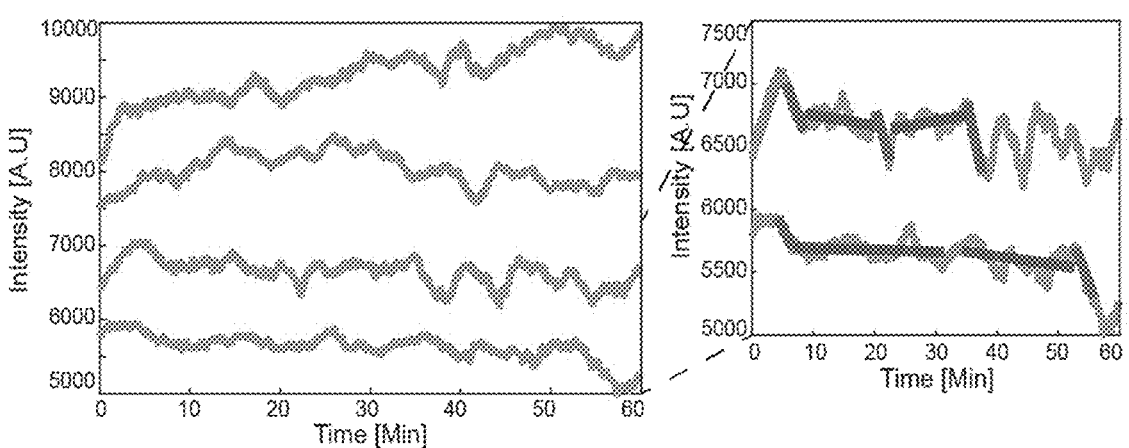
FIGS. 8A-E: Fluorescent puncta are characterized by insertion and shedding events of RNA-RBP complexes. (8A) (left) Sample traces of puncta signal for the Qβ-5x cassette. (Right) Sample annotation of traces with positive bursts (green), negative bursts (red), and non-classified signal (blue), respectively. (8B) Amplitude distribution for the different types of events, from 300 Qβ-5x traces. (8C) Bar-graph showing the number of events for both negative and positive bursts immediately following a long (>2.5 min) non-classified event. From top-left, in clockwise direction: PP7-24x, Qβ-10x, PP7-4x, Qβ-5x. (8D) Violin plots show- ing amplitude distribution as a function of cassette type for both positive (top) and negative (bottom) bursts. (8E) Bar charts of amplitude distributions of different binding sites cassettes. Top—PP7-4x, collected from 256 traces, center— QD-10x, collected from 430 traces, bottom—PP7-24x, col- lected from 390 traces.
Figure 8B:
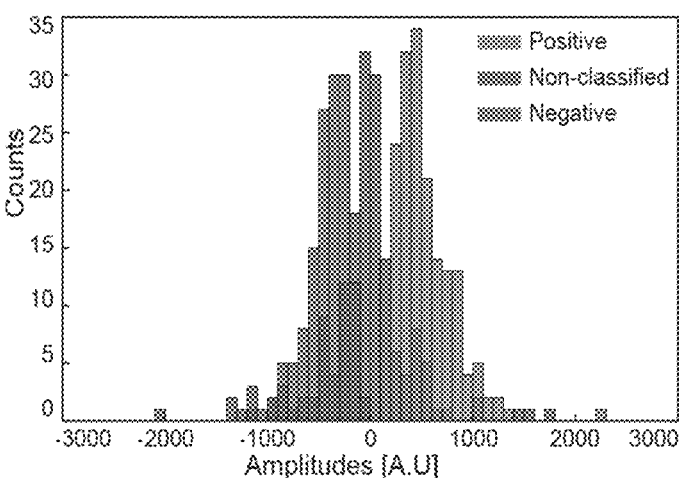
Figure 8C:
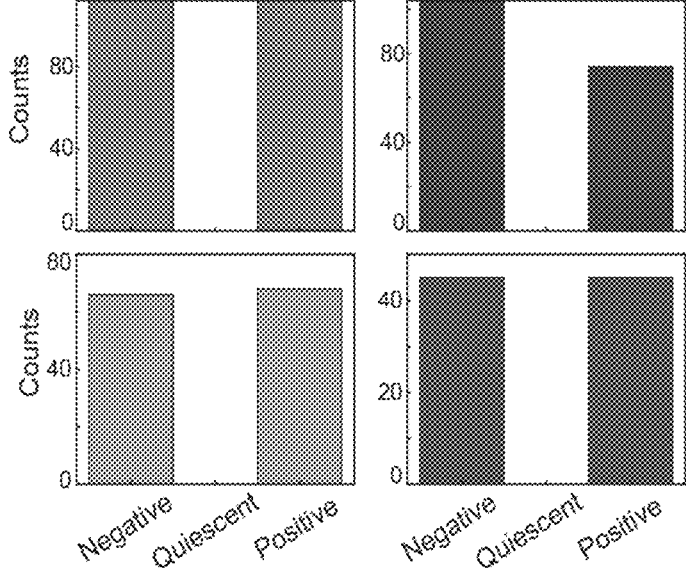
Figure 8D:
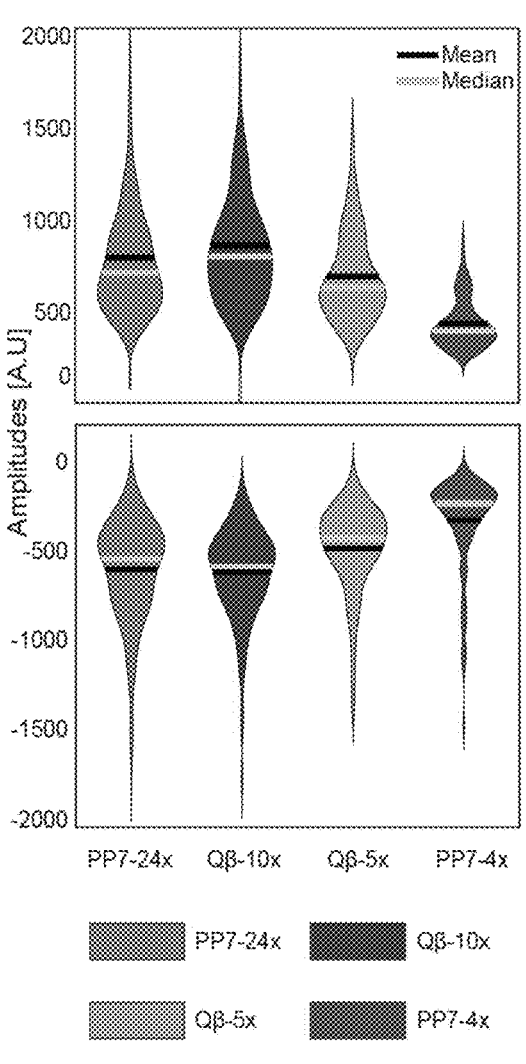
Figure 8E:
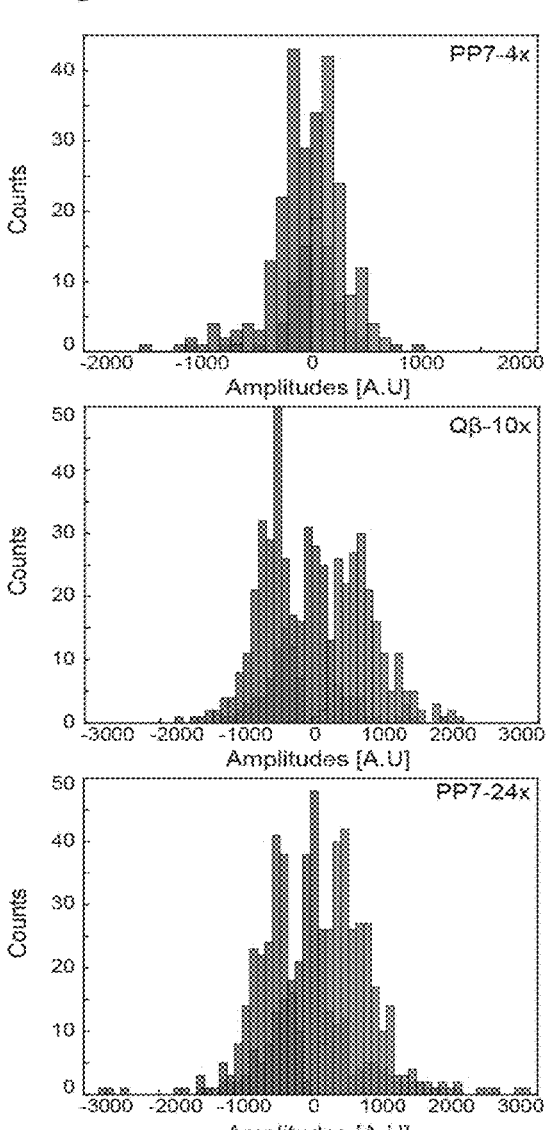

The signal brightness of each punctum was analyzed for
every time point using a customized analysis algorithm (see
Methods). In FIG. 8A, representative intensity vs time
signals was plotted for the Qβ-5x-PP7-4x cassette together
with Qβ-mCherry (denoted Qβ-5x), obtained from multiple
puncta tracked in different fields of view on separate days
(40 repetitions in total). The signals are either decreasing or
increasing in overall intensity and dispersed within them are
sharp variations in brightness, that are also either increasing
or decreasing, which were termed "signal bursts". Next, a
statistical threshold was employed which flagged these
signal variation events whose amplitude was determined to
not be part of the underlying signal noise (p-value<1e−3)
(See Methods). These events were classified as either
increasing signal bursts (green), decreasing signal bursts
(red), and non-classified segments (blue) (FIG. 8A). FIG. 8B
plots the distributions of amplitude (ΔI) for all three event
types, obtained from ~300 puncta traces for the Qβ-5x data.
The plots show the distributions of the three separated
populations of non-classified, increasing, and decreasing
signal bursts, with the number of positive and negative burst
events being approximately equal. Moreover, a similarly
symmetric burst distribution is recorded for the PP7-4x,
Qβ-10x, and PP7-24x cassettes (FIG. 8E).

A hallmark of LLPS is the free exchange of molecules
between the biocondensate droplet and the surrounding
dilute phase. These exchange events are predicted to occur
independently of one another at some rate that depends on
the transient concentration of the molecules in the dilute
phase. It was examined whether the data supports this
prediction, namely, whether positive and negative burst rates
are independent. Specifically, whether there was a bias for
one type of burst or the other after a non-classified period
that lasted more than 2.5 minutes was checked (see Meth-
ods). The results (FIG. 8C) show that no such bias seems to
exist, i.e., either a positive or negative burst seems to occur
after non-classified events with equal probability for all four
cassette types, consistent with the LLPS model. Next, the
amplitudes of the bursts for all four cassette-RBP pairings
were measured and it was found that both positive and
negative amplitudes are proportional to the number of
binding sites within the encoded cassette. (FIG. 8D).
Together, these lines of data provide strong support that the
bursts indeed correspond to insertion and shedding of sln-
cRNA-RBP complexes into and from the denser droplet
phase, respectively.

Example 9: Comparative Measurements Hint at a
Bi-Phasic Cytosol

Figure 9A:
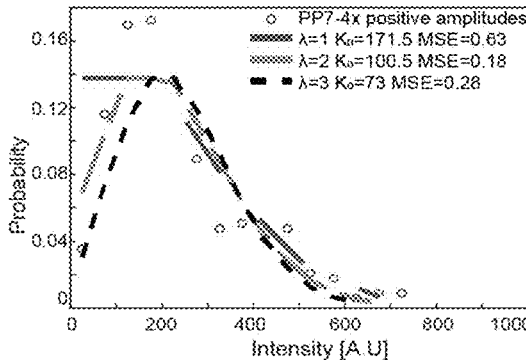
FIGS. 9A-H: Puncta analysis suggests a biphasic cytosol in E. coli. (9A-B) Poisson functions fits for the amplitude distribution of insertion assuming 1, 2, or 3 mean events (9A) and shedding (9B) events. (9C) Extracted fluorescence signal for a single slncRNA-RBP complex, assuming a Poisson distribution with λ=1. (9D) Distribution corre- sponding to the number of slncRNAs per puncta, assuming the value of K0 shown in panel (9C). (9E) Lag-time distribution between insertion events for Qβ-5x r-square of fit is 0.63. (9F) Bar plot showing extracted mean lag times for all four cassette-RBP pairings. Error bars indicate 95% confidence intervals. (9G) Violin plot showing mean background levels from cells expressing the PP7-mCherry fusion protein only (light blue), and cells expressing slncRNAs together with the fitting fusion protein (red, orange, purple and green corresponding to PP7-4x, QD-5x, QD-10x and PP7-24x). (9H) Fitting of amplitude data to Poisson distributions. Top Row—Qβ-5x, middle row—Qβ-10x, bottom row—PP7-24x. Left column—positive amplitudes, right column—negative amplitudes.
Figure 9B:
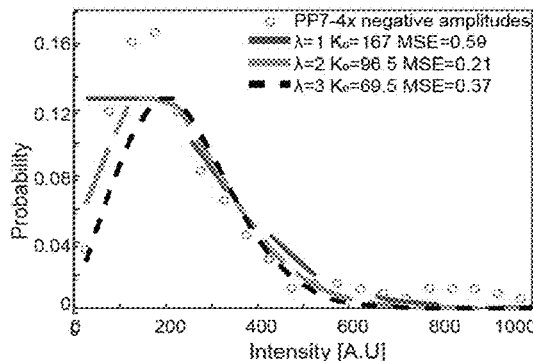
Figure 9C:
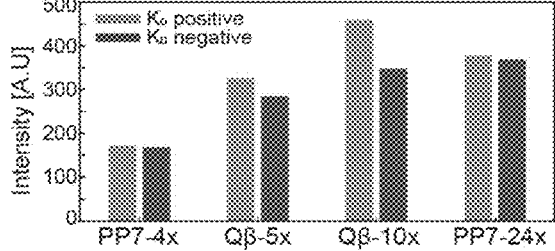
Figure 9D:
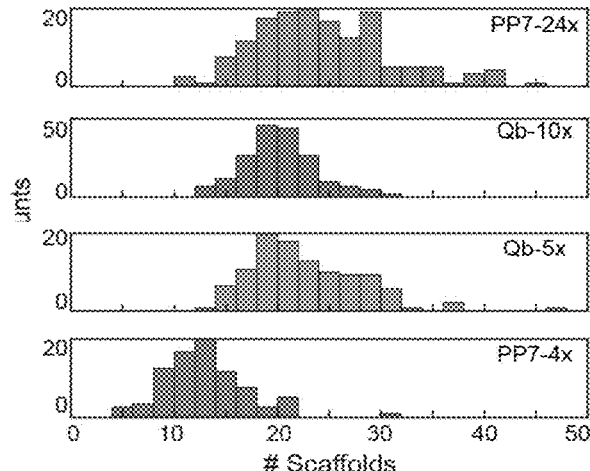
Figure 9E:
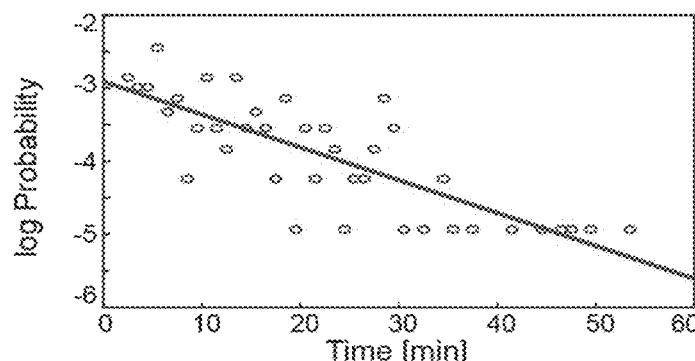
Figure 9F:
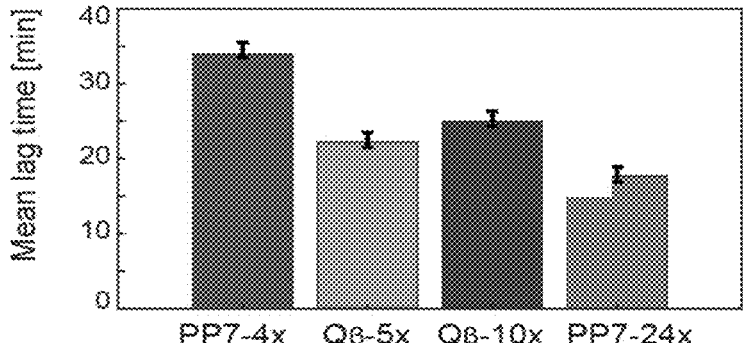
Figure 9G:
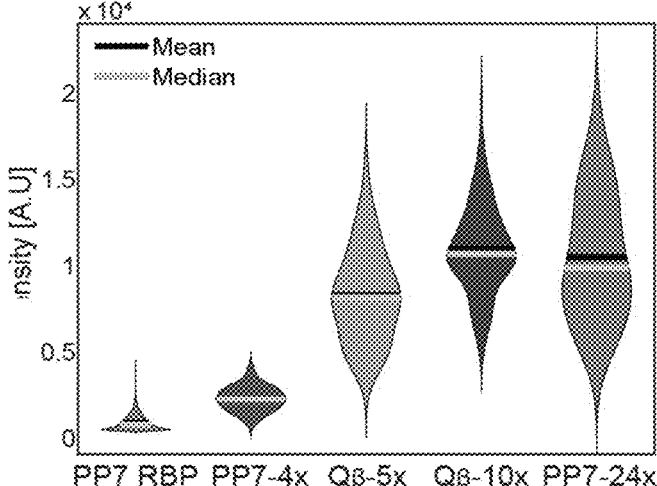
Figure 9H:
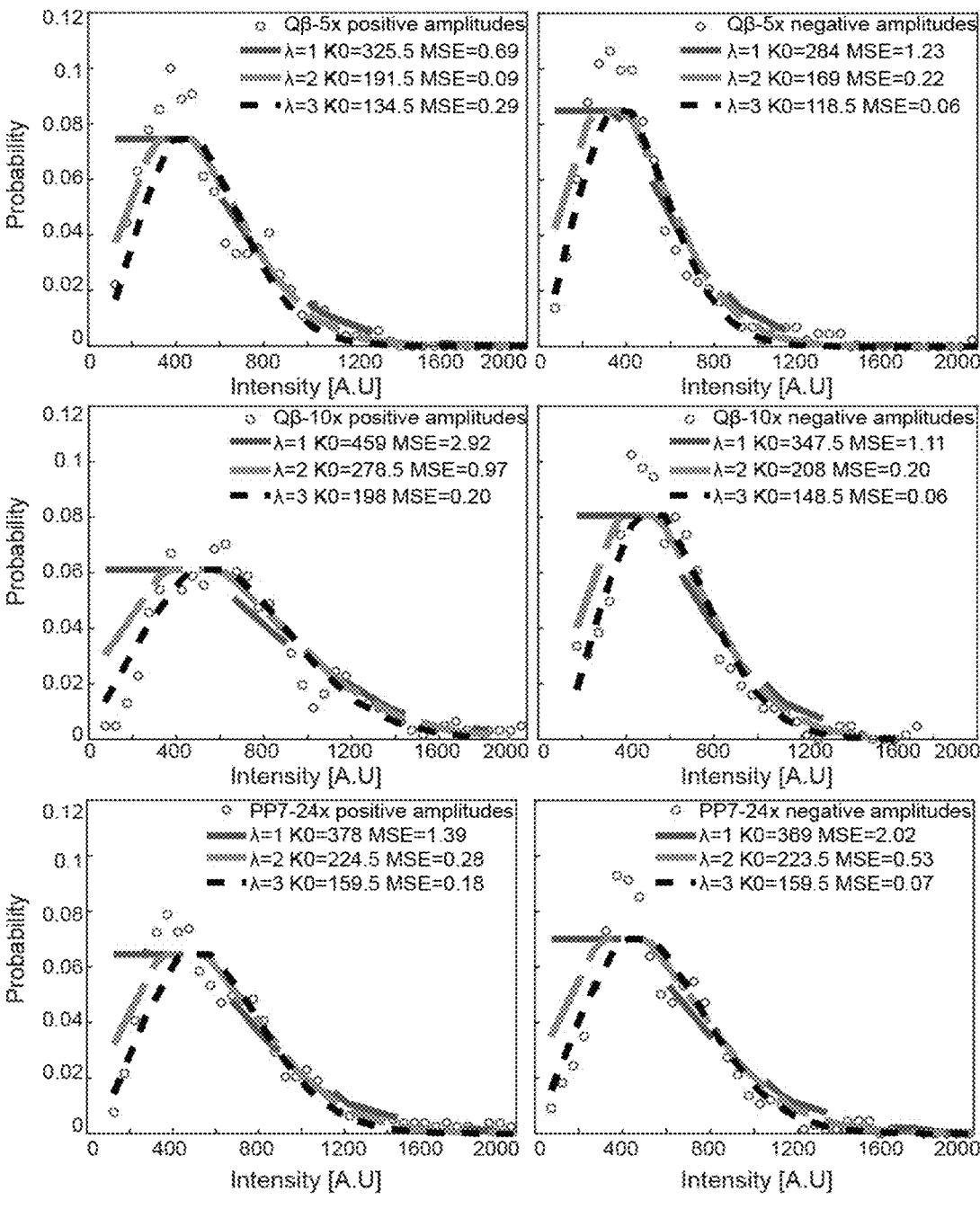

In order to further characterize the shedding and insertion
dynamics occurring between the biocondensate and the
surrounding dilute phase, the number of slncRNA-RBP
complexes that exist within the denser droplet phase was
estimated. To do so, each shedding and insertion event
amplitude distribution was fitted to a Poisson model which
is justified by the uncorrelated occurrence of insertion and
shedding events as a function of time (FIG. 8C). FIG. 9A-B
present a sample fit for the PP7-4x burst amplitude distri-
bution data, with three Poisson functions for λ=1 (red), 2
(green), and 3 (black), corresponding to a mean of 1, 2, and
3 slncRNA-RBP complexes per burst, respectively. The fits
show that while the λ=3 distribution provides the best fit to
the data (corresponding to a mean of three slncRNAs per
burst), the λ=1 distribution provides the best fit to the tail of
the distribution, but fails at lower amplitude values. This
may be due to the analysis threshold that treats many of
these small amplitude events as unclassified. Higher values
of λ provide a progressively worse fit. This analysis was
repeated for the three additional cassette configurations and
computed the estimated intensity per slncRNA-RBP com-
plex (K$_o$) for each slncRNA-type (FIGS. 9A, 9B and 9H).
Both the Poisson fits (FIG. 9C) and empirical distribution
analysis (FIG. 8D) suggest that at least for the range of 4-10
binding sites, the number of sites in a cassette can be
determined by the amplitude distribution at a resolution as
low as a single binding site with a fluorescence signature that
can be estimated to be ~40-60 A.U. Using the single
molecule intensity estimate obtained from the λ=1 approxi-
mation, an estimate was computed for the number of sln-
cRNA-RBP complexes within each punctum, averaged over
the duration of the trace. The distribution of the average
number of complexes per punctum was plotted for each
cassette-RBP pairing (FIG. 9D). The results show that for
the Qβ-5x, Qβ-10x, and PP7-24x slncRNA cassettes puncta
are estimated to contain ~10-30 slncRNA-RBP complexes,
while the puncta for the PP7-4x cassette seem to be com-
prised of about half this number. It is important to note that
when these experiments were repeated with cassettes con-
taining fewer than 4 binding sites the fluorescence was
evenly distributed throughout the cell and puncta did not
form. This indicates that there is a need for at least 4 binding
sites in the cassette in order to induce phase separation.

In the context of liquid-liquid phase-separation, such a
difference between cassettes can occur if the dilute phase
containing the PP7-4x molecules can tolerate a higher
concentration of this slncRNA as compared with the other
slncRNAs (and thus have a higher intensity). This is con-
sistent with the multivalency hypothesis for LLPS, which
suggests that the volume fraction or concentration at which
the LLPS transition occurs could depend strongly on the
number of binding sites in the scaffold molecule. If so, this
then implies that the rate of addition or shedding of a PP7-4x
slncRNA-RBP complex into and from the droplet phase
should be ~×2 faster as compared with the other complexes.
To test this, the time-interval between insertion events for all
four slncRNA-RBP pairs was examined. The time-interval
distributions exhibited an exponential behavior (FIG. 9E),
which is expected from a Markov-type process, as is appar-
ently the case here. However, the average time-intervals
between insertion events for each slncRNA-type (FIG. 9F)
show that contrary to the multivalency model prediction, the
mean time interval between bursts of signal increases for the
PP7-4x cassette was 2× slower as compared with the higher-
valency configurations. To provide further support for this
anomalous observation, the average level of the non-puncta
background signal was directly measured. The result shows
a significantly lower signal intensity for the PP7-4x sln-
cRNA background (FIG. 9G), which is consistent with the
longer mean interval between events observe for this cas-
sette.

In order to accommodate these contradictory findings
within a broader LLPS context, it was hypothesized that the
E. coli cytosol consists of a dense molecular phase in the
central portion of the cell consistent with the location of the
nucleoid, and a dilute molecular phase in the polar regions.

Figure 10A:
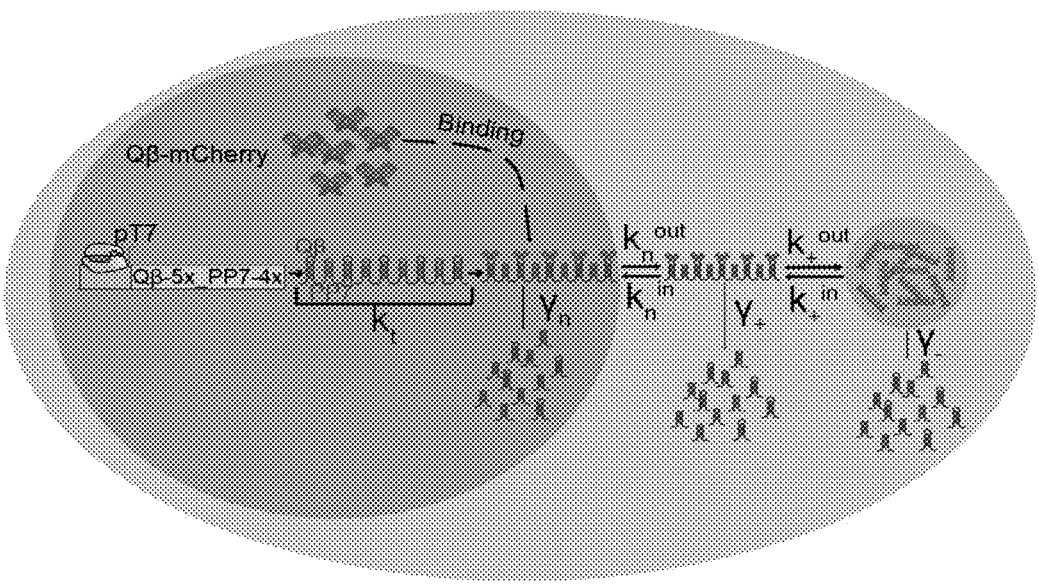
FIGS. 10A-C: Verification of biphasic cytosol hypothesis. (10A) Model showing the effects of the biphasic hypothesis on insertion and shedding of a slncRNA. Parameters: $k_r$ and $\gamma_n$ are the slncRNA transcriptional and degradation rates, $$k_n^{in}, k_n^{out}$$
Figure 10B:
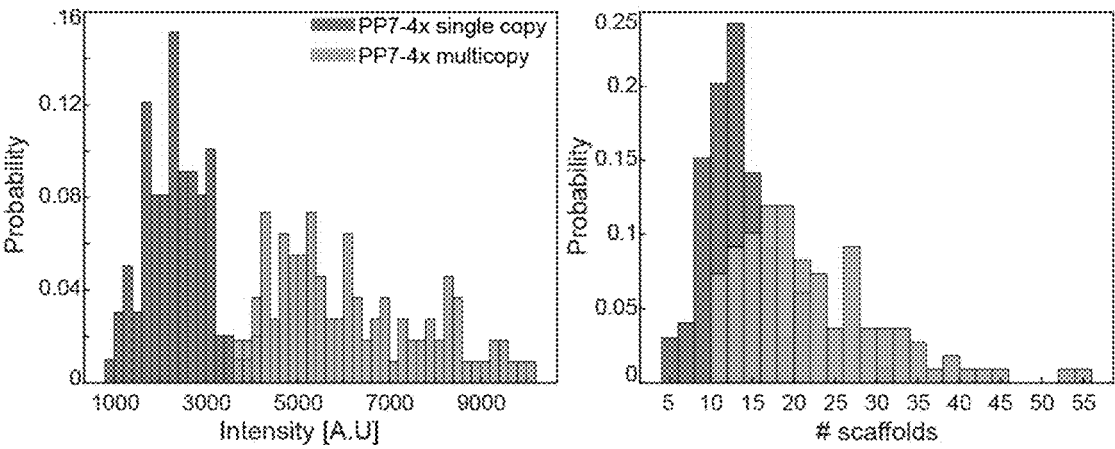
Figure 10C:
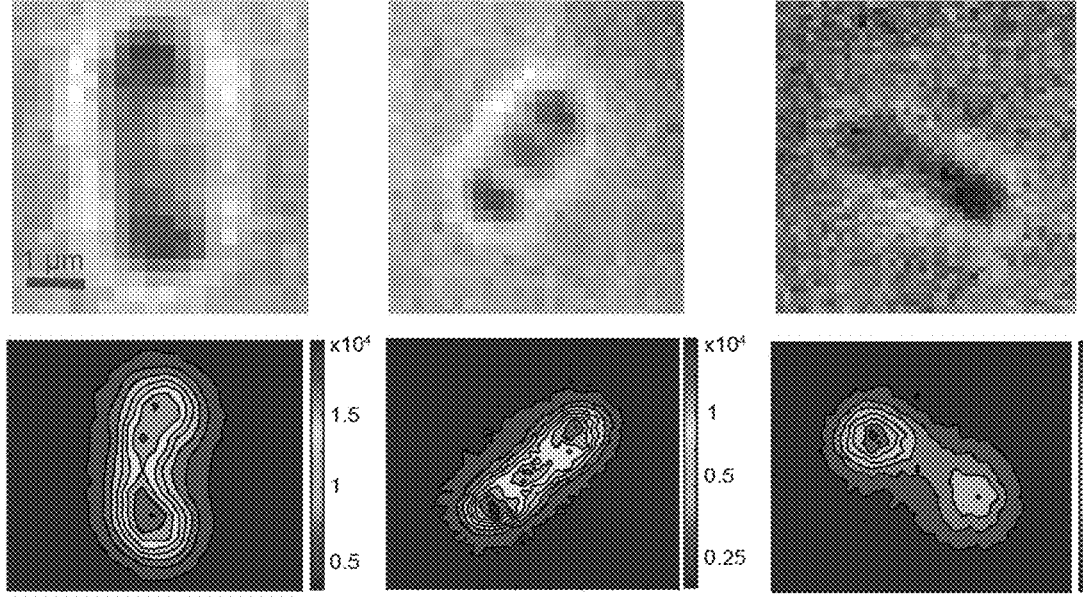

As a result, slncRNAs cannot phase separate and form biocondensates within the dense-nucleoid phase. In contrast, the polar regions of the *E. coli* cell are sufficiently dilute to facilitate formation of biocondensates, as observed in the experiments (FIG. 10A). In this scenario, the dense cytosolic nucleoid phase serves as a reservoir of slncRNA molecules, which when released into the polar regions phase separate into the biocondensate droplets. For the case of PP7-4x, it is assumed that reduced stability of the slncRNA scaffold within the dense nucleoid-region reservoir as compared with the other slncRNAs may lead to a reduced background signal, which in turn leads to a lower mean rate of entry into the droplet and to fewer molecules within the droplet. A possible reason for this instability is misfolding of the scaffold due to the spatial positioning of the occupied binding sites, increasing its vulnerability to degradation. To provide support for the biphasic hypothesis of the bacterial cell, two additional experiments were carried out. In the first, the PP7-4x was expressed on a multicopy plasmid. The purpose of this experiment was to increase the background levels of the cassette, which according to the biphasic model and data from the other slncRNAs is predicted to lead to an increase in the number of cassettes within the biocondensate droplets. As FIG. 10B shows, an increase in both the background signal, and in the number of estimated scaffolds within the puncta to levels similar to the ones observed with the other slncRNAs was indeed witnessed. Further, the cells were grown in starvation conditions for several hours, triggering a transition to stationary phase. In stationary phase the nucleoid is known to condense, thus increasing the amount of cellular volume which is likely to be molecularly dilute. This, in turn, generates a much larger accessible cellular volume for droplet formation, which should lead to different presentation of the phase-separation phenomena as compared with exponentially growing cells. FIG. 10C shows images of bacteria displaying 'bridging' (the formation of a high intensity streak between the spots) of puncta (left), whereby biocondensates seem to fill out the available dilute volume, and the emergence of a third puncta at the center of the cell (center). Both behaviors are substantially different than the puncta appearing under normal conditions (right). Such behavior was observed in >40% of the fluorescent cells and was not detected in non-stationary growth conditions.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

---

The invention claimed is:

1. A synthetic RNA molecule, comprising at least 5 different RNA-binding protein (RBP)-binding motifs, wherein said at least 5 RBP-binding motifs (1) bind the same RBP selected from a phage coat protein selected from PP7 phage coat protein (PCP), QB phage coat protein (QCP) and MS2 phage coat protein (MCP) and (2) comprise non-identical sequences, wherein said RBP is QCP and the at least 5 RBP-binding motifs are QCP-binding motifs selected from the group consisting of SEQ ID NOs 3-102 wherein at least one QCP-binding motif is selected from the group consisting of SEQ ID NOs 3-9, and wherein each non-identical sequence of the at least 5 QCP-binding motifs comprises at least 5 nucleotide differences from all other QCP-binding motifs in the synthetic RNA molecule;

said RBP is MCP and the at least 5 RBP-binding motifs are MCP-binding motifs selected from the group consisting of SEQ ID NOs 103-202 wherein at least one MCP-binding motif is selected from the group consisting of SEQ ID NOs 103-108 and 110, and wherein each non-identical sequence of the at least 5 MCP-binding motifs comprises at least 5 nucleotide differences from all other MCP-binding motifs in the synthetic RNA molecule; or said RBP is PCP and the at least 5 RBP-binding motifs are PCP-binding motifs selected from the group consisting of SEQ ID NOs 203-302 wherein at least one PCP-binding motif is selected from the group consisting of SEQ ID NOs 203-204 and 206-210, and wherein each non-identical sequence of the at least 5 PCP-binding motifs comprises at least 5 nucleotide differences from all other PCP-binding motifs in the synthetic RNA molecule.

2. The synthetic RNA molecule of claim 1, wherein said at least 5 different RBP-binding motifs comprise at least 10 different RBP-binding motifs that all bind the same phage coat protein and all comprise non-identical sequences.

3. The synthetic RNA molecule of claim 1, further comprising at least two different RBP-binding motifs to a second RBP, wherein said RBP and said second RBP are different phage coat proteins selected from PCP, QCP and MCP, and wherein said at least two different RBP-binding motifs to the second RBP comprise a second set of at least 2 non-identical sequences and wherein each RBP-binding motif of said second set of at least 2 non-identical sequences comprises at least 5 nucleotide differences from all other RBP-binding motifs of said second set.

4. The synthetic RNA molecule of claim 3, comprising at least 5 second RBP-binding motifs that bind said second RBP and comprise a second set of at least 5 non-identical sequences, wherein each RBP-binding motif of said second set of at least 5 non-identical sequences comprises at least 5 nucleotide differences from all other RNA-binding motifs of said second set.

5. The synthetic RNA molecule of claim 3, wherein said at least 5 RBP-binding motifs and said at least two second RBP-binding motifs do not overlap with each other.

6. The synthetic RNA molecule of claim 3, further comprising at least two different RBP-binding motifs to a third RBP wherein said at least two different RBP-binding motifs to a third RBP comprise a third set of at least 2 non-identical sequences and wherein each RBP-binding motif of said third set of at least 2 non-identical sequences comprises at least 5 nucleotide differences from all other RBP-binding motifs of said third set, and wherein said RBP is PCP, said second RBP is QCP and said third RBP is MCP.

7. The synthetic RNA molecule of claim 1, wherein said synthetic RNA molecule does not encode a protein.

8. The synthetic RNA molecule of claim 7, wherein said synthetic RNA molecule does not comprise a microRNA (miR) or small interfering RNA (siRNA).

9. The synthetic RNA molecule of claim 8, comprising at least 5 third RBP-binding motifs that bind said third RBP and comprise a third set of at least 5 non-identical sequences, wherein each RBP-binding motif of said third set of at least 5 non-identical sequences comprises at least 5 nucleotide differences from all other RBP-binding motifs of said third set.

* * * * *

SEQUENCE LISTING

```
<160> NUMBER OF SEQ ID NOS: 308

<210> SEQ ID NO 1
<211> LENGTH: 66
<212> TYPE: DNA
<213> ORGANISM: Artificial sequence
<220> FEATURE:
<223> OTHER INFORMATION: Synthetic

<400> SEQUENCE: 1
aattgtgagc gctcacaatt atgatagatt caattggatt aattaaagag gagaaaggta        60
cccatg                                                                   66

<210> SEQ ID NO 2
<211> LENGTH: 238
<212> TYPE: DNA
<213> ORGANISM: Artificial sequence
<220> FEATURE:
<223> OTHER INFORMATION: Synthetic

<400> SEQUENCE: 2
gtgagcaagg gcgaggagga taacatggcc atcatcaagg agttcatgcg cttcaaggtg        60
cacatggagg gctccgtgaa cggccacgag ttcgagatcg agggcgaggg cgagggccgc       120
ccctacgagg gcacccagac cgccaagctg aaggtgacca agggtggccc cctgcccttc       180
gcctgggaca tcctgtcccc tcagttcatg tacggctcca aggcctacgt gaagcacc        238

<210> SEQ ID NO 3
<211> LENGTH: 20
<212> TYPE: RNA
<213> ORGANISM: Artificial sequence
<220> FEATURE:
<223> OTHER INFORMATION: Synthetic

<400> SEQUENCE: 3
auuuacuucu aagaagaaau                                                    20
```

-continued

```
<210> SEQ ID NO 4
<211> LENGTH: 25
<212> TYPE: RNA
<213> ORGANISM: Artificial sequence
<220> FEATURE:
<223> OTHER INFORMATION: Synthetic

<400> SEQUENCE: 4
aaucgagaaa auaugguuuc cgauu                                          25

<210> SEQ ID NO 5
<211> LENGTH: 19
<212> TYPE: RNA
<213> ORGANISM: Artificial sequence
<220> FEATURE:
<223> OTHER INFORMATION: Synthetic

<400> SEQUENCE: 5
gaauaaggau uaccuauuc                                                 19

<210> SEQ ID NO 6
<211> LENGTH: 20
<212> TYPE: RNA
<213> ORGANISM: Artificial sequence
<220> FEATURE:
<223> OTHER INFORMATION: Synthetic

<400> SEQUENCE: 6
uaagacagua uuacugcuua                                                20

<210> SEQ ID NO 7
<211> LENGTH: 25
<212> TYPE: RNA
<213> ORGANISM: Artificial sequence
<220> FEATURE:
<223> OTHER INFORMATION: Synthetic

<400> SEQUENCE: 7
uaaggacuuu auauguaaag ccuua                                          25

<210> SEQ ID NO 8
<211> LENGTH: 19
<212> TYPE: RNA
<213> ORGANISM: Artificial sequence
<220> FEATURE:
<223> OTHER INFORMATION: Synthetic

<400> SEQUENCE: 8
acauaaggau uaccuaugu                                                 19

<210> SEQ ID NO 9
<211> LENGTH: 19
<212> TYPE: RNA
<213> ORGANISM: Artificial sequence
<220> FEATURE:
<223> OTHER INFORMATION: Synthetic

<400> SEQUENCE: 9
ccguaauaau uauauacgg                                                 19

<210> SEQ ID NO 10
<211> LENGTH: 20
<212> TYPE: RNA
<213> ORGANISM: Artificial sequence
<220> FEATURE:
<223> OTHER INFORMATION: Synthetic
```

<400> SEQUENCE: 10
auacaguucu aagaacguau                                                                          20

<210> SEQ ID NO 11
<211> LENGTH: 23
<212> TYPE: RNA
<213> ORGANISM: Artificial sequence
<220> FEATURE:
<223> OTHER INFORMATION: Synthetic

<400> SEQUENCE: 11
aaugcacaug cuaacauggc auu                                                                       23

<210> SEQ ID NO 12
<211> LENGTH: 25
<212> TYPE: RNA
<213> ORGANISM: Artificial sequence
<220> FEATURE:
<223> OTHER INFORMATION: Synthetic

<400> SEQUENCE: 12
aaugcacauu auauggaaug gcauu                                                                     25

<210> SEQ ID NO 13
<211> LENGTH: 25
<212> TYPE: RNA
<213> ORGANISM: Artificial sequence
<220> FEATURE:
<223> OTHER INFORMATION: Synthetic

<400> SEQUENCE: 13
uacagauuuc auaugggaaa cugua                                                                     25

<210> SEQ ID NO 14
<211> LENGTH: 25
<212> TYPE: RNA
<213> ORGANISM: Artificial sequence
<220> FEATURE:
<223> OTHER INFORMATION: Synthetic

<400> SEQUENCE: 14
uaaggaguuu uuauguaaac ccuua                                                                     25

<210> SEQ ID NO 15
<211> LENGTH: 25
<212> TYPE: RNA
<213> ORGANISM: Artificial sequence
<220> FEATURE:
<223> OTHER INFORMATION: Synthetic

<400> SEQUENCE: 15
uaaugaguuu acaucgaaac cauua                                                                     25

<210> SEQ ID NO 16
<211> LENGTH: 25
<212> TYPE: RNA
<213> ORGANISM: Artificial sequence
<220> FEATURE:
<223> OTHER INFORMATION: Synthetic

<400> SEQUENCE: 16
uaaggauuuc gauugggaaa ccuua                                                                     25

<210> SEQ ID NO 17
<211> LENGTH: 20

```
<212> TYPE: RNA
<213> ORGANISM: Artificial sequence
<220> FEATURE:
<223> OTHER INFORMATION: Synthetic

<400> SEQUENCE: 17
aaacaacucu cagaguguuu                                                   20

<210> SEQ ID NO 18
<211> LENGTH: 25
<212> TYPE: RNA
<213> ORGANISM: Artificial sequence
<220> FEATURE:
<223> OTHER INFORMATION: Synthetic

<400> SEQUENCE: 18
uaaccacaau auauggauug gguua                                             25

<210> SEQ ID NO 19
<211> LENGTH: 21
<212> TYPE: RNA
<213> ORGANISM: Artificial sequence
<220> FEATURE:
<223> OTHER INFORMATION: Synthetic

<400> SEQUENCE: 19
aaggauagua augacuaccu u                                                 21

<210> SEQ ID NO 20
<211> LENGTH: 19
<212> TYPE: RNA
<213> ORGANISM: Artificial sequence
<220> FEATURE:
<223> OTHER INFORMATION: Synthetic

<400> SEQUENCE: 20
acauacgaau uaucuaugu                                                    19

<210> SEQ ID NO 21
<211> LENGTH: 25
<212> TYPE: RNA
<213> ORGANISM: Artificial sequence
<220> FEATURE:
<223> OTHER INFORMATION: Synthetic

<400> SEQUENCE: 21
uaucgagauu auauggaauc cgaua                                             25

<210> SEQ ID NO 22
<211> LENGTH: 25
<212> TYPE: RNA
<213> ORGANISM: Artificial sequence
<220> FEATURE:
<223> OTHER INFORMATION: Synthetic

<400> SEQUENCE: 22
uaaggcaauu auaccgaauu ccuua                                             25

<210> SEQ ID NO 23
<211> LENGTH: 21
<212> TYPE: RNA
<213> ORGANISM: Artificial sequence
<220> FEATURE:
<223> OTHER INFORMATION: Synthetic
```

-continued

```
<400> SEQUENCE: 23
acaugacgga uuaccgcaug u                                          21

<210> SEQ ID NO 24
<211> LENGTH: 25
<212> TYPE: RNA
<213> ORGANISM: Artificial sequence
<220> FEATURE:
<223> OTHER INFORMATION: Synthetic

<400> SEQUENCE: 24
aaaguuguuu auguggaaac acuuu                                      25

<210> SEQ ID NO 25
<211> LENGTH: 20
<212> TYPE: RNA
<213> ORGANISM: Artificial sequence
<220> FEATURE:
<223> OTHER INFORMATION: Synthetic

<400> SEQUENCE: 25
auccauguca aagacaggau                                           20

<210> SEQ ID NO 26
<211> LENGTH: 25
<212> TYPE: RNA
<213> ORGANISM: Artificial sequence
<220> FEATURE:
<223> OTHER INFORMATION: Synthetic

<400> SEQUENCE: 26
uaaggaguuu cacaguaaac ccuua                                      25

<210> SEQ ID NO 27
<211> LENGTH: 20
<212> TYPE: RNA
<213> ORGANISM: Artificial sequence
<220> FEATURE:
<223> OTHER INFORMATION: Synthetic

<400> SEQUENCE: 27
aguuauugcu aagcaaaacu                                           20

<210> SEQ ID NO 28
<211> LENGTH: 25
<212> TYPE: RNA
<213> ORGANISM: Artificial sequence
<220> FEATURE:
<223> OTHER INFORMATION: Synthetic

<400> SEQUENCE: 28
auacgagaau auauggauuc cguau                                      25

<210> SEQ ID NO 29
<211> LENGTH: 25
<212> TYPE: RNA
<213> ORGANISM: Artificial sequence
<220> FEATURE:
<223> OTHER INFORMATION: Synthetic

<400> SEQUENCE: 29
uaaggaguuu ugucggaaac ccuua                                      25

<210> SEQ ID NO 30
```

-continued

```
<211> LENGTH: 25
<212> TYPE: RNA
<213> ORGANISM: Artificial sequence
<220> FEATURE:
<223> OTHER INFORMATION: Synthetic

<400> SEQUENCE: 30
augucaaaug cuuaaacauu gacau                                          25

<210> SEQ ID NO 31
<211> LENGTH: 25
<212> TYPE: RNA
<213> ORGANISM: Artificial sequence
<220> FEATURE:
<223> OTHER INFORMATION: Synthetic

<400> SEQUENCE: 31
uaagcacaua auaugguaug gcuua                                          25

<210> SEQ ID NO 32
<211> LENGTH: 25
<212> TYPE: RNA
<213> ORGANISM: Artificial sequence
<220> FEATURE:
<223> OTHER INFORMATION: Synthetic

<400> SEQUENCE: 32
uaaggcguuu ggcucuaaac ccuua                                          25

<210> SEQ ID NO 33
<211> LENGTH: 20
<212> TYPE: RNA
<213> ORGANISM: Artificial sequence
<220> FEATURE:
<223> OTHER INFORMATION: Synthetic

<400> SEQUENCE: 33
uuggaugucc aagacaccaa                                                20

<210> SEQ ID NO 34
<211> LENGTH: 20
<212> TYPE: RNA
<213> ORGANISM: Artificial sequence
<220> FEATURE:
<223> OTHER INFORMATION: Synthetic

<400> SEQUENCE: 34
auacauugau aaucaaguau                                                20

<210> SEQ ID NO 35
<211> LENGTH: 25
<212> TYPE: RNA
<213> ORGANISM: Artificial sequence
<220> FEATURE:
<223> OTHER INFORMATION: Synthetic

<400> SEQUENCE: 35
aauggacaaa auaugguuug ccauu                                          25

<210> SEQ ID NO 36
<211> LENGTH: 25
<212> TYPE: RNA
<213> ORGANISM: Artificial sequence
<220> FEATURE:
<223> OTHER INFORMATION: Synthetic
```

-continued

```
<400> SEQUENCE: 36
uaagcacagu aucaggacug gcuua                                        25

<210> SEQ ID NO 37
<211> LENGTH: 18
<212> TYPE: RNA
<213> ORGANISM: Artificial sequence
<220> FEATURE:
<223> OTHER INFORMATION: Synthetic

<400> SEQUENCE: 37
uaaggaggua gccccuua                                                18

<210> SEQ ID NO 38
<211> LENGTH: 22
<212> TYPE: RNA
<213> ORGANISM: Artificial sequence
<220> FEATURE:
<223> OTHER INFORMATION: Synthetic

<400> SEQUENCE: 38
acaugacgag auacucgcau gu                                           22

<210> SEQ ID NO 39
<211> LENGTH: 25
<212> TYPE: RNA
<213> ORGANISM: Artificial sequence
<220> FEATURE:
<223> OTHER INFORMATION: Synthetic

<400> SEQUENCE: 39
uaaggaguuu uuugacaaac ccuua                                        25

<210> SEQ ID NO 40
<211> LENGTH: 25
<212> TYPE: RNA
<213> ORGANISM: Artificial sequence
<220> FEATURE:
<223> OTHER INFORMATION: Synthetic

<400> SEQUENCE: 40
uaagguguuu ucuaccaaac ccuua                                        25

<210> SEQ ID NO 41
<211> LENGTH: 25
<212> TYPE: RNA
<213> ORGANISM: Artificial sequence
<220> FEATURE:
<223> OTHER INFORMATION: Synthetic

<400> SEQUENCE: 41
uaagguguuu aagguuaaac ccuua                                        25

<210> SEQ ID NO 42
<211> LENGTH: 25
<212> TYPE: RNA
<213> ORGANISM: Artificial sequence
<220> FEATURE:
<223> OTHER INFORMATION: Synthetic

<400> SEQUENCE: 42
uacagaacuu auauggaagu cugua                                        25

<210> SEQ ID NO 43
```

-continued

```
<211> LENGTH: 19
<212> TYPE: RNA
<213> ORGANISM: Artificial sequence
<220> FEATURE:
<223> OTHER INFORMATION: Synthetic

<400> SEQUENCE: 43
gcuauaggau ugccauagc                                          19

<210> SEQ ID NO 44
<211> LENGTH: 20
<212> TYPE: RNA
<213> ORGANISM: Artificial sequence
<220> FEATURE:
<223> OTHER INFORMATION: Synthetic

<400> SEQUENCE: 44
auacaugugc uacacaguau                                         20

<210> SEQ ID NO 45
<211> LENGTH: 20
<212> TYPE: RNA
<213> ORGANISM: Artificial sequence
<220> FEATURE:
<223> OTHER INFORMATION: Synthetic

<400> SEQUENCE: 45
auguaugucc aagacaacau                                         20

<210> SEQ ID NO 46
<211> LENGTH: 20
<212> TYPE: RNA
<213> ORGANISM: Artificial sequence
<220> FEATURE:
<223> OTHER INFORMATION: Synthetic

<400> SEQUENCE: 46
uugcaugucg aagacagcaa                                         20

<210> SEQ ID NO 47
<211> LENGTH: 25
<212> TYPE: RNA
<213> ORGANISM: Artificial sequence
<220> FEATURE:
<223> OTHER INFORMATION: Synthetic

<400> SEQUENCE: 47
uaaaaauuuu aucagcaaaa uuuua                                   25

<210> SEQ ID NO 48
<211> LENGTH: 25
<212> TYPE: RNA
<213> ORGANISM: Artificial sequence
<220> FEATURE:
<223> OTHER INFORMATION: Synthetic

<400> SEQUENCE: 48
auacgagauu auauggaauc cguau                                   25

<210> SEQ ID NO 49
<211> LENGTH: 19
<212> TYPE: RNA
<213> ORGANISM: Artificial sequence
<220> FEATURE:
<223> OTHER INFORMATION: Synthetic
```

-continued

<400> SEQUENCE: 49
aguacacgau uacgguacu                                                                                      19

<210> SEQ ID NO 50
<211> LENGTH: 25
<212> TYPE: RNA
<213> ORGANISM: Artificial sequence
<220> FEATURE:
<223> OTHER INFORMATION: Synthetic

<400> SEQUENCE: 50
aaaggucuuu auguggaaag ccuuu                                                                                25

<210> SEQ ID NO 51
<211> LENGTH: 25
<212> TYPE: RNA
<213> ORGANISM: Artificial sequence
<220> FEATURE:
<223> OTHER INFORMATION: Synthetic

<400> SEQUENCE: 51
gaagaauuug auauggcaaa ucuuc                                                                                25

<210> SEQ ID NO 52
<211> LENGTH: 25
<212> TYPE: RNA
<213> ORGANISM: Artificial sequence
<220> FEATURE:
<223> OTHER INFORMATION: Synthetic

<400> SEQUENCE: 52
uaaggcguuu uuuaagaaac ccuua                                                                                25

<210> SEQ ID NO 53
<211> LENGTH: 19
<212> TYPE: RNA
<213> ORGANISM: Artificial sequence
<220> FEATURE:
<223> OTHER INFORMATION: Synthetic

<400> SEQUENCE: 53
uguacacgau uacgguaca                                                                                       19

<210> SEQ ID NO 54
<211> LENGTH: 20
<212> TYPE: RNA
<213> ORGANISM: Artificial sequence
<220> FEATURE:
<223> OTHER INFORMATION: Synthetic

<400> SEQUENCE: 54
aacgaugucu aagacacguu                                                                                      20

<210> SEQ ID NO 55
<211> LENGTH: 25
<212> TYPE: RNA
<213> ORGANISM: Artificial sequence
<220> FEATURE:
<223> OTHER INFORMATION: Synthetic

<400> SEQUENCE: 55
uaucgacaaa auaugguuug cgaua                                                                                25

<210> SEQ ID NO 56

-continued

```
<211> LENGTH: 19
<212> TYPE: RNA
<213> ORGANISM: Artificial sequence
<220> FEATURE:
<223> OTHER INFORMATION: Synthetic

<400> SEQUENCE: 56
acuacaccau uaggguagu                                                   19

<210> SEQ ID NO 57
<211> LENGTH: 25
<212> TYPE: RNA
<213> ORGANISM: Artificial sequence
<220> FEATURE:
<223> OTHER INFORMATION: Synthetic

<400> SEQUENCE: 57
auugcacuuu auauggaaag gcaau                                            25

<210> SEQ ID NO 58
<211> LENGTH: 22
<212> TYPE: RNA
<213> ORGANISM: Artificial sequence
<220> FEATURE:
<223> OTHER INFORMATION: Synthetic

<400> SEQUENCE: 58
auagcauguc uaagacagcu au                                               22

<210> SEQ ID NO 59
<211> LENGTH: 20
<212> TYPE: RNA
<213> ORGANISM: Artificial sequence
<220> FEATURE:
<223> OTHER INFORMATION: Synthetic

<400> SEQUENCE: 59
gugaauaucu aagauaucac                                                  20

<210> SEQ ID NO 60
<211> LENGTH: 20
<212> TYPE: RNA
<213> ORGANISM: Artificial sequence
<220> FEATURE:
<223> OTHER INFORMATION: Synthetic

<400> SEQUENCE: 60
guuuacuucu aagaagaaac                                                  20

<210> SEQ ID NO 61
<211> LENGTH: 19
<212> TYPE: RNA
<213> ORGANISM: Artificial sequence
<220> FEATURE:
<223> OTHER INFORMATION: Synthetic

<400> SEQUENCE: 61
acauaguauu gauacaugu                                                   19

<210> SEQ ID NO 62
<211> LENGTH: 25
<212> TYPE: RNA
<213> ORGANISM: Artificial sequence
<220> FEATURE:
<223> OTHER INFORMATION: Synthetic
```

-continued

<400> SEQUENCE: 62
uaacgacaau auauggauug cguua                                                                              25

<210> SEQ ID NO 63
<211> LENGTH: 25
<212> TYPE: RNA
<213> ORGANISM: Artificial sequence
<220> FEATURE:
<223> OTHER INFORMATION: Synthetic

<400> SEQUENCE: 63
acaugaagaa cauuaauucu caugu                                                                              25

<210> SEQ ID NO 64
<211> LENGTH: 20
<212> TYPE: RNA
<213> ORGANISM: Artificial sequence
<220> FEATURE:
<223> OTHER INFORMATION: Synthetic

<400> SEQUENCE: 64
uagcaagacu aagucugcua                                                                                   20

<210> SEQ ID NO 65
<211> LENGTH: 20
<212> TYPE: RNA
<213> ORGANISM: Artificial sequence
<220> FEATURE:
<223> OTHER INFORMATION: Synthetic

<400> SEQUENCE: 65
augcauguca aagacagcau                                                                                   20

<210> SEQ ID NO 66
<211> LENGTH: 20
<212> TYPE: RNA
<213> ORGANISM: Artificial sequence
<220> FEATURE:
<223> OTHER INFORMATION: Synthetic

<400> SEQUENCE: 66
augcauugca aagcaagcau                                                                                   20

<210> SEQ ID NO 67
<211> LENGTH: 25
<212> TYPE: RNA
<213> ORGANISM: Artificial sequence
<220> FEATURE:
<223> OTHER INFORMATION: Synthetic

<400> SEQUENCE: 67
uaaggaguuu guuuguaaac ccuua                                                                              25

<210> SEQ ID NO 68
<211> LENGTH: 25
<212> TYPE: RNA
<213> ORGANISM: Artificial sequence
<220> FEATURE:
<223> OTHER INFORMATION: Synthetic

<400> SEQUENCE: 68
uaaggaguuu aaguuuaaac ccuua                                                                              25

<210> SEQ ID NO 69

```
<211> LENGTH: 25
<212> TYPE: RNA
<213> ORGANISM: Artificial sequence
<220> FEATURE:
<223> OTHER INFORMATION: Synthetic

<400> SEQUENCE: 69
uacggagucc auaugggggac ccgua                                          25

<210> SEQ ID NO 70
<211> LENGTH: 23
<212> TYPE: RNA
<213> ORGANISM: Artificial sequence
<220> FEATURE:
<223> OTHER INFORMATION: Synthetic

<400> SEQUENCE: 70
uaaggaguuu auggaaaccc uua                                             23

<210> SEQ ID NO 71
<211> LENGTH: 20
<212> TYPE: RNA
<213> ORGANISM: Artificial sequence
<220> FEATURE:
<223> OTHER INFORMATION: Synthetic

<400> SEQUENCE: 71
aaacaugucu gagacaguuu                                                 20

<210> SEQ ID NO 72
<211> LENGTH: 25
<212> TYPE: RNA
<213> ORGANISM: Artificial sequence
<220> FEATURE:
<223> OTHER INFORMATION: Synthetic

<400> SEQUENCE: 72
uaagcaaagu acaucuacuu gcuua                                           25

<210> SEQ ID NO 73
<211> LENGTH: 25
<212> TYPE: RNA
<213> ORGANISM: Artificial sequence
<220> FEATURE:
<223> OTHER INFORMATION: Synthetic

<400> SEQUENCE: 73
aaugcacaau auauggauug gcauu                                           25

<210> SEQ ID NO 74
<211> LENGTH: 19
<212> TYPE: RNA
<213> ORGANISM: Artificial sequence
<220> FEATURE:
<223> OTHER INFORMATION: Synthetic

<400> SEQUENCE: 74
agaugauaau uguacaucu                                                  19

<210> SEQ ID NO 75
<211> LENGTH: 25
<212> TYPE: RNA
<213> ORGANISM: Artificial sequence
<220> FEATURE:
<223> OTHER INFORMATION: Synthetic
```

-continued

<400> SEQUENCE: 75
aaaccagaau auauggauuc gguuu                                    25

<210> SEQ ID NO 76
<211> LENGTH: 23
<212> TYPE: RNA
<213> ORGANISM: Artificial sequence
<220> FEATURE:
<223> OTHER INFORMATION: Synthetic

<400> SEQUENCE: 76
uaaggauuua uauggaaccc uua                                      23

<210> SEQ ID NO 77
<211> LENGTH: 25
<212> TYPE: RNA
<213> ORGANISM: Artificial sequence
<220> FEATURE:
<223> OTHER INFORMATION: Synthetic

<400> SEQUENCE: 77
aaaggcguug auauggcaac ccuuu                                    25

<210> SEQ ID NO 78
<211> LENGTH: 20
<212> TYPE: RNA
<213> ORGANISM: Artificial sequence
<220> FEATURE:
<223> OTHER INFORMATION: Synthetic

<400> SEQUENCE: 78
uugcgagucc aagacugcaa                                          20

<210> SEQ ID NO 79
<211> LENGTH: 25
<212> TYPE: RNA
<213> ORGANISM: Artificial sequence
<220> FEATURE:
<223> OTHER INFORMATION: Synthetic

<400> SEQUENCE: 79
aaacgagauu auauggaauc cguuu                                    25

<210> SEQ ID NO 80
<211> LENGTH: 23
<212> TYPE: RNA
<213> ORGANISM: Artificial sequence
<220> FEATURE:
<223> OTHER INFORMATION: Synthetic

<400> SEQUENCE: 80
uaaggauuua uauggaaacc uua                                      23

<210> SEQ ID NO 81
<211> LENGTH: 25
<212> TYPE: RNA
<213> ORGANISM: Artificial sequence
<220> FEATURE:
<223> OTHER INFORMATION: Synthetic

<400> SEQUENCE: 81
uuagcacaau auauggauug gcuaa                                    25

<210> SEQ ID NO 82

-continued

```
<211> LENGTH: 25
<212> TYPE: RNA
<213> ORGANISM: Artificial sequence
<220> FEATURE:
<223> OTHER INFORMATION: Synthetic

<400> SEQUENCE: 82
gauugauuuu auguacaaaa caauc                                        25

<210> SEQ ID NO 83
<211> LENGTH: 20
<212> TYPE: RNA
<213> ORGANISM: Artificial sequence
<220> FEATURE:
<223> OTHER INFORMATION: Synthetic

<400> SEQUENCE: 83
aaagauguca aagacacuuu                                              20

<210> SEQ ID NO 84
<211> LENGTH: 20
<212> TYPE: RNA
<213> ORGANISM: Artificial sequence
<220> FEATURE:
<223> OTHER INFORMATION: Synthetic

<400> SEQUENCE: 84
aaggaacugu aacaguccuu                                              20

<210> SEQ ID NO 85
<211> LENGTH: 20
<212> TYPE: RNA
<213> ORGANISM: Artificial sequence
<220> FEATURE:
<223> OTHER INFORMATION: Synthetic

<400> SEQUENCE: 85
augcaagacu gagucugcau                                              20

<210> SEQ ID NO 86
<211> LENGTH: 19
<212> TYPE: RNA
<213> ORGANISM: Artificial sequence
<220> FEATURE:
<223> OTHER INFORMATION: Synthetic

<400> SEQUENCE: 86
auuugaguaa uuaccaaau                                               19

<210> SEQ ID NO 87
<211> LENGTH: 25
<212> TYPE: RNA
<213> ORGANISM: Artificial sequence
<220> FEATURE:
<223> OTHER INFORMATION: Synthetic

<400> SEQUENCE: 87
uaagggguuu ucucggaaac ccuua                                        25

<210> SEQ ID NO 88
<211> LENGTH: 20
<212> TYPE: RNA
<213> ORGANISM: Artificial sequence
<220> FEATURE:
<223> OTHER INFORMATION: Synthetic
```

```
<400> SEQUENCE: 88
guucagaucu aagaucgaac                                                    20

<210> SEQ ID NO 89
<211> LENGTH: 25
<212> TYPE: RNA
<213> ORGANISM: Artificial sequence
<220> FEATURE:
<223> OTHER INFORMATION: Synthetic

<400> SEQUENCE: 89
uaacgagaaa auaucauuuc cguua                                              25

<210> SEQ ID NO 90
<211> LENGTH: 22
<212> TYPE: RNA
<213> ORGANISM: Artificial sequence
<220> FEATURE:
<223> OTHER INFORMATION: Synthetic

<400> SEQUENCE: 90
acaugauacg auacguacau gu                                                 22

<210> SEQ ID NO 91
<211> LENGTH: 19
<212> TYPE: RNA
<213> ORGANISM: Artificial sequence
<220> FEATURE:
<223> OTHER INFORMATION: Synthetic

<400> SEQUENCE: 91
agauauccau ucgguaucu                                                     19

<210> SEQ ID NO 92
<211> LENGTH: 20
<212> TYPE: RNA
<213> ORGANISM: Artificial sequence
<220> FEATURE:
<223> OTHER INFORMATION: Synthetic

<400> SEQUENCE: 92
aucgaacucu aagagucgau                                                    20

<210> SEQ ID NO 93
<211> LENGTH: 25
<212> TYPE: RNA
<213> ORGANISM: Artificial sequence
<220> FEATURE:
<223> OTHER INFORMATION: Synthetic

<400> SEQUENCE: 93
uuugcacaua auaugguaug gcaaa                                              25

<210> SEQ ID NO 94
<211> LENGTH: 25
<212> TYPE: RNA
<213> ORGANISM: Artificial sequence
<220> FEATURE:
<223> OTHER INFORMATION: Synthetic

<400> SEQUENCE: 94
uaaggaguuu ggcauaaaac ccuua                                              25

<210> SEQ ID NO 95
```

-continued

```
<211> LENGTH: 25
<212> TYPE: RNA
<213> ORGANISM: Artificial sequence
<220> FEATURE:
<223> OTHER INFORMATION: Synthetic

<400> SEQUENCE: 95
uaaggaguuu guauguaaac ccuua                                         25

<210> SEQ ID NO 96
<211> LENGTH: 25
<212> TYPE: RNA
<213> ORGANISM: Artificial sequence
<220> FEATURE:
<223> OTHER INFORMATION: Synthetic

<400> SEQUENCE: 96
uaugcacaau auauggauug gcaua                                         25

<210> SEQ ID NO 97
<211> LENGTH: 19
<212> TYPE: RNA
<213> ORGANISM: Artificial sequence
<220> FEATURE:
<223> OTHER INFORMATION: Synthetic

<400> SEQUENCE: 97
cacugagaau uauccagug                                                19

<210> SEQ ID NO 98
<211> LENGTH: 27
<212> TYPE: RNA
<213> ORGANISM: Artificial sequence
<220> FEATURE:
<223> OTHER INFORMATION: Synthetic

<400> SEQUENCE: 98
uaaggaaguu uauauggaaa cuccuua                                       27

<210> SEQ ID NO 99
<211> LENGTH: 20
<212> TYPE: RNA
<213> ORGANISM: Artificial sequence
<220> FEATURE:
<223> OTHER INFORMATION: Synthetic

<400> SEQUENCE: 99
ggucagaucu aagaucgacc                                               20

<210> SEQ ID NO 100
<211> LENGTH: 25
<212> TYPE: RNA
<213> ORGANISM: Artificial sequence
<220> FEATURE:
<223> OTHER INFORMATION: Synthetic

<400> SEQUENCE: 100
uacggauuuu ugauagaaaa ccgua                                         25

<210> SEQ ID NO 101
<211> LENGTH: 20
<212> TYPE: RNA
<213> ORGANISM: Artificial sequence
<220> FEATURE:
<223> OTHER INFORMATION: Synthetic
```

-continued

<400> SEQUENCE: 101
uucgaugacu aagucacgaa                                              20

<210> SEQ ID NO 102
<211> LENGTH: 19
<212> TYPE: RNA
<213> ORGANISM: Artificial sequence
<220> FEATURE:
<223> OTHER INFORMATION: Synthetic

<400> SEQUENCE: 102
aguacaggau uaccguacu                                              19

<210> SEQ ID NO 103
<211> LENGTH: 19
<212> TYPE: RNA
<213> ORGANISM: Artificial sequence
<220> FEATURE:
<223> OTHER INFORMATION: Synthetic

<400> SEQUENCE: 103
acgcaugagg aacaccaau                                              19

<210> SEQ ID NO 104
<211> LENGTH: 19
<212> TYPE: RNA
<213> ORGANISM: Artificial sequence
<220> FEATURE:
<223> OTHER INFORMATION: Synthetic

<400> SEQUENCE: 104
acaugagcau cagccaugg                                              19

<210> SEQ ID NO 105
<211> LENGTH: 19
<212> TYPE: RNA
<213> ORGANISM: Artificial sequence
<220> FEATURE:
<223> OTHER INFORMATION: Synthetic

<400> SEQUENCE: 105
acauaaggau uaccuaugu                                              19

<210> SEQ ID NO 106
<211> LENGTH: 19
<212> TYPE: RNA
<213> ORGANISM: Artificial sequence
<220> FEATURE:
<223> OTHER INFORMATION: Synthetic

<400> SEQUENCE: 106
gcaugagaac cauccaugu                                              19

<210> SEQ ID NO 107
<211> LENGTH: 19
<212> TYPE: RNA
<213> ORGANISM: Artificial sequence
<220> FEATURE:
<223> OTHER INFORMATION: Synthetic

<400> SEQUENCE: 107
ugaagacgau uacgcuuca                                              19

<210> SEQ ID NO 108

-continued

```
<211> LENGTH: 19
<212> TYPE: RNA
<213> ORGANISM: Artificial sequence
<220> FEATURE:
<223> OTHER INFORMATION: Synthetic

<400> SEQUENCE: 108
acgugaggau cacccacgg                                          19

<210> SEQ ID NO 109
<211> LENGTH: 19
<212> TYPE: RNA
<213> ORGANISM: Artificial sequence
<220> FEATURE:
<223> OTHER INFORMATION: Synthetic

<400> SEQUENCE: 109
acaugaggau uacccaugu                                          19

<210> SEQ ID NO 110
<211> LENGTH: 19
<212> TYPE: RNA
<213> ORGANISM: Artificial sequence
<220> FEATURE:
<223> OTHER INFORMATION: Synthetic

<400> SEQUENCE: 110
acgugaggau cacccacgc                                          19

<210> SEQ ID NO 111
<211> LENGTH: 19
<212> TYPE: RNA
<213> ORGANISM: Artificial sequence
<220> FEATURE:
<223> OTHER INFORMATION: Synthetic

<400> SEQUENCE: 111
acgagacgau cacgcucgu                                          19

<210> SEQ ID NO 112
<211> LENGTH: 19
<212> TYPE: RNA
<213> ORGANISM: Artificial sequence
<220> FEATURE:
<223> OTHER INFORMATION: Synthetic

<400> SEQUENCE: 112
aguugaccau uaggcaacu                                          19

<210> SEQ ID NO 113
<211> LENGTH: 19
<212> TYPE: RNA
<213> ORGANISM: Artificial sequence
<220> FEATURE:
<223> OTHER INFORMATION: Synthetic

<400> SEQUENCE: 113
acgugaggau cacccacgu                                          19

<210> SEQ ID NO 114
<211> LENGTH: 18
<212> TYPE: RNA
<213> ORGANISM: Artificial sequence
<220> FEATURE:
<223> OTHER INFORMATION: Synthetic
```

-continued

```
<400> SEQUENCE: 114
uaaggaauuu gauccuua                                              18

<210> SEQ ID NO 115
<211> LENGTH: 19
<212> TYPE: RNA
<213> ORGANISM: Artificial sequence
<220> FEATURE:
<223> OTHER INFORMATION: Synthetic

<400> SEQUENCE: 115
acacgaggau cacccgugc                                            19

<210> SEQ ID NO 116
<211> LENGTH: 19
<212> TYPE: RNA
<213> ORGANISM: Artificial sequence
<220> FEATURE:
<223> OTHER INFORMATION: Synthetic

<400> SEQUENCE: 116
acuuaaggau caccuaagu                                            19

<210> SEQ ID NO 117
<211> LENGTH: 19
<212> TYPE: RNA
<213> ORGANISM: Artificial sequence
<220> FEATURE:
<223> OTHER INFORMATION: Synthetic

<400> SEQUENCE: 117
ggaugaggau cacccaucu                                            19

<210> SEQ ID NO 118
<211> LENGTH: 19
<212> TYPE: RNA
<213> ORGANISM: Artificial sequence
<220> FEATURE:
<223> OTHER INFORMATION: Synthetic

<400> SEQUENCE: 118
cgaugaggau cacccaucu                                            19

<210> SEQ ID NO 119
<211> LENGTH: 19
<212> TYPE: RNA
<213> ORGANISM: Artificial sequence
<220> FEATURE:
<223> OTHER INFORMATION: Synthetic

<400> SEQUENCE: 119
acaacacgau uacgguugu                                            19

<210> SEQ ID NO 120
<211> LENGTH: 19
<212> TYPE: RNA
<213> ORGANISM: Artificial sequence
<220> FEATURE:
<223> OTHER INFORMATION: Synthetic

<400> SEQUENCE: 120
agaacacgau uacgguucu                                            19

<210> SEQ ID NO 121
```

```
<211> LENGTH: 19
<212> TYPE: RNA
<213> ORGANISM: Artificial sequence
<220> FEATURE:
<223> OTHER INFORMATION: Synthetic

<400> SEQUENCE: 121
agaugaggau cacccaucu                                              19

<210> SEQ ID NO 122
<211> LENGTH: 19
<212> TYPE: RNA
<213> ORGANISM: Artificial sequence
<220> FEATURE:
<223> OTHER INFORMATION: Synthetic

<400> SEQUENCE: 122
acuacaggac uaccguagu                                              19

<210> SEQ ID NO 123
<211> LENGTH: 17
<212> TYPE: RNA
<213> ORGANISM: Artificial sequence
<220> FEATURE:
<223> OTHER INFORMATION: Synthetic

<400> SEQUENCE: 123
acauaggauu accaugu                                                17

<210> SEQ ID NO 124
<211> LENGTH: 19
<212> TYPE: RNA
<213> ORGANISM: Artificial sequence
<220> FEATURE:
<223> OTHER INFORMATION: Synthetic

<400> SEQUENCE: 124
agaagaccau uaggcuucu                                              19

<210> SEQ ID NO 125
<211> LENGTH: 19
<212> TYPE: RNA
<213> ORGANISM: Artificial sequence
<220> FEATURE:
<223> OTHER INFORMATION: Synthetic

<400> SEQUENCE: 125
gcuugaggau cacccaagu                                              19

<210> SEQ ID NO 126
<211> LENGTH: 19
<212> TYPE: RNA
<213> ORGANISM: Artificial sequence
<220> FEATURE:
<223> OTHER INFORMATION: Synthetic

<400> SEQUENCE: 126
agaucaccau uagggaucu                                              19

<210> SEQ ID NO 127
<211> LENGTH: 19
<212> TYPE: RNA
<213> ORGANISM: Artificial sequence
<220> FEATURE:
<223> OTHER INFORMATION: Synthetic
```

-continued

<400> SEQUENCE: 127
aguugagcau uagccaacu                                                          19

<210> SEQ ID NO 128
<211> LENGTH: 19
<212> TYPE: RNA
<213> ORGANISM: Artificial sequence
<220> FEATURE:
<223> OTHER INFORMATION: Synthetic

<400> SEQUENCE: 128
agaugaggau cacccaucg                                                          19

<210> SEQ ID NO 129
<211> LENGTH: 19
<212> TYPE: RNA
<213> ORGANISM: Artificial sequence
<220> FEATURE:
<223> OTHER INFORMATION: Synthetic

<400> SEQUENCE: 129
agaugagaaa uauccaucu                                                          19

<210> SEQ ID NO 130
<211> LENGTH: 25
<212> TYPE: RNA
<213> ORGANISM: Artificial sequence
<220> FEATURE:
<223> OTHER INFORMATION: Synthetic

<400> SEQUENCE: 130
aauggagaau auauggauuc ccauu                                                   25

<210> SEQ ID NO 131
<211> LENGTH: 19
<212> TYPE: RNA
<213> ORGANISM: Artificial sequence
<220> FEATURE:
<223> OTHER INFORMATION: Synthetic

<400> SEQUENCE: 131
acacgaggau cacccgugu                                                          19

<210> SEQ ID NO 132
<211> LENGTH: 19
<212> TYPE: RNA
<213> ORGANISM: Artificial sequence
<220> FEATURE:
<223> OTHER INFORMATION: Synthetic

<400> SEQUENCE: 132
agaugagcaa uagccaucu                                                          19

<210> SEQ ID NO 133
<211> LENGTH: 19
<212> TYPE: RNA
<213> ORGANISM: Artificial sequence
<220> FEATURE:
<223> OTHER INFORMATION: Synthetic

<400> SEQUENCE: 133
agaugaggac uacccaucu                                                          19

<210> SEQ ID NO 134

-continued

```
<211> LENGTH: 19
<212> TYPE: RNA
<213> ORGANISM: Artificial sequence
<220> FEATURE:
<223> OTHER INFORMATION: Synthetic

<400> SEQUENCE: 134
acaugaggau uacccaugu                                              19

<210> SEQ ID NO 135
<211> LENGTH: 19
<212> TYPE: RNA
<213> ORGANISM: Artificial sequence
<220> FEATURE:
<223> OTHER INFORMATION: Synthetic

<400> SEQUENCE: 135
agaagagcau uagccuucu                                              19

<210> SEQ ID NO 136
<211> LENGTH: 19
<212> TYPE: RNA
<213> ORGANISM: Artificial sequence
<220> FEATURE:
<223> OTHER INFORMATION: Synthetic

<400> SEQUENCE: 136
augaggauca cccauguua                                              19

<210> SEQ ID NO 137
<211> LENGTH: 19
<212> TYPE: RNA
<213> ORGANISM: Artificial sequence
<220> FEATURE:
<223> OTHER INFORMATION: Synthetic

<400> SEQUENCE: 137
aacaugagga ucacccaug                                              19

<210> SEQ ID NO 138
<211> LENGTH: 19
<212> TYPE: RNA
<213> ORGANISM: Artificial sequence
<220> FEATURE:
<223> OTHER INFORMATION: Synthetic

<400> SEQUENCE: 138
acaugaggau uacccaugu                                              19

<210> SEQ ID NO 139
<211> LENGTH: 25
<212> TYPE: RNA
<213> ORGANISM: Artificial sequence
<220> FEATURE:
<223> OTHER INFORMATION: Synthetic

<400> SEQUENCE: 139
uaaggaguuu cguguuaaac ccuua                                       25

<210> SEQ ID NO 140
<211> LENGTH: 23
<212> TYPE: RNA
<213> ORGANISM: Artificial sequence
<220> FEATURE:
<223> OTHER INFORMATION: Synthetic
```

-continued

<400> SEQUENCE: 140
acauguaagg auuaccuaca ugu                                                                23

<210> SEQ ID NO 141
<211> LENGTH: 19
<212> TYPE: RNA
<213> ORGANISM: Artificial sequence
<220> FEATURE:
<223> OTHER INFORMATION: Synthetic

<400> SEQUENCE: 141
acaugaggau cacccaugu                                                                     19

<210> SEQ ID NO 142
<211> LENGTH: 20
<212> TYPE: RNA
<213> ORGANISM: Artificial sequence
<220> FEATURE:
<223> OTHER INFORMATION: Synthetic

<400> SEQUENCE: 142
acauauaucu aagauaaugu                                                                    20

<210> SEQ ID NO 143
<211> LENGTH: 25
<212> TYPE: RNA
<213> ORGANISM: Artificial sequence
<220> FEATURE:
<223> OTHER INFORMATION: Synthetic

<400> SEQUENCE: 143
auacgagaau auauggauuc cguau                                                              25

<210> SEQ ID NO 144
<211> LENGTH: 19
<212> TYPE: RNA
<213> ORGANISM: Artificial sequence
<220> FEATURE:
<223> OTHER INFORMATION: Synthetic

<400> SEQUENCE: 144
aguugagcag uagccaacu                                                                     19

<210> SEQ ID NO 145
<211> LENGTH: 25
<212> TYPE: RNA
<213> ORGANISM: Artificial sequence
<220> FEATURE:
<223> OTHER INFORMATION: Synthetic

<400> SEQUENCE: 145
uaaagcgcuu auaugaaagc cuuua                                                              25

<210> SEQ ID NO 146
<211> LENGTH: 19
<212> TYPE: RNA
<213> ORGANISM: Artificial sequence
<220> FEATURE:
<223> OTHER INFORMATION: Synthetic

<400> SEQUENCE: 146
acgugagcau cagccaugu                                                                     19

<210> SEQ ID NO 147

```
<211> LENGTH: 19
<212> TYPE: RNA
<213> ORGANISM: Artificial sequence
<220> FEATURE:
<223> OTHER INFORMATION: Synthetic

<400> SEQUENCE: 147
auacgaggaa uacccguau                                                    19

<210> SEQ ID NO 148
<211> LENGTH: 21
<212> TYPE: RNA
<213> ORGANISM: Artificial sequence
<220> FEATURE:
<223> OTHER INFORMATION: Synthetic

<400> SEQUENCE: 148
acauguagga uuaccacaug u                                                  21

<210> SEQ ID NO 149
<211> LENGTH: 19
<212> TYPE: RNA
<213> ORGANISM: Artificial sequence
<220> FEATURE:
<223> OTHER INFORMATION: Synthetic

<400> SEQUENCE: 149
acuugaccau uaggcaagu                                                    19

<210> SEQ ID NO 150
<211> LENGTH: 19
<212> TYPE: RNA
<213> ORGANISM: Artificial sequence
<220> FEATURE:
<223> OTHER INFORMATION: Synthetic

<400> SEQUENCE: 150
aagugaggaa uacccacuu                                                    19

<210> SEQ ID NO 151
<211> LENGTH: 19
<212> TYPE: RNA
<213> ORGANISM: Artificial sequence
<220> FEATURE:
<223> OTHER INFORMATION: Synthetic

<400> SEQUENCE: 151
uaaugaggaa uacccauua                                                    19

<210> SEQ ID NO 152
<211> LENGTH: 19
<212> TYPE: RNA
<213> ORGANISM: Artificial sequence
<220> FEATURE:
<223> OTHER INFORMATION: Synthetic

<400> SEQUENCE: 152
acuacaggau uaccguagu                                                    19

<210> SEQ ID NO 153
<211> LENGTH: 25
<212> TYPE: RNA
<213> ORGANISM: Artificial sequence
<220> FEATURE:
<223> OTHER INFORMATION: Synthetic
```

-continued

---

<400> SEQUENCE: 153
uaaggaguua uuauguuaac ccuua                                    25

<210> SEQ ID NO 154
<211> LENGTH: 24
<212> TYPE: RNA
<213> ORGANISM: Artificial sequence
<220> FEATURE:
<223> OTHER INFORMATION: Synthetic

<400> SEQUENCE: 154
augcacauga ggauuaccca ugug                                     24

<210> SEQ ID NO 155
<211> LENGTH: 19
<212> TYPE: RNA
<213> ORGANISM: Artificial sequence
<220> FEATURE:
<223> OTHER INFORMATION: Synthetic

<400> SEQUENCE: 155
augcgaggau uacccgcau                                           19

<210> SEQ ID NO 156
<211> LENGTH: 19
<212> TYPE: RNA
<213> ORGANISM: Artificial sequence
<220> FEATURE:
<223> OTHER INFORMATION: Synthetic

<400> SEQUENCE: 156
acacgaggau cacccgugg                                           19

<210> SEQ ID NO 157
<211> LENGTH: 21
<212> TYPE: RNA
<213> ORGANISM: Artificial sequence
<220> FEATURE:
<223> OTHER INFORMATION: Synthetic

<400> SEQUENCE: 157
agcaugagga uuacccaugc u                                        21

<210> SEQ ID NO 158
<211> LENGTH: 19
<212> TYPE: RNA
<213> ORGANISM: Artificial sequence
<220> FEATURE:
<223> OTHER INFORMATION: Synthetic

<400> SEQUENCE: 158
gcacgaggau cacccgugu                                           19

<210> SEQ ID NO 159
<211> LENGTH: 19
<212> TYPE: RNA
<213> ORGANISM: Artificial sequence
<220> FEATURE:
<223> OTHER INFORMATION: Synthetic

<400> SEQUENCE: 159
acuugaggau cacccaagu                                           19

<210> SEQ ID NO 160

```
<211> LENGTH: 19
<212> TYPE: RNA
<213> ORGANISM: Artificial sequence
<220> FEATURE:
<223> OTHER INFORMATION: Synthetic

<400> SEQUENCE: 160
agaacaccau uaggguucu                                              19

<210> SEQ ID NO 161
<211> LENGTH: 19
<212> TYPE: RNA
<213> ORGANISM: Artificial sequence
<220> FEATURE:
<223> OTHER INFORMATION: Synthetic

<400> SEQUENCE: 161
caauaaggau uaccuauug                                              19

<210> SEQ ID NO 162
<211> LENGTH: 25
<212> TYPE: RNA
<213> ORGANISM: Artificial sequence
<220> FEATURE:
<223> OTHER INFORMATION: Synthetic

<400> SEQUENCE: 162
uaaggaguuu caggacaaac ccuua                                       25

<210> SEQ ID NO 163
<211> LENGTH: 21
<212> TYPE: RNA
<213> ORGANISM: Artificial sequence
<220> FEATURE:
<223> OTHER INFORMATION: Synthetic

<400> SEQUENCE: 163
aacaugagga uuacccaugu u                                           21

<210> SEQ ID NO 164
<211> LENGTH: 19
<212> TYPE: RNA
<213> ORGANISM: Artificial sequence
<220> FEATURE:
<223> OTHER INFORMATION: Synthetic

<400> SEQUENCE: 164
ugaacacgau uacgguuca                                              19

<210> SEQ ID NO 165
<211> LENGTH: 25
<212> TYPE: RNA
<213> ORGANISM: Artificial sequence
<220> FEATURE:
<223> OTHER INFORMATION: Synthetic

<400> SEQUENCE: 165
uaagaaacuu auauggaagu ucuua                                       25

<210> SEQ ID NO 166
<211> LENGTH: 19
<212> TYPE: RNA
<213> ORGANISM: Artificial sequence
<220> FEATURE:
<223> OTHER INFORMATION: Synthetic
```

-continued

<400> SEQUENCE: 166
agaagaggaa uacccuucu                                                          19

<210> SEQ ID NO 167
<211> LENGTH: 19
<212> TYPE: RNA
<213> ORGANISM: Artificial sequence
<220> FEATURE:
<223> OTHER INFORMATION: Synthetic

<400> SEQUENCE: 167
aguguaggac uaccacacu                                                         19

<210> SEQ ID NO 168
<211> LENGTH: 19
<212> TYPE: RNA
<213> ORGANISM: Artificial sequence
<220> FEATURE:
<223> OTHER INFORMATION: Synthetic

<400> SEQUENCE: 168
acuggaggau caccccagu                                                         19

<210> SEQ ID NO 169
<211> LENGTH: 25
<212> TYPE: RNA
<213> ORGANISM: Artificial sequence
<220> FEATURE:
<223> OTHER INFORMATION: Synthetic

<400> SEQUENCE: 169
aaaccagaaa auaugguuuc gguuu                                                  25

<210> SEQ ID NO 170
<211> LENGTH: 23
<212> TYPE: RNA
<213> ORGANISM: Artificial sequence
<220> FEATURE:
<223> OTHER INFORMATION: Synthetic

<400> SEQUENCE: 170
augucagaug uuaacaucga cau                                                    23

<210> SEQ ID NO 171
<211> LENGTH: 19
<212> TYPE: RNA
<213> ORGANISM: Artificial sequence
<220> FEATURE:
<223> OTHER INFORMATION: Synthetic

<400> SEQUENCE: 171
acguaagaau uaucuacgu                                                         19

<210> SEQ ID NO 172
<211> LENGTH: 19
<212> TYPE: RNA
<213> ORGANISM: Artificial sequence
<220> FEATURE:
<223> OTHER INFORMATION: Synthetic

<400> SEQUENCE: 172
agaacagcau uagcguucu                                                         19

<210> SEQ ID NO 173

-continued

```
<211> LENGTH: 19
<212> TYPE: RNA
<213> ORGANISM: Artificial sequence
<220> FEATURE:
<223> OTHER INFORMATION: Synthetic

<400> SEQUENCE: 173
acgugaggau cacccgcgu                                             19

<210> SEQ ID NO 174
<211> LENGTH: 19
<212> TYPE: RNA
<213> ORGANISM: Artificial sequence
<220> FEATURE:
<223> OTHER INFORMATION: Synthetic

<400> SEQUENCE: 174
acaugaggau cacccaugc                                             19

<210> SEQ ID NO 175
<211> LENGTH: 19
<212> TYPE: RNA
<213> ORGANISM: Artificial sequence
<220> FEATURE:
<223> OTHER INFORMATION: Synthetic

<400> SEQUENCE: 175
guaugaggau cacccaugc                                             19

<210> SEQ ID NO 176
<211> LENGTH: 19
<212> TYPE: RNA
<213> ORGANISM: Artificial sequence
<220> FEATURE:
<223> OTHER INFORMATION: Synthetic

<400> SEQUENCE: 176
augacaaguu aacugucau                                             19

<210> SEQ ID NO 177
<211> LENGTH: 19
<212> TYPE: RNA
<213> ORGANISM: Artificial sequence
<220> FEATURE:
<223> OTHER INFORMATION: Synthetic

<400> SEQUENCE: 177
agcugacgaa uacgcagcu                                             19

<210> SEQ ID NO 178
<211> LENGTH: 25
<212> TYPE: RNA
<213> ORGANISM: Artificial sequence
<220> FEATURE:
<223> OTHER INFORMATION: Synthetic

<400> SEQUENCE: 178
auucgagauu auauggaauc cgaau                                      25

<210> SEQ ID NO 179
<211> LENGTH: 19
<212> TYPE: RNA
<213> ORGANISM: Artificial sequence
<220> FEATURE:
<223> OTHER INFORMATION: Synthetic
```

-continued

<400> SEQUENCE: 179
acuacaggau uaccguagu                                          19

<210> SEQ ID NO 180
<211> LENGTH: 25
<212> TYPE: RNA
<213> ORGANISM: Artificial sequence
<220> FEATURE:
<223> OTHER INFORMATION: Synthetic

<400> SEQUENCE: 180
uaagguguuu uuuaagaaac ccuua                                   25

<210> SEQ ID NO 181
<211> LENGTH: 16
<212> TYPE: RNA
<213> ORGANISM: Artificial sequence
<220> FEATURE:
<223> OTHER INFORMATION: Synthetic

<400> SEQUENCE: 181
uaggagaagg ucccua                                            16

<210> SEQ ID NO 182
<211> LENGTH: 19
<212> TYPE: RNA
<213> ORGANISM: Artificial sequence
<220> FEATURE:
<223> OTHER INFORMATION: Synthetic

<400> SEQUENCE: 182
auaugaggaa uacccauau                                         19

<210> SEQ ID NO 183
<211> LENGTH: 19
<212> TYPE: RNA
<213> ORGANISM: Artificial sequence
<220> FEATURE:
<223> OTHER INFORMATION: Synthetic

<400> SEQUENCE: 183
acaugaggau uacccaugu                                         19

<210> SEQ ID NO 184
<211> LENGTH: 19
<212> TYPE: RNA
<213> ORGANISM: Artificial sequence
<220> FEATURE:
<223> OTHER INFORMATION: Synthetic

<400> SEQUENCE: 184
acgugaggaa cacccacgu                                         19

<210> SEQ ID NO 185
<211> LENGTH: 25
<212> TYPE: RNA
<213> ORGANISM: Artificial sequence
<220> FEATURE:
<223> OTHER INFORMATION: Synthetic

<400> SEQUENCE: 185
uagugagugu auauggacac cacua                                   25

<210> SEQ ID NO 186

<211> LENGTH: 27
<212> TYPE: RNA
<213> ORGANISM: Artificial sequence
<220> FEATURE:
<223> OTHER INFORMATION: Synthetic

<400> SEQUENCE: 186
uaaggaaguu uauauggaaa cuccuua                                    27

<210> SEQ ID NO 187
<211> LENGTH: 25
<212> TYPE: RNA
<213> ORGANISM: Artificial sequence
<220> FEATURE:
<223> OTHER INFORMATION: Synthetic

<400> SEQUENCE: 187
uaaggcguuu cuugauaaac ccuua                                    25

<210> SEQ ID NO 188
<211> LENGTH: 19
<212> TYPE: RNA
<213> ORGANISM: Artificial sequence
<220> FEATURE:
<223> OTHER INFORMATION: Synthetic

<400> SEQUENCE: 188
acaagagcaa uagccuugu                                    19

<210> SEQ ID NO 189
<211> LENGTH: 17
<212> TYPE: RNA
<213> ORGANISM: Artificial sequence
<220> FEATURE:
<223> OTHER INFORMATION: Synthetic

<400> SEQUENCE: 189
acugaggauu acccagu                                    17

<210> SEQ ID NO 190
<211> LENGTH: 25
<212> TYPE: RNA
<213> ORGANISM: Artificial sequence
<220> FEATURE:
<223> OTHER INFORMATION: Synthetic

<400> SEQUENCE: 190
uaaagaguuu auaaggaaac cuuua                                    25

<210> SEQ ID NO 191
<211> LENGTH: 19
<212> TYPE: RNA
<213> ORGANISM: Artificial sequence
<220> FEATURE:
<223> OTHER INFORMATION: Synthetic

<400> SEQUENCE: 191
uugugaggag uacccacaa                                    19

<210> SEQ ID NO 192
<211> LENGTH: 19
<212> TYPE: RNA
<213> ORGANISM: Artificial sequence
<220> FEATURE:
<223> OTHER INFORMATION: Synthetic -continued

<400> SEQUENCE: 192
acaugaggau uacccaugu                                                              19

<210> SEQ ID NO 193
<211> LENGTH: 25
<212> TYPE: RNA
<213> ORGANISM: Artificial sequence
<220> FEATURE:
<223> OTHER INFORMATION: Synthetic

<400> SEQUENCE: 193
auuggacauu auauggaaug ccaau                                                       25

<210> SEQ ID NO 194
<211> LENGTH: 25
<212> TYPE: RNA
<213> ORGANISM: Artificial sequence
<220> FEATURE:
<223> OTHER INFORMATION: Synthetic

<400> SEQUENCE: 194
uaagguguuu uuuaagaaac ccuua                                                       25

<210> SEQ ID NO 195
<211> LENGTH: 19
<212> TYPE: RNA
<213> ORGANISM: Artificial sequence
<220> FEATURE:
<223> OTHER INFORMATION: Synthetic

<400> SEQUENCE: 195
acugaauaau uacaucagu                                                              19

<210> SEQ ID NO 196
<211> LENGTH: 18
<212> TYPE: RNA
<213> ORGANISM: Artificial sequence
<220> FEATURE:
<223> OTHER INFORMATION: Synthetic

<400> SEQUENCE: 196
uaaggacgau acgccuua                                                               18

<210> SEQ ID NO 197
<211> LENGTH: 19
<212> TYPE: RNA
<213> ORGANISM: Artificial sequence
<220> FEATURE:
<223> OTHER INFORMATION: Synthetic

<400> SEQUENCE: 197
auuagaggac uacccuaau                                                              19

<210> SEQ ID NO 198
<211> LENGTH: 19
<212> TYPE: RNA
<213> ORGANISM: Artificial sequence
<220> FEATURE:
<223> OTHER INFORMATION: Synthetic

<400> SEQUENCE: 198
aguucagcau uagcgaacu                                                              19

<210> SEQ ID NO 199

-continued

```
<211> LENGTH: 19
<212> TYPE: RNA
<213> ORGANISM: Artificial sequence
<220> FEATURE:
<223> OTHER INFORMATION: Synthetic

<400> SEQUENCE: 199
aaacgagaau uauccguuu                                           19

<210> SEQ ID NO 200
<211> LENGTH: 25
<212> TYPE: RNA
<213> ORGANISM: Artificial sequence
<220> FEATURE:
<223> OTHER INFORMATION: Synthetic

<400> SEQUENCE: 200
aaaccuguuu acacggaaac gguuu                                    25

<210> SEQ ID NO 201
<211> LENGTH: 19
<212> TYPE: RNA
<213> ORGANISM: Artificial sequence
<220> FEATURE:
<223> OTHER INFORMATION: Synthetic

<400> SEQUENCE: 201
gaauaaggau uaccuauuc                                           19

<210> SEQ ID NO 202
<211> LENGTH: 25
<212> TYPE: RNA
<213> ORGANISM: Artificial sequence
<220> FEATURE:
<223> OTHER INFORMATION: Synthetic

<400> SEQUENCE: 202
uaacgagaaa auaucauuc cguua                                     25

<210> SEQ ID NO 203
<211> LENGTH: 25
<212> TYPE: RNA
<213> ORGANISM: Artificial sequence
<220> FEATURE:
<223> OTHER INFORMATION: Synthetic

<400> SEQUENCE: 203
uaaagacguu auaaggaacg cuuua                                    25

<210> SEQ ID NO 204
<211> LENGTH: 25
<212> TYPE: RNA
<213> ORGANISM: Artificial sequence
<220> FEATURE:
<223> OTHER INFORMATION: Synthetic

<400> SEQUENCE: 204
uuucgacauu auauggaaug cgaaa                                    25

<210> SEQ ID NO 205
<211> LENGTH: 19
<212> TYPE: RNA
<213> ORGANISM: Artificial sequence
<220> FEATURE:
<223> OTHER INFORMATION: Synthetic
```

-continued

```
<400> SEQUENCE: 205
ggaguuuaua uggaaaccc                                              19

<210> SEQ ID NO 206
<211> LENGTH: 25
<212> TYPE: RNA
<213> ORGANISM: Artificial sequence
<220> FEATURE:
<223> OTHER INFORMATION: Synthetic

<400> SEQUENCE: 206
uaucgagaaa auaugguuuc cgaua                                       25

<210> SEQ ID NO 207
<211> LENGTH: 25
<212> TYPE: RNA
<213> ORGANISM: Artificial sequence
<220> FEATURE:
<223> OTHER INFORMATION: Synthetic

<400> SEQUENCE: 207
aaucgaguau auauggauac cgauu                                       25

<210> SEQ ID NO 208
<211> LENGTH: 25
<212> TYPE: RNA
<213> ORGANISM: Artificial sequence
<220> FEATURE:
<223> OTHER INFORMATION: Synthetic

<400> SEQUENCE: 208
uuuggacuuu auauggaaag ccaaa                                       25

<210> SEQ ID NO 209
<211> LENGTH: 25
<212> TYPE: RNA
<213> ORGANISM: Artificial sequence
<220> FEATURE:
<223> OTHER INFORMATION: Synthetic

<400> SEQUENCE: 209
auaccacuuu auauggaaag gguau                                       25

<210> SEQ ID NO 210
<211> LENGTH: 25
<212> TYPE: RNA
<213> ORGANISM: Artificial sequence
<220> FEATURE:
<223> OTHER INFORMATION: Synthetic

<400> SEQUENCE: 210
auagcacaau auauggauug gcuau                                       25

<210> SEQ ID NO 211
<211> LENGTH: 25
<212> TYPE: RNA
<213> ORGANISM: Artificial sequence
<220> FEATURE:
<223> OTHER INFORMATION: Synthetic

<400> SEQUENCE: 211
cagagauuuc auaugggaaa cucug                                       25

<210> SEQ ID NO 212
```

-continued

```
<211> LENGTH: 25
<212> TYPE: RNA
<213> ORGANISM: Artificial sequence
<220> FEATURE:
<223> OTHER INFORMATION: Synthetic

<400> SEQUENCE: 212
uauggagauu auacgcaauc ccaua                                          25

<210> SEQ ID NO 213
<211> LENGTH: 25
<212> TYPE: RNA
<213> ORGANISM: Artificial sequence
<220> FEATURE:
<223> OTHER INFORMATION: Synthetic

<400> SEQUENCE: 213
uuuccacuuu auauggaaag ggaaa                                          25

<210> SEQ ID NO 214
<211> LENGTH: 25
<212> TYPE: RNA
<213> ORGANISM: Artificial sequence
<220> FEATURE:
<223> OTHER INFORMATION: Synthetic

<400> SEQUENCE: 214
aauggacaaa auaugguuug ccauu                                          25

<210> SEQ ID NO 215
<211> LENGTH: 25
<212> TYPE: RNA
<213> ORGANISM: Artificial sequence
<220> FEATURE:
<223> OTHER INFORMATION: Synthetic

<400> SEQUENCE: 215
aaucgacaau auauggauug cgauu                                          25

<210> SEQ ID NO 216
<211> LENGTH: 25
<212> TYPE: RNA
<213> ORGANISM: Artificial sequence
<220> FEATURE:
<223> OTHER INFORMATION: Synthetic

<400> SEQUENCE: 216
caagaagugu auauggacac ucuug                                          25

<210> SEQ ID NO 217
<211> LENGTH: 27
<212> TYPE: RNA
<213> ORGANISM: Artificial sequence
<220> FEATURE:
<223> OTHER INFORMATION: Synthetic

<400> SEQUENCE: 217
uaagggaguu uauauggaaa ccccuua                                        27

<210> SEQ ID NO 218
<211> LENGTH: 25
<212> TYPE: RNA
<213> ORGANISM: Artificial sequence
<220> FEATURE:
<223> OTHER INFORMATION: Synthetic
```

-continued

<400> SEQUENCE: 218
auuccaguuu auauggaaac ggaau                                          25

<210> SEQ ID NO 219
<211> LENGTH: 25
<212> TYPE: RNA
<213> ORGANISM: Artificial sequence
<220> FEATURE:
<223> OTHER INFORMATION: Synthetic

<400> SEQUENCE: 219
uuuccagaau auauggauuc ggaaa                                          25

<210> SEQ ID NO 220
<211> LENGTH: 25
<212> TYPE: RNA
<213> ORGANISM: Artificial sequence
<220> FEATURE:
<223> OTHER INFORMATION: Synthetic

<400> SEQUENCE: 220
uaaccacuuu auauggaaag gguua                                          25

<210> SEQ ID NO 221
<211> LENGTH: 25
<212> TYPE: RNA
<213> ORGANISM: Artificial sequence
<220> FEATURE:
<223> OTHER INFORMATION: Synthetic

<400> SEQUENCE: 221
aaacgacaau auauggauug cguuu                                          25

<210> SEQ ID NO 222
<211> LENGTH: 27
<212> TYPE: RNA
<213> ORGANISM: Artificial sequence
<220> FEATURE:
<223> OTHER INFORMATION: Synthetic

<400> SEQUENCE: 222
uauaggaguu uauauggaaa cccuaua                                        27

<210> SEQ ID NO 223
<211> LENGTH: 25
<212> TYPE: RNA
<213> ORGANISM: Artificial sequence
<220> FEATURE:
<223> OTHER INFORMATION: Synthetic

<400> SEQUENCE: 223
uaaccagaaa auaugguuuc gguua                                          25

<210> SEQ ID NO 224
<211> LENGTH: 25
<212> TYPE: RNA
<213> ORGANISM: Artificial sequence
<220> FEATURE:
<223> OTHER INFORMATION: Synthetic

<400> SEQUENCE: 224
acaugagcga auaugaucgc caugu                                          25

<210> SEQ ID NO 225

```
<211> LENGTH: 25
<212> TYPE: RNA
<213> ORGANISM: Artificial sequence
<220> FEATURE:
<223> OTHER INFORMATION: Synthetic

<400> SEQUENCE: 225
cuaggaguuu auacgcaaac ccuag                                                      25

<210> SEQ ID NO 226
<211> LENGTH: 25
<212> TYPE: RNA
<213> ORGANISM: Artificial sequence
<220> FEATURE:
<223> OTHER INFORMATION: Synthetic

<400> SEQUENCE: 226
uaggaauugu auauggacaa uccua                                                      25

<210> SEQ ID NO 227
<211> LENGTH: 25
<212> TYPE: RNA
<213> ORGANISM: Artificial sequence
<220> FEATURE:
<223> OTHER INFORMATION: Synthetic

<400> SEQUENCE: 227
uaauaaacuc auaugggagu uauua                                                      25

<210> SEQ ID NO 228
<211> LENGTH: 25
<212> TYPE: RNA
<213> ORGANISM: Artificial sequence
<220> FEATURE:
<223> OTHER INFORMATION: Synthetic

<400> SEQUENCE: 228
aaaggagauu auaugaaauc ccuuu                                                      25

<210> SEQ ID NO 229
<211> LENGTH: 25
<212> TYPE: RNA
<213> ORGANISM: Artificial sequence
<220> FEATURE:
<223> OTHER INFORMATION: Synthetic

<400> SEQUENCE: 229
caaugagcgu auauggacgc cauug                                                      25

<210> SEQ ID NO 230
<211> LENGTH: 23
<212> TYPE: RNA
<213> ORGANISM: Artificial sequence
<220> FEATURE:
<223> OTHER INFORMATION: Synthetic

<400> SEQUENCE: 230
aaggaguuua uauggaaacc cuu                                                        23

<210> SEQ ID NO 231
<211> LENGTH: 25
<212> TYPE: RNA
<213> ORGANISM: Artificial sequence
<220> FEATURE:
<223> OTHER INFORMATION: Synthetic
```

-continued

<400> SEQUENCE: 231
ugaguaauuc auaugggaau acuca                                              25

<210> SEQ ID NO 232
<211> LENGTH: 25
<212> TYPE: RNA
<213> ORGANISM: Artificial sequence
<220> FEATURE:
<223> OTHER INFORMATION: Synthetic

<400> SEQUENCE: 232
caaugaguuc auaugggaac cauug                                              25

<210> SEQ ID NO 233
<211> LENGTH: 25
<212> TYPE: RNA
<213> ORGANISM: Artificial sequence
<220> FEATURE:
<223> OTHER INFORMATION: Synthetic

<400> SEQUENCE: 233
auucgagauu auauggaauc cgaau                                              25

<210> SEQ ID NO 234
<211> LENGTH: 25
<212> TYPE: RNA
<213> ORGANISM: Artificial sequence
<220> FEATURE:
<223> OTHER INFORMATION: Synthetic

<400> SEQUENCE: 234
uaaugagucg auauggcgac cauua                                              25

<210> SEQ ID NO 235
<211> LENGTH: 25
<212> TYPE: RNA
<213> ORGANISM: Artificial sequence
<220> FEATURE:
<223> OTHER INFORMATION: Synthetic

<400> SEQUENCE: 235
caguaaguuc auaugggaac uacug                                              25

<210> SEQ ID NO 236
<211> LENGTH: 25
<212> TYPE: RNA
<213> ORGANISM: Artificial sequence
<220> FEATURE:
<223> OTHER INFORMATION: Synthetic

<400> SEQUENCE: 236
aaucgagaaa auaugguuuc cgauu                                              25

<210> SEQ ID NO 237
<211> LENGTH: 25
<212> TYPE: RNA
<213> ORGANISM: Artificial sequence
<220> FEATURE:
<223> OTHER INFORMATION: Synthetic

<400> SEQUENCE: 237
uaugcaguau auauggauac gcaua                                              25

<210> SEQ ID NO 238

-continued

```
<211> LENGTH: 23
<212> TYPE: RNA
<213> ORGANISM: Artificial sequence
<220> FEATURE:
<223> OTHER INFORMATION: Synthetic

<400> SEQUENCE: 238
uacgagucaa uauggugacc gua                                          23

<210> SEQ ID NO 239
<211> LENGTH: 25
<212> TYPE: RNA
<213> ORGANISM: Artificial sequence
<220> FEATURE:
<223> OTHER INFORMATION: Synthetic

<400> SEQUENCE: 239
aaucgacauu auauggaaug cgauu                                        25

<210> SEQ ID NO 240
<211> LENGTH: 25
<212> TYPE: RNA
<213> ORGANISM: Artificial sequence
<220> FEATURE:
<223> OTHER INFORMATION: Synthetic

<400> SEQUENCE: 240
aaugcacuuu auauggaaag gcauu                                        25

<210> SEQ ID NO 241
<211> LENGTH: 25
<212> TYPE: RNA
<213> ORGANISM: Artificial sequence
<220> FEATURE:
<223> OTHER INFORMATION: Synthetic

<400> SEQUENCE: 241
uaaccagaau auauggauuc gguua                                        25

<210> SEQ ID NO 242
<211> LENGTH: 25
<212> TYPE: RNA
<213> ORGANISM: Artificial sequence
<220> FEATURE:
<223> OTHER INFORMATION: Synthetic

<400> SEQUENCE: 242
auugcacauu auauggaaug gcaau                                        25

<210> SEQ ID NO 243
<211> LENGTH: 25
<212> TYPE: RNA
<213> ORGANISM: Artificial sequence
<220> FEATURE:
<223> OTHER INFORMATION: Synthetic

<400> SEQUENCE: 243
uuugcacuuu auauggaaag gcaaa                                        25

<210> SEQ ID NO 244
<211> LENGTH: 25
<212> TYPE: RNA
<213> ORGANISM: Artificial sequence
<220> FEATURE:
<223> OTHER INFORMATION: Synthetic
```

-continued

<400> SEQUENCE: 244
uacgaagcuu auauggaagc ucgua                                         25

<210> SEQ ID NO 245
<211> LENGTH: 25
<212> TYPE: RNA
<213> ORGANISM: Artificial sequence
<220> FEATURE:
<223> OTHER INFORMATION: Synthetic

<400> SEQUENCE: 245
auuccagauu auauggaauc ggaau                                         25

<210> SEQ ID NO 246
<211> LENGTH: 25
<212> TYPE: RNA
<213> ORGANISM: Artificial sequence
<220> FEATURE:
<223> OTHER INFORMATION: Synthetic

<400> SEQUENCE: 246
uuugcaguau auauggauac gcaaa                                         25

<210> SEQ ID NO 247
<211> LENGTH: 25
<212> TYPE: RNA
<213> ORGANISM: Artificial sequence
<220> FEATURE:
<223> OTHER INFORMATION: Synthetic

<400> SEQUENCE: 247
aaacgacaua auaugguaug cguuu                                         25

<210> SEQ ID NO 248
<211> LENGTH: 25
<212> TYPE: RNA
<213> ORGANISM: Artificial sequence
<220> FEATURE:
<223> OTHER INFORMATION: Synthetic

<400> SEQUENCE: 248
uaacgacaau auauggauug cguua                                         25

<210> SEQ ID NO 249
<211> LENGTH: 25
<212> TYPE: RNA
<213> ORGANISM: Artificial sequence
<220> FEATURE:
<223> OTHER INFORMATION: Synthetic

<400> SEQUENCE: 249
gaaguagugu auauggacac acuuc                                         25

<210> SEQ ID NO 250
<211> LENGTH: 25
<212> TYPE: RNA
<213> ORGANISM: Artificial sequence
<220> FEATURE:
<223> OTHER INFORMATION: Synthetic

<400> SEQUENCE: 250
uaaggaguuu auauggaaac ccuua                                         25

<210> SEQ ID NO 251

-continued

```
<211> LENGTH: 25
<212> TYPE: RNA
<213> ORGANISM: Artificial sequence
<220> FEATURE:
<223> OTHER INFORMATION: Synthetic

<400> SEQUENCE: 251
uaaggaguuu guauguaaac ccuua                                          25

<210> SEQ ID NO 252
<211> LENGTH: 25
<212> TYPE: RNA
<213> ORGANISM: Artificial sequence
<220> FEATURE:
<223> OTHER INFORMATION: Synthetic

<400> SEQUENCE: 252
uaaggaguuu auauggaaac ccuua                                          25

<210> SEQ ID NO 253
<211> LENGTH: 25
<212> TYPE: RNA
<213> ORGANISM: Artificial sequence
<220> FEATURE:
<223> OTHER INFORMATION: Synthetic

<400> SEQUENCE: 253
aaaccacaau auauggauug gguuu                                          25

<210> SEQ ID NO 254
<211> LENGTH: 25
<212> TYPE: RNA
<213> ORGANISM: Artificial sequence
<220> FEATURE:
<223> OTHER INFORMATION: Synthetic

<400> SEQUENCE: 254
uaagcacauu auaaggaaug gcuua                                          25

<210> SEQ ID NO 255
<211> LENGTH: 25
<212> TYPE: RNA
<213> ORGANISM: Artificial sequence
<220> FEATURE:
<223> OTHER INFORMATION: Synthetic

<400> SEQUENCE: 255
aaacgagauu auauggaauc cguuu                                          25

<210> SEQ ID NO 256
<211> LENGTH: 25
<212> TYPE: RNA
<213> ORGANISM: Artificial sequence
<220> FEATURE:
<223> OTHER INFORMATION: Synthetic

<400> SEQUENCE: 256
uaacaaguau auaaggauac uguua                                          25

<210> SEQ ID NO 257
<211> LENGTH: 25
<212> TYPE: RNA
<213> ORGANISM: Artificial sequence
<220> FEATURE:
<223> OTHER INFORMATION: Synthetic
```

<400> SEQUENCE: 257
uaagaaacuu auauggaagu ucuua                                             25

<210> SEQ ID NO 258
<211> LENGTH: 25
<212> TYPE: RNA
<213> ORGANISM: Artificial sequence
<220> FEATURE:
<223> OTHER INFORMATION: Synthetic

<400> SEQUENCE: 258
uuucgagaaa auaugguuuc cgaaa                                             25

<210> SEQ ID NO 259
<211> LENGTH: 25
<212> TYPE: RNA
<213> ORGANISM: Artificial sequence
<220> FEATURE:
<223> OTHER INFORMATION: Synthetic

<400> SEQUENCE: 259
gagguaguuu auauggaaac accuc                                             25

<210> SEQ ID NO 260
<211> LENGTH: 25
<212> TYPE: RNA
<213> ORGANISM: Artificial sequence
<220> FEATURE:
<223> OTHER INFORMATION: Synthetic

<400> SEQUENCE: 260
auacgacuuu auauggaaag cguau                                             25

<210> SEQ ID NO 261
<211> LENGTH: 25
<212> TYPE: RNA
<213> ORGANISM: Artificial sequence
<220> FEATURE:
<223> OTHER INFORMATION: Synthetic

<400> SEQUENCE: 261
uuuccagauu auauggaauc ggaaa                                             25

<210> SEQ ID NO 262
<211> LENGTH: 25
<212> TYPE: RNA
<213> ORGANISM: Artificial sequence
<220> FEATURE:
<223> OTHER INFORMATION: Synthetic

<400> SEQUENCE: 262
uaaugaaguu auauggaacu cauua                                             25

<210> SEQ ID NO 263
<211> LENGTH: 25
<212> TYPE: RNA
<213> ORGANISM: Artificial sequence
<220> FEATURE:
<223> OTHER INFORMATION: Synthetic

<400> SEQUENCE: 263
uaugcagaau auauggauuc gcaua                                             25

<210> SEQ ID NO 264

```
<211> LENGTH: 25
<212> TYPE: RNA
<213> ORGANISM: Artificial sequence
<220> FEATURE:
<223> OTHER INFORMATION: Synthetic

<400> SEQUENCE: 264
aauggagaaa auaugguuuc ccauu                                              25

<210> SEQ ID NO 265
<211> LENGTH: 25
<212> TYPE: RNA
<213> ORGANISM: Artificial sequence
<220> FEATURE:
<223> OTHER INFORMATION: Synthetic

<400> SEQUENCE: 265
uaucgacuuu auauggaaag cgaua                                              25

<210> SEQ ID NO 266
<211> LENGTH: 25
<212> TYPE: RNA
<213> ORGANISM: Artificial sequence
<220> FEATURE:
<223> OTHER INFORMATION: Synthetic

<400> SEQUENCE: 266
aaucgagaau auauggauuc cgauu                                              25

<210> SEQ ID NO 267
<211> LENGTH: 25
<212> TYPE: RNA
<213> ORGANISM: Artificial sequence
<220> FEATURE:
<223> OTHER INFORMATION: Synthetic

<400> SEQUENCE: 267
aaucgaguuu auauggaaac cgauu                                              25

<210> SEQ ID NO 268
<211> LENGTH: 25
<212> TYPE: RNA
<213> ORGANISM: Artificial sequence
<220> FEATURE:
<223> OTHER INFORMATION: Synthetic

<400> SEQUENCE: 268
aaugcacauu auauggaaug gcauu                                              25

<210> SEQ ID NO 269
<211> LENGTH: 25
<212> TYPE: RNA
<213> ORGANISM: Artificial sequence
<220> FEATURE:
<223> OTHER INFORMATION: Synthetic

<400> SEQUENCE: 269
aauccacuuu auauggaaag ggauu                                              25

<210> SEQ ID NO 270
<211> LENGTH: 25
<212> TYPE: RNA
<213> ORGANISM: Artificial sequence
<220> FEATURE:
<223> OTHER INFORMATION: Synthetic
```

<400> SEQUENCE: 270
uaagcacuau auauggauag gcuua                                          25

<210> SEQ ID NO 271
<211> LENGTH: 25
<212> TYPE: RNA
<213> ORGANISM: Artificial sequence
<220> FEATURE:
<223> OTHER INFORMATION: Synthetic

<400> SEQUENCE: 271
auugcagaua auauggguauc gcaau                                         25

<210> SEQ ID NO 272
<211> LENGTH: 25
<212> TYPE: RNA
<213> ORGANISM: Artificial sequence
<220> FEATURE:
<223> OTHER INFORMATION: Synthetic

<400> SEQUENCE: 272
uaaccagguu auaugcaacc gguua                                          25

<210> SEQ ID NO 273
<211> LENGTH: 25
<212> TYPE: RNA
<213> ORGANISM: Artificial sequence
<220> FEATURE:
<223> OTHER INFORMATION: Synthetic

<400> SEQUENCE: 273
gcaauagucu auauggagac auugc                                          25

<210> SEQ ID NO 274
<211> LENGTH: 25
<212> TYPE: RNA
<213> ORGANISM: Artificial sequence
<220> FEATURE:
<223> OTHER INFORMATION: Synthetic

<400> SEQUENCE: 274
uaucgacaau auauggauug cgaua                                          25

<210> SEQ ID NO 275
<211> LENGTH: 25
<212> TYPE: RNA
<213> ORGANISM: Artificial sequence
<220> FEATURE:
<223> OTHER INFORMATION: Synthetic

<400> SEQUENCE: 275
caaggaguuu auauguaaac ccuug                                          25

<210> SEQ ID NO 276
<211> LENGTH: 25
<212> TYPE: RNA
<213> ORGANISM: Artificial sequence
<220> FEATURE:
<223> OTHER INFORMATION: Synthetic

<400> SEQUENCE: 276
uuucgacaau auauggauug cgaaa                                          25

<210> SEQ ID NO 277

-continued

```
<211> LENGTH: 25
<212> TYPE: RNA
<213> ORGANISM: Artificial sequence
<220> FEATURE:
<223> OTHER INFORMATION: Synthetic

<400> SEQUENCE: 277
aaagcacaau auauggauug gcuuu                                        25

<210> SEQ ID NO 278
<211> LENGTH: 25
<212> TYPE: RNA
<213> ORGANISM: Artificial sequence
<220> FEATURE:
<223> OTHER INFORMATION: Synthetic

<400> SEQUENCE: 278
gaauuagucc auaugggac aauuc                                         25

<210> SEQ ID NO 279
<211> LENGTH: 25
<212> TYPE: RNA
<213> ORGANISM: Artificial sequence
<220> FEATURE:
<223> OTHER INFORMATION: Synthetic

<400> SEQUENCE: 279
uaaugacauu auaugcaaug cauua                                        25

<210> SEQ ID NO 280
<211> LENGTH: 25
<212> TYPE: RNA
<213> ORGANISM: Artificial sequence
<220> FEATURE:
<223> OTHER INFORMATION: Synthetic

<400> SEQUENCE: 280
uuucgagauu auauggaauc cgaaa                                        25

<210> SEQ ID NO 281
<211> LENGTH: 25
<212> TYPE: RNA
<213> ORGANISM: Artificial sequence
<220> FEATURE:
<223> OTHER INFORMATION: Synthetic

<400> SEQUENCE: 281
uaaagaaguu auauggaacu cuuua                                        25

<210> SEQ ID NO 282
<211> LENGTH: 25
<212> TYPE: RNA
<213> ORGANISM: Artificial sequence
<220> FEATURE:
<223> OTHER INFORMATION: Synthetic

<400> SEQUENCE: 282
uaaggaguuu guaugaaaac ccuua                                        25

<210> SEQ ID NO 283
<211> LENGTH: 19
<212> TYPE: RNA
<213> ORGANISM: Artificial sequence
<220> FEATURE:
<223> OTHER INFORMATION: Synthetic
```

-continued

<400> SEQUENCE: 283
uguugaccau uaggcaaca                                                                    19

<210> SEQ ID NO 284
<211> LENGTH: 25
<212> TYPE: RNA
<213> ORGANISM: Artificial sequence
<220> FEATURE:
<223> OTHER INFORMATION: Synthetic

<400> SEQUENCE: 284
uaacgacaua auaugguaug cguua                                                             25

<210> SEQ ID NO 285
<211> LENGTH: 25
<212> TYPE: RNA
<213> ORGANISM: Artificial sequence
<220> FEATURE:
<223> OTHER INFORMATION: Synthetic

<400> SEQUENCE: 285
uuuggagaaa auaugguuuc ccaaa                                                             25

<210> SEQ ID NO 286
<211> LENGTH: 25
<212> TYPE: RNA
<213> ORGANISM: Artificial sequence
<220> FEATURE:
<223> OTHER INFORMATION: Synthetic

<400> SEQUENCE: 286
aaacgacaaa auaugguuug cguuu                                                             25

<210> SEQ ID NO 287
<211> LENGTH: 25
<212> TYPE: RNA
<213> ORGANISM: Artificial sequence
<220> FEATURE:
<223> OTHER INFORMATION: Synthetic

<400> SEQUENCE: 287
auuccaguau auauggauac ggaau                                                             25

<210> SEQ ID NO 288
<211> LENGTH: 25
<212> TYPE: RNA
<213> ORGANISM: Artificial sequence
<220> FEATURE:
<223> OTHER INFORMATION: Synthetic

<400> SEQUENCE: 288 uaggacaau auauggauug ccaua                                                              25

<210> SEQ ID NO 289
<211> LENGTH: 25
<212> TYPE: RNA
<213> ORGANISM: Artificial sequence
<220> FEATURE:
<223> OTHER INFORMATION: Synthetic

<400> SEQUENCE: 289
aaugcaguau auauggauac gcauu                                                             25

<210> SEQ ID NO 290

```
<211> LENGTH: 25
<212> TYPE: RNA
<213> ORGANISM: Artificial sequence
<220> FEATURE:
<223> OTHER INFORMATION: Synthetic

<400> SEQUENCE: 290
uaucgacaau auauggauug cgaua                                          25

<210> SEQ ID NO 291
<211> LENGTH: 25
<212> TYPE: RNA
<213> ORGANISM: Artificial sequence
<220> FEATURE:
<223> OTHER INFORMATION: Synthetic

<400> SEQUENCE: 291
uuuggagaau auauggauuc ccaaa                                          25

<210> SEQ ID NO 292
<211> LENGTH: 25
<212> TYPE: RNA
<213> ORGANISM: Artificial sequence
<220> FEATURE:
<223> OTHER INFORMATION: Synthetic

<400> SEQUENCE: 292
aaagcaguau auauggauac gcuuu                                          25

<210> SEQ ID NO 293
<211> LENGTH: 25
<212> TYPE: RNA
<213> ORGANISM: Artificial sequence
<220> FEATURE:
<223> OTHER INFORMATION: Synthetic

<400> SEQUENCE: 293
aauggaguau auauggauac ccauu                                          25

<210> SEQ ID NO 294
<211> LENGTH: 25
<212> TYPE: RNA
<213> ORGANISM: Pseudomonas phage PP7

<400> SEQUENCE: 294
uuuccagauu auauggaauc ggaaa                                          25

<210> SEQ ID NO 295
<211> LENGTH: 25
<212> TYPE: RNA
<213> ORGANISM: Escherichia virus Qbeta

<400> SEQUENCE: 295
uaaggaguau auauguauac ccuua                                          25

<210> SEQ ID NO 296
<211> LENGTH: 25
<212> TYPE: RNA
<213> ORGANISM: Escherichia virus MS2

<400> SEQUENCE: 296
ugaauauugu auauggacaa auuca                                          25

<210> SEQ ID NO 297
<211> LENGTH: 25
```

```
<212> TYPE: RNA
<213> ORGANISM: Artificial sequence
<220> FEATURE:
<223> OTHER INFORMATION: Synthetic

<400> SEQUENCE: 297
gcaagauuuc auaugggaaa cuugc                                            25

<210> SEQ ID NO 298
<211> LENGTH: 25
<212> TYPE: RNA
<213> ORGANISM: Artificial sequence
<220> FEATURE:
<223> OTHER INFORMATION: Synthetic

<400> SEQUENCE: 298
uuagcacuuu auauggaaag gcuaa                                            25

<210> SEQ ID NO 299
<211> LENGTH: 25
<212> TYPE: RNA
<213> ORGANISM: Artificial sequence
<220> FEATURE:
<223> OTHER INFORMATION: Synthetic

<400> SEQUENCE: 299
uuucgacuuu auauggaaag cgaaa                                            25

<210> SEQ ID NO 300
<211> LENGTH: 20
<212> TYPE: RNA
<213> ORGANISM: Artificial sequence
<220> FEATURE:
<223> OTHER INFORMATION: Synthetic

<400> SEQUENCE: 300
acgcagguau aauaccgcgu                                                  20

<210> SEQ ID NO 301
<211> LENGTH: 25
<212> TYPE: RNA
<213> ORGANISM: Artificial sequence
<220> FEATURE:
<223> OTHER INFORMATION: Synthetic

<400> SEQUENCE: 301
auuggaguaa auaugguuac ccaau                                            25

<210> SEQ ID NO 302
<211> LENGTH: 25
<212> TYPE: RNA
<213> ORGANISM: Artificial sequence
<220> FEATURE:
<223> OTHER INFORMATION: Synthetic

<400> SEQUENCE: 302
uuuggacaaa auaugguuug ccaaa                                            25

<210> SEQ ID NO 303
<211> LENGTH: 445
<212> TYPE: DNA
<213> ORGANISM: Artificial sequence
<220> FEATURE:
<223> OTHER INFORMATION: Synthetic
```

-continued

```
<400> SEQUENCE: 303
cctaggcgat tatgacgtta ttctactttg attgtgatgc atgtctaaga cagcatcgcc      60
tgctggtcgt gactaaggag tttatatgga aacccttacg agacaatgct accttaccgg     120
tcgggcccac ttgttttttac ccatgatgca tgtctaagac agcatcgcct gctggtcgtg    180
actaaggagt ttatatggaa acccttagaa acagccgtcg ccttgaagcc gagaacaatg     240
catgtctaag acagcatatg gattgcctgt ctgttaagga gttatatgg aaacccttac      300 atcaggcttc gcagtatgca acgcttgcga tgcatgtcta agacagcatt tcaccgcttt     360
cctaagtaag gagtttatat ggaaacccttt agtactaact cgcagatgca tgtctaagac    420
agcatcagaa acgtcacgtc ctggc                                           445

<210> SEQ ID NO 304
<211> LENGTH: 443
<212> TYPE: DNA
<213> ORGANISM: Artificial sequence
<220> FEATURE:
<223> OTHER INFORMATION: Synthetic

<400> SEQUENCE: 304
gaattcttac aaaggaactg taacagtcct tctcgtgctg atcgtgactt ggatgtccaa      60
gacaccaacg agacaatgct accttaccgt cggcccactt gttttttaccc atgacatgac    120 gagatactcg catgtcgcct gctggtcgtg acatgcatgt ctaagacagc atgaaacagc     180
cgtcgccttg aagccgagaa cattgcatgt cgaagacagc aaatggattg ggtctccaat     240
tcctgtctgt ttccatgact aagtcaggaa catcaggctt cgcagtatgc aacgcttgcg     300
atgcattgca aagcaagcat ttcaccgctt tcctaagaag gatagtaatg actaccttgt     360
actaactcgc agatcgaact ctaagagtcg atcagaaacg tcacgtcctg gcaaccatgt     420
cagggacagg tttggaagaa ttc                                            443

<210> SEQ ID NO 305
<211> LENGTH: 13
<212> TYPE: PRT
<213> ORGANISM: Artificial sequence
<220> FEATURE:
<223> OTHER INFORMATION: Synthetic

<400> SEQUENCE: 305

Pro Ala Gly Ala Leu Asp Asp Phe Asp Leu Asp Met Leu
1               5                   10

<210> SEQ ID NO 306
<211> LENGTH: 25
<212> TYPE: RNA
<213> ORGANISM: Escherichia virus PP7

<400> SEQUENCE: 306
uaaggaguuu auauggaaac ccuua                                           25

<210> SEQ ID NO 307
<211> LENGTH: 20
<212> TYPE: RNA
<213> ORGANISM: Escherichia virus Qbeta

<400> SEQUENCE: 307
augcaugucu aagacagcau                                                 20
```

-continued

```
<210> SEQ ID NO 308
<211> LENGTH: 19
<212> TYPE: RNA
<213> ORGANISM: Escherichia virus MS2

<400> SEQUENCE: 308
acaugaggau cacccaugu                                                    19
```